(12) United States Patent
Chen et al.

(10) Patent No.: US 11,434,491 B2
(45) Date of Patent: Sep. 6, 2022

(54) COMPOSITIONS AND METHODS FOR GENE EDITING

(71) Applicant: The Regents of the University of California, Oakland, CA (US)

(72) Inventors: Jin Chen, San Francisco, CA (US); Luke Gilbert, San Francisco, CA (US); James Nunez, San Francisco, CA (US); Jonathan Weissman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/073,588

(22) Filed: Oct. 19, 2020

(65) Prior Publication Data

US 2021/0139918 A1 May 13, 2021

Related U.S. Application Data

(63) Continuation of application No. PCT/US2019/028377, filed on Apr. 19, 2019.

(60) Provisional application No. 62/660,023, filed on Apr. 19, 2018.

(51) Int. Cl.

| C12N 15/62 | (2006.01) |
| C07K 14/47 | (2006.01) |
| C12N 9/10 | (2006.01) |
| C12N 9/20 | (2006.01) |
| C12N 15/113 | (2010.01) |

(52) U.S. Cl.
CPC .......... *C12N 15/62* (2013.01); *C07K 14/4702* (2013.01); *C12N 9/1007* (2013.01); *C12N 9/20* (2013.01); *C12N 15/113* (2013.01); *C07K 2319/09* (2013.01); *C07K 2319/33* (2013.01); *C12Y 201/01072* (2013.01); *C12Y 301/00* (2013.01)

(58) Field of Classification Search
None
See application file for complete search history.

(56) References Cited

U.S. PATENT DOCUMENTS

| 6,919,204 B2 | 7/2005 | Wolffe et al. |
| 8,658,393 B2 | 2/2014 | Reik et al. |
| 8,697,359 B1 | 4/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,993,233 B2 | 3/2015 | Zhang et al. |
| 8,999,641 B2 | 4/2015 | Zhang et al. |
| 9,139,628 B2 | 9/2015 | Minczuk et al. |
| 9,267,135 B2 | 2/2016 | Church et al. |
| 9,322,006 B2 | 4/2016 | Liu et al. |
| 9,526,784 B2 | 12/2016 | Liu et al. |
| 9,771,601 B2 | 9/2017 | May et al. |
| 9,840,713 B2 | 12/2017 | Zhang |
| 9,850,500 B2 | 12/2017 | Yun et al. |
| 10,266,850 B2 | 4/2019 | Doudna et al. |
| 10,323,073 B2 | 6/2019 | Tremblay et al. |
| 10,329,587 B2 | 6/2019 | Church et al. |
| 10,378,027 B2 | 8/2019 | Joung et al. |
| 10,443,076 B2 | 10/2019 | Doudna et al. |
| 10,525,082 B2 | 1/2020 | Crane et al. |
| 10,526,589 B2 | 1/2020 | Tsai et al. |
| 10,570,378 B2 | 2/2020 | Ji et al. |
| 10,583,201 B2 | 3/2020 | Chen et al. |
| 10,604,752 B2 | 3/2020 | Chen et al. |
| 10,612,044 B2 | 4/2020 | Hatada et al. |
| 10,676,726 B2 | 6/2020 | Gersbach et al. |
| 10,676,735 B2 | 6/2020 | Gersbach et al. |
| 10,704,060 B2 | 7/2020 | Gersbach et al. |
| 10,760,064 B2 | 9/2020 | Joung et al. |
| 11,072,782 B2 | 7/2021 | Cathomen et al. |
| 2007/0192880 A1 | 8/2007 | Muyan et al. |
| 2009/0023153 A1 | 1/2009 | Wolffe et al. |
| 2012/0207744 A1 | 8/2012 | Mendlein et al. |
| 2014/0377868 A1 | 12/2014 | Joung et al. |
| 2015/0191744 A1 | 7/2015 | Wolfe et al. |
| 2015/0232883 A1 | 8/2015 | Dahlman et al. |
| 2015/0247150 A1 | 9/2015 | Zhang et al. |
| 2016/0010076 A1 | 1/2016 | Joung et al. |
| 2016/0201089 A1 | 7/2016 | Gersbach et al. |
| 2016/0298135 A1 | 10/2016 | Chen et al. |

(Continued)

FOREIGN PATENT DOCUMENTS

| WO | WO-03/072788 A1 | 9/2003 |
| WO | WO-2013/141680 A1 | 9/2013 |

(Continued)

OTHER PUBLICATIONS

Henriette O'Geen "dCas9-based epigenome editing suggests acquisition of histone methylation is not sufficient for target gene repression". Nucleic Acids Research, 2017, vol. 45, No. 17 9901-9916. (Year: 2017).*

Ashley G. Rivenbark. Epigenetic reprogramming of cancer cells via targeted DNA methylation. Epigenetics 7:4, 350-360; Apr. 2012 (Year: 2012).*

Adamson, B. et al. (Dec. 15, 2016). "A Multiplexed Single-Cell CRISPR Screening Platform Enables Systematic Dissection of the Unfolded Protein Response," *Cell* 167(7):1867-1882.e21.

Amabile, A. et al. (Sep. 22, 2016). "Inheritable Silencing of Endogenous Genes by Hit-and-Run Targeted Epigenetic Editing," *Cell* 167(1):219-232.

(Continued)

Primary Examiner — Kagnew H Gebreyesus
(74) *Attorney, Agent, or Firm* — Mintz Levin Cohn Ferris Glovsky and Popeo, P.C.

(57) ABSTRACT

Provided herein are, inter alia, compositions and methods for manipulation of genomes of living organisms.

41 Claims, 19 Drawing Sheets

Specification includes a Sequence Listing.

(56) References Cited

U.S. PATENT DOCUMENTS

| | | |
|---|---|---|
| 2016/0319281 A1 | 11/2016 | Tsai et al. |
| 2017/0191082 A1 | 7/2017 | Chen et al. |
| 2017/0204407 A1 | 7/2017 | Gilbert et al. |
| 2017/0219596 A1 | 8/2017 | Tanenbaum et al. |
| 2017/0233762 A1 | 8/2017 | Zalatan et al. |
| 2018/0030425 A1 | 2/2018 | Joung et al. |
| 2018/0059373 A1 | 3/2018 | Chen et al. |
| 2018/0216104 A1 | 8/2018 | Abul-Husn et al. |
| 2018/0273976 A1 | 9/2018 | Umit et al. |
| 2019/0010481 A1 | 1/2019 | Joung et al. |
| 2019/0024072 A1 | 1/2019 | Cathomen et al. |
| 2019/0024090 A1 | 1/2019 | Cathomen et al. |
| 2019/0032049 A1 | 1/2019 | Naldini et al. |
| 2019/0062739 A1 | 2/2019 | Church et al. |
| 2019/0100732 A1 | 4/2019 | Hellman et al. |
| 2019/0127713 A1 | 5/2019 | Gersbach et al. |
| 2019/0194633 A1 | 6/2019 | Gersbach et al. |
| 2019/0218261 A1 | 7/2019 | Cheng et al. |
| 2019/0300868 A1 | 10/2019 | Gilbert et al. |
| 2019/0328732 A1 | 10/2019 | Deutzmann et al. |
| 2019/0343865 A1 | 11/2019 | Jones et al. |
| 2019/0350938 A1 | 11/2019 | Hoch et al. |
| 2019/0351074 A1 | 11/2019 | Ahituv et al. |
| 2019/0376090 A1 | 12/2019 | Joung et al. |
| 2019/0382752 A1 | 12/2019 | Zeisberg et al. |
| 2020/0002710 A1 | 1/2020 | Khalil et al. |
| 2020/0003761 A1 | 1/2020 | Studer et al. |
| 2020/0071730 A1 | 3/2020 | Joung et al. |
| 2020/0109406 A1 | 4/2020 | Miller et al. |

FOREIGN PATENT DOCUMENTS

| | | |
|---|---|---|
| WO | WO-2013/176772 A1 | 11/2013 |
| WO | WO-2014/065596 A1 | 5/2014 |
| WO | WO-2014/089290 A1 | 6/2014 |
| WO | WO-2014/099744 A1 | 6/2014 |
| WO | WO-2016/011080 A2 | 1/2016 |
| WO | WO-2016/011080 A3 | 1/2016 |
| WO | WO-2018/031762 A1 | 2/2018 |
| WO | WO-2018/053035 A1 | 3/2018 |
| WO | WO-2018/195540 A1 | 10/2018 |
| WO | WO-2019/092507 A2 | 5/2019 |
| WO | WO-2019/092507 A3 | 5/2019 |
| WO | WO-2019/109051 A1 | 6/2019 |
| WO | WO-2019/113061 A1 | 6/2019 |
| WO | WO-2019/117660 A2 | 6/2019 |
| WO | WO-2019/117660 A3 | 6/2019 |
| WO | WO-2019/117662 A2 | 6/2019 |
| WO | WO-2019/117662 A3 | 6/2019 |
| WO | WO-2019/126799 A1 | 6/2019 |
| WO | WO-2019/168950 A1 | 9/2019 |
| WO | WO-2019/204503 A1 | 10/2019 |
| WO | WO-2019/204766 A1 | 10/2019 |
| WO | WO-2019/209869 A2 | 10/2019 |
| WO | WO-2019/209869 A3 | 10/2019 |
| WO | WO-2019/210279 A1 | 10/2019 |
| WO | WO-2019/222437 A1 | 11/2019 |
| WO | WO-2019/232069 A1 | 12/2019 |
| WO | WO-2020/041679 A1 | 2/2020 |
| WO | WO-2020/041679 A4 | 2/2020 |
| WO | WO-2020/041776 A1 | 2/2020 |
| WO | WO-2020/101042 A1 | 5/2020 |
| WO | WO-2020/101042 A8 | 5/2020 |

OTHER PUBLICATIONS

Braun, C.J. et al. (Jul. 5, 2016, e-published Jun. 20, 2016). "Versatile in vivo regulation of tumor phenotypes by dCas9-mediated transcriptional perturbation," *PNAS USA* 113(27):E3892-E3900.

Chen, B. et al. (Dec. 19, 2013). "Dynamic imaging of genomic loci in living human cells by an optimized CRISPR/Cas system," *Cell* 155(7):1479-1491.

Deans, R.M. et al. (May 2016, e-published Mar. 28, 2016). "Parallel shRNA and CRISPR-Cas9 screens enable antiviral drug target identification," *Nat Chem Biol* 12(5):361-366.

Ecco, G. et al. (Aug. 1, 2017). "KRAB zinc finger proteins," *Development* 144(15):2719-2729.

Gilbert, L.A. et al. (Jul. 18, 2013, e-published Jul. 11, 2013). "CRISPR-mediated modular RNA-guided regulation of transcription in eukaryotes," *Cell* 154(2):442-451.

Gilbert, L.A. et al. (Oct. 23, 2014, e-published Oct. 9, 2014). "Genome-Scale CRISPR-Mediated Control of Gene Repression and Activation," *Cell* 159(3):647-661.

Guilinger, J.P. et al. (Apr. 25, 2014). "Fusion of catalytically inactive Cas9 to FokI nuclease improves the specificity of genome modification," *Nature Biotechnology* 32(6):1-17.

Horlbeck, M.A. et al. (2016). "Compact and highly active next-generation libraries for CRISPR-mediated gene repression and activation," *eLife* 5:e19760.

Horlbeck, M.A. et al. (2016). "Nucleosomes impede Cas9 access to DNA in vivo and in vitro," *eLife* 5:e12677.

International Search Report dated Sep. 10, 2019, for PCT/US2019/028377, filed Apr. 19, 2019, 6 pages.

Larson, M.H. et al. (Nov. 2013, e-published Oct. 17, 2013). "CRISPR interference (CRISPRi) for sequence-specific control of gene expression," *Nat Protoc* 8(11):2180-2196.

Lin, L. et al. (Mar. 1, 2018). "Genome-wide determination of on-target and off-target characteristics for RNA-guided DNA methylation by dCas9 methyltransferases," *Gigascience* 7(3):1-19.

Liu, S.J. et al. (Jan. 6, 2017, e-published Dec. 15, 2016). "CRISPRi-based genome-scale identification of functional long noncoding RNA loci in human cells," 355(6320):aah7111.

Mandegar, M.A et al. (Apr. 7, 2016, e-published Mar. 10, 2016). "CRISPR Interference Efficiently Induces Specific and Reversible Gene Silencing in Human iPSCs," *Cell Stem Cell* 18(4):541-553.

Mlambo, T. et al. (May 18, 2018). "Designer epigenome modifiers enable robust and sustained gene silencing in clinically relevant human cells," *Nucleic Acids Res* 46(9):4456-4468.

Nguyen, D.P. et al. (Jul. 1, 2016). "Ligand-binding domains of nuclear receptors facilitate tight control of split CRISPR activity," *Nat Commun* 7:12009.

Qi, L.S. et al. (Feb. 28, 2013). "Repurposing CRISPR as an RNA-guided platform for sequence-specific control of gene expression," *Cell* 152(5):1173-1183.

Schellenberger, V. et al. (Dec. 2009). "A recombinant polypeptide extends the in vivo half-life of peptides and proteins in a tunable manner," *Nature Biotechnology* 27(12):1186-1190.

Siddique, A.N. et al. (Feb. 8, 2013, e-published Dec. 4, 2012). "Targeted methylation and gene silencing of VEGF-A in human cells by using a designed Dnmt3a-Dnmt3L single-chain fusion protein with increased DNA methylation activity," *J Mol Biol* 425(3):479-491.

Stepper, P. et al. (Feb. 28, 2017, e-published Nov. 28, 2016). "Efficient targeted DNA methylation with chimeric dCas9-Dnmt3a-Dnmt3L methyltransferase," *Nucleic Acids Res* 45(4):1703-1713.

Wilson, R.C. et al. (Feb. 16, 2018, e-published Oct. 19, 2017). "The Promise and Challenge of In Vivo Delivery for Genome Therapeutics," *ACS Chem Biol* 13(2):376-382.

Written Opinion dated Sep. 10, 2019, for PCT/US2019/028377, filed Apr. 19, 2019, 10 pages.

Zalatan, J.G. et al. (Jan. 15, 2015, e-published Dec. 18, 2014). "Engineering complex synthetic transcriptional programs with CRISPR RNA scaffolds," *Cell* 160(1-2):339-350.

Choudhury, S.R. et al. (Jul. 19, 2016). "CRISPR-dCas9 mediated TET1 targeting for selective DNA demethylation at BRCA1 promoter," *Oncotarget* 7(29):46545-46556.

Deuschle U. et al. (Apr. 1995). "Tetracycline-reversible silencing of eukaryotic promoters," *Mol Cell Biol.* 15(4):1907-1914.

Gowher, H. et al. (Apr. 8, 2005, e-published Jan. 24, 2005). "Mechanism of Stimulation of Catalytic Activity of Dnmt3A and Dnmt3B DNA-(Cytosine-C5)-methyltransferases by Dnmt3L", *The Journal of Biological Chemistry*, 280(14):13341-13348.

Kearns, N.A. et al. (Jan. 2014). "Cas9 effector-mediated regulation of transcription and differentiation in human pluripotent stem cells," *Development* 141(1):219-223.

(56) References Cited

OTHER PUBLICATIONS

Kocak, D. D. (2013). "Synthetic Transcription Factors and their Effects on Endogenous DNA Methylation in Human Cells," [Unpublished Master's Thesis], Duke University. Located at https://dukespace.lib.duke.edu/dspace/bitstream/handle/10161/8802/Kocak_duke_0066N_12237.pdf?sequence=1, 35 pages.

Li, H. et al. (Jul. 14, 2006, e-published May 8, 2006). "The Histone Methyltransferase SETDB1 and the DNA Methyltransferase DNMT3A Interact Directly and Localize to Promoters Silenced in Cancer Cells," *The Journal of Biological Chemistry* 281(28):19489-19500.

Liu, X.S. et al. Sep. 22, 2016). "Editing DNA Methylation in the Mammalian Genome," *Cell* 167(1):233-247.e17.

Vojta, A. et al. (Jul. 8, 2016, e-published Mar. 11, 2016). "Repurposing the CRISPR-Cas9 system for targeted DNA methylation," *Nucleic Acids Research* 44(12):5615-5628.

Zhang Z. et al. (Aug. 15, 2013). "Dissecting the roles of miR-302/367 cluster in cellular reprogramming using TALE-based repressor and TALEN," *Stem Cell Reports* 1(3):218-225.

Extended European Search Report dated Jan. 4, 2022, for EP Patent Application No. 19789200.3, 9 pages.

\* cited by examiner

FIG. 1F
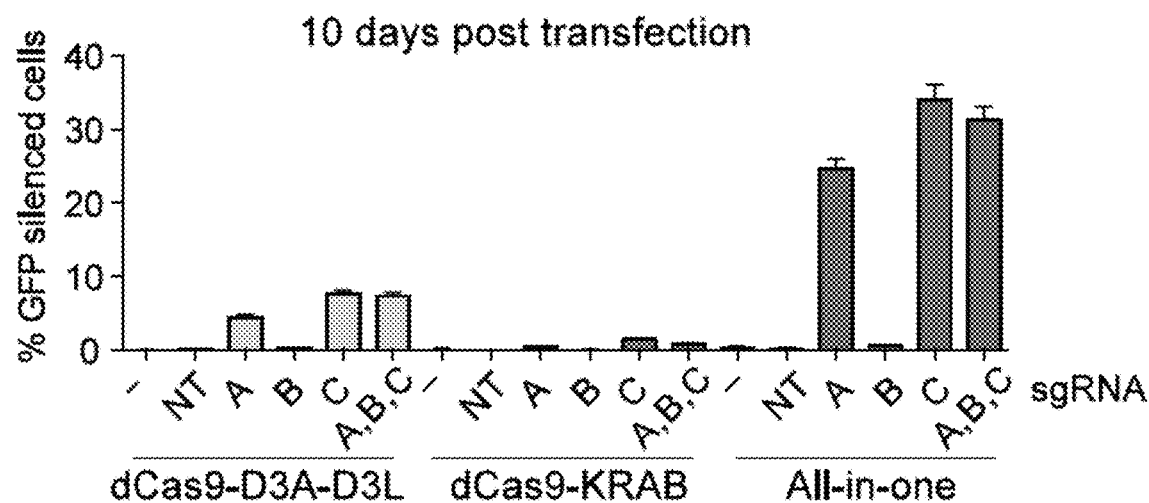
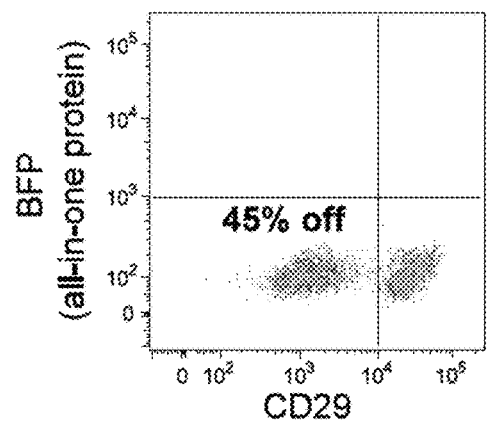
FIG. 2A
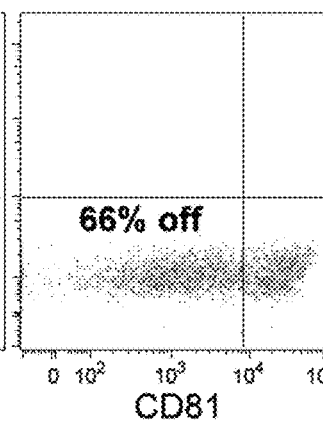
FIG. 2B
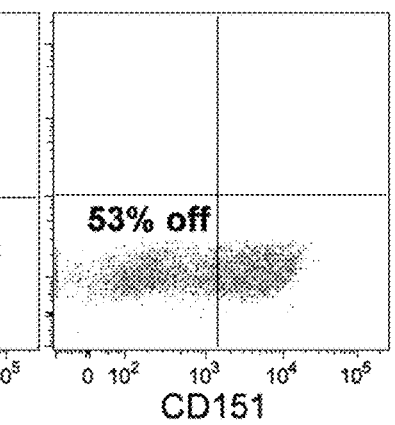
FIG. 2C

SEQUENCE LISTING

<160> NUMBER OF SEQ ID NOS: 96

```
<210> SEQ ID NO 1
<211> LENGTH: 2294
<212> TYPE: PRT
<213> ORGANISM: Artificial sequence
<220> FEATURE:
<223> OTHER INFORMATION: Synthetic polypeptide

<400> SEQUENCE: 1

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
            260                 265                 270

Leu Phe Glu Glu Asn Pro Ile Asn Ala Ser Gly Val Asp Ala Lys Ala
        275                 280                 285

Ile Leu Ser Ala Arg Leu Ser Lys Ser Arg Arg Leu Glu Asn Leu Ile
    290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
        355                 360                 365

Leu Ala Ala Lys Asn Leu Ser Asp Ala Ile Leu Leu Ser Asp Ile Leu
```

-continued

```
            370                 375                 380
Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
                420                 425                 430

Ser Lys Asn Gly Tyr Ala Gly Tyr Ile Asp Gly Gly Ala Ser Gln Glu
                435                 440                 445

Glu Phe Tyr Lys Phe Ile Lys Pro Ile Leu Glu Lys Met Asp Gly Thr
    450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
                500                 505                 510

Asp Asn Arg Glu Lys Ile Glu Lys Ile Leu Thr Phe Arg Ile Pro Tyr
                515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
                580                 585                 590

Tyr Glu Tyr Phe Thr Val Tyr Asn Glu Leu Thr Lys Val Lys Tyr Val
                595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
                660                 665                 670

His Asp Leu Leu Lys Ile Ile Lys Asp Lys Asp Phe Leu Asp Asn Glu
                675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
                740                 745                 750

Ser Gly Lys Thr Ile Leu Asp Phe Leu Lys Ser Asp Gly Phe Ala Asn
                755                 760                 765

Arg Asn Phe Met Gln Leu Ile His Asp Asp Ser Leu Thr Phe Lys Glu
                770                 775                 780

Asp Ile Gln Lys Ala Gln Val Ser Gly Gln Gly Asp Ser Leu His Glu
785                 790                 795                 800
```

```
His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
                885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
        995                 1000                1005

Val Ala  Gln Ile Leu Asp Ser  Arg Met Asn Thr Lys  Tyr Asp Glu
    1010                1015                1020

Asn Asp  Lys Leu Ile Arg Glu  Val Lys Val Ile Thr  Leu Lys Ser
    1025                1030                1035

Lys Leu  Val Ser Asp Phe Arg  Lys Asp Phe Gln Phe  Tyr Lys Val
    1040                1045                1050

Arg Glu  Ile Asn Asn Tyr His  His Ala His Asp Ala  Tyr Leu Asn
    1055                1060                1065

Ala Val  Val Gly Thr Ala Leu  Ile Lys Lys Tyr Pro  Lys Leu Glu
    1070                1075                1080

Ser Glu  Phe Val Tyr Gly Asp  Tyr Lys Val Tyr Asp  Val Arg Lys
    1085                1090                1095

Met Ile  Ala Lys Ser Glu Gln  Glu Ile Gly Lys Ala  Thr Ala Lys
    1100                1105                1110

Tyr Phe  Phe Tyr Ser Asn Ile  Met Asn Phe Phe Lys  Thr Glu Ile
    1115                1120                1125

Thr Leu  Ala Asn Gly Glu Ile  Arg Lys Arg Pro Leu  Ile Glu Thr
    1130                1135                1140

Asn Gly  Glu Thr Gly Glu Ile  Val Trp Asp Lys Gly  Arg Asp Phe
    1145                1150                1155

Ala Thr  Val Arg Lys Val Leu  Ser Met Pro Gln Val  Asn Ile Val
    1160                1165                1170

Lys Lys  Thr Glu Val Gln Thr  Gly Gly Phe Ser Lys  Glu Ser Ile
    1175                1180                1185

Leu Pro  Lys Arg Asn Ser Asp  Lys Leu Ile Ala Arg  Lys Lys Asp
    1190                1195                1200
```

```
Trp Asp Pro Lys Lys Tyr Gly Gly Phe Asp Ser Pro Thr Val Ala
1205                1210                1215

Tyr Ser Val Leu Val Val Ala Lys Val Glu Lys Gly Lys Ser Lys
1220                1225                1230

Lys Leu Lys Ser Val Lys Glu Leu Leu Gly Ile Thr Ile Met Glu
1235                1240                1245

Arg Ser Ser Phe Glu Lys Asn Pro Ile Asp Phe Leu Glu Ala Lys
1250                1255                1260

Gly Tyr Lys Glu Val Lys Lys Asp Leu Ile Ile Lys Leu Pro Lys
1265                1270                1275

Tyr Ser Leu Phe Glu Leu Glu Asn Gly Arg Lys Arg Met Leu Ala
1280                1285                1290

Ser Ala Gly Glu Leu Gln Lys Gly Asn Glu Leu Ala Leu Pro Ser
1295                1300                1305

Lys Tyr Val Asn Phe Leu Tyr Leu Ala Ser His Tyr Glu Lys Leu
1310                1315                1320

Lys Gly Ser Pro Glu Asp Asn Glu Gln Lys Gln Leu Phe Val Glu
1325                1330                1335

Gln His Lys His Tyr Leu Asp Glu Ile Ile Glu Gln Ile Ser Glu
1340                1345                1350

Phe Ser Lys Arg Val Ile Leu Ala Asp Ala Asn Leu Asp Lys Val
1355                1360                1365

Leu Ser Ala Tyr Asn Lys His Arg Asp Lys Pro Ile Arg Glu Gln
1370                1375                1380

Ala Glu Asn Ile Ile His Leu Phe Thr Leu Thr Asn Leu Gly Ala
1385                1390                1395

Pro Ala Ala Phe Lys Tyr Phe Asp Thr Thr Ile Asp Arg Lys Arg
1400                1405                1410

Tyr Thr Ser Thr Lys Glu Val Leu Asp Ala Thr Leu Ile His Gln
1415                1420                1425

Ser Ile Thr Gly Leu Tyr Glu Thr Arg Ile Asp Leu Ser Gln Leu
1430                1435                1440

Gly Gly Asp Ser Arg Ala Asp Tyr Pro Tyr Asp Val Pro Asp Tyr
1445                1450                1455

Ala Ser Gly Ser Pro Lys Lys Arg Lys Val Glu Ala Ser Gly
1460                1465                1470

Ser Gly Arg Ala Ser Pro Gly Ile Pro Gly Ser Thr Arg Asn His
1475                1480                1485

Asp Gln Glu Phe Asp Pro Pro Lys Val Tyr Pro Val Pro Ala
1490                1495                1500

Glu Lys Arg Lys Pro Ile Arg Val Leu Ser Leu Phe Asp Gly Ile
1505                1510                1515

Ala Thr Gly Leu Leu Val Leu Lys Asp Leu Gly Ile Gln Val Asp
1520                1525                1530

Arg Tyr Ile Ala Ser Glu Val Cys Glu Asp Ser Ile Thr Val Gly
1535                1540                1545

Met Val Arg His Gln Gly Lys Ile Met Tyr Val Gly Asp Val Arg
1550                1555                1560

Ser Val Thr Gln Lys His Ile Gln Glu Trp Gly Pro Phe Asp Leu
1565                1570                1575

Val Ile Gly Gly Ser Pro Cys Asn Asp Leu Ser Ile Val Asn Pro
1580                1585                1590

Ala Arg Lys Gly Leu Tyr Glu Gly Thr Gly Arg Leu Phe Phe Glu
```

```
               1595                1600                1605

Phe Tyr Arg Leu Leu His Asp Ala Arg Pro Lys Glu Gly Asp Asp
       1610                1615                1620

Arg Pro Phe Phe Trp Leu Phe Glu Asn Val Val Ala Met Gly Val
       1625                1630                1635

Ser Asp Lys Arg Asp Ile Ser Arg Phe Leu Glu Ser Asn Pro Val
       1640                1645                1650

Met Ile Asp Ala Lys Glu Val Ser Ala Ala His Arg Ala Arg Tyr
       1655                1660                1665

Phe Trp Gly Asn Leu Pro Gly Met Asn Arg Pro Leu Ala Ser Thr
       1670                1675                1680

Val Asn Asp Lys Leu Glu Leu Gln Glu Cys Leu Glu His Gly Arg
       1685                1690                1695

Ile Ala Lys Phe Ser Lys Val Arg Thr Ile Thr Thr Arg Ser Asn
       1700                1705                1710

Ser Ile Lys Gln Gly Lys Asp Gln His Phe Pro Val Phe Met Asn
       1715                1720                1725

Glu Lys Glu Asp Ile Leu Trp Cys Thr Glu Met Glu Arg Val Phe
       1730                1735                1740

Gly Phe Pro Val His Tyr Thr Asp Val Ser Asn Met Ser Arg Leu
       1745                1750                1755

Ala Arg Gln Arg Leu Leu Gly Arg Ser Trp Ser Val Pro Val Ile
       1760                1765                1770

Arg His Leu Phe Ala Pro Leu Lys Glu Tyr Phe Ala Cys Val Ser
       1775                1780                1785

Ser Gly Asn Ser Asn Ala Asn Ser Arg Gly Pro Ser Phe Ser Ser
       1790                1795                1800

Gly Leu Val Pro Leu Ser Leu Arg Gly Ser His Met Gly Pro Met
       1805                1810                1815

Glu Ile Tyr Lys Thr Val Ser Ala Trp Lys Arg Gln Pro Val Arg
       1820                1825                1830

Val Leu Ser Leu Phe Arg Asn Ile Asp Lys Val Leu Lys Ser Leu
       1835                1840                1845

Gly Phe Leu Glu Ser Gly Ser Gly Ser Gly Gly Gly Thr Leu Lys
       1850                1855                1860

Tyr Val Glu Asp Val Thr Asn Val Val Arg Arg Asp Val Glu Lys
       1865                1870                1875

Trp Gly Pro Phe Asp Leu Val Tyr Gly Ser Thr Gln Pro Leu Gly
       1880                1885                1890

Ser Ser Cys Asp Arg Cys Pro Gly Trp Tyr Met Phe Gln Phe His
       1895                1900                1905

Arg Ile Leu Gln Tyr Ala Leu Pro Arg Gln Glu Ser Gln Arg Pro
       1910                1915                1920

Phe Phe Trp Ile Phe Met Asp Asn Leu Leu Leu Thr Glu Asp Asp
       1925                1930                1935

Gln Glu Thr Thr Thr Arg Phe Leu Gln Thr Glu Ala Val Thr Leu
       1940                1945                1950

Gln Asp Val Arg Gly Arg Asp Tyr Gln Asn Ala Met Arg Val Trp
       1955                1960                1965

Ser Asn Ile Pro Gly Leu Lys Ser Lys His Ala Pro Leu Thr Pro
       1970                1975                1980

Lys Glu Glu Glu Tyr Leu Gln Ala Gln Val Arg Ser Arg Ser Lys
       1985                1990                1995
```

```
Leu Asp Ala Pro Lys Val Asp Leu Leu Val Lys Asn Cys Leu Leu
    2000            2005                2010

Pro Leu Arg Glu Tyr Phe Lys Tyr Phe Ser Gln Asn Ser Leu Pro
    2015            2020                2025

Leu Ser Arg Ala Asp Pro Lys Lys Lys Arg Lys Val Gly Ser Gly
    2030            2035                2040

Ala Thr Asn Phe Ser Leu Leu Lys Gln Ala Gly Asp Val Glu Glu
    2045            2050                2055

Asn Pro Gly Pro Ser Glu Leu Ile Lys Glu Asn Met His Met Lys
    2060            2065                2070

Leu Tyr Met Glu Gly Thr Val Asp Asn His His Phe Lys Cys Thr
    2075            2080                2085

Ser Glu Gly Glu Gly Lys Pro Tyr Glu Gly Thr Gln Thr Met Arg
    2090            2095                2100

Ile Lys Val Val Glu Gly Gly Pro Leu Pro Phe Ala Phe Asp Ile
    2105            2110                2115

Leu Ala Thr Ser Phe Leu Tyr Gly Ser Lys Thr Phe Ile Asn His
    2120            2125                2130

Thr Gln Gly Ile Pro Asp Phe Phe Lys Gln Ser Phe Pro Glu Gly
    2135            2140                2145

Phe Thr Trp Glu Arg Val Thr Thr Tyr Glu Asp Gly Gly Val Leu
    2150            2155                2160

Thr Ala Thr Gln Asp Thr Ser Leu Gln Asp Gly Cys Leu Ile Tyr
    2165            2170                2175

Asn Val Lys Ile Arg Gly Val Asn Phe Thr Ser Asn Gly Pro Val
    2180            2185                2190

Met Gln Lys Lys Thr Leu Gly Trp Glu Ala Phe Thr Glu Thr Leu
    2195            2200                2205

Tyr Pro Ala Asp Gly Gly Leu Glu Gly Arg Asn Asp Met Ala Leu
    2210            2215                2220

Lys Leu Val Gly Gly Ser His Leu Ile Ala Asn Ile Lys Thr Thr
    2225            2230                2235

Tyr Arg Ser Lys Lys Pro Ala Lys Asn Leu Lys Met Pro Gly Val
    2240            2245                2250

Tyr Tyr Val Asp Tyr Arg Leu Glu Arg Ile Lys Glu Ala Asn Asn
    2255            2260                2265

Glu Thr Tyr Val Glu Gln His Glu Val Ala Val Ala Arg Tyr Cys
    2270            2275                2280

Asp Leu Pro Ser Lys Leu Gly His Lys Leu Asn
    2285            2290

<210> SEQ ID NO 2
<211> LENGTH: 2296
<212> TYPE: PRT
<213> ORGANISM: Artificial sequence
<220> FEATURE:
<223> OTHER INFORMATION: Synthetic polypeptide

<400> SEQUENCE: 2

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45
```

```
Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
                100                 105                 110

Leu Gly Asn Thr Asp Arg His Ser Ile Lys Lys Asn Leu Ile Gly Ala
                115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
            195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
                260                 265                 270

Leu Phe Glu Glu Asn Pro Ile Asn Ala Ser Gly Val Asp Ala Lys Ala
            275                 280                 285

Ile Leu Ser Ala Arg Leu Ser Lys Ser Arg Arg Leu Glu Asn Leu Ile
    290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
                340                 345                 350

Leu Asp Asn Leu Leu Ala Gln Ile Gly Asp Gln Tyr Ala Asp Leu Phe
            355                 360                 365

Leu Ala Ala Lys Asn Leu Ser Asp Ala Ile Leu Leu Ser Asp Ile Leu
    370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
                420                 425                 430

Ser Lys Asn Gly Tyr Ala Gly Tyr Ile Asp Gly Gly Ala Ser Gln Glu
            435                 440                 445

Glu Phe Tyr Lys Phe Ile Lys Pro Ile Leu Glu Lys Met Asp Gly Thr
    450                 455                 460
```

```
-continued

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
        515                 520                 525

Tyr Val Gly Pro Leu Ala Arg Gly Asn Ser Arg Phe Ala Trp Met Thr
    530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
        595                 600                 605

Thr Glu Gly Met Arg Lys Pro Ala Phe Leu Ser Gly Glu Gln Lys Lys
    610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
        675                 680                 685

Glu Asn Glu Asp Ile Leu Glu Asp Ile Val Leu Thr Leu Thr Leu Phe
    690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
        755                 760                 765

Arg Asn Phe Met Gln Leu Ile His Asp Asp Ser Leu Thr Phe Lys Glu
    770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
        835                 840                 845

Gln Lys Gly Gln Lys Asn Ser Arg Glu Arg Met Lys Arg Ile Glu Glu
    850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
```

-continued

```
            885                 890                 895
Gly Arg Asp Met Tyr Val Asp Gln Glu Leu Asp Ile Asn Arg Leu Ser
                900                 905                 910

Asp Tyr Asp Val Asp Ala Ile Val Pro Gln Ser Phe Leu Lys Asp Asp
        915                 920                 925

Ser Ile Asp Asn Lys Val Leu Thr Arg Ser Asp Lys Asn Arg Gly Lys
    930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
            965                 970                 975

Asn Leu Thr Lys Ala Glu Arg Gly Gly Leu Ser Glu Leu Asp Lys Ala
                980                 985                 990

Gly Phe Ile Lys Arg Gln Leu Val Glu Thr Arg Gln Ile Thr Lys His
            995                1000                1005

Val Ala Gln Ile Leu Asp Ser Arg Met Asn Thr Lys Tyr Asp Glu
    1010                1015                1020

Asn Asp Lys Leu Ile Arg Glu Val Lys Val Ile Thr Leu Lys Ser
    1025                1030                1035

Lys Leu Val Ser Asp Phe Arg Lys Asp Phe Gln Phe Tyr Lys Val
    1040                1045                1050

Arg Glu Ile Asn Asn Tyr His His Ala His Asp Ala Tyr Leu Asn
    1055                1060                1065

Ala Val Val Gly Thr Ala Leu Ile Lys Lys Tyr Pro Lys Leu Glu
    1070                1075                1080

Ser Glu Phe Val Tyr Gly Asp Tyr Lys Val Tyr Asp Val Arg Lys
    1085                1090                1095

Met Ile Ala Lys Ser Glu Gln Glu Ile Gly Lys Ala Thr Ala Lys
    1100                1105                1110

Tyr Phe Phe Tyr Ser Asn Ile Met Asn Phe Phe Lys Thr Glu Ile
    1115                1120                1125

Thr Leu Ala Asn Gly Glu Ile Arg Lys Arg Pro Leu Ile Glu Thr
    1130                1135                1140

Asn Gly Glu Thr Gly Glu Ile Val Trp Asp Lys Gly Arg Asp Phe
    1145                1150                1155

Ala Thr Val Arg Lys Val Leu Ser Met Pro Gln Val Asn Ile Val
    1160                1165                1170

Lys Lys Thr Glu Val Gln Thr Gly Gly Phe Ser Lys Glu Ser Ile
    1175                1180                1185

Leu Pro Lys Arg Asn Ser Asp Lys Leu Ile Ala Arg Lys Lys Asp
    1190                1195                1200

Trp Asp Pro Lys Lys Tyr Gly Gly Phe Asp Ser Pro Thr Val Ala
    1205                1210                1215

Tyr Ser Val Leu Val Val Ala Lys Val Glu Lys Gly Lys Ser Lys
    1220                1225                1230

Lys Leu Lys Ser Val Lys Glu Leu Leu Gly Ile Thr Ile Met Glu
    1235                1240                1245

Arg Ser Ser Phe Glu Lys Asn Pro Ile Asp Phe Leu Glu Ala Lys
    1250                1255                1260

Gly Tyr Lys Glu Val Lys Lys Asp Leu Ile Ile Lys Leu Pro Lys
    1265                1270                1275

Tyr Ser Leu Phe Glu Leu Glu Asn Gly Arg Lys Arg Met Leu Ala
    1280                1285                1290
```

```
Ser Ala Gly Glu Leu Gln Lys Gly Asn Glu Leu Ala Leu Pro Ser
1295            1300                1305

Lys Tyr Val Asn Phe Leu Tyr Leu Ala Ser His Tyr Glu Lys Leu
1310            1315                1320

Lys Gly Ser Pro Glu Asp Asn Glu Gln Lys Gln Leu Phe Val Glu
1325            1330                1335

Gln His Lys His Tyr Leu Asp Glu Ile Ile Glu Gln Ile Ser Glu
1340            1345                1350

Phe Ser Lys Arg Val Ile Leu Ala Asp Ala Asn Leu Asp Lys Val
1355            1360                1365

Leu Ser Ala Tyr Asn Lys His Arg Asp Lys Pro Ile Arg Glu Gln
1370            1375                1380

Ala Glu Asn Ile Ile His Leu Phe Thr Leu Thr Asn Leu Gly Ala
1385            1390                1395

Pro Ala Ala Phe Lys Tyr Phe Asp Thr Thr Ile Asp Arg Lys Arg
1400            1405                1410

Tyr Thr Ser Thr Lys Glu Val Leu Asp Ala Thr Leu Ile His Gln
1415            1420                1425

Ser Ile Thr Gly Leu Tyr Glu Thr Arg Ile Asp Leu Ser Gln Leu
1430            1435                1440

Gly Gly Asp Ser Arg Ala Asp Tyr Pro Tyr Asp Val Pro Asp Tyr
1445            1450                1455

Ala Ser Gly Ser Pro Lys Lys Lys Arg Lys Val Ser Pro Gly Ser
1460            1465                1470

Gly Ser Glu Thr Pro Gly Thr Ser Glu Ser Ala Thr Pro Glu Ser
1475            1480                1485

Asn His Asp Gln Glu Phe Asp Pro Pro Lys Val Tyr Pro Pro Val
1490            1495                1500

Pro Ala Glu Lys Arg Lys Pro Ile Arg Val Leu Ser Leu Phe Asp
1505            1510                1515

Gly Ile Ala Thr Gly Leu Leu Val Leu Lys Asp Leu Gly Ile Gln
1520            1525                1530

Val Asp Arg Tyr Ile Ala Ser Glu Val Cys Glu Asp Ser Ile Thr
1535            1540                1545

Val Gly Met Val Arg His Gln Gly Lys Ile Met Tyr Val Gly Asp
1550            1555                1560

Val Arg Ser Val Thr Gln Lys His Ile Gln Glu Trp Gly Pro Phe
1565            1570                1575

Asp Leu Val Ile Gly Gly Ser Pro Cys Asn Asp Leu Ser Ile Val
1580            1585                1590

Asn Pro Ala Arg Lys Gly Leu Tyr Glu Gly Thr Gly Arg Leu Phe
1595            1600                1605

Phe Glu Phe Tyr Arg Leu Leu His Asp Ala Arg Pro Lys Glu Gly
1610            1615                1620

Asp Asp Arg Pro Phe Phe Trp Leu Phe Glu Asn Val Val Ala Met
1625            1630                1635

Gly Val Ser Asp Lys Arg Asp Ile Ser Arg Phe Leu Glu Ser Asn
1640            1645                1650

Pro Val Met Ile Asp Ala Lys Glu Val Ser Ala Ala His Arg Ala
1655            1660                1665

Arg Tyr Phe Trp Gly Asn Leu Pro Gly Met Asn Arg Pro Leu Ala
1670            1675                1680
```

```
Ser Thr Val Asn Asp Lys Leu Glu Leu Gln Glu Cys Leu Glu His
1685                1690                1695

Gly Arg Ile Ala Lys Phe Ser Lys Val Arg Thr Ile Thr Thr Arg
1700                1705                1710

Ser Asn Ser Ile Lys Gln Gly Lys Asp Gln His Phe Pro Val Phe
1715                1720                1725

Met Asn Glu Lys Glu Asp Ile Leu Trp Cys Thr Glu Met Glu Arg
1730                1735                1740

Val Phe Gly Phe Pro Val His Tyr Thr Asp Val Ser Asn Met Ser
1745                1750                1755

Arg Leu Ala Arg Gln Arg Leu Leu Gly Arg Ser Trp Ser Val Pro
1760                1765                1770

Val Ile Arg His Leu Phe Ala Pro Leu Lys Glu Tyr Phe Ala Cys
1775                1780                1785

Val Ser Ser Gly Asn Ser Asn Ala Asn Ser Arg Gly Pro Ser Phe
1790                1795                1800

Ser Ser Gly Leu Val Pro Leu Ser Leu Arg Gly Ser His Met Gly
1805                1810                1815

Pro Met Glu Ile Tyr Lys Thr Val Ser Ala Trp Lys Arg Gln Pro
1820                1825                1830

Val Arg Val Leu Ser Leu Phe Arg Asn Ile Asp Lys Val Leu Lys
1835                1840                1845

Ser Leu Gly Phe Leu Glu Ser Gly Ser Gly Ser Gly Gly Gly Thr
1850                1855                1860

Leu Lys Tyr Val Glu Asp Val Thr Asn Val Val Arg Arg Asp Val
1865                1870                1875

Glu Lys Trp Gly Pro Phe Asp Leu Val Tyr Gly Ser Thr Gln Pro
1880                1885                1890

Leu Gly Ser Ser Cys Asp Arg Cys Pro Gly Trp Tyr Met Phe Gln
1895                1900                1905

Phe His Arg Ile Leu Gln Tyr Ala Leu Pro Arg Gln Glu Ser Gln
1910                1915                1920

Arg Pro Phe Phe Trp Ile Phe Met Asp Asn Leu Leu Leu Thr Glu
1925                1930                1935

Asp Asp Gln Glu Thr Thr Thr Arg Phe Leu Gln Thr Glu Ala Val
1940                1945                1950

Thr Leu Gln Asp Val Arg Gly Arg Asp Tyr Gln Asn Ala Met Arg
1955                1960                1965

Val Trp Ser Asn Ile Pro Gly Leu Lys Ser Lys His Ala Pro Leu
1970                1975                1980

Thr Pro Lys Glu Glu Glu Tyr Leu Gln Ala Gln Val Arg Ser Arg
1985                1990                1995

Ser Lys Leu Asp Ala Pro Lys Val Asp Leu Leu Val Lys Asn Cys
2000                2005                2010

Leu Leu Pro Leu Arg Glu Tyr Phe Lys Tyr Phe Ser Gln Asn Ser
2015                2020                2025

Leu Pro Leu Ser Arg Ala Asp Pro Lys Lys Arg Lys Val Gly
2030                2035                2040

Ser Gly Ala Thr Asn Phe Ser Leu Leu Lys Gln Ala Gly Asp Val
2045                2050                2055

Glu Glu Asn Pro Gly Pro Ser Glu Leu Ile Lys Glu Asn Met His
2060                2065                2070

Met Lys Leu Tyr Met Glu Gly Thr Val Asp Asn His His Phe Lys
```

```
                   2075                2080                2085
Cys Thr Ser Glu Gly Glu Gly Lys Pro Tyr Glu Gly Thr Gln Thr
        2090                2095                2100

Met Arg Ile Lys Val Val Glu Gly Gly Pro Leu Pro Phe Ala Phe
        2105                2110                2115

Asp Ile Leu Ala Thr Ser Phe Leu Tyr Gly Ser Lys Thr Phe Ile
        2120                2125                2130

Asn His Thr Gln Gly Ile Pro Asp Phe Phe Lys Gln Ser Phe Pro
        2135                2140                2145

Glu Gly Phe Thr Trp Glu Arg Val Thr Thr Tyr Glu Asp Gly Gly
        2150                2155                2160

Val Leu Thr Ala Thr Gln Asp Thr Ser Leu Gln Asp Gly Cys Leu
        2165                2170                2175

Ile Tyr Asn Val Lys Ile Arg Gly Val Asn Phe Thr Ser Asn Gly
        2180                2185                2190

Pro Val Met Gln Lys Lys Thr Leu Gly Trp Glu Ala Phe Thr Glu
        2195                2200                2205

Thr Leu Tyr Pro Ala Asp Gly Gly Leu Glu Gly Arg Asn Asp Met
        2210                2215                2220

Ala Leu Lys Leu Val Gly Gly Ser His Leu Ile Ala Asn Ile Lys
        2225                2230                2235

Thr Thr Tyr Arg Ser Lys Lys Pro Ala Lys Asn Leu Lys Met Pro
        2240                2245                2250

Gly Val Tyr Tyr Val Asp Tyr Arg Leu Glu Arg Ile Lys Glu Ala
        2255                2260                2265

Asn Asn Glu Thr Tyr Val Glu Gln His Glu Val Ala Val Ala Arg
        2270                2275                2280

Tyr Cys Asp Leu Pro Ser Lys Leu Gly His Lys Leu Asn
        2285                2290                2295

<210> SEQ ID NO 3
<211> LENGTH: 2316
<212> TYPE: PRT
<213> ORGANISM: Artificial sequence
<220> FEATURE:
<223> OTHER INFORMATION: Synthetic polypeptide

<400> SEQUENCE: 3

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Ser Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
```

```
                130             135             140
Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Asp Lys Lys His Glu
                180                 185                 190

Arg His Pro Ile Phe Gly Asn Ile Val Asp Glu Val Ala Tyr His Glu
                195                 200                 205

Lys Tyr Pro Thr Ile Tyr His Leu Arg Lys Lys Leu Val Asp Ser Thr
210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
                260                 265                 270

Leu Phe Glu Glu Asn Pro Ile Asn Ala Ser Gly Val Asp Ala Lys Ala
                275                 280                 285

Ile Leu Ser Ala Arg Leu Ser Lys Ser Arg Arg Leu Glu Asn Leu Ile
290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
                340                 345                 350

Leu Asp Asn Leu Leu Ala Gln Ile Gly Asp Gln Tyr Ala Asp Leu Phe
                355                 360                 365

Leu Ala Ala Lys Asn Leu Ser Asp Ala Ile Leu Leu Ser Asp Ile Leu
                370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
                420                 425                 430

Ser Lys Asn Gly Tyr Ala Gly Tyr Ile Asp Gly Gly Ala Ser Gln Glu
                435                 440                 445

Glu Phe Tyr Lys Phe Ile Lys Pro Ile Leu Glu Lys Met Asp Gly Thr
                450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
                500                 505                 510

Asp Asn Arg Glu Lys Ile Glu Lys Ile Leu Thr Phe Arg Ile Pro Tyr
                515                 520                 525

Tyr Val Gly Pro Leu Ala Arg Gly Asn Ser Arg Phe Ala Trp Met Thr
                530                 535                 540

Arg Lys Ser Glu Glu Thr Ile Thr Pro Trp Asn Phe Glu Glu Val Val
545                 550                 555                 560
```

-continued

```
Asp Lys Gly Ala Ser Ala Gln Ser Phe Ile Glu Arg Met Thr Asn Phe
            565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
            595                 600                 605

Thr Glu Gly Met Arg Lys Pro Ala Phe Leu Ser Gly Glu Gln Lys Lys
            610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
            645                 650                 655

Glu Ile Ser Gly Val Glu Asp Arg Phe Asn Ala Ser Leu Gly Thr Tyr
            660                 665                 670

His Asp Leu Leu Lys Ile Ile Lys Asp Lys Asp Phe Leu Asp Asn Glu
            675                 680                 685

Glu Asn Glu Asp Ile Leu Glu Asp Ile Val Leu Thr Leu Thr Leu Phe
            690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Arg Tyr Thr Gly
            725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
            755                 760                 765

Arg Asn Phe Met Gln Leu Ile His Asp Asp Ser Leu Thr Phe Lys Glu
            770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
            805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
            835                 840                 845

Gln Lys Gly Gln Lys Asn Ser Arg Glu Arg Met Lys Arg Ile Glu Glu
850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
            885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
            915                 920                 925

Ser Ile Asp Asn Lys Val Leu Thr Arg Ser Asp Lys Asn Arg Gly Lys
930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
            965                 970                 975
```

-continued

```
Asn Leu Thr Lys Ala Glu Arg Gly Gly Leu Ser Glu Leu Asp Lys Ala
            980                 985                 990
Gly Phe Ile Lys Arg Gln Leu Val Glu Thr Arg Gln Ile Thr Lys His
        995                 1000                1005
Val Ala Gln Ile Leu Asp Ser Arg Met Asn Thr Lys Tyr Asp Glu
    1010                1015                1020
Asn Asp Lys Leu Ile Arg Glu Val Lys Val Ile Thr Leu Lys Ser
    1025                1030                1035
Lys Leu Val Ser Asp Phe Arg Lys Asp Phe Gln Phe Tyr Lys Val
    1040                1045                1050
Arg Glu Ile Asn Asn Tyr His His Ala His Asp Ala Tyr Leu Asn
    1055                1060                1065
Ala Val Val Gly Thr Ala Leu Ile Lys Lys Tyr Pro Lys Leu Glu
    1070                1075                1080
Ser Glu Phe Val Tyr Gly Asp Tyr Lys Val Tyr Asp Val Arg Lys
    1085                1090                1095
Met Ile Ala Lys Ser Glu Gln Glu Ile Gly Lys Ala Thr Ala Lys
    1100                1105                1110
Tyr Phe Phe Tyr Ser Asn Ile Met Asn Phe Phe Lys Thr Glu Ile
    1115                1120                1125
Thr Leu Ala Asn Gly Glu Ile Arg Lys Arg Pro Leu Ile Glu Thr
    1130                1135                1140
Asn Gly Glu Thr Gly Glu Ile Val Trp Asp Lys Gly Arg Asp Phe
    1145                1150                1155
Ala Thr Val Arg Lys Val Leu Ser Met Pro Gln Val Asn Ile Val
    1160                1165                1170
Lys Lys Thr Glu Val Gln Thr Gly Gly Phe Ser Lys Glu Ser Ile
    1175                1180                1185
Leu Pro Lys Arg Asn Ser Asp Lys Leu Ile Ala Arg Lys Lys Asp
    1190                1195                1200
Trp Asp Pro Lys Lys Tyr Gly Gly Phe Asp Ser Pro Thr Val Ala
    1205                1210                1215
Tyr Ser Val Leu Val Val Ala Lys Val Glu Lys Gly Lys Ser Lys
    1220                1225                1230
Lys Leu Lys Ser Val Lys Glu Leu Leu Gly Ile Thr Ile Met Glu
    1235                1240                1245
Arg Ser Ser Phe Glu Lys Asn Pro Ile Asp Phe Leu Glu Ala Lys
    1250                1255                1260
Gly Tyr Lys Glu Val Lys Lys Asp Leu Ile Ile Lys Leu Pro Lys
    1265                1270                1275
Tyr Ser Leu Phe Glu Leu Glu Asn Gly Arg Lys Arg Met Leu Ala
    1280                1285                1290
Ser Ala Gly Glu Leu Gln Lys Gly Asn Glu Leu Ala Leu Pro Ser
    1295                1300                1305
Lys Tyr Val Asn Phe Leu Tyr Leu Ala Ser His Tyr Glu Lys Leu
    1310                1315                1320
Lys Gly Ser Pro Glu Asp Asn Glu Gln Lys Gln Leu Phe Val Glu
    1325                1330                1335
Gln His Lys His Tyr Leu Asp Glu Ile Ile Glu Gln Ile Ser Glu
    1340                1345                1350
Phe Ser Lys Arg Val Ile Leu Ala Asp Ala Asn Leu Asp Lys Val
    1355                1360                1365
Leu Ser Ala Tyr Asn Lys His Arg Asp Lys Pro Ile Arg Glu Gln
```

```
           1370                1375                1380

Ala Glu Asn Ile Ile His Leu Phe Thr Leu Thr Asn Leu Gly Ala
    1385                1390                1395

Pro Ala Ala Phe Lys Tyr Phe Asp Thr Thr Ile Asp Arg Lys Arg
    1400                1405                1410

Tyr Thr Ser Thr Lys Glu Val Leu Asp Ala Thr Leu Ile His Gln
    1415                1420                1425

Ser Ile Thr Gly Leu Tyr Glu Thr Arg Ile Asp Leu Ser Gln Leu
    1430                1435                1440

Gly Gly Asp Ser Arg Ala Asp Tyr Pro Tyr Asp Val Pro Asp Tyr
    1445                1450                1455

Ala Ser Gly Ser Pro Lys Lys Lys Arg Lys Val Glu Ala Ser Gly
    1460                1465                1470

Ser Gly Arg Ala Ser Pro Gly Ile Pro Gly Ser Thr Arg Asn His
    1475                1480                1485

Asp Gln Glu Phe Asp Pro Pro Lys Val Tyr Pro Pro Val Pro Ala
    1490                1495                1500

Glu Lys Arg Lys Pro Ile Arg Val Leu Ser Leu Phe Asp Gly Ile
    1505                1510                1515

Ala Thr Gly Leu Leu Val Leu Lys Asp Leu Gly Ile Gln Val Asp
    1520                1525                1530

Arg Tyr Ile Ala Ser Glu Val Cys Glu Asp Ser Ile Thr Val Gly
    1535                1540                1545

Met Val Arg His Gln Gly Lys Ile Met Tyr Val Gly Asp Val Arg
    1550                1555                1560

Ser Val Thr Gln Lys His Ile Gln Glu Trp Gly Pro Phe Asp Leu
    1565                1570                1575

Val Ile Gly Gly Ser Pro Cys Asn Asp Leu Ser Ile Val Asn Pro
    1580                1585                1590

Ala Arg Lys Gly Leu Tyr Glu Gly Thr Gly Arg Leu Phe Phe Glu
    1595                1600                1605

Phe Tyr Arg Leu Leu His Asp Ala Arg Pro Lys Glu Gly Asp Asp
    1610                1615                1620

Arg Pro Phe Phe Trp Leu Phe Glu Asn Val Val Ala Met Gly Val
    1625                1630                1635

Ser Asp Lys Arg Asp Ile Ser Arg Phe Leu Glu Ser Asn Pro Val
    1640                1645                1650

Met Ile Asp Ala Lys Glu Val Ser Ala Ala His Arg Ala Arg Tyr
    1655                1660                1665

Phe Trp Gly Asn Leu Pro Gly Met Asn Arg Pro Leu Ala Ser Thr
    1670                1675                1680

Val Asn Asp Lys Leu Glu Leu Gln Glu Cys Leu Glu His Gly Arg
    1685                1690                1695

Ile Ala Lys Phe Ser Lys Val Arg Thr Ile Thr Thr Arg Ser Asn
    1700                1705                1710

Ser Ile Lys Gln Gly Lys Asp Gln His Phe Pro Val Phe Met Asn
    1715                1720                1725

Glu Lys Glu Asp Ile Leu Trp Cys Thr Glu Met Glu Arg Val Phe
    1730                1735                1740

Gly Phe Pro Val His Tyr Thr Asp Val Ser Asn Met Ser Arg Leu
    1745                1750                1755

Ala Arg Gln Arg Leu Leu Gly Arg Ser Trp Ser Val Pro Val Ile
    1760                1765                1770
```

```
Arg His Leu Phe Ala Pro Leu Lys Glu Tyr Phe Ala Cys Val Ser
1775                1780                1785

Ser Gly Asn Ser Asn Ala Asn Ser Arg Gly Pro Ser Phe Ser Ser
1790                1795                1800

Gly Leu Val Pro Leu Ser Leu Arg Gly Ser His Met Gly Pro Met
1805                1810                1815

Glu Ile Tyr Lys Thr Val Ser Ala Trp Lys Arg Gln Pro Val Arg
1820                1825                1830

Val Leu Ser Leu Phe Arg Asn Ile Asp Lys Val Leu Lys Ser Leu
1835                1840                1845

Gly Phe Leu Glu Ser Gly Ser Gly Ser Gly Gly Gly Thr Leu Lys
1850                1855                1860

Tyr Val Glu Asp Val Thr Asn Val Val Arg Arg Asp Val Glu Lys
1865                1870                1875

Trp Gly Pro Phe Asp Leu Val Tyr Gly Ser Thr Gln Pro Leu Gly
1880                1885                1890

Ser Ser Cys Asp Arg Cys Pro Gly Trp Tyr Met Phe Gln Phe His
1895                1900                1905

Arg Ile Leu Gln Tyr Ala Leu Pro Arg Gln Glu Ser Gln Arg Pro
1910                1915                1920

Phe Phe Trp Ile Phe Met Asp Asn Leu Leu Leu Thr Glu Asp Asp
1925                1930                1935

Gln Glu Thr Thr Thr Arg Phe Leu Gln Thr Glu Ala Val Thr Leu
1940                1945                1950

Gln Asp Val Arg Gly Arg Asp Tyr Gln Asn Ala Met Arg Val Trp
1955                1960                1965

Ser Asn Ile Pro Gly Leu Lys Ser Lys His Ala Pro Leu Thr Pro
1970                1975                1980

Lys Glu Glu Glu Tyr Leu Gln Ala Gln Val Arg Ser Arg Ser Lys
1985                1990                1995

Leu Asp Ala Pro Lys Val Asp Leu Leu Val Lys Asn Cys Leu Leu
2000                2005                2010

Pro Leu Arg Glu Tyr Phe Lys Tyr Phe Ser Gln Asn Ser Leu Pro
2015                2020                2025

Leu Ser Arg Ala Asp Pro Lys Lys Lys Arg Lys Val Gly Ser Gly
2030                2035                2040

Ala Thr Asn Phe Ser Leu Leu Lys Gln Ala Gly Asp Val Glu Glu
2045                2050                2055

Asn Pro Gly Pro Gly Ser Gly Ala Thr Asn Phe Ser Leu Leu Lys
2060                2065                2070

Gln Ala Gly Asp Val Glu Glu Asn Pro Gly Pro Ser Glu Leu Ile
2075                2080                2085

Lys Glu Asn Met His Met Lys Leu Tyr Met Glu Gly Thr Val Asp
2090                2095                2100

Asn His His Phe Lys Cys Thr Ser Glu Gly Glu Gly Lys Pro Tyr
2105                2110                2115

Glu Gly Thr Gln Thr Met Arg Ile Lys Val Val Glu Gly Gly Pro
2120                2125                2130

Leu Pro Phe Ala Phe Asp Ile Leu Ala Thr Ser Phe Leu Tyr Gly
2135                2140                2145

Ser Lys Thr Phe Ile Asn His Thr Gln Gly Ile Pro Asp Phe Phe
2150                2155                2160
```

```
Lys Gln Ser Phe Pro Glu Gly Phe Thr Trp Glu Arg Val Thr Thr
    2165                2170                2175

Tyr Glu Asp Gly Gly Val Leu Thr Ala Thr Gln Asp Thr Ser Leu
    2180                2185                2190

Gln Asp Gly Cys Leu Ile Tyr Asn Val Lys Ile Arg Gly Val Asn
    2195                2200                2205

Phe Thr Ser Asn Gly Pro Val Met Gln Lys Lys Thr Leu Gly Trp
    2210                2215                2220

Glu Ala Phe Thr Glu Thr Leu Tyr Pro Ala Asp Gly Gly Leu Glu
    2225                2230                2235

Gly Arg Asn Asp Met Ala Leu Lys Leu Val Gly Gly Ser His Leu
    2240                2245                2250

Ile Ala Asn Ile Lys Thr Thr Tyr Arg Ser Lys Lys Pro Ala Lys
    2255                2260                2265

Asn Leu Lys Met Pro Gly Val Tyr Tyr Val Asp Tyr Arg Leu Glu
    2270                2275                2280

Arg Ile Lys Glu Ala Asn Asn Glu Thr Tyr Val Glu Gln His Glu
    2285                2290                2295

Val Ala Val Ala Arg Tyr Cys Asp Leu Pro Ser Lys Leu Gly His
    2300                2305                2310

Lys Leu Asn
    2315

<210> SEQ ID NO 4
<211> LENGTH: 2318
<212> TYPE: PRT
<213> ORGANISM: Artificial sequence
<220> FEATURE:
<223> OTHER INFORMATION: Synthetic polypeptide

<400> SEQUENCE: 4

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45

Leu Val Ser Leu Gly Tyr Gln Leu Thr Lys Pro Asp Val Ile Leu Arg
        50                  55                  60

Leu Glu Lys Gly Glu Glu Pro Gly Gly Ser Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190
```

-continued

```
Arg His Pro Ile Phe Gly Asn Ile Val Asp Glu Val Ala Tyr His Glu
        195                 200                 205
Lys Tyr Pro Thr Ile Tyr His Leu Arg Lys Lys Leu Val Asp Ser Thr
        210                 215                 220
Asp Lys Ala Asp Leu Arg Leu Ile Tyr Leu Ala Leu Ala His Met Ile
225                 230                 235                 240
Lys Phe Arg Gly His Phe Leu Ile Glu Gly Asp Leu Asn Pro Asp Asn
                245                 250                 255
Ser Asp Val Asp Lys Leu Phe Ile Gln Leu Val Gln Thr Tyr Asn Gln
                260                 265                 270
Leu Phe Glu Glu Asn Pro Ile Asn Ala Ser Gly Val Asp Ala Lys Ala
        275                 280                 285
Ile Leu Ser Ala Arg Leu Ser Lys Ser Arg Arg Leu Glu Asn Leu Ile
        290                 295                 300
Ala Gln Leu Pro Gly Glu Lys Lys Asn Gly Leu Phe Gly Asn Leu Ile
305                 310                 315                 320
Ala Leu Ser Leu Gly Leu Thr Pro Asn Phe Lys Ser Asn Phe Asp Leu
                325                 330                 335
Ala Glu Asp Ala Lys Leu Gln Leu Ser Lys Asp Thr Tyr Asp Asp Asp
                340                 345                 350
Leu Asp Asn Leu Leu Ala Gln Ile Gly Asp Gln Tyr Ala Asp Leu Phe
        355                 360                 365
Leu Ala Ala Lys Asn Leu Ser Asp Ala Ile Leu Leu Ser Asp Ile Leu
        370                 375                 380
Arg Val Asn Thr Glu Ile Thr Lys Ala Pro Leu Ser Ala Ser Met Ile
385                 390                 395                 400
Lys Arg Tyr Asp Glu His His Gln Asp Leu Thr Leu Leu Lys Ala Leu
                405                 410                 415
Val Arg Gln Gln Leu Pro Glu Lys Tyr Lys Glu Ile Phe Phe Asp Gln
                420                 425                 430
Ser Lys Asn Gly Tyr Ala Gly Tyr Ile Asp Gly Gly Ala Ser Gln Glu
        435                 440                 445
Glu Phe Tyr Lys Phe Ile Lys Pro Ile Leu Glu Lys Met Asp Gly Thr
        450                 455                 460
Glu Glu Leu Leu Val Lys Leu Asn Arg Glu Asp Leu Leu Arg Lys Gln
465                 470                 475                 480
Arg Thr Phe Asp Asn Gly Ser Ile Pro His Gln Ile His Leu Gly Glu
                485                 490                 495
Leu His Ala Ile Leu Arg Arg Gln Glu Asp Phe Tyr Pro Phe Leu Lys
                500                 505                 510
Asp Asn Arg Glu Lys Ile Glu Lys Ile Leu Thr Phe Arg Ile Pro Tyr
        515                 520                 525
Tyr Val Gly Pro Leu Ala Arg Gly Asn Ser Arg Phe Ala Trp Met Thr
        530                 535                 540
Arg Lys Ser Glu Glu Thr Ile Thr Pro Trp Asn Phe Glu Glu Val Val
545                 550                 555                 560
Asp Lys Gly Ala Ser Ala Gln Ser Phe Ile Glu Arg Met Thr Asn Phe
                565                 570                 575
Asp Lys Asn Leu Pro Asn Glu Lys Val Leu Pro Lys His Ser Leu Leu
                580                 585                 590
Tyr Glu Tyr Phe Thr Val Tyr Asn Glu Leu Thr Lys Val Lys Tyr Val
        595                 600                 605
Thr Glu Gly Met Arg Lys Pro Ala Phe Leu Ser Gly Glu Gln Lys Lys
```

```
            610                 615                 620
Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
                660                 665                 670

His Asp Leu Leu Lys Ile Ile Lys Asp Lys Asp Phe Leu Asp Asn Glu
                675                 680                 685

Glu Asn Glu Asp Ile Leu Glu Asp Ile Val Leu Thr Leu Thr Leu Phe
                690                 695                 700

Glu Asp Arg Glu Met Ile Glu Arg Leu Lys Thr Tyr Ala His Leu
705                 710                 715                 720

Phe Asp Asp Lys Val Met Lys Gln Leu Lys Arg Arg Arg Tyr Thr Gly
                725                 730                 735

Trp Gly Arg Leu Ser Arg Lys Leu Ile Asn Gly Ile Arg Asp Lys Gln
                740                 745                 750

Ser Gly Lys Thr Ile Leu Asp Phe Leu Lys Ser Asp Gly Phe Ala Asn
                755                 760                 765

Arg Asn Phe Met Gln Leu Ile His Asp Asp Ser Leu Thr Phe Lys Glu
770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
                805                 810                 815

Gln Thr Val Lys Val Val Asp Glu Leu Val Lys Val Met Gly Arg His
                820                 825                 830

Lys Pro Glu Asn Ile Val Ile Glu Met Ala Arg Glu Asn Gln Thr Thr
                835                 840                 845

Gln Lys Gly Gln Lys Asn Ser Arg Glu Arg Met Lys Arg Ile Glu Glu
                850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Leu Gln Asn
                885                 890                 895

Gly Arg Asp Met Tyr Val Asp Gln Glu Leu Asp Ile Asn Arg Leu Ser
                900                 905                 910

Asp Tyr Asp Val Asp Ala Ile Val Pro Gln Ser Phe Leu Lys Asp Asp
                915                 920                 925

Ser Ile Asp Asn Lys Val Leu Thr Arg Ser Asp Lys Asn Arg Gly Lys
930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
                965                 970                 975

Asn Leu Thr Lys Ala Glu Arg Gly Gly Leu Ser Glu Leu Asp Lys Ala
                980                 985                 990

Gly Phe Ile Lys Arg Gln Leu Val  Glu Thr Arg Gln Ile  Thr Lys His
                995                 1000                1005

Val Ala  Gln Ile Leu Asp Ser  Arg Met Asn Thr Lys  Tyr Asp Glu
    1010                1015                1020

Asn Asp Lys Leu Ile Arg Glu  Val Lys Val Ile Thr  Leu Lys Ser
    1025                1030                1035
```

-continued

```
Lys Leu Val Ser Asp Phe Arg Lys Asp Phe Gln Phe Tyr Lys Val
    1040                1045                1050

Arg Glu Ile Asn Asn Tyr His His Ala His Asp Ala Tyr Leu Asn
    1055                1060                1065

Ala Val Val Gly Thr Ala Leu Ile Lys Lys Tyr Pro Lys Leu Glu
    1070                1075                1080

Ser Glu Phe Val Tyr Gly Asp Tyr Lys Val Tyr Asp Val Arg Lys
    1085                1090                1095

Met Ile Ala Lys Ser Glu Gln Glu Ile Gly Lys Ala Thr Ala Lys
    1100                1105                1110

Tyr Phe Phe Tyr Ser Asn Ile Met Asn Phe Phe Lys Thr Glu Ile
    1115                1120                1125

Thr Leu Ala Asn Gly Glu Ile Arg Lys Arg Pro Leu Ile Glu Thr
    1130                1135                1140

Asn Gly Glu Thr Gly Glu Ile Val Trp Asp Lys Gly Arg Asp Phe
    1145                1150                1155

Ala Thr Val Arg Lys Val Leu Ser Met Pro Gln Val Asn Ile Val
    1160                1165                1170

Lys Lys Thr Glu Val Gln Thr Gly Gly Phe Ser Lys Glu Ser Ile
    1175                1180                1185

Leu Pro Lys Arg Asn Ser Asp Lys Leu Ile Ala Arg Lys Lys Asp
    1190                1195                1200

Trp Asp Pro Lys Lys Tyr Gly Gly Phe Asp Ser Pro Thr Val Ala
    1205                1210                1215

Tyr Ser Val Leu Val Val Ala Lys Val Glu Lys Gly Lys Ser Lys
    1220                1225                1230

Lys Leu Lys Ser Val Lys Glu Leu Leu Gly Ile Thr Ile Met Glu
    1235                1240                1245

Arg Ser Ser Phe Glu Lys Asn Pro Ile Asp Phe Leu Glu Ala Lys
    1250                1255                1260

Gly Tyr Lys Glu Val Lys Lys Asp Leu Ile Ile Lys Leu Pro Lys
    1265                1270                1275

Tyr Ser Leu Phe Glu Leu Glu Asn Gly Arg Lys Arg Met Leu Ala
    1280                1285                1290

Ser Ala Gly Glu Leu Gln Lys Gly Asn Glu Leu Ala Leu Pro Ser
    1295                1300                1305

Lys Tyr Val Asn Phe Leu Tyr Leu Ala Ser His Tyr Glu Lys Leu
    1310                1315                1320

Lys Gly Ser Pro Glu Asp Asn Glu Gln Lys Gln Leu Phe Val Glu
    1325                1330                1335

Gln His Lys His Tyr Leu Asp Glu Ile Ile Glu Gln Ile Ser Glu
    1340                1345                1350

Phe Ser Lys Arg Val Ile Leu Ala Asp Ala Asn Leu Asp Lys Val
    1355                1360                1365

Leu Ser Ala Tyr Asn Lys His Arg Asp Lys Pro Ile Arg Glu Gln
    1370                1375                1380

Ala Glu Asn Ile Ile His Leu Phe Thr Leu Thr Asn Leu Gly Ala
    1385                1390                1395

Pro Ala Ala Phe Lys Tyr Phe Asp Thr Thr Ile Asp Arg Lys Arg
    1400                1405                1410

Tyr Thr Ser Thr Lys Glu Val Leu Asp Ala Thr Leu Ile His Gln
    1415                1420                1425
```

Ser Ile Thr Gly Leu Tyr Glu Thr Arg Ile Asp Leu Ser Gln Leu
1430                1435                1440

Gly Gly Asp Ser Arg Ala Asp Tyr Pro Tyr Asp Val Pro Asp Tyr
1445                1450                1455

Ala Ser Gly Ser Pro Lys Lys Lys Arg Lys Val Ser Pro Gly Ser
1460                1465                1470

Gly Ser Glu Thr Pro Gly Thr Ser Glu Ser Ala Thr Pro Glu Ser
1475                1480                1485

Asn His Asp Gln Glu Phe Asp Pro Pro Lys Val Tyr Pro Pro Val
1490                1495                1500

Pro Ala Glu Lys Arg Lys Pro Ile Arg Val Leu Ser Leu Phe Asp
1505                1510                1515

Gly Ile Ala Thr Gly Leu Leu Val Leu Lys Asp Leu Gly Ile Gln
1520                1525                1530

Val Asp Arg Tyr Ile Ala Ser Glu Val Cys Glu Asp Ser Ile Thr
1535                1540                1545

Val Gly Met Val Arg His Gln Gly Lys Ile Met Tyr Val Gly Asp
1550                1555                1560

Val Arg Ser Val Thr Gln Lys His Ile Gln Glu Trp Gly Pro Phe
1565                1570                1575

Asp Leu Val Ile Gly Gly Ser Pro Cys Asn Asp Leu Ser Ile Val
1580                1585                1590

Asn Pro Ala Arg Lys Gly Leu Tyr Glu Gly Thr Gly Arg Leu Phe
1595                1600                1605

Phe Glu Phe Tyr Arg Leu Leu His Asp Ala Arg Pro Lys Glu Gly
1610                1615                1620

Asp Asp Arg Pro Phe Phe Trp Leu Phe Glu Asn Val Val Ala Met
1625                1630                1635

Gly Val Ser Asp Lys Arg Asp Ile Ser Arg Phe Leu Glu Ser Asn
1640                1645                1650

Pro Val Met Ile Asp Ala Lys Glu Val Ser Ala Ala His Arg Ala
1655                1660                1665

Arg Tyr Phe Trp Gly Asn Leu Pro Gly Met Asn Arg Pro Leu Ala
1670                1675                1680

Ser Thr Val Asn Asp Lys Leu Glu Leu Gln Glu Cys Leu Glu His
1685                1690                1695

Gly Arg Ile Ala Lys Phe Ser Lys Val Arg Thr Ile Thr Thr Arg
1700                1705                1710

Ser Asn Ser Ile Lys Gln Gly Lys Asp Gln His Phe Pro Val Phe
1715                1720                1725

Met Asn Glu Lys Glu Asp Ile Leu Trp Cys Thr Glu Met Glu Arg
1730                1735                1740

Val Phe Gly Phe Pro Val His Tyr Thr Asp Val Ser Asn Met Ser
1745                1750                1755

Arg Leu Ala Arg Gln Arg Leu Leu Gly Arg Ser Trp Ser Val Pro
1760                1765                1770

Val Ile Arg His Leu Phe Ala Pro Leu Lys Glu Tyr Phe Ala Cys
1775                1780                1785

Val Ser Ser Gly Asn Ser Asn Ala Asn Ser Arg Gly Pro Ser Phe
1790                1795                1800

Ser Ser Gly Leu Val Pro Leu Ser Leu Arg Gly Ser His Met Gly
1805                1810                1815

Pro Met Glu Ile Tyr Lys Thr Val Ser Ala Trp Lys Arg Gln Pro

```
            1820                1825                1830

Val Arg Val Leu Ser Leu Phe Arg Asn Ile Asp Lys Val Leu Lys
    1835                1840                1845

Ser Leu Gly Phe Leu Glu Ser Gly Ser Gly Ser Gly Gly Gly Thr
    1850                1855                1860

Leu Lys Tyr Val Glu Asp Val Thr Asn Val Val Arg Arg Asp Val
    1865                1870                1875

Glu Lys Trp Gly Pro Phe Asp Leu Val Tyr Gly Ser Thr Gln Pro
    1880                1885                1890

Leu Gly Ser Ser Cys Asp Arg Cys Pro Gly Trp Tyr Met Phe Gln
    1895                1900                1905

Phe His Arg Ile Leu Gln Tyr Ala Leu Pro Arg Gln Glu Ser Gln
    1910                1915                1920

Arg Pro Phe Phe Trp Ile Phe Met Asp Asn Leu Leu Leu Thr Glu
    1925                1930                1935

Asp Asp Gln Glu Thr Thr Thr Arg Phe Leu Gln Thr Glu Ala Val
    1940                1945                1950

Thr Leu Gln Asp Val Arg Gly Arg Asp Tyr Gln Asn Ala Met Arg
    1955                1960                1965

Val Trp Ser Asn Ile Pro Gly Leu Lys Ser Lys His Ala Pro Leu
    1970                1975                1980

Thr Pro Lys Glu Glu Tyr Leu Gln Ala Gln Val Arg Ser Arg
    1985                1990                1995

Ser Lys Leu Asp Ala Pro Lys Val Asp Leu Leu Val Lys Asn Cys
    2000                2005                2010

Leu Leu Pro Leu Arg Glu Tyr Phe Lys Tyr Phe Ser Gln Asn Ser
    2015                2020                2025

Leu Pro Leu Ser Arg Ala Asp Pro Lys Lys Lys Arg Lys Val Gly
    2030                2035                2040

Ser Gly Ala Thr Asn Phe Ser Leu Leu Lys Gln Ala Gly Asp Val
    2045                2050                2055

Glu Glu Asn Pro Gly Pro Gly Ser Gly Ala Thr Asn Phe Ser Leu
    2060                2065                2070

Leu Lys Gln Ala Gly Asp Val Glu Glu Asn Pro Gly Pro Ser Glu
    2075                2080                2085

Leu Ile Lys Glu Asn Met His Met Lys Leu Tyr Met Glu Gly Thr
    2090                2095                2100

Val Asp Asn His His Phe Lys Cys Thr Ser Glu Gly Glu Gly Lys
    2105                2110                2115

Pro Tyr Glu Gly Thr Gln Thr Met Arg Ile Lys Val Val Glu Gly
    2120                2125                2130

Gly Pro Leu Pro Phe Ala Phe Asp Ile Leu Ala Thr Ser Phe Leu
    2135                2140                2145

Tyr Gly Ser Lys Thr Phe Ile Asn His Thr Gln Gly Ile Pro Asp
    2150                2155                2160

Phe Phe Lys Gln Ser Phe Pro Glu Gly Phe Thr Trp Glu Arg Val
    2165                2170                2175

Thr Thr Tyr Glu Asp Gly Gly Val Leu Thr Ala Thr Gln Asp Thr
    2180                2185                2190

Ser Leu Gln Asp Gly Cys Leu Ile Tyr Asn Val Lys Ile Arg Gly
    2195                2200                2205

Val Asn Phe Thr Ser Asn Gly Pro Val Met Gln Lys Lys Thr Leu
    2210                2215                2220
```

```
Gly Trp Glu Ala Phe Thr Glu Thr Leu Tyr Pro Ala Asp Gly Gly
    2225                2230                2235

Leu Glu Gly Arg Asn Asp Met Ala Leu Lys Leu Val Gly Gly Ser
    2240                2245                2250

His Leu Ile Ala Asn Ile Lys Thr Thr Tyr Arg Ser Lys Lys Pro
    2255                2260                2265

Ala Lys Asn Leu Lys Met Pro Gly Val Tyr Tyr Val Asp Tyr Arg
    2270                2275                2280

Leu Glu Arg Ile Lys Glu Ala Asn Asn Glu Thr Tyr Val Glu Gln
    2285                2290                2295

His Glu Val Ala Val Ala Arg Tyr Cys Asp Leu Pro Ser Lys Leu
    2300                2305                2310

Gly His Lys Leu Asn
    2315

<210> SEQ ID NO 5
<211> LENGTH: 2360
<212> TYPE: PRT
<213> ORGANISM: Artificial sequence
<220> FEATURE:
<223> OTHER INFORMATION: Synthetic polypeptide

<400> SEQUENCE: 5

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45

Leu Val Ser Leu Gly Tyr Gln Leu Thr Lys Pro Asp Val Ile Leu Arg
        50                  55                  60

Leu Glu Lys Gly Glu Glu Pro Gly Gly Ser Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
                100                 105                 110

Leu Gly Asn Thr Asp Arg His Ser Ile Lys Lys Asn Leu Ile Gly Ala
            115                 120                 125

Leu Leu Phe Asp Ser Gly Glu Thr Ala Glu Ala Thr Arg Leu Lys Arg
        130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255
```

```
Ser Asp Val Asp Lys Leu Phe Ile Gln Leu Val Gln Thr Tyr Asn Gln
            260                 265                 270

Leu Phe Glu Glu Asn Pro Ile Asn Ala Ser Gly Val Asp Ala Lys Ala
            275                 280                 285

Ile Leu Ser Ala Arg Leu Ser Lys Ser Arg Arg Leu Glu Asn Leu Ile
290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
            340                 345                 350

Leu Asp Asn Leu Leu Ala Gln Ile Gly Asp Gln Tyr Ala Asp Leu Phe
            355                 360                 365

Leu Ala Ala Lys Asn Leu Ser Asp Ala Ile Leu Leu Ser Asp Ile Leu
370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
            420                 425                 430

Ser Lys Asn Gly Tyr Ala Gly Tyr Ile Asp Gly Gly Ala Ser Gln Glu
            435                 440                 445

Glu Phe Tyr Lys Phe Ile Lys Pro Ile Leu Glu Lys Met Asp Gly Thr
450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
            500                 505                 510

Asp Asn Arg Glu Lys Ile Glu Lys Ile Leu Thr Phe Arg Ile Pro Tyr
            515                 520                 525

Tyr Val Gly Pro Leu Ala Arg Gly Asn Ser Arg Phe Ala Trp Met Thr
530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
            580                 585                 590

Tyr Glu Tyr Phe Thr Val Tyr Asn Glu Leu Thr Lys Val Lys Tyr Val
            595                 600                 605

Thr Glu Gly Met Arg Lys Pro Ala Phe Leu Ser Gly Glu Gln Lys Lys
            610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
            660                 665                 670
```

```
His Asp Leu Leu Lys Ile Ile Lys Asp Lys Asp Phe Leu Asp Asn Glu
            675                 680                 685
Glu Asn Glu Asp Ile Leu Glu Asp Ile Val Leu Thr Leu Thr Leu Phe
    690                 695                 700
Glu Asp Arg Glu Met Ile Glu Arg Leu Lys Thr Tyr Ala His Leu
705                 710                 715                 720
Phe Asp Asp Lys Val Met Lys Gln Leu Lys Arg Arg Tyr Thr Gly
                725                 730                 735
Trp Gly Arg Leu Ser Arg Lys Leu Ile Asn Gly Ile Arg Asp Lys Gln
                740                 745                 750
Ser Gly Lys Thr Ile Leu Asp Phe Leu Lys Ser Asp Gly Phe Ala Asn
            755                 760                 765
Arg Asn Phe Met Gln Leu Ile His Asp Asp Ser Leu Thr Phe Lys Glu
    770                 775                 780
Asp Ile Gln Lys Ala Gln Val Ser Gly Gln Gly Asp Ser Leu His Glu
785                 790                 795                 800
His Ile Ala Asn Leu Ala Gly Ser Pro Ala Ile Lys Lys Gly Ile Leu
                805                 810                 815
Gln Thr Val Lys Val Val Asp Glu Leu Val Lys Val Met Gly Arg His
            820                 825                 830
Lys Pro Glu Asn Ile Val Ile Glu Met Ala Arg Glu Asn Gln Thr Thr
    835                 840                 845
Gln Lys Gly Gln Lys Asn Ser Arg Glu Arg Met Lys Arg Ile Glu Glu
850                 855                 860
Gly Ile Lys Glu Leu Gly Ser Gln Ile Leu Lys Glu His Pro Val Glu
865                 870                 875                 880
Asn Thr Gln Leu Gln Asn Glu Lys Leu Tyr Leu Tyr Tyr Leu Gln Asn
                885                 890                 895
Gly Arg Asp Met Tyr Val Asp Gln Glu Leu Asp Ile Asn Arg Leu Ser
            900                 905                 910
Asp Tyr Asp Val Asp Ala Ile Val Pro Gln Ser Phe Leu Lys Asp Asp
    915                 920                 925
Ser Ile Asp Asn Lys Val Leu Thr Arg Ser Asp Lys Asn Arg Gly Lys
930                 935                 940
Ser Asp Asn Val Pro Ser Glu Glu Val Val Lys Lys Met Lys Asn Tyr
945                 950                 955                 960
Trp Arg Gln Leu Leu Asn Ala Lys Leu Ile Thr Gln Arg Lys Phe Asp
                965                 970                 975
Asn Leu Thr Lys Ala Glu Arg Gly Gly Leu Ser Glu Leu Asp Lys Ala
            980                 985                 990
Gly Phe Ile Lys Arg Gln Leu Val  Glu Thr Arg Gln Ile  Thr Lys His
    995                 1000                1005
Val Ala  Gln Ile Leu Asp Ser  Arg Met Asn Thr Lys  Tyr Asp Glu
    1010                1015                1020
Asn Asp  Lys Leu Ile Arg Glu  Val Lys Val Ile Thr  Leu Lys Ser
    1025                1030                1035
Lys Leu  Val Ser Asp Phe Arg  Lys Asp Phe Gln Phe  Tyr Lys Val
    1040                1045                1050
Arg Glu  Ile Asn Asn Tyr His  His Ala His Asp Ala  Tyr Leu Asn
    1055                1060                1065
Ala Val  Val Gly Thr Ala Leu  Ile Lys Lys Tyr Pro  Lys Leu Glu
    1070                1075                1080
Ser Glu  Phe Val Tyr Gly Asp  Tyr Lys Val Tyr Asp  Val Arg Lys
```

```
            1085                1090                1095
Met Ile Ala Lys Ser Glu Gln Glu Ile Gly Lys Ala Thr Ala Lys
            1100                1105                1110

Tyr Phe Phe Tyr Ser Asn Ile Met Asn Phe Phe Lys Thr Glu Ile
            1115                1120                1125

Thr Leu Ala Asn Gly Glu Ile Arg Lys Arg Pro Leu Ile Glu Thr
            1130                1135                1140

Asn Gly Glu Thr Gly Glu Ile Val Trp Asp Lys Gly Arg Asp Phe
            1145                1150                1155

Ala Thr Val Arg Lys Val Leu Ser Met Pro Gln Val Asn Ile Val
            1160                1165                1170

Lys Lys Thr Glu Val Gln Thr Gly Gly Phe Ser Lys Glu Ser Ile
            1175                1180                1185

Leu Pro Lys Arg Asn Ser Asp Lys Leu Ile Ala Arg Lys Lys Asp
            1190                1195                1200

Trp Asp Pro Lys Lys Tyr Gly Gly Phe Asp Ser Pro Thr Val Ala
            1205                1210                1215

Tyr Ser Val Leu Val Val Ala Lys Val Glu Lys Gly Lys Ser Lys
            1220                1225                1230

Lys Leu Lys Ser Val Lys Glu Leu Leu Gly Ile Thr Ile Met Glu
            1235                1240                1245

Arg Ser Ser Phe Glu Lys Asn Pro Ile Asp Phe Leu Glu Ala Lys
            1250                1255                1260

Gly Tyr Lys Glu Val Lys Lys Asp Leu Ile Ile Lys Leu Pro Lys
            1265                1270                1275

Tyr Ser Leu Phe Glu Leu Glu Asn Gly Arg Lys Arg Met Leu Ala
            1280                1285                1290

Ser Ala Gly Glu Leu Gln Lys Gly Asn Glu Leu Ala Leu Pro Ser
            1295                1300                1305

Lys Tyr Val Asn Phe Leu Tyr Leu Ala Ser His Tyr Glu Lys Leu
            1310                1315                1320

Lys Gly Ser Pro Glu Asp Asn Glu Gln Lys Gln Leu Phe Val Glu
            1325                1330                1335

Gln His Lys His Tyr Leu Asp Glu Ile Ile Glu Gln Ile Ser Glu
            1340                1345                1350

Phe Ser Lys Arg Val Ile Leu Ala Asp Ala Asn Leu Asp Lys Val
            1355                1360                1365

Leu Ser Ala Tyr Asn Lys His Arg Asp Lys Pro Ile Arg Glu Gln
            1370                1375                1380

Ala Glu Asn Ile Ile His Leu Phe Thr Leu Thr Asn Leu Gly Ala
            1385                1390                1395

Pro Ala Ala Phe Lys Tyr Phe Asp Thr Thr Ile Asp Arg Lys Arg
            1400                1405                1410

Tyr Thr Ser Thr Lys Glu Val Leu Asp Ala Thr Leu Ile His Gln
            1415                1420                1425

Ser Ile Thr Gly Leu Tyr Glu Thr Arg Ile Asp Leu Ser Gln Leu
            1430                1435                1440

Gly Gly Asp Ser Arg Ala Asp Tyr Pro Tyr Asp Val Pro Asp Tyr
            1445                1450                1455

Ala Ser Gly Ser Pro Lys Lys Lys Arg Lys Val Ser Pro Gly Gly
            1460                1465                1470

Gly Pro Ser Ser Gly Ala Pro Pro Pro Ser Gly Gly Ser Pro Ala
            1475                1480                1485
```

-continued

Gly Ser Pro Thr Ser Thr Glu Glu Gly Thr Glu Ser Ala Thr
    1490            1495             1500

Pro Glu Ser Gly Pro Gly Thr Ser Thr Glu Pro Ser Glu Gly Ser
    1505            1510             1515

Ala Pro Gly Ser Pro Ala Gly Ser Pro Thr Ser Thr Glu Glu Gly
    1520            1525             1530

Thr Ser Thr Glu Pro Ser Glu Gly Ser Ala Pro Gly Thr Ser Thr
    1535            1540             1545

Glu Pro Ser Glu Asn His Asp Gln Glu Phe Asp Pro Pro Lys Val
    1550            1555             1560

Tyr Pro Pro Val Pro Ala Glu Lys Arg Lys Pro Ile Arg Val Leu
    1565            1570             1575

Ser Leu Phe Asp Gly Ile Ala Thr Gly Leu Leu Val Leu Lys Asp
    1580            1585             1590

Leu Gly Ile Gln Val Asp Arg Tyr Ile Ala Ser Glu Val Cys Glu
    1595            1600             1605

Asp Ser Ile Thr Val Gly Met Val Arg His Gln Gly Lys Ile Met
    1610            1615             1620

Tyr Val Gly Asp Val Arg Ser Val Thr Gln Lys His Ile Gln Glu
    1625            1630             1635

Trp Gly Pro Phe Asp Leu Val Ile Gly Gly Ser Pro Cys Asn Asp
    1640            1645             1650

Leu Ser Ile Val Asn Pro Ala Arg Lys Gly Leu Tyr Glu Gly Thr
    1655            1660             1665

Gly Arg Leu Phe Phe Glu Phe Tyr Arg Leu Leu His Asp Ala Arg
    1670            1675             1680

Pro Lys Glu Gly Asp Asp Arg Pro Phe Phe Trp Leu Phe Glu Asn
    1685            1690             1695

Val Val Ala Met Gly Val Ser Asp Lys Arg Asp Ile Ser Arg Phe
    1700            1705             1710

Leu Glu Ser Asn Pro Val Met Ile Asp Ala Lys Glu Val Ser Ala
    1715            1720             1725

Ala His Arg Ala Arg Tyr Phe Trp Gly Asn Leu Pro Gly Met Asn
    1730            1735             1740

Arg Pro Leu Ala Ser Thr Val Asn Asp Lys Leu Glu Leu Gln Glu
    1745            1750             1755

Cys Leu Glu His Gly Arg Ile Ala Lys Phe Ser Lys Val Arg Thr
    1760            1765             1770

Ile Thr Thr Arg Ser Asn Ser Ile Lys Gln Gly Lys Asp Gln His
    1775            1780             1785

Phe Pro Val Phe Met Asn Glu Lys Glu Asp Ile Leu Trp Cys Thr
    1790            1795             1800

Glu Met Glu Arg Val Phe Gly Phe Pro Val His Tyr Thr Asp Val
    1805            1810             1815

Ser Asn Met Ser Arg Leu Ala Arg Gln Arg Leu Leu Gly Arg Ser
    1820            1825             1830

Trp Ser Val Pro Val Ile Arg His Leu Phe Ala Pro Leu Lys Glu
    1835            1840             1845

Tyr Phe Ala Cys Val Ser Ser Gly Asn Ser Asn Ala Asn Ser Arg
    1850            1855             1860

Gly Pro Ser Phe Ser Ser Gly Leu Val Pro Leu Ser Leu Arg Gly
    1865            1870             1875

```
Ser His Met Gly Pro Met Glu Ile Tyr Lys Thr Val Ser Ala Trp
    1880            1885                1890

Lys Arg Gln Pro Val Arg Val Leu Ser Leu Phe Arg Asn Ile Asp
    1895            1900                1905

Lys Val Leu Lys Ser Leu Gly Phe Leu Glu Ser Gly Ser Gly Ser
    1910            1915                1920

Gly Gly Gly Thr Leu Lys Tyr Val Glu Asp Val Thr Asn Val Val
    1925            1930                1935

Arg Arg Asp Val Glu Lys Trp Gly Pro Phe Asp Leu Val Tyr Gly
    1940            1945                1950

Ser Thr Gln Pro Leu Gly Ser Ser Cys Asp Arg Cys Pro Gly Trp
    1955            1960                1965

Tyr Met Phe Gln Phe His Arg Ile Leu Gln Tyr Ala Leu Pro Arg
    1970            1975                1980

Gln Glu Ser Gln Arg Pro Phe Phe Trp Ile Phe Met Asp Asn Leu
    1985            1990                1995

Leu Leu Thr Glu Asp Asp Gln Glu Thr Thr Thr Arg Phe Leu Gln
    2000            2005                2010

Thr Glu Ala Val Thr Leu Gln Asp Val Arg Gly Arg Asp Tyr Gln
    2015            2020                2025

Asn Ala Met Arg Val Trp Ser Asn Ile Pro Gly Leu Lys Ser Lys
    2030            2035                2040

His Ala Pro Leu Thr Pro Lys Glu Glu Glu Tyr Leu Gln Ala Gln
    2045            2050                2055

Val Arg Ser Arg Ser Lys Leu Asp Ala Pro Lys Val Asp Leu Leu
    2060            2065                2070

Val Lys Asn Cys Leu Leu Pro Leu Arg Glu Tyr Phe Lys Tyr Phe
    2075            2080                2085

Ser Gln Asn Ser Leu Pro Leu Ser Arg Ala Asp Pro Lys Lys Lys
    2090            2095                2100

Arg Lys Val Gly Ser Gly Ala Thr Asn Phe Ser Leu Leu Lys Gln
    2105            2110                2115

Ala Gly Asp Val Glu Glu Asn Pro Gly Pro Ser Glu Leu Ile Lys
    2120            2125                2130

Glu Asn Met His Met Lys Leu Tyr Met Glu Gly Thr Val Asp Asn
    2135            2140                2145

His His Phe Lys Cys Thr Ser Glu Gly Glu Gly Lys Pro Tyr Glu
    2150            2155                2160

Gly Thr Gln Thr Met Arg Ile Lys Val Val Glu Gly Gly Pro Leu
    2165            2170                2175

Pro Phe Ala Phe Asp Ile Leu Ala Thr Ser Phe Leu Tyr Gly Ser
    2180            2185                2190

Lys Thr Phe Ile Asn His Thr Gln Gly Ile Pro Asp Phe Phe Lys
    2195            2200                2205

Gln Ser Phe Pro Glu Gly Phe Thr Trp Glu Arg Val Thr Thr Tyr
    2210            2215                2220

Glu Asp Gly Gly Val Leu Thr Ala Thr Gln Asp Thr Ser Leu Gln
    2225            2230                2235

Asp Gly Cys Leu Ile Tyr Asn Val Lys Ile Arg Gly Val Asn Phe
    2240            2245                2250

Thr Ser Asn Gly Pro Val Met Gln Lys Lys Thr Leu Gly Trp Glu
    2255            2260                2265

Ala Phe Thr Glu Thr Leu Tyr Pro Ala Asp Gly Gly Leu Glu Gly
```

```
                2270                2275                2280
Arg Asn Asp Met Ala Leu Lys Leu Val Gly Gly Ser His Leu Ile
    2285                2290                2295

Ala Asn Ile Lys Thr Thr Tyr Arg Ser Lys Lys Pro Ala Lys Asn
    2300                2305                2310

Leu Lys Met Pro Gly Val Tyr Tyr Val Asp Tyr Arg Leu Glu Arg
    2315                2320                2325

Ile Lys Glu Ala Asn Asn Glu Thr Tyr Val Glu Gln His Glu Val
    2330                2335                2340

Ala Val Ala Arg Tyr Cys Asp Leu Pro Ser Lys Leu Gly His Lys
    2345                2350                2355

Leu Asn
    2360

<210> SEQ ID NO 6
<211> LENGTH: 2382
<212> TYPE: PRT
<213> ORGANISM: Artificial sequence
<220> FEATURE:
<223> OTHER INFORMATION: Synthetic polypeptide

<400> SEQUENCE: 6

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45

Leu Val Ser Leu Gly Tyr Gln Leu Thr Lys Pro Asp Val Ile Leu Arg
        50                  55                  60

Leu Glu Lys Gly Glu Glu Pro Gly Gly Ser Gly Gly Ser Met Asp
65                  70                  75                  80

Lys Lys Tyr Ser Ile Gly Leu Ala Ile Gly Thr Asn Ser Val Gly Trp
                85                  90                  95

Ala Val Ile Thr Asp Glu Tyr Lys Val Pro Ser Lys Lys Phe Lys Val
            100                 105                 110

Leu Gly Asn Thr Asp Arg His Ser Ile Lys Lys Asn Leu Ile Gly Ala
        115                 120                 125

Leu Leu Phe Asp Ser Gly Glu Thr Ala Glu Ala Thr Arg Leu Lys Arg
    130                 135                 140

Thr Ala Arg Arg Arg Tyr Thr Arg Arg Lys Asn Arg Ile Cys Tyr Leu
145                 150                 155                 160

Gln Glu Ile Phe Ser Asn Glu Met Ala Lys Val Asp Asp Ser Phe Phe
                165                 170                 175

His Arg Leu Glu Glu Ser Phe Leu Val Glu Glu Asp Lys Lys His Glu
            180                 185                 190

Arg His Pro Ile Phe Gly Asn Ile Val Asp Glu Val Ala Tyr His Glu
        195                 200                 205

Lys Tyr Pro Thr Ile Tyr His Leu Arg Lys Lys Leu Val Asp Ser Thr
    210                 215                 220

Asp Lys Ala Asp Leu Arg Leu Ile Tyr Leu Ala Leu Ala His Met Ile
225                 230                 235                 240

Lys Phe Arg Gly His Phe Leu Ile Glu Gly Asp Leu Asn Pro Asp Asn
                245                 250                 255

Ser Asp Val Asp Lys Leu Phe Ile Gln Leu Val Gln Thr Tyr Asn Gln
```

```
                260                 265                 270
Leu Phe Glu Glu Asn Pro Ile Asn Ala Ser Gly Val Asp Ala Lys Ala
                275                 280                 285

Ile Leu Ser Ala Arg Leu Ser Lys Ser Arg Leu Glu Asn Leu Ile
            290                 295                 300

Ala Gln Leu Pro Gly Glu Lys Lys Asn Gly Leu Phe Gly Asn Leu Ile
305                 310                 315                 320

Ala Leu Ser Leu Gly Leu Thr Pro Asn Phe Lys Ser Asn Phe Asp Leu
                325                 330                 335

Ala Glu Asp Ala Lys Leu Gln Leu Ser Lys Asp Thr Tyr Asp Asp Asp
                340                 345                 350

Leu Asp Asn Leu Leu Ala Gln Ile Gly Asp Gln Tyr Ala Asp Leu Phe
                355                 360                 365

Leu Ala Ala Lys Asn Leu Ser Asp Ala Ile Leu Leu Ser Asp Ile Leu
                370                 375                 380

Arg Val Asn Thr Glu Ile Thr Lys Ala Pro Leu Ser Ala Ser Met Ile
385                 390                 395                 400

Lys Arg Tyr Asp Glu His His Gln Asp Leu Thr Leu Leu Lys Ala Leu
                405                 410                 415

Val Arg Gln Gln Leu Pro Glu Lys Tyr Lys Glu Ile Phe Phe Asp Gln
                420                 425                 430

Ser Lys Asn Gly Tyr Ala Gly Tyr Ile Asp Gly Gly Ala Ser Gln Glu
                435                 440                 445

Glu Phe Tyr Lys Phe Ile Lys Pro Ile Leu Glu Lys Met Asp Gly Thr
                450                 455                 460

Glu Glu Leu Leu Val Lys Leu Asn Arg Glu Asp Leu Leu Arg Lys Gln
465                 470                 475                 480

Arg Thr Phe Asp Asn Gly Ser Ile Pro His Gln Ile His Leu Gly Glu
                485                 490                 495

Leu His Ala Ile Leu Arg Arg Gln Glu Asp Phe Tyr Pro Phe Leu Lys
                500                 505                 510

Asp Asn Arg Glu Lys Ile Glu Lys Ile Leu Thr Phe Arg Ile Pro Tyr
                515                 520                 525

Tyr Val Gly Pro Leu Ala Arg Gly Asn Ser Arg Phe Ala Trp Met Thr
                530                 535                 540

Arg Lys Ser Glu Glu Thr Ile Thr Pro Trp Asn Phe Glu Glu Val Val
545                 550                 555                 560

Asp Lys Gly Ala Ser Ala Gln Ser Phe Ile Glu Arg Met Thr Asn Phe
                565                 570                 575

Asp Lys Asn Leu Pro Asn Glu Lys Val Leu Pro Lys His Ser Leu Leu
                580                 585                 590

Tyr Glu Tyr Phe Thr Val Tyr Asn Glu Leu Thr Lys Val Lys Tyr Val
                595                 600                 605

Thr Glu Gly Met Arg Lys Pro Ala Phe Leu Ser Gly Glu Gln Lys Lys
                610                 615                 620

Ala Ile Val Asp Leu Leu Phe Lys Thr Asn Arg Lys Val Thr Val Lys
625                 630                 635                 640

Gln Leu Lys Glu Asp Tyr Phe Lys Lys Ile Glu Cys Phe Asp Ser Val
                645                 650                 655

Glu Ile Ser Gly Val Glu Asp Arg Phe Asn Ala Ser Leu Gly Thr Tyr
                660                 665                 670

His Asp Leu Leu Lys Ile Ile Lys Asp Lys Asp Phe Leu Asp Asn Glu
                675                 680                 685
```

-continued

Glu Asn Glu Asp Ile Leu Glu Asp Ile Val Leu Thr Leu Thr Leu Phe
690                 695                 700

Glu Asp Arg Glu Met Ile Glu Glu Arg Leu Lys Thr Tyr Ala His Leu
705                 710                 715                 720

Phe Asp Asp Lys Val Met Lys Gln Leu Lys Arg Arg Tyr Thr Gly
            725                 730                 735

Trp Gly Arg Leu Ser Arg Lys Leu Ile Asn Gly Ile Arg Asp Lys Gln
            740                 745                 750

Ser Gly Lys Thr Ile Leu Asp Phe Leu Lys Ser Asp Gly Phe Ala Asn
            755                 760                 765

Arg Asn Phe Met Gln Leu Ile His Asp Asp Ser Leu Thr Phe Lys Glu
770                 775                 780

Asp Ile Gln Lys Ala Gln Val Ser Gly Gln Gly Asp Ser Leu His Glu
785                 790                 795                 800

His Ile Ala Asn Leu Ala Gly Ser Pro Ala Ile Lys Lys Gly Ile Leu
            805                 810                 815

Gln Thr Val Lys Val Val Asp Glu Leu Val Lys Val Met Gly Arg His
            820                 825                 830

Lys Pro Glu Asn Ile Val Ile Glu Met Ala Arg Glu Asn Gln Thr Thr
            835                 840                 845

Gln Lys Gly Gln Lys Asn Ser Arg Glu Arg Met Lys Arg Ile Glu Glu
850                 855                 860

Gly Ile Lys Glu Leu Gly Ser Gln Ile Leu Lys Glu His Pro Val Glu
865                 870                 875                 880

Asn Thr Gln Leu Gln Asn Glu Lys Leu Tyr Leu Tyr Tyr Leu Gln Asn
            885                 890                 895

Gly Arg Asp Met Tyr Val Asp Gln Glu Leu Asp Ile Asn Arg Leu Ser
            900                 905                 910

Asp Tyr Asp Val Asp Ala Ile Val Pro Gln Ser Phe Leu Lys Asp Asp
            915                 920                 925

Ser Ile Asp Asn Lys Val Leu Thr Arg Ser Asp Lys Asn Arg Gly Lys
930                 935                 940

Ser Asp Asn Val Pro Ser Glu Glu Val Val Lys Lys Met Lys Asn Tyr
945                 950                 955                 960

Trp Arg Gln Leu Leu Asn Ala Lys Leu Ile Thr Gln Arg Lys Phe Asp
            965                 970                 975

Asn Leu Thr Lys Ala Glu Arg Gly Gly Leu Ser Glu Leu Asp Lys Ala
            980                 985                 990

Gly Phe Ile Lys Arg Gln Leu Val  Glu Thr Arg Gln Ile  Thr Lys His
            995                 1000                 1005

Val Ala Gln Ile Leu Asp Ser Arg Met Asn Thr Lys  Tyr Asp Glu
    1010                 1015                 1020

Asn Asp Lys Leu Ile Arg Glu Val Lys Val Ile Thr  Leu Lys Ser
    1025                 1030                 1035

Lys Leu Val Ser Asp Phe Arg  Lys Asp Phe Gln Phe  Tyr Lys Val
    1040                 1045                 1050

Arg Glu Ile Asn Asn Tyr His  His Ala His Asp Ala  Tyr Leu Asn
    1055                 1060                 1065

Ala Val Val Gly Thr Ala Leu  Ile Lys Lys Tyr Pro  Lys Leu Glu
    1070                 1075                 1080

Ser Glu Phe Val Tyr Gly Asp  Tyr Lys Val Tyr Asp  Val Arg Lys
    1085                 1090                 1095

-continued

Met Ile Ala Lys Ser Glu Gln Glu Ile Gly Lys Ala Thr Ala Lys
1100                1105                1110

Tyr Phe Phe Tyr Ser Asn Ile Met Asn Phe Phe Lys Thr Glu Ile
1115                1120                1125

Thr Leu Ala Asn Gly Glu Ile Arg Lys Arg Pro Leu Ile Glu Thr
1130                1135                1140

Asn Gly Glu Thr Gly Glu Ile Val Trp Asp Lys Gly Arg Asp Phe
1145                1150                1155

Ala Thr Val Arg Lys Val Leu Ser Met Pro Gln Val Asn Ile Val
1160                1165                1170

Lys Lys Thr Glu Val Gln Thr Gly Gly Phe Ser Lys Glu Ser Ile
1175                1180                1185

Leu Pro Lys Arg Asn Ser Asp Lys Leu Ile Ala Arg Lys Lys Asp
1190                1195                1200

Trp Asp Pro Lys Lys Tyr Gly Gly Phe Asp Ser Pro Thr Val Ala
1205                1210                1215

Tyr Ser Val Leu Val Val Ala Lys Val Glu Lys Gly Lys Ser Lys
1220                1225                1230

Lys Leu Lys Ser Val Lys Glu Leu Leu Gly Ile Thr Ile Met Glu
1235                1240                1245

Arg Ser Ser Phe Glu Lys Asn Pro Ile Asp Phe Leu Glu Ala Lys
1250                1255                1260

Gly Tyr Lys Glu Val Lys Lys Asp Leu Ile Ile Lys Leu Pro Lys
1265                1270                1275

Tyr Ser Leu Phe Glu Leu Glu Asn Gly Arg Lys Arg Met Leu Ala
1280                1285                1290

Ser Ala Gly Glu Leu Gln Lys Gly Asn Glu Leu Ala Leu Pro Ser
1295                1300                1305

Lys Tyr Val Asn Phe Leu Tyr Leu Ala Ser His Tyr Glu Lys Leu
1310                1315                1320

Lys Gly Ser Pro Glu Asp Asn Glu Gln Lys Gln Leu Phe Val Glu
1325                1330                1335

Gln His Lys His Tyr Leu Asp Glu Ile Ile Glu Gln Ile Ser Glu
1340                1345                1350

Phe Ser Lys Arg Val Ile Leu Ala Asp Ala Asn Leu Asp Lys Val
1355                1360                1365

Leu Ser Ala Tyr Asn Lys His Arg Asp Lys Pro Ile Arg Glu Gln
1370                1375                1380

Ala Glu Asn Ile Ile His Leu Phe Thr Leu Thr Asn Leu Gly Ala
1385                1390                1395

Pro Ala Ala Phe Lys Tyr Phe Asp Thr Thr Ile Asp Arg Lys Arg
1400                1405                1410

Tyr Thr Ser Thr Lys Glu Val Leu Asp Ala Thr Leu Ile His Gln
1415                1420                1425

Ser Ile Thr Gly Leu Tyr Glu Thr Arg Ile Asp Leu Ser Gln Leu
1430                1435                1440

Gly Gly Asp Ser Arg Ala Asp Tyr Pro Tyr Asp Val Pro Asp Tyr
1445                1450                1455

Ala Ser Gly Ser Pro Lys Lys Lys Arg Lys Val Ser Pro Gly Gly
1460                1465                1470

Gly Pro Ser Ser Gly Ala Pro Pro Pro Ser Gly Gly Ser Pro Ala
1475                1480                1485

Gly Ser Pro Thr Ser Thr Glu Glu Gly Thr Ser Glu Ser Ala Thr

-continued

```
                 1490                1495                1500
Pro Glu Ser Gly Pro Gly Thr Ser Thr Glu Pro Ser Glu Gly Ser
    1505                1510                1515

Ala Pro Gly Ser Pro Ala Gly Ser Pro Thr Ser Thr Glu Glu Gly
    1520                1525                1530

Thr Ser Thr Glu Pro Ser Glu Gly Ser Ala Pro Gly Thr Ser Thr
    1535                1540                1545

Glu Pro Ser Glu Asn His Asp Gln Glu Phe Asp Pro Pro Lys Val
    1550                1555                1560

Tyr Pro Pro Val Pro Ala Glu Lys Arg Lys Pro Ile Arg Val Leu
    1565                1570                1575

Ser Leu Phe Asp Gly Ile Ala Thr Gly Leu Leu Val Leu Lys Asp
    1580                1585                1590

Leu Gly Ile Gln Val Asp Arg Tyr Ile Ala Ser Glu Val Cys Glu
    1595                1600                1605

Asp Ser Ile Thr Val Gly Met Val Arg His Gln Gly Lys Ile Met
    1610                1615                1620

Tyr Val Gly Asp Val Arg Ser Val Thr Gln Lys His Ile Gln Glu
    1625                1630                1635

Trp Gly Pro Phe Asp Leu Val Ile Gly Gly Ser Pro Cys Asn Asp
    1640                1645                1650

Leu Ser Ile Val Asn Pro Ala Arg Lys Gly Leu Tyr Glu Gly Thr
    1655                1660                1665

Gly Arg Leu Phe Phe Glu Phe Tyr Arg Leu Leu His Asp Ala Arg
    1670                1675                1680

Pro Lys Glu Gly Asp Asp Arg Pro Phe Phe Trp Leu Phe Glu Asn
    1685                1690                1695

Val Val Ala Met Gly Val Ser Asp Lys Arg Asp Ile Ser Arg Phe
    1700                1705                1710

Leu Glu Ser Asn Pro Val Met Ile Asp Ala Lys Glu Val Ser Ala
    1715                1720                1725

Ala His Arg Ala Arg Tyr Phe Trp Gly Asn Leu Pro Gly Met Asn
    1730                1735                1740

Arg Pro Leu Ala Ser Thr Val Asn Asp Lys Leu Glu Leu Gln Glu
    1745                1750                1755

Cys Leu Glu His Gly Arg Ile Ala Lys Phe Ser Lys Val Arg Thr
    1760                1765                1770

Ile Thr Thr Arg Ser Asn Ser Ile Lys Gln Gly Lys Asp Gln His
    1775                1780                1785

Phe Pro Val Phe Met Asn Glu Lys Glu Asp Ile Leu Trp Cys Thr
    1790                1795                1800

Glu Met Glu Arg Val Phe Gly Phe Pro Val His Tyr Thr Asp Val
    1805                1810                1815

Ser Asn Met Ser Arg Leu Ala Arg Gln Arg Leu Leu Gly Arg Ser
    1820                1825                1830

Trp Ser Val Pro Val Ile Arg His Leu Phe Ala Pro Leu Lys Glu
    1835                1840                1845

Tyr Phe Ala Cys Val Ser Ser Gly Asn Ser Asn Ala Asn Ser Arg
    1850                1855                1860

Gly Pro Ser Phe Ser Ser Gly Leu Val Pro Leu Ser Leu Arg Gly
    1865                1870                1875

Ser His Met Gly Pro Met Glu Ile Tyr Lys Thr Val Ser Ala Trp
    1880                1885                1890
```

-continued

```
Lys Arg Gln Pro Val Arg Val Leu Ser Leu Phe Arg Asn Ile Asp
1895                1900                1905

Lys Val Leu Lys Ser Leu Gly Phe Leu Glu Ser Gly Ser Gly Ser
1910                1915                1920

Gly Gly Gly Thr Leu Lys Tyr Val Glu Asp Val Thr Asn Val Val
1925                1930                1935

Arg Arg Asp Val Glu Lys Trp Gly Pro Phe Asp Leu Val Tyr Gly
1940                1945                1950

Ser Thr Gln Pro Leu Gly Ser Ser Cys Asp Arg Cys Pro Gly Trp
1955                1960                1965

Tyr Met Phe Gln Phe His Arg Ile Leu Gln Tyr Ala Leu Pro Arg
1970                1975                1980

Gln Glu Ser Gln Arg Pro Phe Phe Trp Ile Phe Met Asp Asn Leu
1985                1990                1995

Leu Leu Thr Glu Asp Asp Gln Glu Thr Thr Arg Phe Leu Gln
2000                2005                2010

Thr Glu Ala Val Thr Leu Gln Asp Val Arg Gly Arg Asp Tyr Gln
2015                2020                2025

Asn Ala Met Arg Val Trp Ser Asn Ile Pro Gly Leu Lys Ser Lys
2030                2035                2040

His Ala Pro Leu Thr Pro Lys Glu Glu Glu Tyr Leu Gln Ala Gln
2045                2050                2055

Val Arg Ser Arg Ser Lys Leu Asp Ala Pro Lys Val Asp Leu Leu
2060                2065                2070

Val Lys Asn Cys Leu Leu Pro Leu Arg Glu Tyr Phe Lys Tyr Phe
2075                2080                2085

Ser Gln Asn Ser Leu Pro Leu Ser Arg Ala Asp Pro Lys Lys Lys
2090                2095                2100

Arg Lys Val Gly Ser Gly Ala Thr Asn Phe Ser Leu Leu Lys Gln
2105                2110                2115

Ala Gly Asp Val Glu Glu Asn Pro Gly Pro Gly Ser Gly Ala Thr
2120                2125                2130

Asn Phe Ser Leu Leu Lys Gln Ala Gly Asp Val Glu Glu Asn Pro
2135                2140                2145

Gly Pro Ser Glu Leu Ile Lys Glu Asn Met His Met Lys Leu Tyr
2150                2155                2160

Met Glu Gly Thr Val Asp Asn His His Phe Lys Cys Thr Ser Glu
2165                2170                2175

Gly Glu Gly Lys Pro Tyr Glu Gly Thr Gln Thr Met Arg Ile Lys
2180                2185                2190

Val Val Glu Gly Gly Pro Leu Pro Phe Ala Phe Asp Ile Leu Ala
2195                2200                2205

Thr Ser Phe Leu Tyr Gly Ser Lys Thr Phe Ile Asn His Thr Gln
2210                2215                2220

Gly Ile Pro Asp Phe Phe Lys Gln Ser Phe Pro Glu Gly Phe Thr
2225                2230                2235

Trp Glu Arg Val Thr Thr Tyr Glu Asp Gly Gly Val Leu Thr Ala
2240                2245                2250

Thr Gln Asp Thr Ser Leu Gln Asp Gly Cys Leu Ile Tyr Asn Val
2255                2260                2265

Lys Ile Arg Gly Val Asn Phe Thr Ser Asn Gly Pro Val Met Gln
2270                2275                2280
```

Lys Lys Thr Leu Gly Trp Glu Ala Phe Thr Glu Thr Leu Tyr Pro
2285                2290                2295

Ala Asp Gly Gly Leu Glu Gly Arg Asn Asp Met Ala Leu Lys Leu
2300                2305                2310

Val Gly Gly Ser His Leu Ile Ala Asn Ile Lys Thr Thr Tyr Arg
2315                2320                2325

Ser Lys Lys Pro Ala Lys Asn Leu Lys Met Pro Gly Val Tyr Tyr
2330                2335                2340

Val Asp Tyr Arg Leu Glu Arg Ile Lys Glu Ala Asn Asn Glu Thr
2345                2350                2355

Tyr Val Glu Gln His Glu Val Ala Val Ala Arg Tyr Cys Asp Leu
2360                2365                2370

Pro Ser Lys Leu Gly His Lys Leu Asn
2375                2380

<210> SEQ ID NO 7
<211> LENGTH: 2303
<212> TYPE: PRT
<213> ORGANISM: Artificial sequence
<220> FEATURE:
<223> OTHER INFORMATION: Synthetic polypeptide

<400> SEQUENCE: 7

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45

Leu Val Ser Leu Gly Tyr Gln Leu Thr Lys Pro Asp Val Ile Leu Arg
        50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

```
Ile Glu Gly Asp Leu Asn Pro Asp Asn Ser Asp Val Asp Lys Leu Phe
             260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

Pro Asn Phe Lys Ser Asn Phe Asp Leu Ala Glu Asp Ala Lys Leu Gln
            340                 345                 350

Leu Ser Lys Asp Thr Tyr Asp Asp Leu Asp Asn Leu Leu Ala Gln
        355                 360                 365

Ile Gly Asp Gln Tyr Ala Asp Leu Phe Leu Ala Ala Lys Asn Leu Ser
    370                 375                 380

Asp Ala Ile Leu Leu Ser Asp Ile Leu Arg Val Asn Thr Glu Ile Thr
385                 390                 395                 400

Lys Ala Pro Leu Ser Ala Ser Met Ile Lys Arg Tyr Asp Glu His His
                405                 410                 415

Gln Asp Leu Thr Leu Leu Lys Ala Leu Val Arg Gln Gln Leu Pro Glu
            420                 425                 430

Lys Tyr Lys Glu Ile Phe Phe Asp Gln Ser Lys Asn Gly Tyr Ala Gly
        435                 440                 445

Tyr Ile Asp Gly Gly Ala Ser Gln Glu Glu Phe Tyr Lys Phe Ile Lys
    450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
                485                 490                 495

Ile Pro His Gln Ile His Leu Gly Glu Leu His Ala Ile Leu Arg Arg
            500                 505                 510

Gln Glu Asp Phe Tyr Pro Phe Leu Lys Asp Asn Arg Glu Lys Ile Glu
        515                 520                 525

Lys Ile Leu Thr Phe Arg Ile Pro Tyr Tyr Val Gly Pro Leu Ala Arg
    530                 535                 540

Gly Asn Ser Arg Phe Ala Trp Met Thr Arg Lys Ser Glu Glu Thr Ile
545                 550                 555                 560

Thr Pro Trp Asn Phe Glu Glu Val Val Asp Lys Gly Ala Ser Ala Gln
                565                 570                 575

Ser Phe Ile Glu Arg Met Thr Asn Phe Asp Lys Asn Leu Pro Asn Glu
            580                 585                 590

Lys Val Leu Pro Lys His Ser Leu Leu Tyr Glu Tyr Phe Thr Val Tyr
        595                 600                 605

Asn Glu Leu Thr Lys Val Lys Tyr Val Thr Glu Gly Met Arg Lys Pro
    610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
                645                 650                 655

Lys Lys Ile Glu Cys Phe Asp Ser Val Glu Ile Ser Gly Val Glu Asp
            660                 665                 670

Arg Phe Asn Ala Ser Leu Gly Thr Tyr His Asp Leu Leu Lys Ile Ile
```

-continued

```
            675                 680                 685
Lys Asp Lys Asp Phe Leu Asp Asn Glu Glu Asn Glu Asp Ile Leu Glu
    690                 695                 700
Asp Ile Val Leu Thr Leu Thr Leu Phe Glu Asp Arg Glu Met Ile Glu
705                 710                 715                 720
Glu Arg Leu Lys Thr Tyr Ala His Leu Phe Asp Asp Lys Val Met Lys
                725                 730                 735
Gln Leu Lys Arg Arg Arg Tyr Thr Gly Trp Gly Arg Leu Ser Arg Lys
            740                 745                 750
Leu Ile Asn Gly Ile Arg Asp Lys Gln Ser Gly Lys Thr Ile Leu Asp
            755                 760                 765
Phe Leu Lys Ser Asp Gly Phe Ala Asn Arg Asn Phe Met Gln Leu Ile
770                 775                 780
His Asp Asp Ser Leu Thr Phe Lys Glu Asp Ile Gln Lys Ala Gln Val
785                 790                 795                 800
Ser Gly Gln Gly Asp Ser Leu His Glu His Ile Ala Asn Leu Ala Gly
                805                 810                 815
Ser Pro Ala Ile Lys Lys Gly Ile Leu Gln Thr Val Lys Val Val Asp
            820                 825                 830
Glu Leu Val Lys Val Met Gly Arg His Lys Pro Glu Asn Ile Val Ile
        835                 840                 845
Glu Met Ala Arg Glu Asn Gln Thr Thr Gln Lys Gly Gln Lys Asn Ser
850                 855                 860
Arg Glu Arg Met Lys Arg Ile Glu Glu Gly Ile Lys Glu Leu Gly Ser
865                 870                 875                 880
Gln Ile Leu Lys Glu His Pro Val Glu Asn Thr Gln Leu Gln Asn Glu
                885                 890                 895
Lys Leu Tyr Leu Tyr Tyr Leu Gln Asn Gly Arg Asp Met Tyr Val Asp
                900                 905                 910
Gln Glu Leu Asp Ile Asn Arg Leu Ser Asp Tyr Asp Val Asp Ala Ile
            915                 920                 925
Val Pro Gln Ser Phe Leu Lys Asp Asp Ser Ile Asp Asn Lys Val Leu
930                 935                 940
Thr Arg Ser Asp Lys Asn Arg Gly Lys Ser Asp Asn Val Pro Ser Glu
945                 950                 955                 960
Glu Val Val Lys Lys Met Lys Asn Tyr Trp Arg Gln Leu Leu Asn Ala
                965                 970                 975
Lys Leu Ile Thr Gln Arg Lys Phe Asp Asn Leu Thr Lys Ala Glu Arg
            980                 985                 990
Gly Gly Leu Ser Glu Leu Asp Lys Ala Gly Phe Ile Lys Arg Gln Leu
            995                 1000                1005
Val Glu Thr Arg Gln Ile Thr Lys His Val Ala Gln Ile Leu Asp
    1010                1015                1020
Ser Arg Met Asn Thr Lys Tyr Asp Glu Asn Asp Lys Leu Ile Arg
    1025                1030                1035
Glu Val Lys Val Ile Thr Leu Lys Ser Lys Leu Val Ser Asp Phe
    1040                1045                1050
Arg Lys Asp Phe Gln Phe Tyr Lys Val Arg Glu Ile Asn Asn Tyr
    1055                1060                1065
His His Ala His Asp Ala Tyr Leu Asn Ala Val Val Gly Thr Ala
    1070                1075                1080
Leu Ile Lys Lys Tyr Pro Lys Leu Glu Ser Glu Phe Val Tyr Gly
    1085                1090                1095
```

```
Asp Tyr Lys Val Tyr Asp Val Arg Lys Met Ile Ala Lys Ser Glu
    1100            1105                1110

Gln Glu Ile Gly Lys Ala Thr Ala Lys Tyr Phe Phe Tyr Ser Asn
    1115            1120                1125

Ile Met Asn Phe Phe Lys Thr Glu Ile Thr Leu Ala Asn Gly Glu
    1130            1135                1140

Ile Arg Lys Arg Pro Leu Ile Glu Thr Asn Gly Glu Thr Gly Glu
    1145            1150                1155

Ile Val Trp Asp Lys Gly Arg Asp Phe Ala Thr Val Arg Lys Val
    1160            1165                1170

Leu Ser Met Pro Gln Val Asn Ile Val Lys Lys Thr Glu Val Gln
    1175            1180                1185

Thr Gly Gly Phe Ser Lys Glu Ser Ile Leu Pro Lys Arg Asn Ser
    1190            1195                1200

Asp Lys Leu Ile Ala Arg Lys Lys Asp Trp Asp Pro Lys Lys Tyr
    1205            1210                1215

Gly Gly Phe Asp Ser Pro Thr Val Ala Tyr Ser Val Leu Val Val
    1220            1225                1230

Ala Lys Val Glu Lys Gly Lys Ser Lys Lys Leu Lys Ser Val Lys
    1235            1240                1245

Glu Leu Leu Gly Ile Thr Ile Met Glu Arg Ser Ser Phe Glu Lys
    1250            1255                1260

Asn Pro Ile Asp Phe Leu Glu Ala Lys Gly Tyr Lys Glu Val Lys
    1265            1270                1275

Lys Asp Leu Ile Ile Lys Leu Pro Lys Tyr Ser Leu Phe Glu Leu
    1280            1285                1290

Glu Asn Gly Arg Lys Arg Met Leu Ala Ser Ala Gly Glu Leu Gln
    1295            1300                1305

Lys Gly Asn Glu Leu Ala Leu Pro Ser Lys Tyr Val Asn Phe Leu
    1310            1315                1320

Tyr Leu Ala Ser His Tyr Glu Lys Leu Lys Gly Ser Pro Glu Asp
    1325            1330                1335

Asn Glu Gln Lys Gln Leu Phe Val Glu Gln His Lys His Tyr Leu
    1340            1345                1350

Asp Glu Ile Ile Glu Gln Ile Ser Glu Phe Ser Lys Arg Val Ile
    1355            1360                1365

Leu Ala Asp Ala Asn Leu Asp Lys Val Leu Ser Ala Tyr Asn Lys
    1370            1375                1380

His Arg Asp Lys Pro Ile Arg Glu Gln Ala Glu Asn Ile Ile His
    1385            1390                1395

Leu Phe Thr Leu Thr Asn Leu Gly Ala Pro Ala Ala Phe Lys Tyr
    1400            1405                1410

Phe Asp Thr Thr Ile Asp Arg Lys Arg Tyr Thr Ser Thr Lys Glu
    1415            1420                1425

Val Leu Asp Ala Thr Leu Ile His Gln Ser Ile Thr Gly Leu Tyr
    1430            1435                1440

Glu Thr Arg Ile Asp Leu Ser Gln Leu Gly Gly Asp Ser Arg Ala
    1445            1450                1455

Asp Tyr Pro Tyr Asp Val Pro Asp Tyr Ala Ser Gly Ser Pro Lys
    1460            1465                1470

Lys Lys Arg Lys Val Glu Ala Ser Gly Ser Gly Arg Ala Ser Pro
    1475            1480                1485
```

```
Gly Ile Pro Gly Ser Thr Arg Asn His Asp Gln Glu Phe Asp Pro
    1490                1495                1500

Pro Lys Val Tyr Pro Pro Val Pro Ala Glu Lys Arg Lys Pro Ile
    1505                1510                1515

Arg Val Leu Ser Leu Phe Asp Gly Ile Ala Thr Gly Leu Leu Val
    1520                1525                1530

Leu Lys Asp Leu Gly Ile Gln Val Asp Arg Tyr Ile Ala Ser Glu
    1535                1540                1545

Val Cys Glu Asp Ser Ile Thr Val Gly Met Val Arg His Gln Gly
    1550                1555                1560

Lys Ile Met Tyr Val Gly Asp Val Arg Ser Val Thr Gln Lys His
    1565                1570                1575

Ile Gln Glu Trp Gly Pro Phe Asp Leu Val Ile Gly Gly Ser Pro
    1580                1585                1590

Cys Asn Asp Leu Ser Ile Val Asn Pro Ala Arg Lys Gly Leu Tyr
    1595                1600                1605

Glu Gly Thr Gly Arg Leu Phe Phe Glu Phe Tyr Arg Leu Leu His
    1610                1615                1620

Asp Ala Arg Pro Lys Glu Gly Asp Asp Arg Pro Phe Phe Trp Leu
    1625                1630                1635

Phe Glu Asn Val Val Ala Met Gly Val Ser Asp Lys Arg Asp Ile
    1640                1645                1650

Ser Arg Phe Leu Glu Ser Asn Pro Val Met Ile Asp Ala Lys Glu
    1655                1660                1665

Val Ser Ala Ala His Arg Ala Arg Tyr Phe Trp Gly Asn Leu Pro
    1670                1675                1680

Gly Met Asn Arg Pro Leu Ala Ser Thr Val Asn Asp Lys Leu Glu
    1685                1690                1695

Leu Gln Glu Cys Leu Glu His Gly Arg Ile Ala Lys Phe Ser Lys
    1700                1705                1710

Val Arg Thr Ile Thr Thr Arg Ser Asn Ser Ile Lys Gln Gly Lys
    1715                1720                1725

Asp Gln His Phe Pro Val Phe Met Asn Glu Lys Glu Asp Ile Leu
    1730                1735                1740

Trp Cys Thr Glu Met Glu Arg Val Phe Gly Phe Pro Val His Tyr
    1745                1750                1755

Thr Asp Val Ser Asn Met Ser Arg Leu Ala Arg Gln Arg Leu Leu
    1760                1765                1770

Gly Arg Ser Trp Ser Val Pro Val Ile Arg His Leu Phe Ala Pro
    1775                1780                1785

Leu Lys Glu Tyr Phe Ala Cys Val Ser Ser Gly Asn Ser Asn Ala
    1790                1795                1800

Asn Ser Arg Gly Pro Ser Phe Ser Ser Gly Leu Val Pro Leu Ser
    1805                1810                1815

Leu Arg Gly Ser His Met Gly Pro Met Glu Ile Tyr Lys Thr Val
    1820                1825                1830

Ser Ala Trp Lys Arg Gln Pro Val Arg Val Leu Ser Leu Phe Arg
    1835                1840                1845

Asn Ile Asp Lys Val Leu Lys Ser Leu Gly Phe Leu Glu Ser Gly
    1850                1855                1860

Ser Gly Ser Gly Gly Gly Thr Leu Lys Tyr Val Glu Asp Val Thr
    1865                1870                1875

Asn Val Val Arg Arg Asp Val Glu Lys Trp Gly Pro Phe Asp Leu
```

|  | 1880 |  |  | 1885 |  |  | 1890 |  |  |
| --- | --- | --- | --- | --- | --- | --- | --- | --- | --- |
| Val | Tyr | Gly | Ser | Thr | Gln | Pro | Leu | Gly | Ser | Ser | Cys | Asp | Arg | Cys |
|  | 1895 |  |  | 1900 |  |  | 1905 |  |  |
| Pro | Gly | Trp | Tyr | Met | Phe | Gln | Phe | His | Arg | Ile | Leu | Gln | Tyr | Ala |
|  | 1910 |  |  | 1915 |  |  | 1920 |  |  |
| Leu | Pro | Arg | Gln | Glu | Ser | Gln | Arg | Pro | Phe | Phe | Trp | Ile | Phe | Met |
|  | 1925 |  |  | 1930 |  |  | 1935 |  |  |
| Asp | Asn | Leu | Leu | Leu | Thr | Glu | Asp | Asp | Gln | Glu | Thr | Thr | Thr | Arg |
|  | 1940 |  |  | 1945 |  |  | 1950 |  |  |
| Phe | Leu | Gln | Thr | Glu | Ala | Val | Thr | Leu | Gln | Asp | Val | Arg | Gly | Arg |
|  | 1955 |  |  | 1960 |  |  | 1965 |  |  |
| Asp | Tyr | Gln | Asn | Ala | Met | Arg | Val | Trp | Ser | Asn | Ile | Pro | Gly | Leu |
|  | 1970 |  |  | 1975 |  |  | 1980 |  |  |
| Lys | Ser | Lys | His | Ala | Pro | Leu | Thr | Pro | Lys | Glu | Glu | Tyr | Leu |
|  | 1985 |  |  | 1990 |  |  | 1995 |  |  |
| Gln | Ala | Gln | Val | Arg | Ser | Arg | Ser | Lys | Leu | Asp | Ala | Pro | Lys | Val |
|  | 2000 |  |  | 2005 |  |  | 2010 |  |  |
| Asp | Leu | Leu | Val | Lys | Asn | Cys | Leu | Leu | Pro | Leu | Arg | Glu | Tyr | Phe |
|  | 2015 |  |  | 2020 |  |  | 2025 |  |  |
| Lys | Tyr | Phe | Ser | Gln | Asn | Ser | Leu | Pro | Leu | Ser | Arg | Ala | Asp | Pro |
|  | 2030 |  |  | 2035 |  |  | 2040 |  |  |
| Lys | Lys | Lys | Arg | Lys | Val | Gly | Ser | Gly | Ala | Thr | Asn | Phe | Ser | Leu |
|  | 2045 |  |  | 2050 |  |  | 2055 |  |  |
| Leu | Lys | Gln | Ala | Gly | Asp | Val | Glu | Glu | Asn | Pro | Gly | Pro | Ser | Glu |
|  | 2060 |  |  | 2065 |  |  | 2070 |  |  |
| Leu | Ile | Lys | Glu | Asn | Met | His | Met | Lys | Leu | Tyr | Met | Glu | Gly | Thr |
|  | 2075 |  |  | 2080 |  |  | 2085 |  |  |
| Val | Asp | Asn | His | His | Phe | Lys | Cys | Thr | Ser | Glu | Gly | Glu | Gly | Lys |
|  | 2090 |  |  | 2095 |  |  | 2100 |  |  |
| Pro | Tyr | Glu | Gly | Thr | Gln | Thr | Met | Arg | Ile | Lys | Val | Val | Glu | Gly |
|  | 2105 |  |  | 2110 |  |  | 2115 |  |  |
| Gly | Pro | Leu | Pro | Phe | Ala | Phe | Asp | Ile | Leu | Ala | Thr | Ser | Phe | Leu |
|  | 2120 |  |  | 2125 |  |  | 2130 |  |  |
| Tyr | Gly | Ser | Lys | Thr | Phe | Ile | Asn | His | Thr | Gln | Gly | Ile | Pro | Asp |
|  | 2135 |  |  | 2140 |  |  | 2145 |  |  |
| Phe | Phe | Lys | Gln | Ser | Phe | Pro | Glu | Gly | Phe | Thr | Trp | Glu | Arg | Val |
|  | 2150 |  |  | 2155 |  |  | 2160 |  |  |
| Thr | Thr | Tyr | Glu | Asp | Gly | Gly | Val | Leu | Thr | Ala | Thr | Gln | Asp | Thr |
|  | 2165 |  |  | 2170 |  |  | 2175 |  |  |
| Ser | Leu | Gln | Asp | Gly | Cys | Leu | Ile | Tyr | Asn | Val | Lys | Ile | Arg | Gly |
|  | 2180 |  |  | 2185 |  |  | 2190 |  |  |
| Val | Asn | Phe | Thr | Ser | Asn | Gly | Pro | Val | Met | Gln | Lys | Lys | Thr | Leu |
|  | 2195 |  |  | 2200 |  |  | 2205 |  |  |
| Gly | Trp | Glu | Ala | Phe | Thr | Glu | Thr | Leu | Tyr | Pro | Ala | Asp | Gly | Gly |
|  | 2210 |  |  | 2215 |  |  | 2220 |  |  |
| Leu | Glu | Gly | Arg | Asn | Asp | Met | Ala | Leu | Lys | Leu | Val | Gly | Gly | Ser |
|  | 2225 |  |  | 2230 |  |  | 2235 |  |  |
| His | Leu | Ile | Ala | Asn | Ile | Lys | Thr | Thr | Tyr | Arg | Ser | Lys | Lys | Pro |
|  | 2240 |  |  | 2245 |  |  | 2250 |  |  |
| Ala | Lys | Asn | Leu | Lys | Met | Pro | Gly | Val | Tyr | Tyr | Val | Asp | Tyr | Arg |
|  | 2255 |  |  | 2260 |  |  | 2265 |  |  |
| Leu | Glu | Arg | Ile | Lys | Glu | Ala | Asn | Asn | Glu | Thr | Tyr | Val | Glu | Gln |
|  | 2270 |  |  | 2275 |  |  | 2280 |  |  |

His Glu Val Ala Val Ala Arg Tyr Cys Asp Leu Pro Ser Lys Leu
      2285                2290                2295

Gly His Lys Leu Asn
      2300

<210> SEQ ID NO 8
<211> LENGTH: 2325
<212> TYPE: PRT
<213> ORGANISM: Artificial sequence
<220> FEATURE:
<223> OTHER INFORMATION: Synthetic polypeptide

<400> SEQUENCE: 8

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

-continued

```
Pro Asn Phe Lys Ser Asn Phe Asp Leu Ala Glu Asp Ala Lys Leu Gln
        340                 345                 350

Leu Ser Lys Asp Thr Tyr Asp Asp Leu Asp Asn Leu Leu Ala Gln
        355                 360                 365

Ile Gly Asp Gln Tyr Ala Asp Leu Phe Leu Ala Ala Lys Asn Leu Ser
370                 375                 380

Asp Ala Ile Leu Leu Ser Asp Ile Leu Arg Val Asn Thr Glu Ile Thr
385                 390                 395                 400

Lys Ala Pro Leu Ser Ala Ser Met Ile Lys Arg Tyr Asp Glu His His
                405                 410                 415

Gln Asp Leu Thr Leu Leu Lys Ala Leu Val Arg Gln Gln Leu Pro Glu
            420                 425                 430

Lys Tyr Lys Glu Ile Phe Phe Asp Gln Ser Lys Asn Gly Tyr Ala Gly
        435                 440                 445

Tyr Ile Asp Gly Gly Ala Ser Gln Glu Glu Phe Tyr Lys Phe Ile Lys
450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
                485                 490                 495

Ile Pro His Gln Ile His Leu Gly Glu Leu His Ala Ile Leu Arg Arg
            500                 505                 510

Gln Glu Asp Phe Tyr Pro Phe Leu Lys Asp Asn Arg Glu Lys Ile Glu
        515                 520                 525

Lys Ile Leu Thr Phe Arg Ile Pro Tyr Tyr Val Gly Pro Leu Ala Arg
530                 535                 540

Gly Asn Ser Arg Phe Ala Trp Met Thr Arg Lys Ser Glu Glu Thr Ile
545                 550                 555                 560

Thr Pro Trp Asn Phe Glu Glu Val Val Asp Lys Gly Ala Ser Ala Gln
                565                 570                 575

Ser Phe Ile Glu Arg Met Thr Asn Phe Asp Lys Asn Leu Pro Asn Glu
            580                 585                 590

Lys Val Leu Pro Lys His Ser Leu Leu Tyr Glu Tyr Phe Thr Val Tyr
        595                 600                 605

Asn Glu Leu Thr Lys Val Lys Tyr Val Thr Glu Gly Met Arg Lys Pro
610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
                645                 650                 655

Lys Lys Ile Glu Cys Phe Asp Ser Val Glu Ile Ser Gly Val Glu Asp
            660                 665                 670

Arg Phe Asn Ala Ser Leu Gly Thr Tyr His Asp Leu Leu Lys Ile Ile
        675                 680                 685

Lys Asp Lys Asp Phe Leu Asp Asn Glu Glu Asn Glu Asp Ile Leu Glu
690                 695                 700

Asp Ile Val Leu Thr Leu Thr Leu Phe Glu Asp Arg Glu Met Ile Glu
705                 710                 715                 720

Glu Arg Leu Lys Thr Tyr Ala His Leu Phe Asp Asp Lys Val Met Lys
                725                 730                 735

Gln Leu Lys Arg Arg Arg Tyr Thr Gly Trp Gly Arg Leu Ser Arg Lys
            740                 745                 750
```

```
Leu Ile Asn Gly Ile Arg Asp Lys Gln Ser Gly Lys Thr Ile Leu Asp
            755                 760                 765
Phe Leu Lys Ser Asp Gly Phe Ala Asn Arg Asn Phe Met Gln Leu Ile
    770                 775                 780
His Asp Asp Ser Leu Thr Phe Lys Glu Asp Ile Gln Lys Ala Gln Val
785                 790                 795                 800
Ser Gly Gln Gly Asp Ser Leu His Glu His Ile Ala Asn Leu Ala Gly
                805                 810                 815
Ser Pro Ala Ile Lys Lys Gly Ile Leu Gln Thr Val Lys Val Val Asp
            820                 825                 830
Glu Leu Val Lys Val Met Gly Arg His Lys Pro Glu Asn Ile Val Ile
    835                 840                 845
Glu Met Ala Arg Glu Asn Gln Thr Thr Gln Lys Gly Gln Lys Asn Ser
850                 855                 860
Arg Glu Arg Met Lys Arg Ile Glu Glu Gly Ile Lys Glu Leu Gly Ser
865                 870                 875                 880
Gln Ile Leu Lys Glu His Pro Val Glu Asn Thr Gln Leu Gln Asn Glu
                885                 890                 895
Lys Leu Tyr Leu Tyr Tyr Leu Gln Asn Gly Arg Asp Met Tyr Val Asp
            900                 905                 910
Gln Glu Leu Asp Ile Asn Arg Leu Ser Asp Tyr Asp Val Asp Ala Ile
    915                 920                 925
Val Pro Gln Ser Phe Leu Lys Asp Asp Ser Ile Asp Asn Lys Val Leu
            930                 935                 940
Thr Arg Ser Asp Lys Asn Arg Gly Lys Ser Asp Asn Val Pro Ser Glu
945                 950                 955                 960
Glu Val Val Lys Lys Met Lys Asn Tyr Trp Arg Gln Leu Leu Asn Ala
                965                 970                 975
Lys Leu Ile Thr Gln Arg Lys Phe Asp Asn Leu Thr Lys Ala Glu Arg
            980                 985                 990
Gly Gly Leu Ser Glu Leu Asp Lys Ala Gly Phe Ile Lys Arg Gln Leu
        995                 1000                1005
Val Glu Thr Arg Gln Ile Thr Lys His Val Ala Gln Ile Leu Asp
    1010                1015                1020
Ser Arg Met Asn Thr Lys Tyr Asp Glu Asn Asp Lys Leu Ile Arg
    1025                1030                1035
Glu Val Lys Val Ile Thr Leu Lys Ser Lys Leu Val Ser Asp Phe
    1040                1045                1050
Arg Lys Asp Phe Gln Phe Tyr Lys Val Arg Glu Ile Asn Asn Tyr
    1055                1060                1065
His His Ala His Asp Ala Tyr Leu Asn Ala Val Val Gly Thr Ala
    1070                1075                1080
Leu Ile Lys Lys Tyr Pro Lys Leu Glu Ser Glu Phe Val Tyr Gly
    1085                1090                1095
Asp Tyr Lys Val Tyr Asp Val Arg Lys Met Ile Ala Lys Ser Glu
    1100                1105                1110
Gln Glu Ile Gly Lys Ala Thr Ala Lys Tyr Phe Phe Tyr Ser Asn
    1115                1120                1125
Ile Met Asn Phe Phe Lys Thr Glu Ile Thr Leu Ala Asn Gly Glu
    1130                1135                1140
Ile Arg Lys Arg Pro Leu Ile Glu Thr Asn Gly Glu Thr Gly Glu
    1145                1150                1155
Ile Val Trp Asp Lys Gly Arg Asp Phe Ala Thr Val Arg Lys Val
```

-continued

```
              1160                1165                1170
Leu Ser  Met Pro Gln Val Asn Ile Val Lys Lys Thr Glu Val Gln
     1175                1180                1185

Thr Gly  Gly Phe Ser Lys Glu Ser Ile Leu Pro Lys Arg Asn Ser
     1190                1195                1200

Asp Lys  Leu Ile Ala Arg Lys Lys Asp Trp Asp Pro Lys Lys Tyr
     1205                1210                1215

Gly Gly  Phe Asp Ser Pro Thr Val Ala Tyr Ser Val Leu Val Val
     1220                1225                1230

Ala Lys  Val Glu Lys Gly Lys Ser Lys Lys Leu Lys Ser Val Lys
     1235                1240                1245

Glu Leu  Leu Gly Ile Thr Ile Met Glu Arg Ser Ser Phe Glu Lys
     1250                1255                1260

Asn Pro  Ile Asp Phe Leu Glu Ala Lys Gly Tyr Lys Glu Val Lys
     1265                1270                1275

Lys Asp  Leu Ile Ile Lys Leu Pro Lys Tyr Ser Leu Phe Glu Leu
     1280                1285                1290

Glu Asn  Gly Arg Lys Arg Met Leu Ala Ser Ala Gly Glu Leu Gln
     1295                1300                1305

Lys Gly  Asn Glu Leu Ala Leu Pro Ser Lys Tyr Val Asn Phe Leu
     1310                1315                1320

Tyr Leu  Ala Ser His Tyr Glu Lys Leu Lys Gly Ser Pro Glu Asp
     1325                1330                1335

Asn Glu  Gln Lys Gln Leu Phe Val Glu Gln His Lys His Tyr Leu
     1340                1345                1350

Asp Glu  Ile Ile Glu Gln Ile Ser Glu Phe Ser Lys Arg Val Ile
     1355                1360                1365

Leu Ala  Asp Ala Asn Leu Asp Lys Val Leu Ser Ala Tyr Asn Lys
     1370                1375                1380

His Arg  Asp Lys Pro Ile Arg Glu Gln Ala Glu Asn Ile Ile His
     1385                1390                1395

Leu Phe  Thr Leu Thr Asn Leu Gly Ala Pro Ala Ala Phe Lys Tyr
     1400                1405                1410

Phe Asp  Thr Thr Ile Asp Arg Lys Arg Tyr Thr Ser Thr Lys Glu
     1415                1420                1425

Val Leu  Asp Ala Thr Leu Ile His Gln Ser Ile Thr Gly Leu Tyr
     1430                1435                1440

Glu Thr  Arg Ile Asp Leu Ser Gln Leu Gly Gly Asp Ser Arg Ala
     1445                1450                1455

Asp Tyr  Pro Tyr Asp Val Pro Asp Tyr Ala Ser Gly Ser Pro Lys
     1460                1465                1470

Lys Lys  Arg Lys Val Glu Ala Ser Gly Ser Gly Arg Ala Ser Pro
     1475                1480                1485

Gly Ile  Pro Gly Ser Thr Arg Asn His Asp Gln Glu Phe Asp Pro
     1490                1495                1500

Pro Lys  Val Tyr Pro Pro Val Pro Ala Glu Lys Arg Lys Pro Ile
     1505                1510                1515

Arg Val  Leu Ser Leu Phe Asp Gly Ile Ala Thr Gly Leu Leu Val
     1520                1525                1530

Leu Lys  Asp Leu Gly Ile Gln Val Asp Arg Tyr Ile Ala Ser Glu
     1535                1540                1545

Val Cys  Glu Asp Ser Ile Thr Val Gly Met Val Arg His Gln Gly
     1550                1555                1560
```

-continued

```
Lys Ile Met Tyr Val Gly Asp Val Arg Ser Val Thr Gln Lys His
1565                1570                1575

Ile Gln Glu Trp Gly Pro Phe Asp Leu Val Ile Gly Gly Ser Pro
1580                1585                1590

Cys Asn Asp Leu Ser Ile Val Asn Pro Ala Arg Lys Gly Leu Tyr
1595                1600                1605

Glu Gly Thr Gly Arg Leu Phe Phe Glu Phe Tyr Arg Leu Leu His
1610                1615                1620

Asp Ala Arg Pro Lys Glu Gly Asp Arg Pro Phe Phe Trp Leu
1625                1630                1635

Phe Glu Asn Val Val Ala Met Gly Val Ser Asp Lys Arg Asp Ile
1640                1645                1650

Ser Arg Phe Leu Glu Ser Asn Pro Val Met Ile Asp Ala Lys Glu
1655                1660                1665

Val Ser Ala Ala His Arg Ala Arg Tyr Phe Trp Gly Asn Leu Pro
1670                1675                1680

Gly Met Asn Arg Pro Leu Ala Ser Thr Val Asn Asp Lys Leu Glu
1685                1690                1695

Leu Gln Glu Cys Leu Glu His Gly Arg Ile Ala Lys Phe Ser Lys
1700                1705                1710

Val Arg Thr Ile Thr Thr Arg Ser Asn Ser Ile Lys Gln Gly Lys
1715                1720                1725

Asp Gln His Phe Pro Val Phe Met Asn Glu Lys Glu Asp Ile Leu
1730                1735                1740

Trp Cys Thr Glu Met Glu Arg Val Phe Gly Phe Pro Val His Tyr
1745                1750                1755

Thr Asp Val Ser Asn Met Ser Arg Leu Ala Arg Gln Arg Leu Leu
1760                1765                1770

Gly Arg Ser Trp Ser Val Pro Val Ile Arg His Leu Phe Ala Pro
1775                1780                1785

Leu Lys Glu Tyr Phe Ala Cys Val Ser Ser Gly Asn Ser Asn Ala
1790                1795                1800

Asn Ser Arg Gly Pro Ser Phe Ser Ser Gly Leu Val Pro Leu Ser
1805                1810                1815

Leu Arg Gly Ser His Met Gly Pro Met Glu Ile Tyr Lys Thr Val
1820                1825                1830

Ser Ala Trp Lys Arg Gln Pro Val Arg Val Leu Ser Leu Phe Arg
1835                1840                1845

Asn Ile Asp Lys Val Leu Lys Ser Leu Gly Phe Leu Glu Ser Gly
1850                1855                1860

Ser Gly Ser Gly Gly Gly Thr Leu Lys Tyr Val Glu Asp Val Thr
1865                1870                1875

Asn Val Val Arg Arg Asp Val Glu Lys Trp Gly Pro Phe Asp Leu
1880                1885                1890

Val Tyr Gly Ser Thr Gln Pro Leu Gly Ser Ser Cys Asp Arg Cys
1895                1900                1905

Pro Gly Trp Tyr Met Phe Gln Phe His Arg Ile Leu Gln Tyr Ala
1910                1915                1920

Leu Pro Arg Gln Glu Ser Gln Arg Pro Phe Phe Trp Ile Phe Met
1925                1930                1935

Asp Asn Leu Leu Leu Thr Glu Asp Asp Gln Glu Thr Thr Thr Arg
1940                1945                1950
```

Phe Leu Gln Thr Glu Ala Val Thr Leu Gln Asp Val Arg Gly Arg
1955                1960                1965

Asp Tyr Gln Asn Ala Met Arg Val Trp Ser Asn Ile Pro Gly Leu
1970                1975                1980

Lys Ser Lys His Ala Pro Leu Thr Pro Lys Glu Glu Tyr Leu
1985                1990                1995

Gln Ala Gln Val Arg Ser Arg Ser Lys Leu Asp Ala Pro Lys Val
2000                2005                2010

Asp Leu Leu Val Lys Asn Cys Leu Leu Pro Leu Arg Glu Tyr Phe
2015                2020                2025

Lys Tyr Phe Ser Gln Asn Ser Leu Pro Leu Ser Arg Ala Asp Pro
2030                2035                2040

Lys Lys Lys Arg Lys Val Gly Ser Gly Ala Thr Asn Phe Ser Leu
2045                2050                2055

Leu Lys Gln Ala Gly Asp Val Glu Glu Asn Pro Gly Pro Gly Ser
2060                2065                2070

Gly Ala Thr Asn Phe Ser Leu Leu Lys Gln Ala Gly Asp Val Glu
2075                2080                2085

Glu Asn Pro Gly Pro Ser Glu Leu Ile Lys Glu Asn Met His Met
2090                2095                2100

Lys Leu Tyr Met Glu Gly Thr Val Asp Asn His His Phe Lys Cys
2105                2110                2115

Thr Ser Glu Gly Glu Gly Lys Pro Tyr Glu Gly Thr Gln Thr Met
2120                2125                2130

Arg Ile Lys Val Val Glu Gly Gly Pro Leu Pro Phe Ala Phe Asp
2135                2140                2145

Ile Leu Ala Thr Ser Phe Leu Tyr Gly Ser Lys Thr Phe Ile Asn
2150                2155                2160

His Thr Gln Gly Ile Pro Asp Phe Phe Lys Gln Ser Phe Pro Glu
2165                2170                2175

Gly Phe Thr Trp Glu Arg Val Thr Thr Tyr Glu Asp Gly Gly Val
2180                2185                2190

Leu Thr Ala Thr Gln Asp Thr Ser Leu Gln Asp Gly Cys Leu Ile
2195                2200                2205

Tyr Asn Val Lys Ile Arg Gly Val Asn Phe Thr Ser Asn Gly Pro
2210                2215                2220

Val Met Gln Lys Lys Thr Leu Gly Trp Glu Ala Phe Thr Glu Thr
2225                2230                2235

Leu Tyr Pro Ala Asp Gly Gly Leu Glu Gly Arg Asn Asp Met Ala
2240                2245                2250

Leu Lys Leu Val Gly Gly Ser His Leu Ile Ala Asn Ile Lys Thr
2255                2260                2265

Thr Tyr Arg Ser Lys Lys Pro Ala Lys Asn Leu Lys Met Pro Gly
2270                2275                2280

Val Tyr Tyr Val Asp Tyr Arg Leu Glu Arg Ile Lys Glu Ala Asn
2285                2290                2295

Asn Glu Thr Tyr Val Glu Gln His Glu Val Ala Val Ala Arg Tyr
2300                2305                2310

Cys Asp Leu Pro Ser Lys Leu Gly His Lys Leu Asn
2315                2320                2325

<210> SEQ ID NO 9
<211> LENGTH: 2367
<212> TYPE: PRT

<213> ORGANISM: Artificial sequence
<220> FEATURE:
<223> OTHER INFORMATION: Synthetic polypeptide

<400> SEQUENCE: 9

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys
    370                 375                 380

Lys Asn Gly Leu Phe Gly Asn Leu Ile Ala Leu Ser Leu Gly Leu Thr
```

```
            385                 390                 395                 400
        Pro Asn Phe Lys Ser Asn Phe Asp Leu Ala Glu Asp Ala Lys Leu Gln
                        405                 410                 415
        Leu Ser Lys Asp Thr Tyr Asp Asp Leu Asp Asn Leu Leu Ala Gln
                        420                 425                 430
        Ile Gly Asp Gln Tyr Ala Asp Leu Phe Leu Ala Ala Lys Asn Leu Ser
                        435                 440                 445
        Asp Ala Ile Leu Leu Ser Asp Ile Leu Arg Val Asn Thr Glu Ile Thr
                        450                 455                 460
        Lys Ala Pro Leu Ser Ala Ser Met Ile Lys Arg Tyr Asp Glu His His
        465                 470                 475                 480
        Gln Asp Leu Thr Leu Leu Lys Ala Leu Val Arg Gln Gln Leu Pro Glu
                        485                 490                 495
        Lys Tyr Lys Glu Ile Phe Phe Asp Gln Ser Lys Asn Gly Tyr Ala Gly
                        500                 505                 510
        Tyr Ile Asp Gly Gly Ala Ser Gln Glu Glu Phe Tyr Lys Phe Ile Lys
                        515                 520                 525
        Pro Ile Leu Glu Lys Met Asp Gly Thr Glu Glu Leu Leu Val Lys Leu
                        530                 535                 540
        Asn Arg Glu Asp Leu Leu Arg Lys Gln Arg Thr Phe Asp Asn Gly Ser
        545                 550                 555                 560
        Ile Pro His Gln Ile His Leu Gly Glu Leu His Ala Ile Leu Arg Arg
                        565                 570                 575
        Gln Glu Asp Phe Tyr Pro Phe Leu Lys Asp Asn Arg Glu Lys Ile Glu
                        580                 585                 590
        Lys Ile Leu Thr Phe Arg Ile Pro Tyr Tyr Val Gly Pro Leu Ala Arg
                        595                 600                 605
        Gly Asn Ser Arg Phe Ala Trp Met Thr Arg Lys Ser Glu Glu Thr Ile
                        610                 615                 620
        Thr Pro Trp Asn Phe Glu Glu Val Val Asp Lys Gly Ala Ser Ala Gln
        625                 630                 635                 640
        Ser Phe Ile Glu Arg Met Thr Asn Phe Asp Lys Asn Leu Pro Asn Glu
                        645                 650                 655
        Lys Val Leu Pro Lys His Ser Leu Leu Tyr Glu Tyr Phe Thr Val Tyr
                        660                 665                 670
        Asn Glu Leu Thr Lys Val Lys Tyr Val Thr Glu Gly Met Arg Lys Pro
                        675                 680                 685
        Ala Phe Leu Ser Gly Glu Gln Lys Lys Ala Ile Val Asp Leu Leu Phe
                        690                 695                 700
        Lys Thr Asn Arg Lys Val Thr Val Lys Gln Leu Lys Glu Asp Tyr Phe
        705                 710                 715                 720
        Lys Lys Ile Glu Cys Phe Asp Ser Val Glu Ile Ser Gly Val Glu Asp
                        725                 730                 735
        Arg Phe Asn Ala Ser Leu Gly Thr Tyr His Asp Leu Leu Lys Ile Ile
                        740                 745                 750
        Lys Asp Lys Asp Phe Leu Asp Asn Glu Glu Asn Glu Asp Ile Leu Glu
                        755                 760                 765
        Asp Ile Val Leu Thr Leu Thr Leu Phe Glu Asp Arg Glu Met Ile Glu
                        770                 775                 780
        Glu Arg Leu Lys Thr Tyr Ala His Leu Phe Asp Asp Lys Val Met Lys
        785                 790                 795                 800
        Gln Leu Lys Arg Arg Arg Tyr Thr Gly Trp Gly Arg Leu Ser Arg Lys
                        805                 810                 815
```

-continued

Leu Ile Asn Gly Ile Arg Asp Lys Gln Ser Gly Lys Thr Ile Leu Asp
            820                 825                 830

Phe Leu Lys Ser Asp Gly Phe Ala Asn Arg Asn Phe Met Gln Leu Ile
            835                 840                 845

His Asp Asp Ser Leu Thr Phe Lys Glu Asp Ile Gln Lys Ala Gln Val
850                 855                 860

Ser Gly Gln Gly Asp Ser Leu His Glu His Ile Ala Asn Leu Ala Gly
865                 870                 875                 880

Ser Pro Ala Ile Lys Lys Gly Ile Leu Gln Thr Val Lys Val Val Asp
                885                 890                 895

Glu Leu Val Lys Val Met Gly Arg His Lys Pro Glu Asn Ile Val Ile
            900                 905                 910

Glu Met Ala Arg Glu Asn Gln Thr Thr Gln Lys Gly Gln Lys Asn Ser
            915                 920                 925

Arg Glu Arg Met Lys Arg Ile Glu Glu Gly Ile Lys Glu Leu Gly Ser
            930                 935                 940

Gln Ile Leu Lys Glu His Pro Val Glu Asn Thr Gln Leu Gln Asn Glu
945                 950                 955                 960

Lys Leu Tyr Leu Tyr Tyr Leu Gln Asn Gly Arg Asp Met Tyr Val Asp
                965                 970                 975

Gln Glu Leu Asp Ile Asn Arg Leu Ser Asp Tyr Asp Val Asp Ala Ile
            980                 985                 990

Val Pro Gln Ser Phe Leu Lys Asp Asp Ser Ile Asp Asn Lys Val Leu
            995                 1000                1005

Thr Arg Ser Asp Lys Asn Arg Gly Lys Ser Asp Asn Val Pro Ser
    1010                1015                1020

Glu Glu Val Val Lys Lys Met Lys Asn Tyr Trp Arg Gln Leu Leu
    1025                1030                1035

Asn Ala Lys Leu Ile Thr Gln Arg Lys Phe Asp Asn Leu Thr Lys
    1040                1045                1050

Ala Glu Arg Gly Gly Leu Ser Glu Leu Asp Lys Ala Gly Phe Ile
    1055                1060                1065

Lys Arg Gln Leu Val Glu Thr Arg Gln Ile Thr Lys His Val Ala
    1070                1075                1080

Gln Ile Leu Asp Ser Arg Met Asn Thr Lys Tyr Asp Glu Asn Asp
    1085                1090                1095

Lys Leu Ile Arg Glu Val Lys Val Ile Thr Leu Lys Ser Lys Leu
    1100                1105                1110

Val Ser Asp Phe Arg Lys Asp Phe Gln Phe Tyr Lys Val Arg Glu
    1115                1120                1125

Ile Asn Asn Tyr His His Ala His Asp Ala Tyr Leu Asn Ala Val
    1130                1135                1140

Val Gly Thr Ala Leu Ile Lys Lys Tyr Pro Lys Leu Glu Ser Glu
    1145                1150                1155

Phe Val Tyr Gly Asp Tyr Lys Val Tyr Asp Val Arg Lys Met Ile
    1160                1165                1170

Ala Lys Ser Glu Gln Glu Ile Gly Lys Ala Thr Ala Lys Tyr Phe
    1175                1180                1185

Phe Tyr Ser Asn Ile Met Asn Phe Phe Lys Thr Glu Ile Thr Leu
    1190                1195                1200

Ala Asn Gly Glu Ile Arg Lys Arg Pro Leu Ile Glu Thr Asn Gly
    1205                1210                1215

Glu Thr Gly Glu Ile Val Trp Asp Lys Gly Arg Asp Phe Ala Thr
1220                    1225                1230

Val Arg Lys Val Leu Ser Met Pro Gln Val Asn Ile Val Lys Lys
1235                    1240                1245

Thr Glu Val Gln Thr Gly Gly Phe Ser Lys Glu Ser Ile Leu Pro
1250                    1255                1260

Lys Arg Asn Ser Asp Lys Leu Ile Ala Arg Lys Lys Asp Trp Asp
1265                    1270                1275

Pro Lys Lys Tyr Gly Gly Phe Asp Ser Pro Thr Val Ala Tyr Ser
1280                    1285                1290

Val Leu Val Val Ala Lys Val Glu Lys Gly Lys Ser Lys Lys Leu
1295                    1300                1305

Lys Ser Val Lys Glu Leu Leu Gly Ile Thr Ile Met Glu Arg Ser
1310                    1315                1320

Ser Phe Glu Lys Asn Pro Ile Asp Phe Leu Glu Ala Lys Gly Tyr
1325                    1330                1335

Lys Glu Val Lys Lys Asp Leu Ile Ile Lys Leu Pro Lys Tyr Ser
1340                    1345                1350

Leu Phe Glu Leu Glu Asn Gly Arg Lys Arg Met Leu Ala Ser Ala
1355                    1360                1365

Gly Glu Leu Gln Lys Gly Asn Glu Leu Ala Leu Pro Ser Lys Tyr
1370                    1375                1380

Val Asn Phe Leu Tyr Leu Ala Ser His Tyr Glu Lys Leu Lys Gly
1385                    1390                1395

Ser Pro Glu Asp Asn Glu Gln Lys Gln Leu Phe Val Glu Gln His
1400                    1405                1410

Lys His Tyr Leu Asp Glu Ile Ile Glu Gln Ile Ser Glu Phe Ser
1415                    1420                1425

Lys Arg Val Ile Leu Ala Asp Ala Asn Leu Asp Lys Val Leu Ser
1430                    1435                1440

Ala Tyr Asn Lys His Arg Asp Lys Pro Ile Arg Glu Gln Ala Glu
1445                    1450                1455

Asn Ile Ile His Leu Phe Thr Leu Thr Asn Leu Gly Ala Pro Ala
1460                    1465                1470

Ala Phe Lys Tyr Phe Asp Thr Thr Ile Asp Arg Lys Arg Tyr Thr
1475                    1480                1485

Ser Thr Lys Glu Val Leu Asp Ala Thr Leu Ile His Gln Ser Ile
1490                    1495                1500

Thr Gly Leu Tyr Glu Thr Arg Ile Asp Leu Ser Gln Leu Gly Gly
1505                    1510                1515

Asp Ser Arg Ala Asp Tyr Pro Tyr Asp Val Pro Asp Tyr Ala Ser
1520                    1525                1530

Gly Ser Pro Lys Lys Lys Arg Lys Val Glu Ala Ser Gly Ser Gly
1535                    1540                1545

Arg Ala Ser Pro Gly Ile Pro Gly Ser Thr Arg Asn His Asp Gln
1550                    1555                1560

Glu Phe Asp Pro Pro Lys Val Tyr Pro Pro Val Pro Ala Glu Lys
1565                    1570                1575

Arg Lys Pro Ile Arg Val Leu Ser Leu Phe Asp Gly Ile Ala Thr
1580                    1585                1590

Gly Leu Leu Val Leu Lys Asp Leu Gly Ile Gln Val Asp Arg Tyr
1595                    1600                1605

Ile Ala Ser Glu Val Cys Glu Asp Ser Ile Thr Val Gly Met Val

```
            1610                1615                1620

Arg His Gln Gly Lys Ile Met Tyr Val Gly Asp Val Arg Ser Val
    1625                1630                1635

Thr Gln Lys His Ile Gln Glu Trp Gly Pro Phe Asp Leu Val Ile
    1640                1645                1650

Gly Gly Ser Pro Cys Asn Asp Leu Ser Ile Val Asn Pro Ala Arg
    1655                1660                1665

Lys Gly Leu Tyr Glu Gly Thr Gly Arg Leu Phe Phe Glu Phe Tyr
    1670                1675                1680

Arg Leu Leu His Asp Ala Arg Pro Lys Glu Gly Asp Asp Arg Pro
    1685                1690                1695

Phe Phe Trp Leu Phe Glu Asn Val Val Ala Met Gly Val Ser Asp
    1700                1705                1710

Lys Arg Asp Ile Ser Arg Phe Leu Glu Ser Asn Pro Val Met Ile
    1715                1720                1725

Asp Ala Lys Glu Val Ser Ala Ala His Arg Ala Arg Tyr Phe Trp
    1730                1735                1740

Gly Asn Leu Pro Gly Met Asn Arg Pro Leu Ala Ser Thr Val Asn
    1745                1750                1755

Asp Lys Leu Glu Leu Gln Glu Cys Leu Glu His Gly Arg Ile Ala
    1760                1765                1770

Lys Phe Ser Lys Val Arg Thr Ile Thr Thr Arg Ser Asn Ser Ile
    1775                1780                1785

Lys Gln Gly Lys Asp Gln His Phe Pro Val Phe Met Asn Glu Lys
    1790                1795                1800

Glu Asp Ile Leu Trp Cys Thr Glu Met Glu Arg Val Phe Gly Phe
    1805                1810                1815

Pro Val His Tyr Thr Asp Val Ser Asn Met Ser Arg Leu Ala Arg
    1820                1825                1830

Gln Arg Leu Leu Gly Arg Ser Trp Ser Val Pro Val Ile Arg His
    1835                1840                1845

Leu Phe Ala Pro Leu Lys Glu Tyr Phe Ala Cys Val Ser Ser Gly
    1850                1855                1860

Asn Ser Asn Ala Asn Ser Arg Gly Pro Ser Phe Ser Ser Gly Leu
    1865                1870                1875

Val Pro Leu Ser Leu Arg Gly Ser His Met Gly Pro Met Glu Ile
    1880                1885                1890

Tyr Lys Thr Val Ser Ala Trp Lys Arg Gln Pro Val Arg Val Leu
    1895                1900                1905

Ser Leu Phe Arg Asn Ile Asp Lys Val Leu Lys Ser Leu Gly Phe
    1910                1915                1920

Leu Glu Ser Gly Ser Gly Ser Gly Gly Gly Thr Leu Lys Tyr Val
    1925                1930                1935

Glu Asp Val Thr Asn Val Val Arg Arg Asp Val Glu Lys Trp Gly
    1940                1945                1950

Pro Phe Asp Leu Val Tyr Gly Ser Thr Gln Pro Leu Gly Ser Ser
    1955                1960                1965

Cys Asp Arg Cys Pro Gly Trp Tyr Met Phe Gln Phe His Arg Ile
    1970                1975                1980

Leu Gln Tyr Ala Leu Pro Arg Gln Glu Ser Gln Arg Pro Phe Phe
    1985                1990                1995

Trp Ile Phe Met Asp Asn Leu Leu Leu Thr Glu Asp Asp Gln Glu
    2000                2005                2010
```

Thr Thr Thr Arg Phe Leu Gln Thr Glu Ala Val Thr Leu Gln Asp
    2015                2020                2025

Val Arg Gly Arg Asp Tyr Gln Asn Ala Met Arg Val Trp Ser Asn
    2030                2035                2040

Ile Pro Gly Leu Lys Ser Lys His Ala Pro Leu Thr Pro Lys Glu
    2045                2050                2055

Glu Glu Tyr Leu Gln Ala Gln Val Arg Ser Arg Ser Lys Leu Asp
    2060                2065                2070

Ala Pro Lys Val Asp Leu Val Lys Asn Cys Leu Leu Pro Leu
    2075                2080                2085

Arg Glu Tyr Phe Lys Tyr Phe Ser Gln Asn Ser Leu Pro Leu Ser
    2090                2095                2100

Arg Ala Asp Pro Lys Lys Lys Arg Lys Val Gly Ser Gly Ala Thr
    2105                2110                2115

Asn Phe Ser Leu Leu Lys Gln Ala Gly Asp Val Glu Glu Asn Pro
    2120                2125                2130

Gly Pro Ser Glu Leu Ile Lys Glu Asn Met His Met Lys Leu Tyr
    2135                2140                2145

Met Glu Gly Thr Val Asp Asn His His Phe Lys Cys Thr Ser Glu
    2150                2155                2160

Gly Glu Gly Lys Pro Tyr Glu Gly Thr Gln Thr Met Arg Ile Lys
    2165                2170                2175

Val Val Glu Gly Gly Pro Leu Pro Phe Ala Phe Asp Ile Leu Ala
    2180                2185                2190

Thr Ser Phe Leu Tyr Gly Ser Lys Thr Phe Ile Asn His Thr Gln
    2195                2200                2205

Gly Ile Pro Asp Phe Phe Lys Gln Ser Phe Pro Glu Gly Phe Thr
    2210                2215                2220

Trp Glu Arg Val Thr Thr Tyr Glu Asp Gly Gly Val Leu Thr Ala
    2225                2230                2235

Thr Gln Asp Thr Ser Leu Gln Asp Gly Cys Leu Ile Tyr Asn Val
    2240                2245                2250

Lys Ile Arg Gly Val Asn Phe Thr Ser Asn Gly Pro Val Met Gln
    2255                2260                2265

Lys Lys Thr Leu Gly Trp Glu Ala Phe Thr Glu Thr Leu Tyr Pro
    2270                2275                2280

Ala Asp Gly Gly Leu Glu Gly Arg Asn Asp Met Ala Leu Lys Leu
    2285                2290                2295

Val Gly Gly Ser His Leu Ile Ala Asn Ile Lys Thr Thr Tyr Arg
    2300                2305                2310

Ser Lys Lys Pro Ala Lys Asn Leu Lys Met Pro Gly Val Tyr Tyr
    2315                2320                2325

Val Asp Tyr Arg Leu Glu Arg Ile Lys Glu Ala Asn Asn Glu Thr
    2330                2335                2340

Tyr Val Glu Gln His Glu Val Ala Val Ala Arg Tyr Cys Asp Leu
    2345                2350                2355

Pro Ser Lys Leu Gly His Lys Leu Asn
    2360                2365

<210> SEQ ID NO 10
<211> LENGTH: 2389
<212> TYPE: PRT
<213> ORGANISM: Artificial sequence
<220> FEATURE:

<223> OTHER INFORMATION: Synthetic polypeptide

<400> SEQUENCE: 10

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Pro Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys
    370                 375                 380

Lys Asn Gly Leu Phe Gly Asn Leu Ile Ala Leu Ser Leu Gly Leu Thr
385                 390                 395                 400

```
Pro Asn Phe Lys Ser Asn Phe Asp Leu Ala Glu Asp Ala Lys Leu Gln
                405                 410                 415
Leu Ser Lys Asp Thr Tyr Asp Asp Leu Asp Asn Leu Leu Ala Gln
        420                 425                 430
Ile Gly Asp Gln Tyr Ala Asp Leu Phe Leu Ala Ala Lys Asn Leu Ser
    435                 440                 445
Asp Ala Ile Leu Leu Ser Asp Ile Leu Arg Val Asn Thr Glu Ile Thr
450                 455                 460
Lys Ala Pro Leu Ser Ala Ser Met Ile Lys Arg Tyr Asp Glu His His
465                 470                 475                 480
Gln Asp Leu Thr Leu Leu Lys Ala Leu Val Arg Gln Gln Leu Pro Glu
                485                 490                 495
Lys Tyr Lys Glu Ile Phe Phe Asp Gln Ser Lys Asn Gly Tyr Ala Gly
            500                 505                 510
Tyr Ile Asp Gly Gly Ala Ser Gln Glu Glu Phe Tyr Lys Phe Ile Lys
        515                 520                 525
Pro Ile Leu Glu Lys Met Asp Gly Thr Glu Glu Leu Leu Val Lys Leu
    530                 535                 540
Asn Arg Glu Asp Leu Leu Arg Lys Gln Arg Thr Phe Asp Asn Gly Ser
545                 550                 555                 560
Ile Pro His Gln Ile His Leu Gly Glu Leu His Ala Ile Leu Arg Arg
                565                 570                 575
Gln Glu Asp Phe Tyr Pro Phe Leu Lys Asp Asn Arg Glu Lys Ile Glu
            580                 585                 590
Lys Ile Leu Thr Phe Arg Ile Pro Tyr Tyr Val Gly Pro Leu Ala Arg
        595                 600                 605
Gly Asn Ser Arg Phe Ala Trp Met Thr Arg Lys Ser Glu Glu Thr Ile
    610                 615                 620
Thr Pro Trp Asn Phe Glu Glu Val Val Asp Lys Gly Ala Ser Ala Gln
625                 630                 635                 640
Ser Phe Ile Glu Arg Met Thr Asn Phe Asp Lys Asn Leu Pro Asn Glu
                645                 650                 655
Lys Val Leu Pro Lys His Ser Leu Leu Tyr Glu Tyr Phe Thr Val Tyr
            660                 665                 670
Asn Glu Leu Thr Lys Val Lys Tyr Val Thr Glu Gly Met Arg Lys Pro
        675                 680                 685
Ala Phe Leu Ser Gly Glu Gln Lys Lys Ala Ile Val Asp Leu Leu Phe
    690                 695                 700
Lys Thr Asn Arg Lys Val Thr Val Lys Gln Leu Lys Glu Asp Tyr Phe
705                 710                 715                 720
Lys Lys Ile Glu Cys Phe Asp Ser Val Glu Ile Ser Gly Val Glu Asp
                725                 730                 735
Arg Phe Asn Ala Ser Leu Gly Thr Tyr His Asp Leu Leu Lys Ile Ile
            740                 745                 750
Lys Asp Lys Asp Phe Leu Asp Asn Glu Glu Asn Glu Asp Ile Leu Glu
        755                 760                 765
Asp Ile Val Leu Thr Leu Thr Leu Phe Glu Asp Arg Glu Met Ile Glu
    770                 775                 780
Glu Arg Leu Lys Thr Tyr Ala His Leu Phe Asp Asp Lys Val Met Lys
785                 790                 795                 800
Gln Leu Lys Arg Arg Arg Tyr Thr Gly Trp Gly Arg Leu Ser Arg Lys
                805                 810                 815
Leu Ile Asn Gly Ile Arg Asp Lys Gln Ser Gly Lys Thr Ile Leu Asp
```

-continued

```
                820                 825                 830
Phe Leu Lys Ser Asp Gly Phe Ala Asn Arg Asn Phe Met Gln Leu Ile
                835                 840                 845
His Asp Asp Ser Leu Thr Phe Lys Glu Asp Ile Gln Lys Ala Gln Val
                850                 855                 860
Ser Gly Gln Gly Asp Ser Leu His Glu His Ile Ala Asn Leu Ala Gly
865                 870                 875                 880
Ser Pro Ala Ile Lys Lys Gly Ile Leu Gln Thr Val Lys Val Val Asp
                885                 890                 895
Glu Leu Val Lys Val Met Gly Arg His Lys Pro Glu Asn Ile Val Ile
                900                 905                 910
Glu Met Ala Arg Glu Asn Gln Thr Thr Gln Lys Gly Gln Lys Asn Ser
                915                 920                 925
Arg Glu Arg Met Lys Arg Ile Glu Glu Gly Ile Lys Glu Leu Gly Ser
                930                 935                 940
Gln Ile Leu Lys Glu His Pro Val Glu Asn Thr Gln Leu Gln Asn Glu
945                 950                 955                 960
Lys Leu Tyr Leu Tyr Tyr Leu Gln Asn Gly Arg Asp Met Tyr Val Asp
                965                 970                 975
Gln Glu Leu Asp Ile Asn Arg Leu Ser Asp Tyr Asp Val Asp Ala Ile
                980                 985                 990
Val Pro Gln Ser Phe Leu Lys Asp Asp Ser Ile Asp Asn Lys Val Leu
                995                 1000                1005
Thr Arg Ser Asp Lys Asn Arg Gly Lys Ser Asp Asn Val Pro Ser
                1010                1015                1020
Glu Glu Val Val Lys Lys Met Lys Asn Tyr Trp Arg Gln Leu Leu
                1025                1030                1035
Asn Ala Lys Leu Ile Thr Gln Arg Lys Phe Asp Asn Leu Thr Lys
                1040                1045                1050
Ala Glu Arg Gly Gly Leu Ser Glu Leu Asp Lys Ala Gly Phe Ile
                1055                1060                1065
Lys Arg Gln Leu Val Glu Thr Arg Gln Ile Thr Lys His Val Ala
                1070                1075                1080
Gln Ile Leu Asp Ser Arg Met Asn Thr Lys Tyr Asp Glu Asn Asp
                1085                1090                1095
Lys Leu Ile Arg Glu Val Lys Val Ile Thr Leu Lys Ser Lys Leu
                1100                1105                1110
Val Ser Asp Phe Arg Lys Asp Phe Gln Phe Tyr Lys Val Arg Glu
                1115                1120                1125
Ile Asn Asn Tyr His His Ala His Asp Ala Tyr Leu Asn Ala Val
                1130                1135                1140
Val Gly Thr Ala Leu Ile Lys Lys Tyr Pro Lys Leu Glu Ser Glu
                1145                1150                1155
Phe Val Tyr Gly Asp Tyr Lys Val Tyr Asp Val Arg Lys Met Ile
                1160                1165                1170
Ala Lys Ser Glu Gln Glu Ile Gly Lys Ala Thr Ala Lys Tyr Phe
                1175                1180                1185
Phe Tyr Ser Asn Ile Met Asn Phe Phe Lys Thr Glu Ile Thr Leu
                1190                1195                1200
Ala Asn Gly Glu Ile Arg Lys Arg Pro Leu Ile Glu Thr Asn Gly
                1205                1210                1215
Glu Thr Gly Glu Ile Val Trp Asp Lys Gly Arg Asp Phe Ala Thr
                1220                1225                1230
```

```
Val Arg Lys Val Leu Ser Met Pro Gln Val Asn Ile Val Lys Lys
1235                1240                1245

Thr Glu Val Gln Thr Gly Gly Phe Ser Lys Glu Ser Ile Leu Pro
1250                1255                1260

Lys Arg Asn Ser Asp Lys Leu Ile Ala Arg Lys Lys Asp Trp Asp
1265                1270                1275

Pro Lys Lys Tyr Gly Gly Phe Asp Ser Pro Thr Val Ala Tyr Ser
1280                1285                1290

Val Leu Val Val Ala Lys Val Glu Lys Gly Lys Ser Lys Lys Leu
1295                1300                1305

Lys Ser Val Lys Glu Leu Leu Gly Ile Thr Ile Met Glu Arg Ser
1310                1315                1320

Ser Phe Glu Lys Asn Pro Ile Asp Phe Leu Glu Ala Lys Gly Tyr
1325                1330                1335

Lys Glu Val Lys Lys Asp Leu Ile Ile Lys Leu Pro Lys Tyr Ser
1340                1345                1350

Leu Phe Glu Leu Glu Asn Gly Arg Lys Arg Met Leu Ala Ser Ala
1355                1360                1365

Gly Glu Leu Gln Lys Gly Asn Glu Leu Ala Leu Pro Ser Lys Tyr
1370                1375                1380

Val Asn Phe Leu Tyr Leu Ala Ser His Tyr Glu Lys Leu Lys Gly
1385                1390                1395

Ser Pro Glu Asp Asn Glu Gln Lys Gln Leu Phe Val Glu Gln His
1400                1405                1410

Lys His Tyr Leu Asp Glu Ile Ile Glu Gln Ile Ser Glu Phe Ser
1415                1420                1425

Lys Arg Val Ile Leu Ala Asp Ala Asn Leu Asp Lys Val Leu Ser
1430                1435                1440

Ala Tyr Asn Lys His Arg Asp Lys Pro Ile Arg Glu Gln Ala Glu
1445                1450                1455

Asn Ile Ile His Leu Phe Thr Leu Thr Asn Leu Gly Ala Pro Ala
1460                1465                1470

Ala Phe Lys Tyr Phe Asp Thr Thr Ile Asp Arg Lys Arg Tyr Thr
1475                1480                1485

Ser Thr Lys Glu Val Leu Asp Ala Thr Leu Ile His Gln Ser Ile
1490                1495                1500

Thr Gly Leu Tyr Glu Thr Arg Ile Asp Leu Ser Gln Leu Gly Gly
1505                1510                1515

Asp Ser Arg Ala Asp Tyr Pro Tyr Asp Val Pro Asp Tyr Ala Ser
1520                1525                1530

Gly Ser Pro Lys Lys Lys Arg Lys Val Glu Ala Ser Gly Ser Gly
1535                1540                1545

Arg Ala Ser Pro Gly Ile Pro Gly Ser Thr Arg Asn His Asp Gln
1550                1555                1560

Glu Phe Asp Pro Pro Lys Val Tyr Pro Pro Val Pro Ala Glu Lys
1565                1570                1575

Arg Lys Pro Ile Arg Val Leu Ser Leu Phe Asp Gly Ile Ala Thr
1580                1585                1590

Gly Leu Leu Val Leu Lys Asp Leu Gly Ile Gln Val Asp Arg Tyr
1595                1600                1605

Ile Ala Ser Glu Val Cys Glu Asp Ser Ile Thr Val Gly Met Val
1610                1615                1620
```

-continued

```
Arg His Gln Gly Lys Ile Met Tyr Val Gly Asp Val Arg Ser Val
1625                1630                1635

Thr Gln Lys His Ile Gln Glu Trp Gly Pro Phe Asp Leu Val Ile
1640                1645                1650

Gly Gly Ser Pro Cys Asn Asp Leu Ser Ile Val Asn Pro Ala Arg
1655                1660                1665

Lys Gly Leu Tyr Glu Gly Thr Gly Arg Leu Phe Phe Glu Phe Tyr
1670                1675                1680

Arg Leu Leu His Asp Ala Arg Pro Lys Glu Gly Asp Asp Arg Pro
1685                1690                1695

Phe Phe Trp Leu Phe Glu Asn Val Val Ala Met Gly Val Ser Asp
1700                1705                1710

Lys Arg Asp Ile Ser Arg Phe Leu Glu Ser Asn Pro Val Met Ile
1715                1720                1725

Asp Ala Lys Glu Val Ser Ala Ala His Arg Ala Arg Tyr Phe Trp
1730                1735                1740

Gly Asn Leu Pro Gly Met Asn Arg Pro Leu Ala Ser Thr Val Asn
1745                1750                1755

Asp Lys Leu Glu Leu Gln Glu Cys Leu Glu His Gly Arg Ile Ala
1760                1765                1770

Lys Phe Ser Lys Val Arg Thr Ile Thr Thr Arg Ser Asn Ser Ile
1775                1780                1785

Lys Gln Gly Lys Asp Gln His Phe Pro Val Phe Met Asn Glu Lys
1790                1795                1800

Glu Asp Ile Leu Trp Cys Thr Glu Met Glu Arg Val Phe Gly Phe
1805                1810                1815

Pro Val His Tyr Thr Asp Val Ser Asn Met Ser Arg Leu Ala Arg
1820                1825                1830

Gln Arg Leu Leu Gly Arg Ser Trp Ser Val Pro Val Ile Arg His
1835                1840                1845

Leu Phe Ala Pro Leu Lys Glu Tyr Phe Ala Cys Val Ser Ser Gly
1850                1855                1860

Asn Ser Asn Ala Asn Ser Arg Gly Pro Ser Phe Ser Ser Gly Leu
1865                1870                1875

Val Pro Leu Ser Leu Arg Gly Ser His Met Gly Pro Met Glu Ile
1880                1885                1890

Tyr Lys Thr Val Ser Ala Trp Lys Arg Gln Pro Val Arg Val Leu
1895                1900                1905

Ser Leu Phe Arg Asn Ile Asp Lys Val Leu Lys Ser Leu Gly Phe
1910                1915                1920

Leu Glu Ser Gly Ser Gly Ser Gly Gly Gly Thr Leu Lys Tyr Val
1925                1930                1935

Glu Asp Val Thr Asn Val Val Arg Arg Asp Val Glu Lys Trp Gly
1940                1945                1950

Pro Phe Asp Leu Val Tyr Gly Ser Thr Gln Pro Leu Gly Ser Ser
1955                1960                1965

Cys Asp Arg Cys Pro Gly Trp Tyr Met Phe Gln Phe His Arg Ile
1970                1975                1980

Leu Gln Tyr Ala Leu Pro Arg Gln Glu Ser Gln Arg Pro Phe Phe
1985                1990                1995

Trp Ile Phe Met Asp Asn Leu Leu Leu Thr Glu Asp Asp Gln Glu
2000                2005                2010

Thr Thr Thr Arg Phe Leu Gln Thr Glu Ala Val Thr Leu Gln Asp
```

```
                    2015                2020                2025
Val Arg Gly Arg Asp Tyr Gln Asn Ala Met Arg Val Trp Ser Asn
                2030                2035            2040

Ile Pro Gly Leu Lys Ser Lys His Ala Pro Leu Thr Pro Lys Glu
            2045            2050            2055

Glu Glu Tyr Leu Gln Ala Gln Val Arg Ser Arg Ser Lys Leu Asp
        2060            2065            2070

Ala Pro Lys Val Asp Leu Leu Val Lys Asn Cys Leu Leu Pro Leu
    2075            2080            2085

Arg Glu Tyr Phe Lys Tyr Phe Ser Gln Asn Ser Leu Pro Leu Ser
2090            2095            2100

Arg Ala Asp Pro Lys Lys Lys Arg Lys Val Gly Ser Gly Ala Thr
        2105            2110            2115

Asn Phe Ser Leu Leu Lys Gln Ala Gly Asp Val Glu Glu Asn Pro
    2120            2125            2130

Gly Pro Gly Ser Gly Ala Thr Asn Phe Ser Leu Leu Lys Gln Ala
2135            2140            2145

Gly Asp Val Glu Glu Asn Pro Gly Pro Ser Glu Leu Ile Lys Glu
        2150            2155            2160

Asn Met His Met Lys Leu Tyr Met Glu Gly Thr Val Asp Asn His
    2165            2170            2175

His Phe Lys Cys Thr Ser Glu Gly Glu Gly Lys Pro Tyr Glu Gly
2180            2185            2190

Thr Gln Thr Met Arg Ile Lys Val Val Glu Gly Gly Pro Leu Pro
        2195            2200            2205

Phe Ala Phe Asp Ile Leu Ala Thr Ser Phe Leu Tyr Gly Ser Lys
    2210            2215            2220

Thr Phe Ile Asn His Thr Gln Gly Ile Pro Asp Phe Phe Lys Gln
2225            2230            2235

Ser Phe Pro Glu Gly Phe Thr Trp Glu Arg Val Thr Thr Tyr Glu
        2240            2245            2250

Asp Gly Gly Val Leu Thr Ala Thr Gln Asp Thr Ser Leu Gln Asp
    2255            2260            2265

Gly Cys Leu Ile Tyr Asn Val Lys Ile Arg Gly Val Asn Phe Thr
2270            2275            2280

Ser Asn Gly Pro Val Met Gln Lys Lys Thr Leu Gly Trp Glu Ala
        2285            2290            2295

Phe Thr Glu Thr Leu Tyr Pro Ala Asp Gly Gly Leu Glu Gly Arg
    2300            2305            2310

Asn Asp Met Ala Leu Lys Leu Val Gly Gly Ser His Leu Ile Ala
2315            2320            2325

Asn Ile Lys Thr Thr Tyr Arg Ser Lys Lys Pro Ala Lys Asn Leu
        2330            2335            2340

Lys Met Pro Gly Val Tyr Tyr Val Asp Tyr Arg Leu Glu Arg Ile
    2345            2350            2355

Lys Glu Ala Asn Asn Glu Thr Tyr Val Glu Gln His Glu Val Ala
2360            2365            2370

Val Ala Arg Tyr Cys Asp Leu Pro Ser Lys Leu Gly His Lys Leu
        2375            2380            2385

Asn

<210> SEQ ID NO 11
<211> LENGTH: 2369
```

<212> TYPE: PRT
<213> ORGANISM: Artificial sequence
<220> FEATURE:
<223> OTHER INFORMATION: Synthetic polypeptide

<400> SEQUENCE: 11

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

Pro Asn Phe Lys Ser Asn Phe Asp Leu Ala Glu Asp Ala Lys Leu Gln
            340                 345                 350

Leu Ser Lys Asp Thr Tyr Asp Asp Asp Leu Asp Asn Leu Leu Ala Gln
        355                 360                 365

Ile Gly Asp Gln Tyr Ala Asp Leu Phe Leu Ala Ala Lys Asn Leu Ser
    370                 375                 380
```

```
Asp Ala Ile Leu Leu Ser Asp Ile Leu Arg Val Asn Thr Glu Ile Thr
385                 390                 395                 400

Lys Ala Pro Leu Ser Ala Ser Met Ile Lys Arg Tyr Asp Glu His His
            405                 410                 415

Gln Asp Leu Thr Leu Leu Lys Ala Leu Val Arg Gln Leu Pro Glu
            420                 425                 430

Lys Tyr Lys Glu Ile Phe Phe Asp Gln Ser Lys Asn Gly Tyr Ala Gly
            435                 440                 445

Tyr Ile Asp Gly Gly Ala Ser Gln Glu Glu Phe Tyr Lys Phe Ile Lys
450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
            485                 490                 495

Ile Pro His Gln Ile His Leu Gly Glu Leu His Ala Ile Leu Arg Arg
            500                 505                 510

Gln Glu Asp Phe Tyr Pro Phe Leu Lys Asp Asn Arg Glu Lys Ile Glu
            515                 520                 525

Lys Ile Leu Thr Phe Arg Ile Pro Tyr Tyr Val Gly Pro Leu Ala Arg
            530                 535                 540

Gly Asn Ser Arg Phe Ala Trp Met Thr Arg Lys Ser Glu Glu Thr Ile
545                 550                 555                 560

Thr Pro Trp Asn Phe Glu Val Val Asp Lys Gly Ala Ser Ala Gln
                565                 570                 575

Ser Phe Ile Glu Arg Met Thr Asn Phe Asp Lys Asn Leu Pro Asn Glu
            580                 585                 590

Lys Val Leu Pro Lys His Ser Leu Leu Tyr Glu Tyr Phe Thr Val Tyr
            595                 600                 605

Asn Glu Leu Thr Lys Val Lys Tyr Val Thr Glu Gly Met Arg Lys Pro
            610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
            645                 650                 655

Lys Lys Ile Glu Cys Phe Asp Ser Val Glu Ile Ser Gly Val Glu Asp
            660                 665                 670

Arg Phe Asn Ala Ser Leu Gly Thr Tyr His Asp Leu Leu Lys Ile Ile
            675                 680                 685

Lys Asp Lys Asp Phe Leu Asp Asn Glu Glu Asn Glu Asp Ile Leu Glu
            690                 695                 700

Asp Ile Val Leu Thr Leu Thr Leu Phe Glu Asp Arg Glu Met Ile Glu
705                 710                 715                 720

Glu Arg Leu Lys Thr Tyr Ala His Leu Phe Asp Asp Lys Val Met Lys
            725                 730                 735

Gln Leu Lys Arg Arg Arg Tyr Thr Gly Trp Gly Arg Leu Ser Arg Lys
            740                 745                 750

Leu Ile Asn Gly Ile Arg Asp Lys Gln Ser Gly Lys Thr Ile Leu Asp
            755                 760                 765

Phe Leu Lys Ser Asp Gly Phe Ala Asn Arg Asn Phe Met Gln Leu Ile
            770                 775                 780

His Asp Asp Ser Leu Thr Phe Lys Glu Asp Ile Gln Lys Ala Gln Val
785                 790                 795                 800

Ser Gly Gln Gly Asp Ser Leu His Glu His Ile Ala Asn Leu Ala Gly
```

```
                    805                 810                 815
Ser Pro Ala Ile Lys Lys Gly Ile Leu Gln Thr Val Lys Val Val Asp
                820                 825                 830
Glu Leu Val Lys Val Met Gly Arg His Lys Pro Glu Asn Ile Val Ile
                835                 840                 845
Glu Met Ala Arg Glu Asn Gln Thr Thr Gln Lys Gly Gln Lys Asn Ser
                850                 855                 860
Arg Glu Arg Met Lys Arg Ile Glu Glu Gly Ile Lys Glu Leu Gly Ser
865                 870                 875                 880
Gln Ile Leu Lys Glu His Pro Val Glu Asn Thr Gln Leu Gln Asn Glu
                885                 890                 895
Lys Leu Tyr Leu Tyr Tyr Leu Gln Asn Gly Arg Asp Met Tyr Val Asp
                900                 905                 910
Gln Glu Leu Asp Ile Asn Arg Leu Ser Asp Tyr Asp Val Asp Ala Ile
                915                 920                 925
Val Pro Gln Ser Phe Leu Lys Asp Asp Ser Ile Asp Asn Lys Val Leu
                930                 935                 940
Thr Arg Ser Asp Lys Asn Arg Gly Lys Ser Asp Asn Val Pro Ser Glu
945                 950                 955                 960
Glu Val Val Lys Lys Met Lys Asn Tyr Trp Arg Gln Leu Leu Asn Ala
                965                 970                 975
Lys Leu Ile Thr Gln Arg Lys Phe Asp Asn Leu Thr Lys Ala Glu Arg
                980                 985                 990
Gly Gly Leu Ser Glu Leu Asp Lys Ala Gly Phe Ile Lys Arg Gln Leu
                995                 1000                1005
Val Glu Thr Arg Gln Ile Thr Lys His Val Ala Gln Ile Leu Asp
                1010                1015                1020
Ser Arg Met Asn Thr Lys Tyr Asp Glu Asn Asp Lys Leu Ile Arg
                1025                1030                1035
Glu Val Lys Val Ile Thr Leu Lys Ser Lys Leu Val Ser Asp Phe
                1040                1045                1050
Arg Lys Asp Phe Gln Phe Tyr Lys Val Arg Glu Ile Asn Asn Tyr
                1055                1060                1065
His His Ala His Asp Ala Tyr Leu Asn Ala Val Val Gly Thr Ala
                1070                1075                1080
Leu Ile Lys Lys Tyr Pro Lys Leu Glu Ser Glu Phe Val Tyr Gly
                1085                1090                1095
Asp Tyr Lys Val Tyr Asp Val Arg Lys Met Ile Ala Lys Ser Glu
                1100                1105                1110
Gln Glu Ile Gly Lys Ala Thr Ala Lys Tyr Phe Phe Tyr Ser Asn
                1115                1120                1125
Ile Met Asn Phe Phe Lys Thr Glu Ile Thr Leu Ala Asn Gly Glu
                1130                1135                1140
Ile Arg Lys Arg Pro Leu Ile Glu Thr Asn Gly Glu Thr Gly Glu
                1145                1150                1155
Ile Val Trp Asp Lys Gly Arg Asp Phe Ala Thr Val Arg Lys Val
                1160                1165                1170
Leu Ser Met Pro Gln Val Asn Ile Val Lys Lys Thr Glu Val Gln
                1175                1180                1185
Thr Gly Gly Phe Ser Lys Glu Ser Ile Leu Pro Lys Arg Asn Ser
                1190                1195                1200
Asp Lys Leu Ile Ala Arg Lys Lys Asp Trp Asp Pro Lys Lys Tyr
                1205                1210                1215
```

```
Gly Gly Phe Asp Ser Pro Thr Val Ala Tyr Ser Val Leu Val Val
    1220            1225            1230

Ala Lys Val Glu Lys Gly Lys Ser Lys Lys Leu Lys Ser Val Lys
    1235            1240            1245

Glu Leu Leu Gly Ile Thr Ile Met Glu Arg Ser Ser Phe Glu Lys
    1250            1255            1260

Asn Pro Ile Asp Phe Leu Glu Ala Lys Gly Tyr Lys Glu Val Lys
    1265            1270            1275

Lys Asp Leu Ile Ile Lys Leu Pro Lys Tyr Ser Leu Phe Glu Leu
    1280            1285            1290

Glu Asn Gly Arg Lys Arg Met Leu Ala Ser Ala Gly Glu Leu Gln
    1295            1300            1305

Lys Gly Asn Glu Leu Ala Leu Pro Ser Lys Tyr Val Asn Phe Leu
    1310            1315            1320

Tyr Leu Ala Ser His Tyr Glu Lys Leu Lys Gly Ser Pro Glu Asp
    1325            1330            1335

Asn Glu Gln Lys Gln Leu Phe Val Glu Gln His Lys His Tyr Leu
    1340            1345            1350

Asp Glu Ile Ile Glu Gln Ile Ser Glu Phe Ser Lys Arg Val Ile
    1355            1360            1365

Leu Ala Asp Ala Asn Leu Asp Lys Val Leu Ser Ala Tyr Asn Lys
    1370            1375            1380

His Arg Asp Lys Pro Ile Arg Glu Gln Ala Glu Asn Ile Ile His
    1385            1390            1395

Leu Phe Thr Leu Thr Asn Leu Gly Ala Pro Ala Ala Phe Lys Tyr
    1400            1405            1410

Phe Asp Thr Thr Ile Asp Arg Lys Arg Tyr Thr Ser Thr Lys Glu
    1415            1420            1425

Val Leu Asp Ala Thr Leu Ile His Gln Ser Ile Thr Gly Leu Tyr
    1430            1435            1440

Glu Thr Arg Ile Asp Leu Ser Gln Leu Gly Gly Asp Ser Arg Ala
    1445            1450            1455

Asp Tyr Pro Tyr Asp Val Pro Asp Tyr Ala Ser Gly Ser Pro Lys
    1460            1465            1470

Lys Lys Arg Lys Val Ser Pro Gly Gly Gly Pro Ser Ser Gly Ala
    1475            1480            1485

Pro Pro Pro Ser Gly Gly Ser Pro Ala Gly Ser Pro Thr Ser Thr
    1490            1495            1500

Glu Glu Gly Thr Ser Glu Ser Ala Thr Pro Glu Ser Gly Pro Gly
    1505            1510            1515

Thr Ser Thr Glu Pro Ser Glu Gly Ser Ala Pro Gly Ser Pro Ala
    1520            1525            1530

Gly Ser Pro Thr Ser Thr Glu Glu Gly Thr Ser Thr Glu Pro Ser
    1535            1540            1545

Glu Gly Ser Ala Pro Gly Thr Ser Thr Glu Pro Ser Glu Asn His
    1550            1555            1560

Asp Gln Glu Phe Asp Pro Pro Lys Val Tyr Pro Pro Val Pro Ala
    1565            1570            1575

Glu Lys Arg Lys Pro Ile Arg Val Leu Ser Leu Phe Asp Gly Ile
    1580            1585            1590

Ala Thr Gly Leu Leu Val Leu Lys Asp Leu Gly Ile Gln Val Asp
    1595            1600            1605
```

-continued

```
Arg Tyr Ile Ala Ser Glu Val Cys Glu Asp Ser Ile Thr Val Gly
    1610                1615                1620

Met Val Arg His Gln Gly Lys Ile Met Tyr Val Gly Asp Val Arg
    1625                1630                1635

Ser Val Thr Gln Lys His Ile Gln Glu Trp Gly Pro Phe Asp Leu
    1640                1645                1650

Val Ile Gly Gly Ser Pro Cys Asn Asp Leu Ser Ile Val Asn Pro
    1655                1660                1665

Ala Arg Lys Gly Leu Tyr Glu Gly Thr Gly Arg Leu Phe Phe Glu
    1670                1675                1680

Phe Tyr Arg Leu Leu His Asp Ala Arg Pro Lys Glu Gly Asp Asp
    1685                1690                1695

Arg Pro Phe Phe Trp Leu Phe Glu Asn Val Val Ala Met Gly Val
    1700                1705                1710

Ser Asp Lys Arg Asp Ile Ser Arg Phe Leu Glu Ser Asn Pro Val
    1715                1720                1725

Met Ile Asp Ala Lys Glu Val Ser Ala Ala His Arg Ala Arg Tyr
    1730                1735                1740

Phe Trp Gly Asn Leu Pro Gly Met Asn Arg Pro Leu Ala Ser Thr
    1745                1750                1755

Val Asn Asp Lys Leu Glu Leu Gln Glu Cys Leu Glu His Gly Arg
    1760                1765                1770

Ile Ala Lys Phe Ser Lys Val Arg Thr Ile Thr Thr Arg Ser Asn
    1775                1780                1785

Ser Ile Lys Gln Gly Lys Asp Gln His Phe Pro Val Phe Met Asn
    1790                1795                1800

Glu Lys Glu Asp Ile Leu Trp Cys Thr Glu Met Glu Arg Val Phe
    1805                1810                1815

Gly Phe Pro Val His Tyr Thr Asp Val Ser Asn Met Ser Arg Leu
    1820                1825                1830

Ala Arg Gln Arg Leu Leu Gly Arg Ser Trp Ser Val Pro Val Ile
    1835                1840                1845

Arg His Leu Phe Ala Pro Leu Lys Glu Tyr Phe Ala Cys Val Ser
    1850                1855                1860

Ser Gly Asn Ser Asn Ala Asn Ser Arg Gly Pro Ser Phe Ser Ser
    1865                1870                1875

Gly Leu Val Pro Leu Ser Leu Arg Gly Ser His Met Gly Pro Met
    1880                1885                1890

Glu Ile Tyr Lys Thr Val Ser Ala Trp Lys Arg Gln Pro Val Arg
    1895                1900                1905

Val Leu Ser Leu Phe Arg Asn Ile Asp Lys Val Leu Lys Ser Leu
    1910                1915                1920

Gly Phe Leu Glu Ser Gly Ser Gly Ser Gly Gly Thr Leu Lys
    1925                1930                1935

Tyr Val Glu Asp Val Thr Asn Val Val Arg Asp Val Glu Lys
    1940                1945                1950

Trp Gly Pro Phe Asp Leu Val Tyr Gly Ser Thr Gln Pro Leu Gly
    1955                1960                1965

Ser Ser Cys Asp Arg Cys Pro Gly Trp Tyr Met Phe Gln Phe His
    1970                1975                1980

Arg Ile Leu Gln Tyr Ala Leu Pro Arg Gln Glu Ser Gln Arg Pro
    1985                1990                1995

Phe Phe Trp Ile Phe Met Asp Asn Leu Leu Leu Thr Glu Asp Asp
```

```
              2000                2005                2010

Gln Glu Thr Thr Thr Arg Phe Leu Gln Thr Glu Ala Val Thr Leu
    2015                2020                2025

Gln Asp Val Arg Gly Arg Asp Tyr Gln Asn Ala Met Arg Val Trp
    2030                2035                2040

Ser Asn Ile Pro Gly Leu Lys Ser Lys His Ala Pro Leu Thr Pro
    2045                2050                2055

Lys Glu Glu Tyr Leu Gln Ala Gln Val Arg Ser Arg Ser Lys
    2060                2065                2070

Leu Asp Ala Pro Lys Val Asp Leu Leu Val Lys Asn Cys Leu Leu
    2075                2080                2085

Pro Leu Arg Glu Tyr Phe Lys Tyr Phe Ser Gln Asn Ser Leu Pro
    2090                2095                2100

Leu Ser Arg Ala Asp Pro Lys Lys Lys Arg Lys Val Gly Ser Gly
    2105                2110                2115

Ala Thr Asn Phe Ser Leu Leu Lys Gln Ala Gly Asp Val Glu Glu
    2120                2125                2130

Asn Pro Gly Pro Ser Glu Leu Ile Lys Glu Asn Met His Met Lys
    2135                2140                2145

Leu Tyr Met Glu Gly Thr Val Asp Asn His His Phe Lys Cys Thr
    2150                2155                2160

Ser Glu Gly Glu Gly Lys Pro Tyr Glu Gly Thr Gln Thr Met Arg
    2165                2170                2175

Ile Lys Val Val Glu Gly Gly Pro Leu Pro Phe Ala Phe Asp Ile
    2180                2185                2190

Leu Ala Thr Ser Phe Leu Tyr Gly Ser Lys Thr Phe Ile Asn His
    2195                2200                2205

Thr Gln Gly Ile Pro Asp Phe Phe Lys Gln Ser Phe Pro Glu Gly
    2210                2215                2220

Phe Thr Trp Glu Arg Val Thr Thr Tyr Glu Asp Gly Gly Val Leu
    2225                2230                2235

Thr Ala Thr Gln Asp Thr Ser Leu Gln Asp Gly Cys Leu Ile Tyr
    2240                2245                2250

Asn Val Lys Ile Arg Gly Val Asn Phe Thr Ser Asn Gly Pro Val
    2255                2260                2265

Met Gln Lys Lys Thr Leu Gly Trp Glu Ala Phe Thr Glu Thr Leu
    2270                2275                2280

Tyr Pro Ala Asp Gly Gly Leu Glu Gly Arg Asn Asp Met Ala Leu
    2285                2290                2295

Lys Leu Val Gly Gly Ser His Leu Ile Ala Asn Ile Lys Thr Thr
    2300                2305                2310

Tyr Arg Ser Lys Lys Pro Ala Lys Asn Leu Lys Met Pro Gly Val
    2315                2320                2325

Tyr Tyr Val Asp Tyr Arg Leu Glu Arg Ile Lys Glu Ala Asn Asn
    2330                2335                2340

Glu Thr Tyr Val Glu Gln His Glu Val Ala Val Ala Arg Tyr Cys
    2345                2350                2355

Asp Leu Pro Ser Lys Leu Gly His Lys Leu Asn
    2360                2365

<210> SEQ ID NO 12
<211> LENGTH: 2391
<212> TYPE: PRT
<213> ORGANISM: Artificial sequence
```

<220> FEATURE:
<223> OTHER INFORMATION: Synthetic polypeptide

<400> SEQUENCE: 12

```
Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Ser Gly Ser Glu Thr Pro Gly Thr Ser
65                  70                  75                  80

Glu Ser Ala Thr Pro Glu Ser Met Asp Lys Lys Tyr Ser Ile Gly Leu
                85                  90                  95

Ala Ile Gly Thr Asn Ser Val Gly Trp Ala Val Ile Thr Asp Glu Tyr
            100                 105                 110

Lys Val Pro Ser Lys Lys Phe Lys Val Leu Gly Asn Thr Asp Arg His
        115                 120                 125

Ser Ile Lys Lys Asn Leu Ile Gly Ala Leu Leu Phe Asp Ser Gly Glu
    130                 135                 140

Thr Ala Glu Ala Thr Arg Leu Lys Arg Thr Ala Arg Arg Arg Tyr Thr
145                 150                 155                 160

Arg Arg Lys Asn Arg Ile Cys Tyr Leu Gln Glu Ile Phe Ser Asn Glu
                165                 170                 175

Met Ala Lys Val Asp Asp Ser Phe Phe His Arg Leu Glu Glu Ser Phe
            180                 185                 190

Leu Val Glu Glu Asp Lys Lys His Glu Arg His Pro Ile Phe Gly Asn
        195                 200                 205

Ile Val Asp Glu Val Ala Tyr His Glu Lys Tyr Pro Thr Ile Tyr His
    210                 215                 220

Leu Arg Lys Lys Leu Val Asp Ser Thr Asp Lys Ala Asp Leu Arg Leu
225                 230                 235                 240

Ile Tyr Leu Ala Leu Ala His Met Ile Lys Phe Arg Gly His Phe Leu
                245                 250                 255

Ile Glu Gly Asp Leu Asn Pro Asp Asn Ser Asp Val Asp Lys Leu Phe
            260                 265                 270

Ile Gln Leu Val Gln Thr Tyr Asn Gln Leu Phe Glu Glu Asn Pro Ile
        275                 280                 285

Asn Ala Ser Gly Val Asp Ala Lys Ala Ile Leu Ser Ala Arg Leu Ser
    290                 295                 300

Lys Ser Arg Arg Leu Glu Asn Leu Ile Ala Gln Leu Pro Gly Glu Lys
305                 310                 315                 320

Lys Asn Gly Leu Phe Gly Asn Leu Ile Ala Leu Ser Leu Gly Leu Thr
                325                 330                 335

Pro Asn Phe Lys Ser Asn Phe Asp Leu Ala Glu Asp Ala Lys Leu Gln
            340                 345                 350

Leu Ser Lys Asp Thr Tyr Asp Asp Asp Leu Asp Asn Leu Leu Ala Gln
        355                 360                 365

Ile Gly Asp Gln Tyr Ala Asp Leu Phe Leu Ala Ala Lys Asn Leu Ser
    370                 375                 380

Asp Ala Ile Leu Leu Ser Asp Ile Leu Arg Val Asn Thr Glu Ile Thr
385                 390                 395                 400
```

```
Lys Ala Pro Leu Ser Ala Ser Met Ile Lys Arg Tyr Asp Glu His His
            405                 410                 415

Gln Asp Leu Thr Leu Leu Lys Ala Leu Val Arg Gln Gln Leu Pro Glu
            420                 425                 430

Lys Tyr Lys Glu Ile Phe Phe Asp Gln Ser Lys Asn Gly Tyr Ala Gly
            435                 440                 445

Tyr Ile Asp Gly Gly Ala Ser Gln Glu Glu Phe Tyr Lys Phe Ile Lys
            450                 455                 460

Pro Ile Leu Glu Lys Met Asp Gly Thr Glu Glu Leu Leu Val Lys Leu
465                 470                 475                 480

Asn Arg Glu Asp Leu Leu Arg Lys Gln Arg Thr Phe Asp Asn Gly Ser
                485                 490                 495

Ile Pro His Gln Ile His Leu Gly Glu Leu His Ala Ile Leu Arg Arg
                500                 505                 510

Gln Glu Asp Phe Tyr Pro Phe Leu Lys Asp Asn Arg Glu Lys Ile Glu
                515                 520                 525

Lys Ile Leu Thr Phe Arg Ile Pro Tyr Tyr Val Gly Pro Leu Ala Arg
            530                 535                 540

Gly Asn Ser Arg Phe Ala Trp Met Thr Arg Lys Ser Glu Glu Thr Ile
545                 550                 555                 560

Thr Pro Trp Asn Phe Glu Glu Val Val Asp Lys Gly Ala Ser Ala Gln
                565                 570                 575

Ser Phe Ile Glu Arg Met Thr Asn Phe Asp Lys Asn Leu Pro Asn Glu
                580                 585                 590

Lys Val Leu Pro Lys His Ser Leu Leu Tyr Glu Tyr Phe Thr Val Tyr
                595                 600                 605

Asn Glu Leu Thr Lys Val Lys Tyr Val Thr Glu Gly Met Arg Lys Pro
            610                 615                 620

Ala Phe Leu Ser Gly Glu Gln Lys Lys Ala Ile Val Asp Leu Leu Phe
625                 630                 635                 640

Lys Thr Asn Arg Lys Val Thr Val Lys Gln Leu Lys Glu Asp Tyr Phe
                645                 650                 655

Lys Lys Ile Glu Cys Phe Asp Ser Val Glu Ile Ser Gly Val Glu Asp
                660                 665                 670

Arg Phe Asn Ala Ser Leu Gly Thr Tyr His Asp Leu Leu Lys Ile Ile
                675                 680                 685

Lys Asp Lys Asp Phe Leu Asp Asn Glu Glu Asn Glu Asp Ile Leu Glu
            690                 695                 700

Asp Ile Val Leu Thr Leu Thr Leu Phe Glu Asp Arg Glu Met Ile Glu
705                 710                 715                 720

Glu Arg Leu Lys Thr Tyr Ala His Leu Phe Asp Asp Lys Val Met Lys
                725                 730                 735

Gln Leu Lys Arg Arg Arg Tyr Thr Gly Trp Gly Arg Leu Ser Arg Lys
            740                 745                 750

Leu Ile Asn Gly Ile Arg Asp Lys Gln Ser Gly Lys Thr Ile Leu Asp
            755                 760                 765

Phe Leu Lys Ser Asp Gly Phe Ala Asn Arg Asn Phe Met Gln Leu Ile
            770                 775                 780

His Asp Asp Ser Leu Thr Phe Lys Glu Asp Ile Gln Lys Ala Gln Val
785                 790                 795                 800

Ser Gly Gln Gly Asp Ser Leu His Glu His Ile Ala Asn Leu Ala Gly
                805                 810                 815
```

Ser Pro Ala Ile Lys Lys Gly Ile Leu Gln Thr Val Lys Val Val Asp
            820                 825                 830

Glu Leu Val Lys Val Met Gly Arg His Lys Pro Glu Asn Ile Val Ile
            835                 840                 845

Glu Met Ala Arg Glu Asn Gln Thr Thr Gln Lys Gly Gln Lys Asn Ser
            850                 855                 860

Arg Glu Arg Met Lys Arg Ile Glu Glu Gly Ile Lys Glu Leu Gly Ser
865                 870                 875                 880

Gln Ile Leu Lys Glu His Pro Val Glu Asn Thr Gln Leu Gln Asn Glu
                885                 890                 895

Lys Leu Tyr Leu Tyr Tyr Leu Gln Asn Gly Arg Asp Met Tyr Val Asp
            900                 905                 910

Gln Glu Leu Asp Ile Asn Arg Leu Ser Asp Tyr Asp Val Asp Ala Ile
            915                 920                 925

Val Pro Gln Ser Phe Leu Lys Asp Asp Ser Ile Asp Asn Lys Val Leu
            930                 935                 940

Thr Arg Ser Asp Lys Asn Arg Gly Lys Ser Asp Asn Val Pro Ser Glu
945                 950                 955                 960

Glu Val Val Lys Lys Met Lys Asn Tyr Trp Arg Gln Leu Leu Asn Ala
                965                 970                 975

Lys Leu Ile Thr Gln Arg Lys Phe Asp Asn Leu Thr Lys Ala Glu Arg
            980                 985                 990

Gly Gly Leu Ser Glu Leu Asp Lys Ala Gly Phe Ile Lys Arg Gln Leu
                995                 1000                1005

Val Glu Thr Arg Gln Ile Thr Lys His Val Ala Gln Ile Leu Asp
            1010                1015                1020

Ser Arg Met Asn Thr Lys Tyr Asp Glu Asn Asp Lys Leu Ile Arg
            1025                1030                1035

Glu Val Lys Val Ile Thr Leu Lys Ser Lys Leu Val Ser Asp Phe
            1040                1045                1050

Arg Lys Asp Phe Gln Phe Tyr Lys Val Arg Glu Ile Asn Asn Tyr
            1055                1060                1065

His His Ala His Asp Ala Tyr Leu Asn Ala Val Val Gly Thr Ala
            1070                1075                1080

Leu Ile Lys Lys Tyr Pro Lys Leu Glu Ser Glu Phe Val Tyr Gly
            1085                1090                1095

Asp Tyr Lys Val Tyr Asp Val Arg Lys Met Ile Ala Lys Ser Glu
            1100                1105                1110

Gln Glu Ile Gly Lys Ala Thr Ala Lys Tyr Phe Phe Tyr Ser Asn
            1115                1120                1125

Ile Met Asn Phe Phe Lys Thr Glu Ile Thr Leu Ala Asn Gly Glu
            1130                1135                1140

Ile Arg Lys Arg Pro Leu Ile Glu Thr Asn Gly Glu Thr Gly Glu
            1145                1150                1155

Ile Val Trp Asp Lys Gly Arg Asp Phe Ala Thr Val Arg Lys Val
            1160                1165                1170

Leu Ser Met Pro Gln Val Asn Ile Val Lys Lys Thr Glu Val Gln
            1175                1180                1185

Thr Gly Gly Phe Ser Lys Glu Ser Ile Leu Pro Lys Arg Asn Ser
            1190                1195                1200

Asp Lys Leu Ile Ala Arg Lys Lys Asp Trp Asp Pro Lys Lys Tyr
            1205                1210                1215

Gly Gly Phe Asp Ser Pro Thr Val Ala Tyr Ser Val Leu Val Val

```
              1220                1225                1230

Ala Lys Val Glu Lys Gly Lys Ser Lys Lys Leu Lys Ser Val Lys
              1235                1240                1245

Glu Leu Leu Gly Ile Thr Ile Met Glu Arg Ser Ser Phe Glu Lys
              1250                1255                1260

Asn Pro Ile Asp Phe Leu Glu Ala Lys Gly Tyr Lys Glu Val Lys
              1265                1270                1275

Lys Asp Leu Ile Ile Lys Leu Pro Lys Tyr Ser Leu Phe Glu Leu
              1280                1285                1290

Glu Asn Gly Arg Lys Arg Met Leu Ala Ser Ala Gly Glu Leu Gln
              1295                1300                1305

Lys Gly Asn Glu Leu Ala Leu Pro Ser Lys Tyr Val Asn Phe Leu
              1310                1315                1320

Tyr Leu Ala Ser His Tyr Glu Lys Leu Lys Gly Ser Pro Glu Asp
              1325                1330                1335

Asn Glu Gln Lys Gln Leu Phe Val Glu Gln His Lys His Tyr Leu
              1340                1345                1350

Asp Glu Ile Ile Glu Gln Ile Ser Glu Phe Ser Lys Arg Val Ile
              1355                1360                1365

Leu Ala Asp Ala Asn Leu Asp Lys Val Leu Ser Ala Tyr Asn Lys
              1370                1375                1380

His Arg Asp Lys Pro Ile Arg Glu Gln Ala Glu Asn Ile Ile His
              1385                1390                1395

Leu Phe Thr Leu Thr Asn Leu Gly Ala Pro Ala Ala Phe Lys Tyr
              1400                1405                1410

Phe Asp Thr Thr Ile Asp Arg Lys Arg Tyr Thr Ser Thr Lys Glu
              1415                1420                1425

Val Leu Asp Ala Thr Leu Ile His Gln Ser Ile Thr Gly Leu Tyr
              1430                1435                1440

Glu Thr Arg Ile Asp Leu Ser Gln Leu Gly Gly Asp Ser Arg Ala
              1445                1450                1455

Asp Tyr Pro Tyr Asp Val Pro Asp Tyr Ala Ser Gly Ser Pro Lys
              1460                1465                1470

Lys Lys Arg Lys Val Ser Pro Gly Gly Gly Pro Ser Ser Gly Ala
              1475                1480                1485

Pro Pro Pro Ser Gly Gly Ser Pro Ala Gly Ser Pro Thr Ser Thr
              1490                1495                1500

Glu Glu Gly Thr Ser Glu Ser Ala Thr Pro Glu Ser Gly Pro Gly
              1505                1510                1515

Thr Ser Thr Glu Pro Ser Glu Gly Ser Ala Pro Gly Ser Pro Ala
              1520                1525                1530

Gly Ser Pro Thr Ser Thr Glu Glu Gly Thr Ser Thr Glu Pro Ser
              1535                1540                1545

Glu Gly Ser Ala Pro Gly Thr Ser Thr Glu Pro Ser Glu Asn His
              1550                1555                1560

Asp Gln Glu Phe Asp Pro Pro Lys Val Tyr Pro Pro Val Pro Ala
              1565                1570                1575

Glu Lys Arg Lys Pro Ile Arg Val Leu Ser Leu Phe Asp Gly Ile
              1580                1585                1590

Ala Thr Gly Leu Leu Val Leu Lys Asp Leu Gly Ile Gln Val Asp
              1595                1600                1605

Arg Tyr Ile Ala Ser Glu Val Cys Glu Asp Ser Ile Thr Val Gly
              1610                1615                1620
```

-continued

```
Met Val Arg His Gln Gly Lys Ile Met Tyr Val Gly Asp Val Arg
    1625              1630                1635
Ser Val Thr Gln Lys His Ile Gln Glu Trp Gly Pro Phe Asp Leu
    1640              1645                1650
Val Ile Gly Gly Ser Pro Cys Asn Asp Leu Ser Ile Val Asn Pro
    1655              1660                1665
Ala Arg Lys Gly Leu Tyr Glu Gly Thr Gly Arg Leu Phe Phe Glu
    1670              1675                1680
Phe Tyr Arg Leu Leu His Asp Ala Arg Pro Lys Glu Gly Asp Asp
    1685              1690                1695
Arg Pro Phe Phe Trp Leu Phe Glu Asn Val Val Ala Met Gly Val
    1700              1705                1710
Ser Asp Lys Arg Asp Ile Ser Arg Phe Leu Glu Ser Asn Pro Val
    1715              1720                1725
Met Ile Asp Ala Lys Glu Val Ser Ala Ala His Arg Ala Arg Tyr
    1730              1735                1740
Phe Trp Gly Asn Leu Pro Gly Met Asn Arg Pro Leu Ala Ser Thr
    1745              1750                1755
Val Asn Asp Lys Leu Glu Leu Gln Glu Cys Leu Glu His Gly Arg
    1760              1765                1770
Ile Ala Lys Phe Ser Lys Val Arg Thr Ile Thr Arg Arg Ser Asn
    1775              1780                1785
Ser Ile Lys Gln Gly Lys Asp Gln His Phe Pro Val Phe Met Asn
    1790              1795                1800
Glu Lys Glu Asp Ile Leu Trp Cys Thr Glu Met Glu Arg Val Phe
    1805              1810                1815
Gly Phe Pro Val His Tyr Thr Asp Val Ser Asn Met Ser Arg Leu
    1820              1825                1830
Ala Arg Gln Arg Leu Leu Gly Arg Ser Trp Ser Val Pro Val Ile
    1835              1840                1845
Arg His Leu Phe Ala Pro Leu Lys Glu Tyr Phe Ala Cys Val Ser
    1850              1855                1860
Ser Gly Asn Ser Asn Ala Asn Ser Arg Gly Pro Ser Phe Ser Ser
    1865              1870                1875
Gly Leu Val Pro Leu Ser Leu Arg Gly Ser His Met Gly Pro Met
    1880              1885                1890
Glu Ile Tyr Lys Thr Val Ser Ala Trp Lys Arg Gln Pro Val Arg
    1895              1900                1905
Val Leu Ser Leu Phe Arg Asn Ile Asp Lys Val Leu Lys Ser Leu
    1910              1915                1920
Gly Phe Leu Glu Ser Gly Ser Gly Ser Gly Gly Thr Leu Lys
    1925              1930                1935
Tyr Val Glu Asp Val Thr Asn Val Val Arg Arg Asp Val Glu Lys
    1940              1945                1950
Trp Gly Pro Phe Asp Leu Val Tyr Gly Ser Thr Gln Pro Leu Gly
    1955              1960                1965
Ser Ser Cys Asp Arg Cys Pro Gly Trp Tyr Met Phe Gln Phe His
    1970              1975                1980
Arg Ile Leu Gln Tyr Ala Leu Pro Arg Gln Glu Ser Gln Arg Pro
    1985              1990                1995
Phe Phe Trp Ile Phe Met Asp Asn Leu Leu Leu Thr Glu Asp Asp
    2000              2005                2010
```

| | | | | | | | | | | | | |
|---|---|---|---|---|---|---|---|---|---|---|---|---|
| Gln | Glu | Thr | Thr | Thr | Arg | Phe | Leu | Gln | Thr | Glu | Ala | Val | Thr | Leu |
| 2015 | | | | | 2020 | | | | | 2025 | | | | |
| Gln | Asp | Val | Arg | Gly | Arg | Asp | Tyr | Gln | Asn | Ala | Met | Arg | Val | Trp |
| 2030 | | | | | 2035 | | | | | 2040 | | | | |
| Ser | Asn | Ile | Pro | Gly | Leu | Lys | Ser | Lys | His | Ala | Pro | Leu | Thr | Pro |
| 2045 | | | | | 2050 | | | | | 2055 | | | | |
| Lys | Glu | Glu | Glu | Tyr | Leu | Gln | Ala | Gln | Val | Arg | Ser | Arg | Ser | Lys |
| 2060 | | | | | 2065 | | | | | 2070 | | | | |
| Leu | Asp | Ala | Pro | Lys | Val | Asp | Leu | Leu | Val | Lys | Asn | Cys | Leu | Leu |
| 2075 | | | | | 2080 | | | | | 2085 | | | | |
| Pro | Leu | Arg | Glu | Tyr | Phe | Lys | Tyr | Phe | Ser | Gln | Asn | Ser | Leu | Pro |
| 2090 | | | | | 2095 | | | | | 2100 | | | | |
| Leu | Ser | Arg | Ala | Asp | Pro | Lys | Lys | Arg | Lys | Val | Gly | Ser | Gly |
| 2105 | | | | | 2110 | | | | | 2115 | | | | |
| Ala | Thr | Asn | Phe | Ser | Leu | Leu | Lys | Gln | Ala | Gly | Asp | Val | Glu | Glu |
| 2120 | | | | | 2125 | | | | | 2130 | | | | |
| Asn | Pro | Gly | Pro | Gly | Ser | Gly | Ala | Thr | Asn | Phe | Ser | Leu | Leu | Lys |
| 2135 | | | | | 2140 | | | | | 2145 | | | | |
| Gln | Ala | Gly | Asp | Val | Glu | Glu | Asn | Pro | Gly | Pro | Ser | Glu | Leu | Ile |
| 2150 | | | | | 2155 | | | | | 2160 | | | | |
| Lys | Glu | Asn | Met | His | Met | Lys | Leu | Tyr | Met | Glu | Gly | Thr | Val | Asp |
| 2165 | | | | | 2170 | | | | | 2175 | | | | |
| Asn | His | His | Phe | Lys | Cys | Thr | Ser | Glu | Gly | Glu | Gly | Lys | Pro | Tyr |
| 2180 | | | | | 2185 | | | | | 2190 | | | | |
| Glu | Gly | Thr | Gln | Thr | Met | Arg | Ile | Lys | Val | Val | Glu | Gly | Gly | Pro |
| 2195 | | | | | 2200 | | | | | 2205 | | | | |
| Leu | Pro | Phe | Ala | Phe | Asp | Ile | Leu | Ala | Thr | Ser | Phe | Leu | Tyr | Gly |
| 2210 | | | | | 2215 | | | | | 2220 | | | | |
| Ser | Lys | Thr | Phe | Ile | Asn | His | Thr | Gln | Gly | Ile | Pro | Asp | Phe | Phe |
| 2225 | | | | | 2230 | | | | | 2235 | | | | |
| Lys | Gln | Ser | Phe | Pro | Glu | Gly | Phe | Thr | Trp | Glu | Arg | Val | Thr | Thr |
| 2240 | | | | | 2245 | | | | | 2250 | | | | |
| Tyr | Glu | Asp | Gly | Gly | Val | Leu | Thr | Ala | Thr | Gln | Asp | Thr | Ser | Leu |
| 2255 | | | | | 2260 | | | | | 2265 | | | | |
| Gln | Asp | Gly | Cys | Leu | Ile | Tyr | Asn | Val | Lys | Ile | Arg | Gly | Val | Asn |
| 2270 | | | | | 2275 | | | | | 2280 | | | | |
| Phe | Thr | Ser | Asn | Gly | Pro | Val | Met | Gln | Lys | Lys | Thr | Leu | Gly | Trp |
| 2285 | | | | | 2290 | | | | | 2295 | | | | |
| Glu | Ala | Phe | Thr | Glu | Thr | Leu | Tyr | Pro | Ala | Asp | Gly | Gly | Leu | Glu |
| 2300 | | | | | 2305 | | | | | 2310 | | | | |
| Gly | Arg | Asn | Asp | Met | Ala | Leu | Lys | Leu | Val | Gly | Gly | Ser | His | Leu |
| 2315 | | | | | 2320 | | | | | 2325 | | | | |
| Ile | Ala | Asn | Ile | Lys | Thr | Thr | Tyr | Arg | Ser | Lys | Lys | Pro | Ala | Lys |
| 2330 | | | | | 2335 | | | | | 2340 | | | | |
| Asn | Leu | Lys | Met | Pro | Gly | Val | Tyr | Tyr | Val | Asp | Tyr | Arg | Leu | Glu |
| 2345 | | | | | 2350 | | | | | 2355 | | | | |
| Arg | Ile | Lys | Glu | Ala | Asn | Asn | Glu | Thr | Tyr | Val | Glu | Gln | His | Glu |
| 2360 | | | | | 2365 | | | | | 2370 | | | | |
| Val | Ala | Val | Ala | Arg | Tyr | Cys | Asp | Leu | Pro | Ser | Lys | Leu | Gly | His |
| 2375 | | | | | 2380 | | | | | 2385 | | | | |
| Lys | Leu | Asn | | | | | | | | | | | | |
| 2390 | | | | | | | | | | | | | | |

-continued

```
<210> SEQ ID NO 13
<211> LENGTH: 2369
<212> TYPE: PRT
<213> ORGANISM: Artificial sequence
<220> FEATURE:
<223> OTHER INFORMATION: Synthetic polypeptide

<400> SEQUENCE: 13
```

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Gly Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
            100                 105                 110

Pro Ser Glu Gly Ser Ala Pro Gly Ser Pro Ala Gly Ser Pro Thr Ser
        115                 120                 125

Thr Glu Glu Gly Thr Ser Thr Glu Pro Ser Glu Gly Ser Ala Pro Gly
    130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
            180                 185                 190

Ser Ile Lys Lys Asn Leu Ile Gly Ala Leu Leu Phe Asp Ser Gly Glu
        195                 200                 205

Thr Ala Glu Ala Thr Arg Leu Lys Arg Thr Ala Arg Arg Arg Tyr Thr
    210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
            260                 265                 270

Ile Val Asp Glu Val Ala Tyr His Glu Lys Tyr Pro Thr Ile Tyr His
        275                 280                 285

Leu Arg Lys Lys Leu Val Asp Ser Thr Asp Lys Ala Asp Leu Arg Leu
    290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
            340                 345                 350

Asn Ala Ser Gly Val Asp Ala Lys Ala Ile Leu Ser Ala Arg Leu Ser
        355                 360                 365

Lys Ser Arg Arg Leu Glu Asn Leu Ile Ala Gln Leu Pro Gly Glu Lys

```
              370                 375                 380
Lys Asn Gly Leu Phe Gly Asn Leu Ile Ala Leu Ser Leu Gly Leu Thr
385                 390                 395                 400

Pro Asn Phe Lys Ser Asn Phe Asp Leu Ala Glu Asp Ala Lys Leu Gln
                405                 410                 415

Leu Ser Lys Asp Thr Tyr Asp Asp Leu Asp Asn Leu Leu Ala Gln
                420                 425                 430

Ile Gly Asp Gln Tyr Ala Asp Leu Phe Leu Ala Ala Lys Asn Leu Ser
                435                 440                 445

Asp Ala Ile Leu Leu Ser Asp Ile Leu Arg Val Asn Thr Glu Ile Thr
450                 455                 460

Lys Ala Pro Leu Ser Ala Ser Met Ile Lys Arg Tyr Asp Glu His His
465                 470                 475                 480

Gln Asp Leu Thr Leu Leu Lys Ala Leu Val Arg Gln Gln Leu Pro Glu
                485                 490                 495

Lys Tyr Lys Glu Ile Phe Phe Asp Gln Ser Lys Asn Gly Tyr Ala Gly
                500                 505                 510

Tyr Ile Asp Gly Gly Ala Ser Gln Glu Glu Phe Tyr Lys Phe Ile Lys
                515                 520                 525

Pro Ile Leu Glu Lys Met Asp Gly Thr Glu Glu Leu Leu Val Lys Leu
                530                 535                 540

Asn Arg Glu Asp Leu Leu Arg Lys Gln Arg Thr Phe Asp Asn Gly Ser
545                 550                 555                 560

Ile Pro His Gln Ile His Leu Gly Glu Leu His Ala Ile Leu Arg Arg
                565                 570                 575

Gln Glu Asp Phe Tyr Pro Phe Leu Lys Asp Asn Arg Glu Lys Ile Glu
                580                 585                 590

Lys Ile Leu Thr Phe Arg Ile Pro Tyr Tyr Val Gly Pro Leu Ala Arg
                595                 600                 605

Gly Asn Ser Arg Phe Ala Trp Met Thr Arg Lys Ser Glu Glu Thr Ile
610                 615                 620

Thr Pro Trp Asn Phe Glu Glu Val Val Asp Lys Gly Ala Ser Ala Gln
625                 630                 635                 640

Ser Phe Ile Glu Arg Met Thr Asn Phe Asp Lys Asn Leu Pro Asn Glu
                645                 650                 655

Lys Val Leu Pro Lys His Ser Leu Leu Tyr Glu Tyr Phe Thr Val Tyr
                660                 665                 670

Asn Glu Leu Thr Lys Val Lys Tyr Val Thr Glu Gly Met Arg Lys Pro
                675                 680                 685

Ala Phe Leu Ser Gly Glu Gln Lys Lys Ala Ile Val Asp Leu Leu Phe
                690                 695                 700

Lys Thr Asn Arg Lys Val Thr Val Lys Gln Leu Lys Glu Asp Tyr Phe
705                 710                 715                 720

Lys Lys Ile Glu Cys Phe Asp Ser Val Glu Ile Ser Gly Val Glu Asp
                725                 730                 735

Arg Phe Asn Ala Ser Leu Gly Thr Tyr His Asp Leu Leu Lys Ile Ile
                740                 745                 750

Lys Asp Lys Asp Phe Leu Asp Asn Glu Glu Asn Glu Asp Ile Leu Glu
                755                 760                 765

Asp Ile Val Leu Thr Leu Thr Leu Phe Glu Asp Arg Glu Met Ile Glu
                770                 775                 780

Glu Arg Leu Lys Thr Tyr Ala His Leu Phe Asp Asp Lys Val Met Lys
785                 790                 795                 800
```

```
Gln Leu Lys Arg Arg Tyr Thr Gly Trp Gly Arg Leu Ser Arg Lys
            805                 810                 815

Leu Ile Asn Gly Ile Arg Asp Lys Gln Ser Gly Lys Thr Ile Leu Asp
            820                 825                 830

Phe Leu Lys Ser Asp Gly Phe Ala Asn Arg Asn Phe Met Gln Leu Ile
            835                 840                 845

His Asp Asp Ser Leu Thr Phe Lys Glu Asp Ile Gln Lys Ala Gln Val
            850                 855                 860

Ser Gly Gln Gly Asp Ser Leu His Glu His Ile Ala Asn Leu Ala Gly
865                 870                 875                 880

Ser Pro Ala Ile Lys Lys Gly Ile Leu Gln Thr Val Lys Val Val Asp
            885                 890                 895

Glu Leu Val Lys Val Met Gly Arg His Lys Pro Glu Asn Ile Val Ile
            900                 905                 910

Glu Met Ala Arg Glu Asn Gln Thr Thr Gln Lys Gly Gln Lys Asn Ser
            915                 920                 925

Arg Glu Arg Met Lys Arg Ile Glu Glu Gly Ile Lys Glu Leu Gly Ser
            930                 935                 940

Gln Ile Leu Lys Glu His Pro Val Glu Asn Thr Gln Leu Gln Asn Glu
945                 950                 955                 960

Lys Leu Tyr Leu Tyr Tyr Leu Gln Asn Gly Arg Asp Met Tyr Val Asp
            965                 970                 975

Gln Glu Leu Asp Ile Asn Arg Leu Ser Asp Tyr Asp Val Asp Ala Ile
            980                 985                 990

Val Pro Gln Ser Phe Leu Lys Asp Asp Ser Ile Asp Asn Lys Val Leu
            995                 1000                1005

Thr Arg Ser Asp Lys Asn Arg Gly Lys Ser Asp Asn Val Pro Ser
            1010                1015                1020

Glu Glu Val Val Lys Lys Met Lys Asn Tyr Trp Arg Gln Leu Leu
1025                1030                1035

Asn Ala Lys Leu Ile Thr Gln Arg Lys Phe Asp Asn Leu Thr Lys
1040                1045                1050

Ala Glu Arg Gly Gly Leu Ser Glu Leu Asp Lys Ala Gly Phe Ile
1055                1060                1065

Lys Arg Gln Leu Val Glu Thr Arg Gln Ile Thr Lys His Val Ala
1070                1075                1080

Gln Ile Leu Asp Ser Arg Met Asn Thr Lys Tyr Asp Glu Asn Asp
1085                1090                1095

Lys Leu Ile Arg Glu Val Lys Val Ile Thr Leu Lys Ser Lys Leu
1100                1105                1110

Val Ser Asp Phe Arg Lys Asp Phe Gln Phe Tyr Lys Val Arg Glu
1115                1120                1125

Ile Asn Asn Tyr His His Ala His Asp Ala Tyr Leu Asn Ala Val
1130                1135                1140

Val Gly Thr Ala Leu Ile Lys Lys Tyr Pro Lys Leu Glu Ser Glu
1145                1150                1155

Phe Val Tyr Gly Asp Tyr Lys Val Tyr Asp Val Arg Lys Met Ile
1160                1165                1170

Ala Lys Ser Glu Gln Glu Ile Gly Lys Ala Thr Ala Lys Tyr Phe
1175                1180                1185

Phe Tyr Ser Asn Ile Met Asn Phe Phe Lys Thr Glu Ile Thr Leu
1190                1195                1200
```

```
Ala Asn Gly Glu Ile Arg Lys Arg Pro Leu Ile Glu Thr Asn Gly
1205                1210                1215

Glu Thr Gly Glu Ile Val Trp Asp Lys Gly Arg Asp Phe Ala Thr
1220                1225                1230

Val Arg Lys Val Leu Ser Met Pro Gln Val Asn Ile Val Lys Lys
1235                1240                1245

Thr Glu Val Gln Thr Gly Gly Phe Ser Lys Glu Ser Ile Leu Pro
1250                1255                1260

Lys Arg Asn Ser Asp Lys Leu Ile Ala Arg Lys Lys Asp Trp Asp
1265                1270                1275

Pro Lys Lys Tyr Gly Gly Phe Asp Ser Pro Thr Val Ala Tyr Ser
1280                1285                1290

Val Leu Val Val Ala Lys Val Glu Lys Gly Lys Ser Lys Lys Leu
1295                1300                1305

Lys Ser Val Lys Glu Leu Leu Gly Ile Thr Ile Met Glu Arg Ser
1310                1315                1320

Ser Phe Glu Lys Asn Pro Ile Asp Phe Leu Glu Ala Lys Gly Tyr
1325                1330                1335

Lys Glu Val Lys Lys Asp Leu Ile Ile Lys Leu Pro Lys Tyr Ser
1340                1345                1350

Leu Phe Glu Leu Glu Asn Gly Arg Lys Arg Met Leu Ala Ser Ala
1355                1360                1365

Gly Glu Leu Gln Lys Gly Asn Glu Leu Ala Leu Pro Ser Lys Tyr
1370                1375                1380

Val Asn Phe Leu Tyr Leu Ala Ser His Tyr Glu Lys Leu Lys Gly
1385                1390                1395

Ser Pro Glu Asp Asn Glu Gln Lys Gln Leu Phe Val Glu Gln His
1400                1405                1410

Lys His Tyr Leu Asp Glu Ile Ile Glu Gln Ile Ser Glu Phe Ser
1415                1420                1425

Lys Arg Val Ile Leu Ala Asp Ala Asn Leu Asp Lys Val Leu Ser
1430                1435                1440

Ala Tyr Asn Lys His Arg Asp Lys Pro Ile Arg Glu Gln Ala Glu
1445                1450                1455

Asn Ile Ile His Leu Phe Thr Leu Thr Asn Leu Gly Ala Pro Ala
1460                1465                1470

Ala Phe Lys Tyr Phe Asp Thr Thr Ile Asp Arg Lys Arg Tyr Thr
1475                1480                1485

Ser Thr Lys Glu Val Leu Asp Ala Thr Leu Ile His Gln Ser Ile
1490                1495                1500

Thr Gly Leu Tyr Glu Thr Arg Ile Asp Leu Ser Gln Leu Gly Gly
1505                1510                1515

Asp Ser Arg Ala Asp Tyr Pro Tyr Asp Val Pro Asp Tyr Ala Ser
1520                1525                1530

Gly Ser Pro Lys Lys Lys Arg Lys Val Ser Pro Gly Ser Gly Ser
1535                1540                1545

Glu Thr Pro Gly Thr Ser Glu Ser Ala Thr Pro Glu Ser Asn His
1550                1555                1560

Asp Gln Glu Phe Asp Pro Pro Lys Val Tyr Pro Pro Val Pro Ala
1565                1570                1575

Glu Lys Arg Lys Pro Ile Arg Val Leu Ser Leu Phe Asp Gly Ile
1580                1585                1590

Ala Thr Gly Leu Leu Val Leu Lys Asp Leu Gly Ile Gln Val Asp
```

-continued

```
            1595                1600                1605

Arg Tyr Ile Ala Ser Glu Val Cys Glu Asp Ser Ile Thr Val Gly
    1610                1615                1620

Met Val Arg His Gln Gly Lys Ile Met Tyr Val Gly Asp Val Arg
    1625                1630                1635

Ser Val Thr Gln Lys His Ile Gln Glu Trp Gly Pro Phe Asp Leu
    1640                1645                1650

Val Ile Gly Gly Ser Pro Cys Asn Asp Leu Ser Ile Val Asn Pro
    1655                1660                1665

Ala Arg Lys Gly Leu Tyr Glu Gly Thr Gly Arg Leu Phe Phe Glu
    1670                1675                1680

Phe Tyr Arg Leu Leu His Asp Ala Arg Pro Lys Glu Gly Asp Asp
    1685                1690                1695

Arg Pro Phe Phe Trp Leu Phe Glu Asn Val Val Ala Met Gly Val
    1700                1705                1710

Ser Asp Lys Arg Asp Ile Ser Arg Phe Leu Glu Ser Asn Pro Val
    1715                1720                1725

Met Ile Asp Ala Lys Glu Val Ser Ala Ala His Arg Ala Arg Tyr
    1730                1735                1740

Phe Trp Gly Asn Leu Pro Gly Met Asn Arg Pro Leu Ala Ser Thr
    1745                1750                1755

Val Asn Asp Lys Leu Glu Leu Gln Glu Cys Leu Glu His Gly Arg
    1760                1765                1770

Ile Ala Lys Phe Ser Lys Val Arg Thr Ile Thr Thr Arg Ser Asn
    1775                1780                1785

Ser Ile Lys Gln Gly Lys Asp Gln His Phe Pro Val Phe Met Asn
    1790                1795                1800

Glu Lys Glu Asp Ile Leu Trp Cys Thr Glu Met Glu Arg Val Phe
    1805                1810                1815

Gly Phe Pro Val His Tyr Thr Asp Val Ser Asn Met Ser Arg Leu
    1820                1825                1830

Ala Arg Gln Arg Leu Leu Gly Arg Ser Trp Ser Val Pro Val Ile
    1835                1840                1845

Arg His Leu Phe Ala Pro Leu Lys Glu Tyr Phe Ala Cys Val Ser
    1850                1855                1860

Ser Gly Asn Ser Asn Ala Asn Ser Arg Gly Pro Ser Phe Ser Ser
    1865                1870                1875

Gly Leu Val Pro Leu Ser Leu Arg Gly Ser His Met Gly Pro Met
    1880                1885                1890

Glu Ile Tyr Lys Thr Val Ser Ala Trp Lys Arg Gln Pro Val Arg
    1895                1900                1905

Val Leu Ser Leu Phe Arg Asn Ile Asp Lys Val Leu Lys Ser Leu
    1910                1915                1920

Gly Phe Leu Glu Ser Gly Ser Gly Ser Gly Gly Thr Leu Lys
    1925                1930                1935

Tyr Val Glu Asp Val Thr Asn Val Val Arg Arg Asp Val Glu Lys
    1940                1945                1950

Trp Gly Pro Phe Asp Leu Val Tyr Gly Ser Thr Gln Pro Leu Gly
    1955                1960                1965

Ser Ser Cys Asp Arg Cys Pro Gly Trp Tyr Met Phe Gln Phe His
    1970                1975                1980

Arg Ile Leu Gln Tyr Ala Leu Pro Arg Gln Glu Ser Gln Arg Pro
    1985                1990                1995
```

Phe Phe Trp Ile Phe Met Asp Asn Leu Leu Thr Glu Asp Asp
2000                2005                2010

Gln Glu Thr Thr Thr Arg Phe Leu Gln Thr Glu Ala Val Thr Leu
2015                2020                2025

Gln Asp Val Arg Gly Arg Asp Tyr Gln Asn Ala Met Arg Val Trp
2030                2035                2040

Ser Asn Ile Pro Gly Leu Lys Ser Lys His Ala Pro Leu Thr Pro
2045                2050                2055

Lys Glu Glu Glu Tyr Leu Gln Ala Gln Val Arg Ser Arg Ser Lys
2060                2065                2070

Leu Asp Ala Pro Lys Val Asp Leu Leu Val Lys Asn Cys Leu Leu
2075                2080                2085

Pro Leu Arg Glu Tyr Phe Lys Tyr Phe Ser Gln Asn Ser Leu Pro
2090                2095                2100

Leu Ser Arg Ala Asp Pro Lys Lys Arg Lys Val Gly Ser Gly
2105                2110                2115

Ala Thr Asn Phe Ser Leu Leu Lys Gln Ala Gly Asp Val Glu Glu
2120                2125                2130

Asn Pro Gly Pro Ser Glu Leu Ile Lys Glu Asn Met His Met Lys
2135                2140                2145

Leu Tyr Met Glu Gly Thr Val Asp Asn His His Phe Lys Cys Thr
2150                2155                2160

Ser Glu Gly Glu Gly Lys Pro Tyr Glu Gly Thr Gln Thr Met Arg
2165                2170                2175

Ile Lys Val Val Glu Gly Gly Pro Leu Pro Phe Ala Phe Asp Ile
2180                2185                2190

Leu Ala Thr Ser Phe Leu Tyr Gly Ser Lys Thr Phe Ile Asn His
2195                2200                2205

Thr Gln Gly Ile Pro Asp Phe Phe Lys Gln Ser Phe Pro Glu Gly
2210                2215                2220

Phe Thr Trp Glu Arg Val Thr Thr Tyr Glu Asp Gly Gly Val Leu
2225                2230                2235

Thr Ala Thr Gln Asp Thr Ser Leu Gln Asp Gly Cys Leu Ile Tyr
2240                2245                2250

Asn Val Lys Ile Arg Gly Val Asn Phe Thr Ser Asn Gly Pro Val
2255                2260                2265

Met Gln Lys Lys Thr Leu Gly Trp Glu Ala Phe Thr Glu Thr Leu
2270                2275                2280

Tyr Pro Ala Asp Gly Gly Leu Glu Gly Arg Asn Asp Met Ala Leu
2285                2290                2295

Lys Leu Val Gly Gly Ser His Leu Ile Ala Asn Ile Lys Thr Thr
2300                2305                2310

Tyr Arg Ser Lys Lys Pro Ala Lys Asn Leu Lys Met Pro Gly Val
2315                2320                2325

Tyr Tyr Val Asp Tyr Arg Leu Glu Arg Ile Lys Glu Ala Asn Asn
2330                2335                2340

Glu Thr Tyr Val Glu Gln His Glu Val Ala Val Ala Arg Tyr Cys
2345                2350                2355

Asp Leu Pro Ser Lys Leu Gly His Lys Leu Asn
2360                2365

<210> SEQ ID NO 14
<211> LENGTH: 2391

```
<212> TYPE: PRT
<213> ORGANISM: Artificial sequence
<220> FEATURE:
<223> OTHER INFORMATION: Synthetic polypeptide

<400> SEQUENCE: 14
```

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
                20                  25                  30

Ala Gln Gln Ile Val Tyr Arg Asn Val Met Leu Glu Asn Tyr Lys Asn
            35                  40                  45

Leu Val Ser Leu Gly Tyr Gln Leu Thr Lys Pro Asp Val Ile Leu Arg
        50                  55                  60

Leu Glu Lys Gly Glu Glu Pro Gly Pro Ser Ser Gly Ala Pro Pro
65                  70                  75                  80

Pro Ser Gly Gly Ser Pro Ala Gly Ser Pro Thr Ser Thr Glu Glu Gly
                85                  90                  95

Thr Ser Glu Ser Ala Thr Pro Glu Ser Gly Pro Gly Thr Ser Thr Glu
                100                 105                 110

Pro Ser Glu Gly Ser Ala Pro Gly Ser Pro Ala Gly Ser Pro Thr Ser
                115                 120                 125

Thr Glu Glu Gly Thr Ser Thr Glu Pro Ser Glu Gly Ser Ala Pro Gly
130                 135                 140

Thr Ser Thr Glu Pro Ser Glu Met Asp Lys Lys Tyr Ser Ile Gly Leu
145                 150                 155                 160

Ala Ile Gly Thr Asn Ser Val Gly Trp Ala Val Ile Thr Asp Glu Tyr
                165                 170                 175

Lys Val Pro Ser Lys Lys Phe Lys Val Leu Gly Asn Thr Asp Arg His
                180                 185                 190

Ser Ile Lys Lys Asn Leu Ile Gly Ala Leu Leu Phe Asp Ser Gly Glu
            195                 200                 205

Thr Ala Glu Ala Thr Arg Leu Lys Arg Thr Ala Arg Arg Arg Tyr Thr
210                 215                 220

Arg Arg Lys Asn Arg Ile Cys Tyr Leu Gln Glu Ile Phe Ser Asn Glu
225                 230                 235                 240

Met Ala Lys Val Asp Asp Ser Phe Phe His Arg Leu Glu Glu Ser Phe
                245                 250                 255

Leu Val Glu Glu Asp Lys Lys His Glu Arg His Pro Ile Phe Gly Asn
                260                 265                 270

Ile Val Asp Glu Val Ala Tyr His Glu Lys Tyr Pro Thr Ile Tyr His
            275                 280                 285

Leu Arg Lys Lys Leu Val Asp Ser Thr Asp Lys Ala Asp Leu Arg Leu
        290                 295                 300

Ile Tyr Leu Ala Leu Ala His Met Ile Lys Phe Arg Gly His Phe Leu
305                 310                 315                 320

Ile Glu Gly Asp Leu Asn Pro Asp Asn Ser Asp Val Asp Lys Leu Phe
                325                 330                 335

Ile Gln Leu Val Gln Thr Tyr Asn Gln Leu Phe Glu Glu Asn Pro Ile
                340                 345                 350

Asn Ala Ser Gly Val Asp Ala Lys Ala Ile Leu Ser Ala Arg Leu Ser
            355                 360                 365

Lys Ser Arg Arg Leu Glu Asn Leu Ile Ala Gln Leu Pro Gly Glu Lys
        370                 375                 380

-continued

```
Lys Asn Gly Leu Phe Gly Asn Leu Ile Ala Leu Ser Leu Gly Leu Thr
385                 390                 395                 400

Pro Asn Phe Lys Ser Asn Phe Asp Leu Ala Glu Asp Ala Lys Leu Gln
                405                 410                 415

Leu Ser Lys Asp Thr Tyr Asp Asp Leu Asp Asn Leu Leu Ala Gln
            420                 425                 430

Ile Gly Asp Gln Tyr Ala Asp Leu Phe Leu Ala Ala Lys Asn Leu Ser
                435                 440                 445

Asp Ala Ile Leu Leu Ser Asp Ile Leu Arg Val Asn Thr Glu Ile Thr
450                 455                 460

Lys Ala Pro Leu Ser Ala Ser Met Ile Lys Arg Tyr Asp Glu His His
465                 470                 475                 480

Gln Asp Leu Thr Leu Leu Lys Ala Leu Val Arg Gln Gln Leu Pro Glu
                485                 490                 495

Lys Tyr Lys Glu Ile Phe Phe Asp Gln Ser Lys Asn Gly Tyr Ala Gly
                500                 505                 510

Tyr Ile Asp Gly Gly Ala Ser Gln Glu Glu Phe Tyr Lys Phe Ile Lys
                515                 520                 525

Pro Ile Leu Glu Lys Met Asp Gly Thr Glu Glu Leu Leu Val Lys Leu
530                 535                 540

Asn Arg Glu Asp Leu Leu Arg Lys Gln Arg Thr Phe Asp Asn Gly Ser
545                 550                 555                 560

Ile Pro His Gln Ile His Leu Gly Glu Leu His Ala Ile Leu Arg Arg
                565                 570                 575

Gln Glu Asp Phe Tyr Pro Phe Leu Lys Asp Asn Arg Glu Lys Ile Glu
                580                 585                 590

Lys Ile Leu Thr Phe Arg Ile Pro Tyr Tyr Val Gly Pro Leu Ala Arg
                595                 600                 605

Gly Asn Ser Arg Phe Ala Trp Met Thr Arg Lys Ser Glu Glu Thr Ile
            610                 615                 620

Thr Pro Trp Asn Phe Glu Glu Val Val Asp Lys Gly Ala Ser Ala Gln
625                 630                 635                 640

Ser Phe Ile Glu Arg Met Thr Asn Phe Asp Lys Asn Leu Pro Asn Glu
                645                 650                 655

Lys Val Leu Pro Lys His Ser Leu Leu Tyr Glu Tyr Phe Thr Val Tyr
                660                 665                 670

Asn Glu Leu Thr Lys Val Lys Tyr Val Thr Glu Gly Met Arg Lys Pro
                675                 680                 685

Ala Phe Leu Ser Gly Glu Gln Lys Lys Ala Ile Val Asp Leu Leu Phe
690                 695                 700

Lys Thr Asn Arg Lys Val Thr Val Lys Gln Leu Lys Glu Asp Tyr Phe
705                 710                 715                 720

Lys Lys Ile Glu Cys Phe Asp Ser Val Glu Ile Ser Gly Val Glu Asp
                725                 730                 735

Arg Phe Asn Ala Ser Leu Gly Thr Tyr His Asp Leu Leu Lys Ile Ile
                740                 745                 750

Lys Asp Lys Asp Phe Leu Asp Asn Glu Glu Asn Glu Asp Ile Leu Glu
                755                 760                 765

Asp Ile Val Leu Thr Leu Thr Leu Phe Glu Asp Arg Glu Met Ile Glu
                770                 775                 780

Glu Arg Leu Lys Thr Tyr Ala His Leu Phe Asp Asp Lys Val Met Lys
785                 790                 795                 800

Gln Leu Lys Arg Arg Arg Tyr Thr Gly Trp Gly Arg Leu Ser Arg Lys
```

```
                805                 810                 815
Leu Ile Asn Gly Ile Arg Asp Lys Gln Ser Gly Lys Thr Ile Leu Asp
            820                 825                 830
Phe Leu Lys Ser Asp Gly Phe Ala Asn Arg Asn Phe Met Gln Leu Ile
            835                 840                 845
His Asp Asp Ser Leu Thr Phe Lys Glu Asp Ile Gln Lys Ala Gln Val
            850                 855                 860
Ser Gly Gln Gly Asp Ser Leu His Glu His Ile Ala Asn Leu Ala Gly
865                 870                 875                 880
Ser Pro Ala Ile Lys Lys Gly Ile Leu Gln Thr Val Lys Val Val Asp
                885                 890                 895
Glu Leu Val Lys Val Met Gly Arg His Lys Pro Glu Asn Ile Val Ile
                900                 905                 910
Glu Met Ala Arg Glu Asn Gln Thr Thr Gln Lys Gly Gln Lys Asn Ser
                915                 920                 925
Arg Glu Arg Met Lys Arg Ile Glu Glu Gly Ile Lys Glu Leu Gly Ser
            930                 935                 940
Gln Ile Leu Lys Glu His Pro Val Glu Asn Thr Gln Leu Gln Asn Glu
945                 950                 955                 960
Lys Leu Tyr Leu Tyr Tyr Leu Gln Asn Gly Arg Asp Met Tyr Val Asp
                965                 970                 975
Gln Glu Leu Asp Ile Asn Arg Leu Ser Asp Tyr Asp Val Asp Ala Ile
            980                 985                 990
Val Pro Gln Ser Phe Leu Lys Asp Asp Ser Ile Asp Asn Lys Val Leu
            995                 1000                1005
Thr Arg Ser Asp Lys Asn Arg Gly Lys Ser Asp Asn Val Pro Ser
    1010                1015                1020
Glu Glu Val Val Lys Lys Met Lys Asn Tyr Trp Arg Gln Leu Leu
    1025                1030                1035
Asn Ala Lys Leu Ile Thr Gln Arg Lys Phe Asp Asn Leu Thr Lys
    1040                1045                1050
Ala Glu Arg Gly Gly Leu Ser Glu Leu Asp Lys Ala Gly Phe Ile
    1055                1060                1065
Lys Arg Gln Leu Val Glu Thr Arg Gln Ile Thr Lys His Val Ala
    1070                1075                1080
Gln Ile Leu Asp Ser Arg Met Asn Thr Lys Tyr Asp Glu Asn Asp
    1085                1090                1095
Lys Leu Ile Arg Glu Val Lys Val Ile Thr Leu Lys Ser Lys Leu
    1100                1105                1110
Val Ser Asp Phe Arg Lys Asp Phe Gln Phe Tyr Lys Val Arg Glu
    1115                1120                1125
Ile Asn Asn Tyr His His Ala His Asp Ala Tyr Leu Asn Ala Val
    1130                1135                1140
Val Gly Thr Ala Leu Ile Lys Lys Tyr Pro Lys Leu Glu Ser Glu
    1145                1150                1155
Phe Val Tyr Gly Asp Tyr Lys Val Tyr Asp Val Arg Lys Met Ile
    1160                1165                1170
Ala Lys Ser Glu Gln Glu Ile Gly Lys Ala Thr Ala Lys Tyr Phe
    1175                1180                1185
Phe Tyr Ser Asn Ile Met Asn Phe Phe Lys Thr Glu Ile Thr Leu
    1190                1195                1200
Ala Asn Gly Glu Ile Arg Lys Arg Pro Leu Ile Glu Thr Asn Gly
    1205                1210                1215
```

-continued

```
Glu Thr Gly Glu Ile Val Trp Asp Lys Gly Arg Asp Phe Ala Thr
1220                1225                1230

Val Arg Lys Val Leu Ser Met Pro Gln Val Asn Ile Val Lys Lys
1235                1240                1245

Thr Glu Val Gln Thr Gly Gly Phe Ser Lys Glu Ser Ile Leu Pro
1250                1255                1260

Lys Arg Asn Ser Asp Lys Leu Ile Ala Arg Lys Lys Asp Trp Asp
1265                1270                1275

Pro Lys Lys Tyr Gly Gly Phe Asp Ser Pro Thr Val Ala Tyr Ser
1280                1285                1290

Val Leu Val Val Ala Lys Val Glu Lys Gly Lys Ser Lys Lys Leu
1295                1300                1305

Lys Ser Val Lys Glu Leu Leu Gly Ile Thr Ile Met Glu Arg Ser
1310                1315                1320

Ser Phe Glu Lys Asn Pro Ile Asp Phe Leu Glu Ala Lys Gly Tyr
1325                1330                1335

Lys Glu Val Lys Lys Asp Leu Ile Ile Lys Leu Pro Lys Tyr Ser
1340                1345                1350

Leu Phe Glu Leu Glu Asn Gly Arg Lys Arg Met Leu Ala Ser Ala
1355                1360                1365

Gly Glu Leu Gln Lys Gly Asn Glu Leu Ala Leu Pro Ser Lys Tyr
1370                1375                1380

Val Asn Phe Leu Tyr Leu Ala Ser His Tyr Glu Lys Leu Lys Gly
1385                1390                1395

Ser Pro Glu Asp Asn Glu Gln Lys Gln Leu Phe Val Glu Gln His
1400                1405                1410

Lys His Tyr Leu Asp Glu Ile Ile Glu Gln Ile Ser Glu Phe Ser
1415                1420                1425

Lys Arg Val Ile Leu Ala Asp Ala Asn Leu Asp Lys Val Leu Ser
1430                1435                1440

Ala Tyr Asn Lys His Arg Asp Lys Pro Ile Arg Glu Gln Ala Glu
1445                1450                1455

Asn Ile Ile His Leu Phe Thr Leu Thr Asn Leu Gly Ala Pro Ala
1460                1465                1470

Ala Phe Lys Tyr Phe Asp Thr Thr Ile Asp Arg Lys Arg Tyr Thr
1475                1480                1485

Ser Thr Lys Glu Val Leu Asp Ala Thr Leu Ile His Gln Ser Ile
1490                1495                1500

Thr Gly Leu Tyr Glu Thr Arg Ile Asp Leu Ser Gln Leu Gly Gly
1505                1510                1515

Asp Ser Arg Ala Asp Tyr Pro Tyr Asp Val Pro Asp Tyr Ala Ser
1520                1525                1530

Gly Ser Pro Lys Lys Lys Arg Lys Val Ser Pro Gly Ser Gly Ser
1535                1540                1545

Glu Thr Pro Gly Thr Ser Glu Ser Ala Thr Pro Glu Ser Asn His
1550                1555                1560

Asp Gln Glu Phe Asp Pro Pro Lys Val Tyr Pro Pro Val Pro Ala
1565                1570                1575

Glu Lys Arg Lys Pro Ile Arg Val Leu Ser Leu Phe Asp Gly Ile
1580                1585                1590

Ala Thr Gly Leu Leu Val Leu Lys Asp Leu Gly Ile Gln Val Asp
1595                1600                1605
```

```
Arg Tyr Ile Ala Ser Glu Val Cys Glu Asp Ser Ile Thr Val Gly
    1610                1615                1620

Met Val Arg His Gln Gly Lys Ile Met Tyr Val Gly Asp Val Arg
    1625                1630                1635

Ser Val Thr Gln Lys His Ile Gln Glu Trp Gly Pro Phe Asp Leu
    1640                1645                1650

Val Ile Gly Gly Ser Pro Cys Asn Asp Leu Ser Ile Val Asn Pro
    1655                1660                1665

Ala Arg Lys Gly Leu Tyr Glu Gly Thr Gly Arg Leu Phe Phe Glu
    1670                1675                1680

Phe Tyr Arg Leu Leu His Asp Ala Arg Pro Lys Glu Gly Asp Asp
    1685                1690                1695

Arg Pro Phe Phe Trp Leu Phe Glu Asn Val Val Ala Met Gly Val
    1700                1705                1710

Ser Asp Lys Arg Asp Ile Ser Arg Phe Leu Glu Ser Asn Pro Val
    1715                1720                1725

Met Ile Asp Ala Lys Glu Val Ser Ala Ala His Arg Ala Arg Tyr
    1730                1735                1740

Phe Trp Gly Asn Leu Pro Gly Met Asn Arg Pro Leu Ala Ser Thr
    1745                1750                1755

Val Asn Asp Lys Leu Glu Leu Gln Glu Cys Leu Glu His Gly Arg
    1760                1765                1770

Ile Ala Lys Phe Ser Lys Val Arg Thr Ile Thr Thr Arg Ser Asn
    1775                1780                1785

Ser Ile Lys Gln Gly Lys Asp Gln His Phe Pro Val Phe Met Asn
    1790                1795                1800

Glu Lys Glu Asp Ile Leu Trp Cys Thr Glu Met Glu Arg Val Phe
    1805                1810                1815

Gly Phe Pro Val His Tyr Thr Asp Val Ser Asn Met Ser Arg Leu
    1820                1825                1830

Ala Arg Gln Arg Leu Leu Gly Arg Ser Trp Ser Val Pro Val Ile
    1835                1840                1845

Arg His Leu Phe Ala Pro Leu Lys Glu Tyr Phe Ala Cys Val Ser
    1850                1855                1860

Ser Gly Asn Ser Asn Ala Asn Ser Arg Gly Pro Ser Phe Ser Ser
    1865                1870                1875

Gly Leu Val Pro Leu Ser Leu Arg Gly Ser His Met Gly Pro Met
    1880                1885                1890

Glu Ile Tyr Lys Thr Val Ser Ala Trp Lys Arg Gln Pro Val Arg
    1895                1900                1905

Val Leu Ser Leu Phe Arg Asn Ile Asp Lys Val Leu Lys Ser Leu
    1910                1915                1920

Gly Phe Leu Glu Ser Gly Ser Gly Ser Gly Gly Thr Leu Lys
    1925                1930                1935

Tyr Val Glu Asp Val Thr Asn Val Val Arg Asp Val Glu Lys
    1940                1945                1950

Trp Gly Pro Phe Asp Leu Val Tyr Gly Ser Thr Gln Pro Leu Gly
    1955                1960                1965

Ser Ser Cys Asp Arg Cys Pro Gly Trp Tyr Met Phe Gln Phe His
    1970                1975                1980

Arg Ile Leu Gln Tyr Ala Leu Pro Arg Gln Glu Ser Gln Arg Pro
    1985                1990                1995

Phe Phe Trp Ile Phe Met Asp Asn Leu Leu Leu Thr Glu Asp Asp
```

```
                2000                2005                 2010
Gln Glu Thr Thr Thr Arg Phe Leu Gln Thr Glu Ala Val Thr Leu
    2015                2020                2025

Gln Asp Val Arg Gly Arg Asp Tyr Gln Asn Ala Met Arg Val Trp
    2030                2035                2040

Ser Asn Ile Pro Gly Leu Lys Ser Lys His Ala Pro Leu Thr Pro
    2045                2050                2055

Lys Glu Glu Glu Tyr Leu Gln Ala Gln Val Arg Ser Arg Ser Lys
    2060                2065                2070

Leu Asp Ala Pro Lys Val Asp Leu Leu Val Lys Asn Cys Leu Leu
    2075                2080                2085

Pro Leu Arg Glu Tyr Phe Lys Tyr Phe Ser Gln Asn Ser Leu Pro
    2090                2095                2100

Leu Ser Arg Ala Asp Pro Lys Lys Arg Lys Val Gly Ser Gly
    2105                2110                2115

Ala Thr Asn Phe Ser Leu Leu Lys Gln Ala Gly Asp Val Glu Glu
    2120                2125                2130

Asn Pro Gly Pro Gly Ser Gly Ala Thr Asn Phe Ser Leu Leu Lys
    2135                2140                2145

Gln Ala Gly Asp Val Glu Glu Asn Pro Gly Pro Ser Glu Leu Ile
    2150                2155                2160

Lys Glu Asn Met His Met Lys Leu Tyr Met Glu Gly Thr Val Asp
    2165                2170                2175

Asn His His Phe Lys Cys Thr Ser Glu Gly Glu Gly Lys Pro Tyr
    2180                2185                2190

Glu Gly Thr Gln Thr Met Arg Ile Lys Val Val Glu Gly Gly Pro
    2195                2200                2205

Leu Pro Phe Ala Phe Asp Ile Leu Ala Thr Ser Phe Leu Tyr Gly
    2210                2215                2220

Ser Lys Thr Phe Ile Asn His Thr Gln Gly Ile Pro Asp Phe Phe
    2225                2230                2235

Lys Gln Ser Phe Pro Glu Gly Phe Thr Trp Glu Arg Val Thr Thr
    2240                2245                2250

Tyr Glu Asp Gly Gly Val Leu Thr Ala Thr Gln Asp Thr Ser Leu
    2255                2260                2265

Gln Asp Gly Cys Leu Ile Tyr Asn Val Lys Ile Arg Gly Val Asn
    2270                2275                2280

Phe Thr Ser Asn Gly Pro Val Met Gln Lys Lys Thr Leu Gly Trp
    2285                2290                2295

Glu Ala Phe Thr Glu Thr Leu Tyr Pro Ala Asp Gly Gly Leu Glu
    2300                2305                2310

Gly Arg Asn Asp Met Ala Leu Lys Leu Val Gly Gly Ser His Leu
    2315                2320                2325

Ile Ala Asn Ile Lys Thr Thr Tyr Arg Ser Lys Lys Pro Ala Lys
    2330                2335                2340

Asn Leu Lys Met Pro Gly Val Tyr Tyr Val Asp Tyr Arg Leu Glu
    2345                2350                2355

Arg Ile Lys Glu Ala Asn Asn Glu Thr Tyr Val Glu Gln His Glu
    2360                2365                2370

Val Ala Val Ala Arg Tyr Cys Asp Leu Pro Ser Lys Leu Gly His
    2375                2380                2385

Lys Leu Asn
    2390
```

<210> SEQ ID NO 15
<211> LENGTH: 2345
<212> TYPE: PRT
<213> ORGANISM: Artificial sequence
<220> FEATURE:
<223> OTHER INFORMATION: Synthetic polypeptide

<400> SEQUENCE: 15

```
Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val Ser Ser Gly
    290                 295                 300

Asn Ser Asn Ala Asn Ser Arg Gly Pro Ser Phe Ser Ser Gly Leu Val
305                 310                 315                 320

Pro Leu Ser Leu Arg Gly Ser His Met Gly Pro Met Glu Ile Tyr Lys
                325                 330                 335

Thr Val Ser Ala Trp Lys Arg Gln Pro Val Arg Val Leu Ser Leu Phe
            340                 345                 350

Arg Asn Ile Asp Lys Val Leu Lys Ser Leu Gly Phe Leu Glu Ser Gly
        355                 360                 365
```

```
Ser Gly Ser Gly Gly Thr Leu Lys Tyr Val Glu Asp Val Thr Asn
    370             375             380

Val Val Arg Arg Asp Val Glu Lys Trp Gly Pro Phe Asp Leu Val Tyr
385             390             395             400

Gly Ser Thr Gln Pro Leu Gly Ser Ser Cys Asp Arg Cys Pro Gly Trp
            405             410             415

Tyr Met Phe Gln Phe His Arg Ile Leu Gln Tyr Ala Leu Pro Arg Gln
            420             425             430

Glu Ser Gln Arg Pro Phe Phe Trp Ile Phe Met Asp Asn Leu Leu Leu
        435             440             445

Thr Glu Asp Asp Gln Glu Thr Thr Thr Arg Phe Leu Gln Thr Glu Ala
    450             455             460

Val Thr Leu Gln Asp Val Arg Gly Arg Asp Tyr Gln Asn Ala Met Arg
465             470             475             480

Val Trp Ser Asn Ile Pro Gly Leu Lys Ser Lys His Ala Pro Leu Thr
            485             490             495

Pro Lys Glu Glu Glu Tyr Leu Gln Ala Gln Val Arg Ser Arg Ser Lys
        500             505             510

Leu Asp Ala Pro Lys Val Asp Leu Leu Val Lys Asn Cys Leu Leu Pro
    515             520             525

Leu Arg Glu Tyr Phe Lys Tyr Phe Ser Gln Asn Ser Leu Pro Leu Gly
    530             535             540

Gly Pro Ser Ser Gly Ala Pro Pro Ser Gly Ser Pro Ala Gly
545             550             555             560

Ser Pro Thr Ser Thr Glu Glu Gly Thr Ser Glu Ser Ala Thr Pro Glu
            565             570             575

Ser Gly Pro Gly Thr Ser Thr Glu Pro Ser Glu Gly Ser Ala Pro Gly
            580             585             590

Ser Pro Ala Gly Ser Pro Thr Ser Thr Glu Glu Gly Thr Ser Thr Glu
    595             600             605

Pro Ser Glu Gly Ser Ala Pro Gly Thr Ser Thr Glu Pro Ser Glu Met
    610             615             620

Asp Lys Lys Tyr Ser Ile Gly Leu Ala Ile Gly Thr Asn Ser Val Gly
625             630             635             640

Trp Ala Val Ile Thr Asp Glu Tyr Lys Val Pro Ser Lys Lys Phe Lys
            645             650             655

Val Leu Gly Asn Thr Asp Arg His Ser Ile Lys Lys Asn Leu Ile Gly
            660             665             670

Ala Leu Leu Phe Asp Ser Gly Glu Thr Ala Glu Ala Thr Arg Leu Lys
    675             680             685

Arg Thr Ala Arg Arg Arg Tyr Thr Arg Arg Lys Asn Arg Ile Cys Tyr
    690             695             700

Leu Gln Glu Ile Phe Ser Asn Glu Met Ala Lys Val Asp Asp Ser Phe
705             710             715             720

Phe His Arg Leu Glu Glu Ser Phe Leu Val Glu Glu Asp Lys Lys His
            725             730             735

Glu Arg His Pro Ile Phe Gly Asn Ile Val Asp Glu Val Ala Tyr His
            740             745             750

Glu Lys Tyr Pro Thr Ile Tyr His Leu Arg Lys Lys Leu Val Asp Ser
    755             760             765

Thr Asp Lys Ala Asp Leu Arg Leu Ile Tyr Leu Ala Leu Ala His Met
    770             775             780
```

```
Ile Lys Phe Arg Gly His Phe Leu Ile Glu Gly Asp Leu Asn Pro Asp
785                 790                 795                 800

Asn Ser Asp Val Asp Lys Leu Phe Ile Gln Leu Val Gln Thr Tyr Asn
            805                 810                 815

Gln Leu Phe Glu Glu Asn Pro Ile Asn Ala Ser Gly Val Asp Ala Lys
        820                 825                 830

Ala Ile Leu Ser Ala Arg Leu Ser Lys Ser Arg Arg Leu Glu Asn Leu
            835                 840                 845

Ile Ala Gln Leu Pro Gly Glu Lys Lys Asn Gly Leu Phe Gly Asn Leu
        850                 855                 860

Ile Ala Leu Ser Leu Gly Leu Thr Pro Asn Phe Lys Ser Asn Phe Asp
865                 870                 875                 880

Leu Ala Glu Asp Ala Lys Leu Gln Leu Ser Lys Asp Thr Tyr Asp Asp
            885                 890                 895

Asp Leu Asp Asn Leu Leu Ala Gln Ile Gly Asp Gln Tyr Ala Asp Leu
        900                 905                 910

Phe Leu Ala Ala Lys Asn Leu Ser Asp Ala Ile Leu Leu Ser Asp Ile
        915                 920                 925

Leu Arg Val Asn Thr Glu Ile Thr Lys Ala Pro Leu Ser Ala Ser Met
930                 935                 940

Ile Lys Arg Tyr Asp Glu His His Gln Asp Leu Thr Leu Leu Lys Ala
945                 950                 955                 960

Leu Val Arg Gln Gln Leu Pro Glu Lys Tyr Lys Glu Ile Phe Phe Asp
                965                 970                 975

Gln Ser Lys Asn Gly Tyr Ala Gly Tyr Ile Asp Gly Gly Ala Ser Gln
            980                 985                 990

Glu Glu Phe Tyr Lys Phe Ile Lys Pro Ile Leu Glu Lys Met Asp Gly
        995                 1000                1005

Thr Glu Glu Leu Leu Val Lys Leu Asn Arg Glu Asp Leu Leu Arg
    1010            1015            1020

Lys Gln Arg Thr Phe Asp Asn Gly Ser Ile Pro His Gln Ile His
    1025            1030            1035

Leu Gly Glu Leu His Ala Ile Leu Arg Arg Gln Glu Asp Phe Tyr
    1040            1045            1050

Pro Phe Leu Lys Asp Asn Arg Glu Lys Ile Glu Lys Ile Leu Thr
    1055            1060            1065

Phe Arg Ile Pro Tyr Tyr Val Gly Pro Leu Ala Arg Gly Asn Ser
    1070            1075            1080

Arg Phe Ala Trp Met Thr Arg Lys Ser Glu Glu Thr Ile Thr Pro
    1085            1090            1095

Trp Asn Phe Glu Glu Val Val Asp Lys Gly Ala Ser Ala Gln Ser
    1100            1105            1110

Phe Ile Glu Arg Met Thr Asn Phe Asp Lys Asn Leu Pro Asn Glu
    1115            1120            1125

Lys Val Leu Pro Lys His Ser Leu Leu Tyr Glu Tyr Phe Thr Val
    1130            1135            1140

Tyr Asn Glu Leu Thr Lys Val Lys Tyr Val Thr Glu Gly Met Arg
    1145            1150            1155

Lys Pro Ala Phe Leu Ser Gly Glu Gln Lys Lys Ala Ile Val Asp
    1160            1165            1170

Leu Leu Phe Lys Thr Asn Arg Lys Val Thr Val Lys Gln Leu Lys
    1175            1180            1185

Glu Asp Tyr Phe Lys Lys Ile Glu Cys Phe Asp Ser Val Glu Ile
```

-continued

```
                 1190                1195                1200
Ser Gly Val Glu Asp Arg Phe Asn Ala Ser Leu Gly Thr Tyr His
    1205                1210                1215
Asp Leu Leu Lys Ile Ile Lys Asp Lys Asp Phe Leu Asp Asn Glu
    1220                1225                1230
Glu Asn Glu Asp Ile Leu Glu Asp Ile Val Leu Thr Leu Thr Leu
    1235                1240                1245
Phe Glu Asp Arg Glu Met Ile Glu Glu Arg Leu Lys Thr Tyr Ala
    1250                1255                1260
His Leu Phe Asp Asp Lys Val Met Lys Gln Leu Lys Arg Arg Arg
    1265                1270                1275
Tyr Thr Gly Trp Gly Arg Leu Ser Arg Lys Leu Ile Asn Gly Ile
    1280                1285                1290
Arg Asp Lys Gln Ser Gly Lys Thr Ile Leu Asp Phe Leu Lys Ser
    1295                1300                1305
Asp Gly Phe Ala Asn Arg Asn Phe Met Gln Leu Ile His Asp Asp
    1310                1315                1320
Ser Leu Thr Phe Lys Glu Asp Ile Gln Lys Ala Gln Val Ser Gly
    1325                1330                1335
Gln Gly Asp Ser Leu His Glu His Ile Ala Asn Leu Ala Gly Ser
    1340                1345                1350
Pro Ala Ile Lys Lys Gly Ile Leu Gln Thr Val Lys Val Val Asp
    1355                1360                1365
Glu Leu Val Lys Val Met Gly Arg His Lys Pro Glu Asn Ile Val
    1370                1375                1380
Ile Glu Met Ala Arg Glu Asn Gln Thr Thr Gln Lys Gly Gln Lys
    1385                1390                1395
Asn Ser Arg Glu Arg Met Lys Arg Ile Glu Glu Gly Ile Lys Glu
    1400                1405                1410
Leu Gly Ser Gln Ile Leu Lys Glu His Pro Val Glu Asn Thr Gln
    1415                1420                1425
Leu Gln Asn Glu Lys Leu Tyr Leu Tyr Tyr Leu Gln Asn Gly Arg
    1430                1435                1440
Asp Met Tyr Val Asp Gln Glu Leu Asp Ile Asn Arg Leu Ser Asp
    1445                1450                1455
Tyr Asp Val Asp Ala Ile Val Pro Gln Ser Phe Leu Lys Asp Asp
    1460                1465                1470
Ser Ile Asp Asn Lys Val Leu Thr Arg Ser Asp Lys Asn Arg Gly
    1475                1480                1485
Lys Ser Asp Asn Val Pro Ser Glu Glu Val Val Lys Lys Met Lys
    1490                1495                1500
Asn Tyr Trp Arg Gln Leu Leu Asn Ala Lys Leu Ile Thr Gln Arg
    1505                1510                1515
Lys Phe Asp Asn Leu Thr Lys Ala Glu Arg Gly Gly Leu Ser Glu
    1520                1525                1530
Leu Asp Lys Ala Gly Phe Ile Lys Arg Gln Leu Val Glu Thr Arg
    1535                1540                1545
Gln Ile Thr Lys His Val Ala Gln Ile Leu Asp Ser Arg Met Asn
    1550                1555                1560
Thr Lys Tyr Asp Glu Asn Asp Lys Leu Ile Arg Glu Val Lys Val
    1565                1570                1575
Ile Thr Leu Lys Ser Lys Leu Val Ser Asp Phe Arg Lys Asp Phe
    1580                1585                1590
```

-continued

```
Gln Phe Tyr Lys Val Arg Glu Ile Asn Asn Tyr His His Ala His
1595                1600                1605

Asp Ala Tyr Leu Asn Ala Val Val Gly Thr Ala Leu Ile Lys Lys
1610                1615                1620

Tyr Pro Lys Leu Glu Ser Glu Phe Val Tyr Gly Asp Tyr Lys Val
1625                1630                1635

Tyr Asp Val Arg Lys Met Ile Ala Lys Ser Glu Gln Glu Ile Gly
1640                1645                1650

Lys Ala Thr Ala Lys Tyr Phe Phe Tyr Ser Asn Ile Met Asn Phe
1655                1660                1665

Phe Lys Thr Glu Ile Thr Leu Ala Asn Gly Glu Ile Arg Lys Arg
1670                1675                1680

Pro Leu Ile Glu Thr Asn Gly Glu Thr Gly Glu Ile Val Trp Asp
1685                1690                1695

Lys Gly Arg Asp Phe Ala Thr Val Arg Lys Val Leu Ser Met Pro
1700                1705                1710

Gln Val Asn Ile Val Lys Lys Thr Glu Val Gln Thr Gly Gly Phe
1715                1720                1725

Ser Lys Glu Ser Ile Leu Pro Lys Arg Asn Ser Asp Lys Leu Ile
1730                1735                1740

Ala Arg Lys Lys Asp Trp Asp Pro Lys Lys Tyr Gly Gly Phe Asp
1745                1750                1755

Ser Pro Thr Val Ala Tyr Ser Val Leu Val Val Ala Lys Val Glu
1760                1765                1770

Lys Gly Lys Ser Lys Lys Leu Lys Ser Val Lys Glu Leu Leu Gly
1775                1780                1785

Ile Thr Ile Met Glu Arg Ser Ser Phe Glu Lys Asn Pro Ile Asp
1790                1795                1800

Phe Leu Glu Ala Lys Gly Tyr Lys Glu Val Lys Lys Asp Leu Ile
1805                1810                1815

Ile Lys Leu Pro Lys Tyr Ser Leu Phe Glu Leu Glu Asn Gly Arg
1820                1825                1830

Lys Arg Met Leu Ala Ser Ala Gly Glu Leu Gln Lys Gly Asn Glu
1835                1840                1845

Leu Ala Leu Pro Ser Lys Tyr Val Asn Phe Leu Tyr Leu Ala Ser
1850                1855                1860

His Tyr Glu Lys Leu Lys Gly Ser Pro Glu Asp Asn Glu Gln Lys
1865                1870                1875

Gln Leu Phe Val Glu Gln His Lys His Tyr Leu Asp Glu Ile Ile
1880                1885                1890

Glu Gln Ile Ser Glu Phe Ser Lys Arg Val Ile Leu Ala Asp Ala
1895                1900                1905

Asn Leu Asp Lys Val Leu Ser Ala Tyr Asn Lys His Arg Asp Lys
1910                1915                1920

Pro Ile Arg Glu Gln Ala Glu Asn Ile Ile His Leu Phe Thr Leu
1925                1930                1935

Thr Asn Leu Gly Ala Pro Ala Ala Phe Lys Tyr Phe Asp Thr Thr
1940                1945                1950

Ile Asp Arg Lys Arg Tyr Thr Ser Thr Lys Glu Val Leu Asp Ala
1955                1960                1965

Thr Leu Ile His Gln Ser Ile Thr Gly Leu Tyr Glu Thr Arg Ile
1970                1975                1980
```

```
Asp Leu Ser Gln Leu Gly Gly Asp Ala Tyr Pro Tyr Asp Val Pro
    1985                1990                1995

Asp Tyr Ala Ser Leu Gly Ser Gly Ser Pro Lys Lys Lys Arg Lys
    2000                2005                2010

Val Glu Asp Pro Lys Lys Arg Lys Val Asp Gly Ile Gly Ser
    2015                2020                2025

Gly Ser Asn Gly Ser Ser Gly Ser Ser Glu Leu Ile Lys Glu Asn
    2030                2035                2040

Met His Met Lys Leu Tyr Met Glu Gly Thr Val Asp Asn His His
    2045                2050                2055

Phe Lys Cys Thr Ser Glu Gly Glu Gly Lys Pro Tyr Glu Gly Thr
    2060                2065                2070

Gln Thr Met Arg Ile Lys Val Val Glu Gly Gly Pro Leu Pro Phe
    2075                2080                2085

Ala Phe Asp Ile Leu Ala Thr Ser Phe Leu Tyr Gly Ser Lys Thr
    2090                2095                2100

Phe Ile Asn His Thr Gln Gly Ile Pro Asp Phe Phe Lys Gln Ser
    2105                2110                2115

Phe Pro Glu Gly Phe Thr Trp Glu Arg Val Thr Thr Tyr Glu Asp
    2120                2125                2130

Gly Gly Val Leu Thr Ala Thr Gln Asp Thr Ser Leu Gln Asp Gly
    2135                2140                2145

Cys Leu Ile Tyr Asn Val Lys Ile Arg Gly Val Asn Phe Thr Ser
    2150                2155                2160

Asn Gly Pro Val Met Gln Lys Lys Thr Leu Gly Trp Glu Ala Phe
    2165                2170                2175

Thr Glu Thr Leu Tyr Pro Ala Asp Gly Gly Leu Glu Gly Arg Asn
    2180                2185                2190

Asp Met Ala Leu Lys Leu Val Gly Gly Ser His Leu Ile Ala Asn
    2195                2200                2205

Ile Lys Thr Thr Tyr Arg Ser Lys Lys Pro Ala Lys Asn Leu Lys
    2210                2215                2220

Met Pro Gly Val Tyr Tyr Val Asp Tyr Arg Leu Glu Arg Ile Lys
    2225                2230                2235

Glu Ala Asn Asn Glu Thr Tyr Val Glu Gln His Glu Val Ala Val
    2240                2245                2250

Ala Arg Tyr Cys Asp Leu Pro Ser Lys Leu Gly His Lys Leu Asn
    2255                2260                2265

Gly Gly Gly Gly Met Asp Ala Lys Ser Leu Thr Ala Trp Ser
    2270                2275                2280

Arg Thr Leu Val Thr Phe Lys Asp Val Phe Val Asp Phe Thr Arg
    2285                2290                2295

Glu Glu Trp Lys Leu Leu Asp Thr Ala Gln Gln Ile Val Tyr Arg
    2300                2305                2310

Asn Val Met Leu Glu Asn Tyr Lys Asn Leu Val Ser Leu Gly Tyr
    2315                2320                2325

Gln Leu Thr Lys Pro Asp Val Ile Leu Arg Leu Glu Lys Gly Glu
    2330                2335                2340

Glu Pro
    2345

<210> SEQ ID NO 16
<211> LENGTH: 71
<212> TYPE: PRT
```

```
<213> ORGANISM: Artificial sequence
<220> FEATURE:
<223> OTHER INFORMATION: Synthetic polypeptide

<400> SEQUENCE: 16

Asp Ala Lys Ser Leu Thr Ala Trp Ser Arg Thr Leu Val Thr Phe Lys
1               5                   10                  15

Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro
65                  70

<210> SEQ ID NO 17
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 17

Gly Gly Ser Gly Gly Gly Ser
1               5

<210> SEQ ID NO 18
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 18

Ser Gly Ser
1

<210> SEQ ID NO 19
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 19

Glu Ala Ser Gly Ser Gly Arg Ala Ser Pro Gly Ile Pro Gly Ser Thr
1               5                   10                  15

Arg

<210> SEQ ID NO 20
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 20

Ser Arg Ala Asp
1

<210> SEQ ID NO 21
<211> LENGTH: 3
<212> TYPE: PRT
```

<213> ORGANISM: Artificial sequence
<220> FEATURE:
<223> OTHER INFORMATION: Synthetic polypeptide

<400> SEQUENCE: 21

Gly Ser Gly
1

<210> SEQ ID NO 22
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 22

Ser Pro Gly
1

<210> SEQ ID NO 23
<211> LENGTH: 1368
<212> TYPE: PRT
<213> ORGANISM: Artificial sequence
<220> FEATURE:
<223> OTHER INFORMATION: Synthetic polypeptide

<400> SEQUENCE: 23

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

```
Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
             675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
             725                 730                 735

Ile Leu Gln Thr Val Lys Val Val Asp Glu Leu Val Lys Val Met Gly
             740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
             805                 810                 815

Gln Asn Gly Arg Asp Met Tyr Val Asp Gln Glu Leu Asp Ile Asn Arg
        820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
             885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
             965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
```

-continued

```
            1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 24
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 24

```
Tyr Pro Tyr Asp Val Pro Asp Tyr Ala
1               5
```

<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 25

```
Pro Lys Lys Lys Arg Lys Val
1               5
```

<210> SEQ ID NO 26
<211> LENGTH: 301
<212> TYPE: PRT
<213> ORGANISM: Artificial sequence
<220> FEATURE:
<223> OTHER INFORMATION: Synthetic polypeptide

<400> SEQUENCE: 26

```
Asn His Asp Gln Glu Phe Asp Pro Pro Lys Val Tyr Pro Pro Val Pro
1               5                   10                  15

Ala Glu Lys Arg Lys Pro Ile Arg Val Leu Ser Leu Phe Asp Gly Ile
            20                  25                  30

Ala Thr Gly Leu Leu Val Leu Lys Asp Leu Gly Ile Gln Val Asp Arg
        35                  40                  45

Tyr Ile Ala Ser Glu Val Cys Glu Asp Ser Ile Thr Val Gly Met Val
    50                  55                  60

Arg His Gln Gly Lys Ile Met Tyr Val Gly Asp Val Arg Ser Val Thr
65                  70                  75                  80

Gln Lys His Ile Gln Glu Trp Gly Pro Phe Asp Leu Val Ile Gly Gly
                85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val
    290                 295                 300
```

<210> SEQ ID NO 27
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 27

Ser Ser Gly Asn Ser Asn Ala Asn Ser Arg Gly Pro Ser Phe Ser Ser
1               5                   10                  15

Gly Leu Val Pro Leu Ser Leu Arg Gly Ser His
            20                  25

<210> SEQ ID NO 28
<211> LENGTH: 215
<212> TYPE: PRT
<213> ORGANISM: Artificial sequence
<220> FEATURE:
<223> OTHER INFORMATION: Synthetic polypeptide

<400> SEQUENCE: 28

Met Gly Pro Met Glu Ile Tyr Lys Thr Val Ser Ala Trp Lys Arg Gln
1               5                   10                  15

Pro Val Arg Val Leu Ser Leu Phe Arg Asn Ile Asp Lys Val Leu Lys
            20                  25                  30

Ser Leu Gly Phe Leu Glu Ser Gly Ser Gly Ser Gly Gly Gly Thr Leu
        35                  40                  45

Lys Tyr Val Glu Asp Val Thr Asn Val Val Arg Arg Asp Val Glu Lys
    50                  55                  60

Trp Gly Pro Phe Asp Leu Val Tyr Gly Ser Thr Gln Pro Leu Gly Ser
65                  70                  75                  80

Ser Cys Asp Arg Cys Pro Gly Trp Tyr Met Phe Gln Phe His Arg Ile
                85                  90                  95

Leu Gln Tyr Ala Leu Pro Arg Gln Glu Ser Gln Arg Pro Phe Phe Trp
            100                 105                 110

Ile Phe Met Asp Asn Leu Leu Leu Thr Glu Asp Asp Gln Glu Thr Thr
        115                 120                 125

Thr Arg Phe Leu Gln Thr Glu Ala Val Thr Leu Gln Asp Val Arg Gly
    130                 135                 140

Arg Asp Tyr Gln Asn Ala Met Arg Val Trp Ser Asn Ile Pro Gly Leu
145                 150                 155                 160

Lys Ser Lys His Ala Pro Leu Thr Pro Lys Glu Glu Glu Tyr Leu Gln
                165                 170                 175

Ala Gln Val Arg Ser Arg Ser Lys Leu Asp Ala Pro Lys Val Asp Leu
            180                 185                 190

Leu Val Lys Asn Cys Leu Leu Pro Leu Arg Glu Tyr Phe Lys Tyr Phe
        195                 200                 205

Ser Gln Asn Ser Leu Pro Leu
    210                 215

<210> SEQ ID NO 29
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 29

Ala Thr Asn Phe Ser Leu Leu Lys Gln Ala Gly Asp Val Glu Glu Asn
1               5                   10                  15

Pro Gly Pro

<210> SEQ ID NO 30
<211> LENGTH: 232
<212> TYPE: PRT
<213> ORGANISM: Artificial sequence

```
<220> FEATURE:
<223> OTHER INFORMATION: Synthetic polypeptide

<400> SEQUENCE: 30

Ser Glu Leu Ile Lys Glu Asn Met His Met Lys Leu Tyr Met Glu Gly
1               5                   10                  15

Thr Val Asp Asn His His Phe Lys Cys Thr Ser Glu Gly Glu Gly Lys
            20                  25                  30

Pro Tyr Glu Gly Thr Gln Thr Met Arg Ile Lys Val Val Glu Gly Gly
        35                  40                  45

Pro Leu Pro Phe Ala Phe Asp Ile Leu Ala Thr Ser Phe Leu Tyr Gly
    50                  55                  60

Ser Lys Thr Phe Ile Asn His Thr Gln Gly Ile Pro Asp Phe Phe Lys
65                  70                  75                  80

Gln Ser Phe Pro Glu Gly Phe Thr Trp Glu Arg Val Thr Thr Tyr Glu
                85                  90                  95

Asp Gly Gly Val Leu Thr Ala Thr Gln Asp Thr Ser Leu Gln Asp Gly
            100                 105                 110

Cys Leu Ile Tyr Asn Val Lys Ile Arg Gly Val Asn Phe Thr Ser Asn
        115                 120                 125

Gly Pro Val Met Gln Lys Lys Thr Leu Gly Trp Glu Ala Phe Thr Glu
    130                 135                 140

Thr Leu Tyr Pro Ala Asp Gly Gly Leu Glu Gly Arg Asn Asp Met Ala
145                 150                 155                 160

Leu Lys Leu Val Gly Gly Ser His Leu Ile Ala Asn Ile Lys Thr Thr
                165                 170                 175

Tyr Arg Ser Lys Lys Pro Ala Lys Asn Leu Lys Met Pro Gly Val Tyr
            180                 185                 190

Tyr Val Asp Tyr Arg Leu Glu Arg Ile Lys Glu Ala Asn Asn Glu Thr
        195                 200                 205

Tyr Val Glu Gln His Glu Val Ala Val Ala Arg Tyr Cys Asp Leu Pro
    210                 215                 220

Ser Lys Leu Gly His Lys Leu Asn
225                 230

<210> SEQ ID NO 31
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 31

Ser Gly Ser Glu Thr Pro Gly Thr Ser Glu Ser Ala Thr Pro Glu Ser
1               5                   10                  15

<210> SEQ ID NO 32
<211> LENGTH: 80
<212> TYPE: PRT
<213> ORGANISM: Artificial sequence
<220> FEATURE:
<223> OTHER INFORMATION: Synthetic polypeptide

<400> SEQUENCE: 32

Gly Gly Pro Ser Ser Gly Ala Pro Pro Ser Gly Gly Ser Pro Ala
1               5                   10                  15

Gly Ser Pro Thr Ser Thr Glu Glu Gly Thr Ser Glu Ser Ala Thr Pro
            20                  25                  30
```

```
Glu Ser Gly Pro Gly Thr Ser Thr Glu Pro Ser Glu Gly Ser Ala Pro
             35                  40                  45

Gly Ser Pro Ala Gly Ser Pro Thr Ser Thr Glu Gly Thr Ser Thr
 50                  55                  60

Glu Pro Ser Glu Gly Ser Ala Pro Gly Thr Ser Thr Glu Pro Ser Glu
 65                  70                  75                  80

<210> SEQ ID NO 33
<211> LENGTH: 543
<212> TYPE: PRT
<213> ORGANISM: Artificial sequence
<220> FEATURE:
<223> OTHER INFORMATION: Synthetic polypeptide

<400> SEQUENCE: 33

Asn His Asp Gln Glu Phe Asp Pro Pro Lys Val Tyr Pro Pro Val Pro
 1               5                  10                  15

Ala Glu Lys Arg Lys Pro Ile Arg Val Leu Ser Leu Phe Asp Gly Ile
             20                  25                  30

Ala Thr Gly Leu Leu Val Leu Lys Asp Leu Gly Ile Gln Val Asp Arg
         35                  40                  45

Tyr Ile Ala Ser Glu Val Cys Glu Asp Ser Ile Thr Val Gly Met Val
 50                  55                  60

Arg His Gln Gly Lys Ile Met Tyr Val Gly Asp Val Arg Ser Val Thr
 65                  70                  75                  80

Gln Lys His Ile Gln Glu Trp Gly Pro Phe Asp Leu Val Ile Gly Gly
             85                  90                  95

Ser Pro Cys Asn Asp Leu Ser Ile Val Asn Pro Ala Arg Lys Gly Leu
            100                 105                 110

Tyr Glu Gly Thr Gly Arg Leu Phe Phe Glu Phe Tyr Arg Leu Leu His
        115                 120                 125

Asp Ala Arg Pro Lys Glu Gly Asp Asp Arg Pro Phe Phe Trp Leu Phe
    130                 135                 140

Glu Asn Val Val Ala Met Gly Val Ser Asp Lys Arg Asp Ile Ser Arg
145                 150                 155                 160

Phe Leu Glu Ser Asn Pro Val Met Ile Asp Ala Lys Glu Val Ser Ala
                165                 170                 175

Ala His Arg Ala Arg Tyr Phe Trp Gly Asn Leu Pro Gly Met Asn Arg
            180                 185                 190

Pro Leu Ala Ser Thr Val Asn Asp Lys Leu Glu Leu Gln Glu Cys Leu
        195                 200                 205

Glu His Gly Arg Ile Ala Lys Phe Ser Lys Val Arg Thr Ile Thr Thr
    210                 215                 220

Arg Ser Asn Ser Ile Lys Gln Gly Lys Asp Gln His Phe Pro Val Phe
225                 230                 235                 240

Met Asn Glu Lys Glu Asp Ile Leu Trp Cys Thr Glu Met Glu Arg Val
                245                 250                 255

Phe Gly Phe Pro Val His Tyr Thr Asp Val Ser Asn Met Ser Arg Leu
            260                 265                 270

Ala Arg Gln Arg Leu Leu Gly Arg Ser Trp Ser Val Pro Val Ile Arg
        275                 280                 285

His Leu Phe Ala Pro Leu Lys Glu Tyr Phe Ala Cys Val Ser Ser Gly
    290                 295                 300

Asn Ser Asn Ala Asn Ser Arg Gly Pro Ser Phe Ser Ser Gly Leu Val
305                 310                 315                 320
```

```
Pro Leu Ser Leu Arg Gly Ser His Met Gly Pro Met Glu Ile Tyr Lys
            325                 330                 335

Thr Val Ser Ala Trp Lys Arg Gln Pro Val Arg Val Leu Ser Leu Phe
        340                 345                 350

Arg Asn Ile Asp Lys Val Leu Lys Ser Leu Gly Phe Leu Glu Ser Gly
            355                 360                 365

Ser Gly Ser Gly Gly Thr Leu Lys Tyr Val Glu Asp Val Thr Asn
        370                 375                 380

Val Val Arg Arg Asp Val Glu Lys Trp Gly Pro Phe Asp Leu Val Tyr
385                 390                 395                 400

Gly Ser Thr Gln Pro Leu Gly Ser Ser Cys Asp Arg Cys Pro Gly Trp
            405                 410                 415

Tyr Met Phe Gln Phe His Arg Ile Leu Gln Tyr Ala Leu Pro Arg Gln
        420                 425                 430

Glu Ser Gln Arg Pro Phe Phe Trp Ile Phe Met Asp Asn Leu Leu Leu
            435                 440                 445

Thr Glu Asp Asp Gln Gly Thr Thr Thr Arg Phe Leu Gln Thr Glu Ala
        450                 455                 460

Val Thr Leu Gln Asp Val Arg Gly Arg Asp Tyr Gln Asn Ala Met Arg
465                 470                 475                 480

Val Trp Ser Asn Ile Pro Gly Leu Lys Ser Lys His Ala Pro Leu Thr
            485                 490                 495

Pro Lys Glu Glu Glu Tyr Leu Gln Ala Gln Val Arg Ser Arg Ser Lys
        500                 505                 510

Leu Asp Ala Pro Lys Val Asp Leu Leu Val Lys Asn Cys Leu Leu Pro
            515                 520                 525

Leu Arg Glu Tyr Phe Lys Tyr Phe Ser Gln Asn Ser Leu Pro Leu
        530                 535                 540

<210> SEQ ID NO 34
<211> LENGTH: 1307
<212> TYPE: PRT
<213> ORGANISM: Artificial sequence
<220> FEATURE:
<223> OTHER INFORMATION: Synthetic polypeptide

<400> SEQUENCE: 34

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140
```

```
Gln Leu Gly Thr Val Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
            165                 170                 175

Lys Asn Val Phe Ser Ala Glu Asp Ile Ser Thr Ala Ile Pro His Arg
        180                 185                 190

Ile Val Gln Asp Asn Phe Pro Lys Phe Lys Glu Asn Cys His Ile Phe
    195                 200                 205

Thr Arg Leu Ile Thr Ala Val Pro Ser Leu Arg Glu His Phe Glu Asn
210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
```

```
              565                 570                 575
Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990
```

```
Ala Asn Leu Asn Phe Gly Phe Lys  Ser Lys Arg Thr Gly  Ile Ala Glu
        995                 1000                 1005

Lys Ala Val Tyr Gln Gln Phe  Glu Lys Met Leu Ile  Asp Lys Leu
        1010                1015               1020

Asn Cys Leu Val Leu Lys Asp  Tyr Pro Ala Glu Lys  Val Gly Gly
        1025                1030               1035

Val Leu Asn Pro Tyr Gln Leu  Thr Asp Gln Phe Thr  Ser Phe Ala
        1040                1045               1050

Lys Met Gly Thr Gln Ser Gly  Phe Leu Phe Tyr Val  Pro Ala Pro
        1055                1060               1065

Tyr Thr Ser Lys Ile Asp Pro  Leu Thr Gly Phe Val  Asp Pro Phe
        1070                1075               1080

Val Trp Lys Thr Ile Lys Asn  His Glu Ser Arg Lys  His Phe Leu
        1085                1090               1095

Glu Gly Phe Asp Phe Leu His  Tyr Asp Val Lys Thr  Gly Asp Phe
        1100                1105               1110

Ile Leu His Phe Lys Met Asn  Arg Asn Leu Ser Phe  Gln Arg Gly
        1115                1120               1125

Leu Pro Gly Phe Met Pro Ala  Trp Asp Ile Val Phe  Glu Lys Asn
        1130                1135               1140

Glu Thr Gln Phe Asp Ala Lys  Gly Thr Pro Phe Ile  Ala Gly Lys
        1145                1150               1155

Arg Ile Val Pro Val Ile Glu  Asn His Arg Phe Thr  Gly Arg Tyr
        1160                1165               1170

Arg Asp Leu Tyr Pro Ala Asn  Glu Leu Ile Ala Leu  Leu Glu Glu
        1175                1180               1185

Lys Gly Ile Val Phe Arg Asp  Gly Ser Asn Ile Leu  Pro Lys Leu
        1190                1195               1200

Leu Glu Asn Asp Asp Ser His  Ala Ile Asp Thr Met  Val Ala Leu
        1205                1210               1215

Ile Arg Ser Val Leu Gln Met  Arg Asn Ser Asn Ala  Ala Thr Gly
        1220                1225               1230

Glu Asp Tyr Ile Asn Ser Pro  Val Arg Asp Leu Asn  Gly Val Cys
        1235                1240               1245

Phe Asp Ser Arg Phe Gln Asn  Pro Glu Trp Pro Met  Asp Ala Asp
        1250                1255               1260

Ala Asn Gly Ala Tyr His Ile  Ala Leu Lys Gly Gln  Leu Leu Leu
        1265                1270               1275

Asn His Leu Lys Glu Ser Lys  Asp Leu Lys Leu Gln  Asn Gly Ile
        1280                1285               1290

Ser Asn Gln Asp Trp Leu Ala  Tyr Ile Gln Glu Leu  Arg Asn
        1295                1300               1305

<210> SEQ ID NO 35
<211> LENGTH: 1228
<212> TYPE: PRT
<213> ORGANISM: Artificial sequence
<220> FEATURE:
<223> OTHER INFORMATION: Synthetic polypeptide

<400> SEQUENCE: 35

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30
```

```
Asn Lys Arg Leu Leu Val Glu Asp Glu Lys Arg Ala Glu Asp Tyr Lys
         35                  40                  45

Gly Val Lys Lys Leu Leu Asp Arg Tyr Tyr Leu Ser Phe Ile Asn Asp
     50                  55                  60

Val Leu His Ser Ile Lys Leu Lys Asn Leu Asn Asn Tyr Ile Ser Leu
 65                  70                  75                  80

Phe Arg Lys Lys Thr Arg Thr Glu Lys Glu Asn Lys Glu Leu Glu Asn
                 85                  90                  95

Leu Glu Ile Asn Leu Arg Lys Glu Ile Ala Lys Ala Phe Lys Gly Asn
             100                 105                 110

Glu Gly Tyr Lys Ser Leu Phe Lys Lys Asp Ile Ile Glu Thr Ile Leu
             115                 120                 125

Pro Glu Phe Leu Asp Asp Lys Asp Glu Ile Ala Leu Val Asn Ser Phe
         130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                 165                 170                 175

Asn Glu Asn Leu Thr Arg Tyr Ile Ser Asn Met Asp Ile Phe Glu Lys
             180                 185                 190

Val Asp Ala Ile Phe Asp Lys His Glu Val Gln Glu Ile Lys Glu Lys
         195                 200                 205

Ile Leu Asn Ser Asp Tyr Asp Val Glu Asp Phe Phe Glu Gly Glu Phe
     210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                 245                 250                 255

Glu Tyr Ile Asn Leu Tyr Asn Gln Lys Thr Lys Gln Lys Leu Pro Lys
             260                 265                 270

Phe Lys Pro Leu Tyr Lys Gln Val Leu Ser Asp Arg Glu Ser Leu Ser
         275                 280                 285

Phe Tyr Gly Glu Gly Tyr Thr Ser Asp Glu Glu Val Leu Glu Val Phe
     290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                 325                 330                 335

Phe Val Lys Asn Gly Pro Ala Ile Ser Thr Ile Ser Lys Asp Ile Phe
             340                 345                 350

Gly Glu Trp Asn Val Ile Arg Asp Lys Trp Asn Ala Glu Tyr Asp Asp
         355                 360                 365

Ile His Leu Lys Lys Lys Ala Val Val Thr Glu Lys Tyr Glu Asp Asp
     370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                 405                 410                 415

Ile Ile Ile Gln Lys Val Asp Glu Ile Tyr Lys Val Tyr Gly Ser Ser
             420                 425                 430

Glu Lys Leu Phe Asp Ala Asp Phe Val Leu Glu Lys Ser Leu Lys Lys
         435                 440                 445
```

```
Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
    755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Ala
                820                 825                 830

Arg Gly Glu Arg Asn Leu Leu Tyr Ile Val Val Asp Gly Lys Gly
            835                 840                 845

Asn Ile Val Glu Gln Tyr Ser Leu Asn Glu Ile Asn Asn Phe Asn
    850                 855                 860

Gly Ile Arg Ile Lys Thr Asp Tyr His Ser Leu Leu Asp Lys Lys Glu
```

```
                865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
                900                 905                 910
Glu Leu Val Glu Lys Tyr Asp Ala Val Ile Ala Leu Ala Asp Leu Asn
                915                 920                 925
Ser Gly Phe Lys Asn Ser Arg Val Lys Val Lys Gln Val Tyr Gln
        930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Asn Gly Phe
        980                 985                 990
Ile Phe Tyr Ile Pro Ala Trp Leu Thr Ser Lys Ile Asp Pro Ser Thr
        995                 1000                1005
Gly Phe Val Asn Leu Leu Lys Thr Lys Tyr Thr Ser Ile Ala Asp
    1010                1015                1020
Ser Lys Lys Phe Ile Ser Ser Phe Asp Arg Ile Met Tyr Val Pro
    1025                1030                1035
Glu Glu Asp Leu Phe Glu Phe Ala Leu Asp Tyr Lys Asn Phe Ser
    1040                1045                1050
Arg Thr Asp Ala Asp Tyr Ile Lys Lys Trp Lys Leu Tyr Ser Tyr
    1055                1060                1065
Gly Asn Arg Ile Arg Ile Phe Arg Asn Pro Lys Lys Asn Asn Val
    1070                1075                1080
Phe Asp Trp Glu Glu Val Cys Leu Thr Ser Ala Tyr Lys Glu Leu
    1085                1090                1095
Phe Asn Lys Tyr Gly Ile Asn Tyr Gln Gln Gly Asp Ile Arg Ala
    1100                1105                1110
Leu Leu Cys Glu Gln Ser Asp Lys Ala Phe Tyr Ser Ser Phe Met
    1115                1120                1125
Ala Leu Met Ser Leu Met Leu Gln Met Arg Asn Ser Ile Thr Gly
    1130                1135                1140
Arg Thr Asp Val Asp Phe Leu Ile Ser Pro Val Lys Asn Ser Asp
    1145                1150                1155
Gly Ile Phe Tyr Asp Ser Arg Asn Tyr Glu Ala Gln Glu Asn Ala
    1160                1165                1170
Ile Leu Pro Lys Asn Ala Asp Ala Asn Gly Ala Tyr Asn Ile Ala
    1175                1180                1185
Arg Lys Val Leu Trp Ala Ile Gly Gln Phe Lys Lys Ala Glu Asp
    1190                1195                1200
Glu Lys Leu Asp Lys Val Lys Ile Ala Ile Ser Asn Lys Glu Trp
    1205                1210                1215
Leu Glu Tyr Ala Gln Thr Ser Val Lys His
    1220                1225

<210> SEQ ID NO 36
<211> LENGTH: 1314
<212> TYPE: PRT
<213> ORGANISM: Artificial sequence
<220> FEATURE:
<223> OTHER INFORMATION: Synthetic polypeptide
```

<400> SEQUENCE: 36

```
Met Tyr Pro Tyr Asp Val Pro Asp Tyr Ala Ser Gly Ser Gly Met Ser
1               5                   10                  15

Ile Tyr Gln Glu Phe Val Asn Lys Tyr Ser Leu Ser Lys Thr Leu Arg
            20                  25                  30

Phe Glu Leu Ile Pro Gln Gly Lys Thr Leu Glu Asn Ile Lys Ala Arg
        35                  40                  45

Gly Leu Ile Leu Asp Asp Glu Lys Arg Ala Lys Asp Tyr Lys Lys Ala
    50                  55                  60

Lys Gln Ile Ile Asp Lys Tyr His Gln Phe Phe Ile Glu Glu Ile Leu
65                  70                  75                  80

Ser Ser Val Cys Ile Ser Glu Asp Leu Leu Gln Asn Tyr Ser Asp Val
                85                  90                  95

Tyr Phe Lys Leu Lys Lys Ser Asp Asp Asn Leu Gln Lys Asp Phe
            100                 105                 110

Lys Ser Ala Lys Asp Thr Ile Lys Lys Gln Ile Ser Glu Tyr Ile Lys
            115                 120                 125

Asp Ser Glu Lys Phe Lys Asn Leu Phe Asn Gln Asn Leu Ile Asp Ala
    130                 135                 140

Lys Lys Gly Gln Glu Ser Asp Leu Ile Leu Trp Leu Lys Gln Ser Lys
145                 150                 155                 160

Asp Asn Gly Ile Glu Leu Phe Lys Ala Asn Ser Asp Ile Thr Asp Ile
                165                 170                 175

Asp Glu Ala Leu Glu Ile Ile Lys Ser Phe Lys Gly Trp Thr Thr Tyr
            180                 185                 190

Phe Lys Gly Phe His Glu Asn Arg Lys Asn Val Tyr Ser Ser Asn Asp
        195                 200                 205

Ile Pro Thr Ser Ile Ile Tyr Arg Ile Val Asp Asp Asn Leu Pro Lys
    210                 215                 220

Phe Leu Glu Asn Lys Ala Lys Tyr Glu Ser Leu Lys Asp Lys Ala Pro
225                 230                 235                 240

Glu Ala Ile Asn Tyr Glu Gln Ile Lys Lys Asp Leu Ala Glu Glu Leu
                245                 250                 255

Thr Phe Asp Ile Asp Tyr Lys Thr Ser Glu Val Asn Gln Arg Val Phe
            260                 265                 270

Ser Leu Asp Glu Val Phe Glu Ile Ala Asn Phe Asn Asn Tyr Leu Asn
        275                 280                 285

Gln Ser Gly Ile Thr Lys Phe Asn Thr Ile Ile Gly Gly Lys Phe Val
    290                 295                 300

Asn Gly Glu Asn Thr Lys Arg Lys Gly Ile Asn Glu Tyr Ile Asn Leu
305                 310                 315                 320

Tyr Ser Gln Gln Ile Asn Asp Lys Thr Leu Lys Lys Tyr Lys Met Ser
                325                 330                 335

Val Leu Phe Lys Gln Ile Leu Ser Asp Thr Glu Ser Lys Ser Phe Val
            340                 345                 350

Ile Asp Lys Leu Glu Asp Asp Ser Asp Val Val Thr Thr Met Gln Ser
        355                 360                 365

Phe Tyr Glu Gln Ile Ala Ala Phe Lys Thr Val Glu Glu Lys Ser Ile
    370                 375                 380

Lys Glu Thr Leu Ser Leu Leu Phe Asp Asp Leu Lys Ala Gln Lys Leu
385                 390                 395                 400

Asp Leu Ser Lys Ile Tyr Phe Lys Asn Asp Lys Ser Leu Thr Asp Leu
                405                 410                 415
```

```
Ser Gln Gln Val Phe Asp Asp Tyr Ser Val Ile Gly Thr Ala Val Leu
            420                 425                 430

Glu Tyr Ile Thr Gln Gln Ile Ala Pro Lys Asn Leu Asp Asn Pro Ser
            435                 440                 445

Lys Lys Glu Gln Glu Leu Ile Ala Lys Lys Thr Glu Lys Ala Lys Tyr
            450                 455                 460

Leu Ser Leu Glu Thr Ile Lys Leu Ala Leu Glu Glu Phe Asn Lys His
465                 470                 475                 480

Arg Asp Ile Asp Lys Gln Cys Arg Phe Glu Glu Ile Leu Ala Asn Phe
            485                 490                 495

Ala Ala Ile Pro Met Ile Phe Asp Glu Ile Ala Gln Asn Lys Asp Asn
            500                 505                 510

Leu Ala Gln Ile Ser Ile Lys Tyr Gln Asn Gln Gly Lys Lys Asp Leu
            515                 520                 525

Leu Gln Ala Ser Ala Glu Asp Asp Val Lys Ala Ile Lys Asp Leu Leu
            530                 535                 540

Asp Gln Thr Asn Asn Leu Leu His Lys Leu Lys Ile Phe His Ile Ser
545                 550                 555                 560

Gln Ser Glu Asp Lys Ala Asn Ile Leu Asp Lys Asp Glu His Phe Tyr
            565                 570                 575

Leu Val Phe Glu Glu Cys Tyr Phe Glu Leu Ala Asn Ile Val Pro Leu
            580                 585                 590

Tyr Asn Lys Ile Arg Asn Tyr Ile Thr Gln Lys Pro Tyr Ser Asp Glu
            595                 600                 605

Lys Phe Lys Leu Asn Phe Glu Asn Ser Thr Leu Ala Asn Gly Trp Asp
            610                 615                 620

Lys Asn Lys Glu Pro Asp Asn Thr Ala Ile Leu Phe Ile Lys Asp Asp
625                 630                 635                 640

Lys Tyr Tyr Leu Gly Val Met Asn Lys Lys Asn Asn Lys Ile Phe Asp
            645                 650                 655

Asp Lys Ala Ile Lys Glu Asn Lys Gly Glu Gly Tyr Lys Lys Ile Val
            660                 665                 670

Tyr Lys Leu Leu Pro Gly Ala Asn Lys Met Leu Pro Lys Val Phe Phe
            675                 680                 685

Ser Ala Lys Ser Ile Lys Phe Tyr Asn Pro Ser Glu Asp Ile Leu Arg
            690                 695                 700

Ile Arg Asn His Ser Thr His Thr Lys Asn Gly Ser Pro Gln Lys Gly
705                 710                 715                 720

Tyr Glu Lys Phe Glu Phe Asn Ile Glu Asp Cys Arg Lys Phe Ile Asp
            725                 730                 735

Phe Tyr Lys Gln Ser Ile Ser Lys His Pro Glu Trp Lys Asp Phe Gly
            740                 745                 750

Phe Arg Phe Ser Asp Thr Gln Arg Tyr Asn Ser Ile Asp Glu Phe Tyr
            755                 760                 765

Arg Glu Val Glu Asn Gln Gly Tyr Lys Leu Thr Phe Glu Asn Ile Ser
            770                 775                 780

Glu Ser Tyr Ile Asp Ser Val Val Asn Gln Gly Lys Leu Tyr Leu Phe
785                 790                 795                 800

Gln Ile Tyr Asn Lys Asp Phe Ser Ala Tyr Ser Lys Gly Arg Pro Asn
            805                 810                 815

Leu His Thr Leu Tyr Trp Lys Ala Leu Phe Asp Glu Arg Asn Leu Gln
            820                 825                 830
```

```
Asp Val Val Tyr Lys Leu Asn Gly Glu Ala Glu Leu Phe Tyr Arg Lys
            835                 840                 845

Gln Ser Ile Pro Lys Lys Ile Thr His Pro Ala Lys Glu Ala Ile Ala
        850                 855                 860

Asn Lys Asn Lys Asp Asn Pro Lys Lys Glu Ser Val Phe Glu Tyr Asp
865                 870                 875                 880

Leu Ile Lys Asp Lys Arg Phe Thr Glu Asp Lys Phe Phe His Cys
                885                 890                 895

Pro Ile Thr Ile Asn Phe Lys Ser Gly Ala Asn Lys Phe Asn Asp
        900                 905                 910

Glu Ile Asn Leu Leu Lys Glu Lys Ala Asn Asp Val His Ile Leu
        915                 920                 925

Ser Ile Ala Arg Gly Glu Arg His Leu Ala Tyr Tyr Thr Leu Val Asp
        930                 935                 940

Gly Lys Gly Asn Ile Ile Lys Gln Asp Thr Phe Asn Ile Ile Gly Asn
945                 950                 955                 960

Asp Arg Met Lys Thr Asn Tyr His Asp Lys Leu Ala Ala Ile Glu Lys
                965                 970                 975

Asp Arg Asp Ser Ala Arg Lys Asp Trp Lys Lys Ile Asn Asn Ile Lys
                980                 985                 990

Glu Met Lys Glu Gly Tyr Leu Ser Gln Val Val His Glu Ile Ala Lys
            995                1000                1005

Leu Val Ile Glu Tyr Asn Ala Ile Val Val Phe Glu Asp Leu Asn
        1010                1015                1020

Phe Gly Phe Lys Arg Gly Arg Phe Lys Val Glu Lys Gln Val Tyr
        1025                1030                1035

Gln Lys Leu Glu Lys Met Leu Ile Glu Lys Leu Asn Tyr Leu Val
        1040                1045                1050

Phe Lys Asp Asn Glu Phe Asp Lys Thr Gly Gly Val Leu Arg Ala
        1055                1060                1065

Tyr Gln Leu Thr Ala Pro Phe Glu Thr Phe Lys Lys Met Gly Lys
        1070                1075                1080

Gln Thr Gly Ile Ile Tyr Tyr Val Pro Ala Gly Phe Thr Ser Lys
        1085                1090                1095

Ile Cys Pro Val Thr Gly Phe Val Asn Gln Leu Tyr Pro Lys Tyr
        1100                1105                1110

Glu Ser Val Ser Lys Ser Gln Glu Phe Phe Ser Lys Phe Asp Lys
        1115                1120                1125

Ile Cys Tyr Asn Leu Asp Lys Gly Tyr Phe Glu Phe Ser Phe Asp
        1130                1135                1140

Tyr Lys Asn Phe Gly Asp Lys Ala Ala Lys Gly Lys Trp Thr Ile
        1145                1150                1155

Ala Ser Phe Gly Ser Arg Leu Ile Asn Phe Arg Asn Ser Asp Lys
        1160                1165                1170

Asn His Asn Trp Asp Thr Arg Glu Val Tyr Pro Thr Lys Glu Leu
        1175                1180                1185

Glu Lys Leu Leu Lys Asp Tyr Ser Ile Glu Tyr Gly His Gly Glu
        1190                1195                1200

Cys Ile Lys Ala Ala Ile Cys Gly Glu Ser Asp Lys Lys Phe Phe
        1205                1210                1215

Ala Lys Leu Thr Ser Val Leu Asn Thr Ile Leu Gln Met Arg Asn
        1220                1225                1230

Ser Lys Thr Gly Thr Glu Leu Asp Tyr Leu Ile Ser Pro Val Ala
```

Asp Val Asn Gly Asn Phe Phe Asp Ser Arg Gln Ala Pro Lys Asn
          1250                1255                1260

Met Pro Gln Asp Ala Asp Ala Asn Gly Ala Tyr His Ile Gly Leu
    1265                1270                1275

Lys Gly Leu Met Leu Leu Gly Arg Ile Lys Asn Asn Gln Glu Gly
    1280                1285                1290

Lys Lys Leu Asn Leu Val Ile Lys Asn Glu Glu Tyr Phe Glu Phe
    1295                1300                1305

Val Gln Asn Arg Asn Asn
    1310

<210> SEQ ID NO 37
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 37
actgcggaaa tttgagcgt                                                  19

<210> SEQ ID NO 38
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 38
acgctcaaat ttccgcagt                                                  19

<210> SEQ ID NO 39
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 39
aggcaatggc tgcacatgc                                                  19

<210> SEQ ID NO 40
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 40
gcatgtgcag ccattgcct                                                  19

<210> SEQ ID NO 41
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 41
gacgcttggt tctgaggag                                                  19

<210> SEQ ID NO 42

```
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 42
ctcctcagaa ccaagcgtc                                                    19

<210> SEQ ID NO 43
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 43
tccggaaacg cattcctct                                                    19

<210> SEQ ID NO 44
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 44
agaggaatgc gtttccgga                                                    19

<210> SEQ ID NO 45
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 45
ccgcgtcagc ccggcccgg                                                    19

<210> SEQ ID NO 46
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 46
ccgggccggg ctgacgcgg                                                    19

<210> SEQ ID NO 47
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 47
cgactcccgc tgggcctct                                                    19

<210> SEQ ID NO 48
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 48
```
agaggcccag cgggagtcg                                           19

<210> SEQ ID NO 49
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 49
ccgttgcgcg ctcgctctc                                           19

<210> SEQ ID NO 50
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 50
gagagcgagc gcgcaacgg                                           19

<210> SEQ ID NO 51
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 51
ccgcgcatcc tgccaggcc                                           19

<210> SEQ ID NO 52
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 52
ggcctggcag gatgcgcgg                                           19

<210> SEQ ID NO 53
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 53
ccaacttggc gcgtttcgg                                           19

<210> SEQ ID NO 54
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 54
ccgaaacgcg ccaagttgg                                           19

<210> SEQ ID NO 55
<211> LENGTH: 19
<212> TYPE: DNA

<213> ORGANISM: Artificial sequence
<220> FEATURE:
<223> OTHER INFORMATION: Synthetic polynucleotide

<400> SEQUENCE: 55
accacgcgtc cgagtccgg                                                19

<210> SEQ ID NO 56
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 56
ccggactcgg acgcgtggt                                                19

<210> SEQ ID NO 57
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 57
tgctcattgt ccctggaca                                                19

<210> SEQ ID NO 58
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 58
tgtccaggga caatgagca                                                19

<210> SEQ ID NO 59
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 59
ggacaccctg ctcattgtc                                                19

<210> SEQ ID NO 60
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 60
gacaatgagc agggtgtcc                                                19

<210> SEQ ID NO 61
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 61
accggcagcc tgcgcgtcc                                                19

<210> SEQ ID NO 62
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 62
ggacgcgcag gctgccggt                                              19

<210> SEQ ID NO 63
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 63
cgatgggcac ccactgctc                                              19

<210> SEQ ID NO 64
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 64
gagcagtggg tgcccatcg                                              19

<210> SEQ ID NO 65
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 65
ccttcacgtg gacgcgcag                                              19

<210> SEQ ID NO 66
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 66
ctgcgcgtcc acgtgaagg                                              19

<210> SEQ ID NO 67
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 67
cgtgaaggtg gaagccttc                                              19

<210> SEQ ID NO 68
<211> LENGTH: 19
<212> TYPE: DNA
<213> ORGANISM: Artificial sequence
<220> FEATURE:

<223> OTHER INFORMATION: Synthetic polynucleotide

<400> SEQUENCE: 68
gaaggcttcc accttcacg                                                    19

<210> SEQ ID NO 69
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 69
ctccttggtc aggcgccgg                                                    19

<210> SEQ ID NO 70
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 70
ccggcgcctg accaaggag                                                    19

<210> SEQ ID NO 71
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 71
tggtcaggcg ccggttccg                                                    19

<210> SEQ ID NO 72
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 72
cggaaccggc gcctgacca                                                    19

<210> SEQ ID NO 73
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 73
tagaggtcgc cttctcctc                                                    19

<210> SEQ ID NO 74
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 74
gaggagaagg cgacctcta                                                    19

<210> SEQ ID NO 75
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 75
cgacgctcgg gtcgcggtg                                              19

<210> SEQ ID NO 76
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 76
caccgcgacc cgagcgtcg                                              19

<210> SEQ ID NO 77
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 77
atgctgtcgc cgcgcgggg                                              19

<210> SEQ ID NO 78
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 78
ccccgcgcgg cgacagcat                                              19

<210> SEQ ID NO 79
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 79
ctcaccctca ccggagcca                                              19

<210> SEQ ID NO 80
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 80
tggctccggt gagggtgag                                              19

<210> SEQ ID NO 81
<211> LENGTH: 19
<212> TYPE: DNA
<213> ORGANISM: Artificial sequence
<220> FEATURE:
<223> OTHER INFORMATION: Synthetic polynucleotide -continued

```
<400> SEQUENCE: 81
ccgcaaactt tactcctta                                                19

<210> SEQ ID NO 82
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 82
taaggagtaa agtttgcgg                                                19

<210> SEQ ID NO 83
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 83
ctcctaagat tggcttcac                                                19

<210> SEQ ID NO 84
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 84
gtgaagccaa tcttaggag                                                19

<210> SEQ ID NO 85
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 85
ccggagccac tcctaagat                                                19

<210> SEQ ID NO 86
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 86
atcttaggag tggctccgg                                                19

<210> SEQ ID NO 87
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 87
ttctctaccc tacgtctca                                                19

<210> SEQ ID NO 88
<211> LENGTH: 19
```

```
<212> TYPE: DNA
<213> ORGANISM: Artificial sequence
<220> FEATURE:
<223> OTHER INFORMATION: Synthetic polynucleotide

<400> SEQUENCE: 88
tgagacgtag ggtagagaa                                          19

<210> SEQ ID NO 89
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 89
tacgtctcat tctccgcaa                                          19

<210> SEQ ID NO 90
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 90
ttgcggagaa tgagacgta                                          19

<210> SEQ ID NO 91
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 91
gctaggcctc cagcccttc                                          19

<210> SEQ ID NO 92
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 92
gaagggctgg aggcctagc                                          19

<210> SEQ ID NO 93
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 93
acaggtggcg ccgcaactt                                          19

<210> SEQ ID NO 94
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 94
```

```
aagttgcggc gccacctgt                                              19

<210> SEQ ID NO 95
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 95
agccggaggc gcgagagtc                                              19

<210> SEQ ID NO 96
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 96
gactctcgcg cctccggct                                              19
```

COMPOSITIONS AND METHODS FOR GENE EDITING

STATEMENT AS TO RIGHTS TO INVENTIONS MADE UNDER FEDERALLY SPONSORED RESEARCH AND DEVELOPMENT

This invention was made with government support under grant no. HR0011-17-2-0043 awarded by the Department of Defense, Defense Advanced Research Projects Agency and grant no. R01 DA036858 awarded by the National Institutes of Health. The government has certain rights in the invention.

CROSS-REFERENCE TO RELATED APPLICATIONS

The protein constructs shown in FIG. 5 were tested for silencing of the CLTA gene in HEK293T cells for 18 days post-transfection (FIGS. 6A-6B). Variable levels of gene silencing activities were detected, including a panel of variants with more durable gene silencing compared to the p76 (V1) design such as p99 (SEQ ID NO:11), p100 (SEQ ID NO:12), and p112 (SEQ ID NO:15). FIGS. 6A and 6B show that the dCas9-KRAB and dCas9-Dnmt3A-Dnmt3L constructs showed transient and lower efficiency of long term silencing.

REFERENCE TO A "SEQUENCE LISTING," A TABLE, OR A COMPUTER PROGRAM LISTING APPENDIX SUBMITTED AS AN ASCII FILE

The Sequence Listing written in file 048536-620001WO_SequenceListing_ST25.txt, created May 14, 2019, 382,771 bytes, machine format IBM-PC, MS Windows operating system, is hereby incorporated by reference.

BACKGROUND

Although considered a promising therapeutic approach for treatment of disease, genome editing carries inherent risks due to the potential for genotoxicity from double strand breaks. Further, genome editing often is associated with an all-or-none effect on the target gene (i.e., it produces a full knockout). In contrast, targeted epigenome engineering does not carry the risk of DSB-induced genotoxicity; further, it affords the opportunity to create a more graded effect on gene expression and thus function from a complete silencing through a less pronounced effect.

Provided herein are solutions to these and other needs in the art.

BRIEF SUMMARY

In an aspect is provided a fusion protein including a nuclease-deficient RNA-guided DNA endonuclease enzyme, a Krüppel associated box (KRAB) domain and a DNA methyltransferase domain. In an aspect is provided a fusion protein of any one of SEQ ID NOS:1-15.

In an aspect is provided a nucleic acid sequence encoding the fusion protein as described herein, including embodiments and aspects thereof.

In an aspect is provided a complex including a fusion protein as described herein, including embodiments and aspects thereof, and a polynucleotide including (1) a DNA-targeting sequence that is complementary to a target polynucleotide sequence and (2) a binding sequence for the nuclease-deficient RNA-guided DNA endonuclease enzyme, wherein the nuclease-deficient RNA-guided DNA endonuclease enzyme is bound to the polynucleotide via the binding sequence.

In an aspect is provided a vector including the nucleic acid sequence of a fusion protein as described herein, including embodiments and aspects thereof.

In an aspect is provided a cell including a fusion protein as described herein, including embodiments and aspects thereof, a nucleic acid as described herein, including embodiments and aspects thereof, a complex as described herein, including embodiments and aspects thereof, or a vector as described herein, including embodiments and aspects thereof.

In an aspect is provided a method of silencing a target nucleic acid sequence in a cell, including delivering a first polynucleotide encoding a fusion protein as described herein, including embodiments and aspects thereof, to a cell containing the target nucleic acid, and delivering to the cell a second polynucleotide including (i) a DNA-targeting sequence that is complementary to the target nucleic acid sequence, and (ii) a binding sequence for the nuclease-deficient RNA-guide DNA endonuclease enzyme. Without intending to be bound by any theory, it is believed that the fusion protein silences the target nucleic acid sequence in the cell by methylating a chromatin containing the target nucleic acid sequence and/or by introducing repressive chromatin marks to a chromatin containing the target nucleic acid sequence. Thus, in aspects, the fusion protein silences the target nucleic acid sequence in the cell by methylating a chromatin containing the target nucleic acid sequence and/or by introducing repressive chromatin marks to a chromatin containing the target nucleic acid sequence.

In an aspect is provided a method of silencing a target nucleic acid sequence in a cell, including delivering a complex as described herein, including embodiments and aspects thereof, to a cell containing the target nucleic acid, wherein the complex silences the target nucleic acid sequence in the cell. Without intending to be bound by any theory, it is believed that the complex silences the target nucleic acid sequence in the cell by methylating a chromatin containing the target nucleic acid sequence and/or by introducing repressive chromatin marks to a chromatin containing the target nucleic acid sequence. Thus, in aspects, the complex silences the target nucleic acid sequence in the cell by methylating a chromatin containing the target nucleic acid sequence and/or by introducing repressive chromatin marks to a chromatin containing the target nucleic acid sequence

BRIEF DESCRIPTION OF THE DRAWINGS

FIG. 1A-1F describe engineering of an all-in-one protein for long-term gene silencing. FIG. 1A is a schematic of an all-in-one protein (SEQ ID NO:1) of the disclosure that has the KRAB domain fused to the —N-terminus of dCas9 (SEQ ID NO:23), separated by a GGSGGGS (SEQ ID NO:17) linker, and Dnmt3A-Dnmt3L at the C-terminus of dCas9 (separated by a EASGSGRASPGIPGSTR (SEQ ID NO:19) linker). FIG. 1B provides schematics of dCas9-fused epigenetic modulators tested for permanent gene silencing. The dCas9-KRAB protein is adapted from Gilbert et al., Cell 2013 for CRISPR interference (CRISPRi) applications. The dCas9-Dnmt3A-Dnmt3L fusion is adapted from Stepper et al., Nucleic Acids Research, 2016. The inventors engineered a novel all-in-one protein that combines the KRAB domain (SEQ ID NO:16), dCas9 (D10A, H208A), Dnmt3A-Dnmt3L (SEQ ID NO:33; where Dnmt3A is SEQ ID NO:26 and Dnmt3L is SEQ ID NO:28) into one polypeptide. FIG. 1C provides schematics of a methylation-sensitive GFP reporter (adapted from Stelzer et al., Cell 2015) that was used to assess long-term silencing by the all-in-one protein. FIGS. 1D-1E provide a diagram and results of a hit-and-run experimental workflow in HEK293T cells expressing the GFP reporter shown in FIG. 3. FIG. 1D shows that plasmids were co-transfected into cells, one encoding the hit-and-run protein and the other plasmid encoding a sgRNA. FIG. 1E shows the results of the hit-and-run assay sorted for cells that were co-transfected with the all-in-one plasmid and sgRNA plasmid. FIG. 1F shows the results of the silencing of the GFP reporter is dependent on the sgRNA sequence.

FIGS. 2A-2F describe long-term silencing of endogenous genes. FIGS. 2A-2C are representative flow cytometry data shown taken 22 days post-transfection following gene (CD29, CD81, CD151) targeting for long term silencing using the all-in-one protein. Quadrant IV represents cells that have turned off the gene, indicated by the percentage of cells with the gene off (i.e., 45%, 66%, and 53%, respectively). FIG. 2D provides quantification of silencing of CD29, CD81, and CD151 with three different sgRNA. FIG. 2E provides quantification of silencing of two or three genes simultaneously to show that the all-in-protein can be multiplexed by co-delivery of sgRNAs targeting different genes. FIG. 2F provides a plot representing a time point taken 9 months post transfection of the all-in-one protein and sgRNA targeting the CLTA gene, signifying that the majority of cells have stably turned off the CLTA gene.

FIGS. 3A-3C shows that harvested cells lost expression of CD29 (FIG. 3A), CD81 (FIG. 3B), and CD151 (FIG. 3C) thirty-six days post-transfection, as determined by their RNA expression profiles. FIGS. 3D-3F are volcano plots showing that the targeted genes CD29 (FIG. 3D), CD81 (FIG. 3E) and CD151 (FIG. 3F) is the only significant gene knocked down for each experiment, signifying high specificity of gene silencing. FIGS. 3G-3I provides quantification of transcript levels of CD151 (FIG. 3G), CD81 (GIF. 3H), and CD29 (FIG. 3I) showing more than 96% knockdown of each of the targeted genes.

FIGS. 4A-4F are flow cytometry plots showing BFP expression (which is fused to the all-in-one protein) in HeLa (cervical)(FIG. 4A), U20S (bone)(FIG. 4B), and human induced pluripotent cells (iPSC) (FIG. 4C). FIGS. 4D-4F are the untransfected controls for FIGS. 4A-4C, respectively. FIG. 4G shows that stable silencing of endogenous genes in HeLa and U20S cells, measured at 18 days post-transfection with the all-in-one protein, was achieved. In FIGS. 4A-4F, the x-axis is BFP (fused to all-in-one protein), and the y-axis is mCherry. FIG. 4H shows that gene silencing was detected 14 days post transfection by qPCR in AML12 mouse hepatocyte cell lines when targeting Pcsk9, Npc1, Spcs1 and Cd81.

FIGS. 6A-6B shows the gene silencing results 18 days post-transfection of the fusion proteins of SEQ ID NOS:1-15 transfected into HEK293T cells for targeted silencing of the CLTA gene. The dCas9-KRAB and dCas9-Dnmt3A-Dnmt3L designs showed transient and lower efficiency of long term silencing. FIGS. 6C-6D provide a comparison of SEQ ID NO:1 (p76) and SEQ ID NO:15 (p112) for silencing the HIST2H2BE (H2B) endogenous gene (FIG. 6C) and a synthetic Snrpn-GFP reporter gene (FIG. 6D) stably expressed in HEK293T cells. FIG. 6E provides a plot of protein expression (dotted lines) of p76 and p112 over the 50 day time course to turn off the HIST2H2BE (H2B) gene. Protein levels were measured by flow cytometry detection of BFP, which is co-expressed with the all-in-one protein.

FIG. 7A is a Western blot analysis of the all-in-one protein variants p76 and p90-p102 using an antibody against Steptococcuspyogenes Cas9. The top band represents full-length protein and smaller-sized bands represent proteolysis of the all-in-one protein. FIG. 7B is a Western blot analysis of all-in-one protein variants to detect free Dnmt3A that is cleaved from the fusion protein.

FIG. 8A is a schematic of a pooled screen to determine the optimal sgRNAs that leads to long term gene silencing. FIGS. 8B-8E are flow cytometry histograms of the percent of cells undergoing gene silencing four weeks post-transfection. Four HEK293T cell lines were used, each with a different gene with a GFP tag, including CLTA (FIG. 8B), VIM (FIG. 8C), HIST2H2BE (H2B) (FIG. 8D), and RAB11A (FIG. 8E).

FIG. 10A is a workflow of a pooled screen in HEK293T cells to determine optimal sgRNA targeting positions for the all-in-one protein, adapted from a previous ricin tiling screen in K562 cells to determine optimal sgRNAs for dCas9-KRAB (Gilbert, Horlbeck et al., Cell 2014). FIGS. 10B-10E are representative plots showing growth phenotypes for four genes, including ARL1 (FIG. 10B), EIF6 (FIG. 10C), SMC3 (FIG. 10D), HEATRI (FIG. 10E), from existing dCas9-KRAB/CRISPRi datasets in K562 cells (Gilbert, Horlbeck et al., 2014) and with the all-in-one protein (bottom plot). Each dot represents an sgRNA. The TSS and annotated CpG island are shown for each gene.

FIG. 12A shows the in vitro transcription of two all-in-one variants (p102 and p112) show full length synthesis of each design. FIG. 12B provides a flow cytometry plot showing expression of p102 and p112 one day post-transfection of mRNA into HEK293T cells. FIG. 12C provides the time course of CLTA endogenous gene silencing in HEK293T cells after transfecting mRNA expressing the p102 and p112 all-in-one variants.

FIG. 13A provides flow cytometry plots showing induced expression of the all-in-one protein by addition of doxycycline in K562 cells that stably encode the all-in-one protein under a doxycycline-inducible promoter. The dotted line represents the baseline median BFP fluorescence without doxycycline administration. FIG. 13B provides a Western blot of cells to detect expression of the all-in-one protein before and after doxycycline treatment. FIGS. 13C-13F are flow cytometry plots of CD81 (FIGS. 13C-13D) and CD151 (FIGS. 13E-13F) knockdown 14 days post-doxycycline treatment of K562 cells. FIG. 13G shows the quantification of CD81 and CD151 knockdown 14 days post-doxycycline treatment or without doxycycline treatment.

DETAILED DESCRIPTION

Figure 1A:
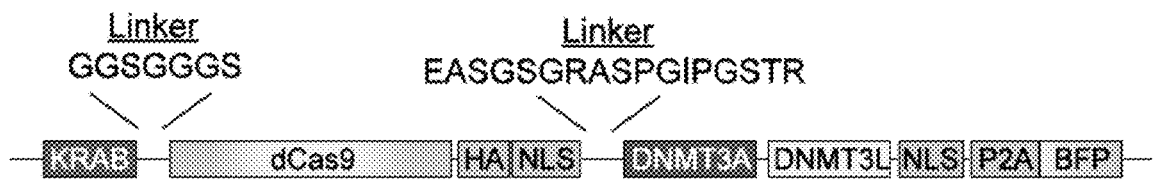

The technology described herein allows for, inter alia, permanent silencing of genes in mammalian cells without generating double stranded DNA breaks in the host genome. In embodiments, the central component is a single polypeptide chain composed of catalytically inactive Cas9 (dCas9) fused to Dnmt3A, Dnmt3L, and a KRAB domain (herein referred to as an "all-in-one protein"). This fusion protein provided herein can be directed to a specific site in a mammalian genome using a single guide RNA (sgRNA) and may add DNA methylation and/or repressive chromatin marks to the site. In embodiments, the result is gene silencing that is inheritable across subsequent cell divisions. In embodiments, the fusion protein provided herein (and sgRNA) are only expressed transiently, bypassing the use of viral delivery methods to induce permanent silencing.

In embodiments, the fusion proteins provided herein provide a robust long-term or permanent silencing of endogenous gene expression by epigenome editing rather than genome editing. Both alleles of a gene may be targeted or a single pathogenic allele may be selectively targeted. In embodiments, an advantage of the fusion protein provided herein is that epigenetic editing is reversible and therefore inherently safer than genome editing. Thus, in embodiments, fusion protein provided herein is useful in prophylactic applications. For example, gene silencing can enable acute protection from an infection/biologic toxin and then be reversed after the risk of infection or intoxication is absent. Thus, in embodiments, fusion protein provided herein is useful for viral or toxin that enters a cell through interaction with a protein that is required for long term organ function or homeostasis. In embodiments, fusion protein provided herein is useful in genome editing based therapeutics.

In embodiments, permanent gene silencing in mammalian cells can be accomplished with two components: a single polypeptide chain composed of dCas9 fused to three epigenetic modulators and a single guide RNA that directs the protein to a specific site in the host genome. In embodiments, the components are only expressed transiently in the host cell, thus reducing toxicity and off-target events.

In embodiments, the fusion protein provided herein does not induce DNA breaks in the host cell for permanent gene silencing. In embodiments, the epigenetic marks that are added to the genomic site of interest are reversible, thus allowing for removal of any off-target events that may occur.

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acids, e.g. polynucleotides, contemplated herein include, but are not limited to, any type of RNA, e.g., mRNA, siRNA, miRNA, sgRNA, and guide RNA and any type of DNA, genomic DNA, plasmid DNA, and minicircle DNA, and any fragments thereof. In aspects, the nucleic acid is messenger RNA. In aspects, the messenger RNA is messenger ribonucleoprotein (RNP). The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, sgRNA, guide RNA, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions (i.e., stringent hybridization conditions).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. One of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al., supra.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 Molecular Cloning: A Laboratory Manual, 18.1-18.88.

The term "transcriptional regulatory sequence" as provided herein refers to a segment of DNA that is capable of increasing or decreasing transcription (e.g., expression) of a specific gene within an organism. Non-limiting examples of transcriptional regulatory sequences include promoters, enhancers, and silencers.

The terms "transcription start site" and transcription initiation site" may be used interchangeably to refer herein to the 5' end of a gene sequence (e.g., DNA sequence) where RNA polymerase (e.g., DNA-directed RNA polymerase) begins synthesizing the RNA transcript. The transcription start site may be the first nucleotide of a transcribed DNA sequence where RNA polymerase begins synthesizing the RNA transcript. A skilled artisan can determine a transcription start site via routine experimentation and analysis, for example, by performing a run-off transcription assay or by definitions according to FANTOM5 database.

The term "promoter" as used herein refers to a region of DNA that initiates transcription of a particular gene. Promoters are typically located near the transcription start site of a gene, upstream of the gene and on the same strand (i.e., 5' on the sense strand) on the DNA. Promoters may be about 100 to about 1000 base pairs in length.

The term "enhancer" as used herein refers to a region of DNA that may be bound by proteins (e.g., transcription factors) to increase the likelihood that transcription of a gene will occur. Enhancers may be about 50 to about 1500 base pairs in length. Enhancers may be located downstream or upstream of the transcription initiation site that it regulates and may be several hundreds of base pairs away from the transcription initiation site.

The term "silencer" as used herein refers to a DNA sequence capable of binding transcription regulation factors known as repressors, thereby negatively effecting transcription of a gene. Silencer DNA sequences may be found at many different positions throughout the DNA, including, but not limited to, upstream of a target gene for which it acts to repress transcription of the gene (e.g., silence gene expression).

A "guide RNA" or "gRNA" as provided herein refers to any polynucleotide sequence having sufficient complementarity with a target polynucleotide sequence to hybridize with the target sequence and direct sequence-specific binding of a CRISPR complex to the target sequence. In aspects, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

In embodiments, the polynucleotide (e.g., gRNA) is a single-stranded ribonucleic acid. In aspects, the polynucleotide (e.g., gRNA) is 10, 20, 30, 40, 50, 60, 70, 80, 90, 100 or more nucleic acid residues in length. In aspects, the polynucleotide (e.g., gRNA) is from 10 to 30 nucleic acid residues in length. In aspects, the polynucleotide (e.g., gRNA) is 20 nucleic acid residues in length. In aspects, the length of the polynucleotide (e.g., gRNA) can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In aspects, the polynucleotide (e.g., gRNA) is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In aspects, the polynucleotide (e.g., gRNA) is from 10 to 15, 10 to 20, 10 to 30, 10 to 40, or 10 to 50 residues in length.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may, in aspects, be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

For specific proteins described herein (e.g., KRAB, dCas9, Dnmt3A, Dnmt3L), the named protein includes any of the protein's naturally occurring forms, or variants or homologs that maintain the protein activity (e.g., within at least 50%, 80%, 90%, 95%, 96%, 97%, 98%, 99% or 100% activity compared to the native protein). In aspects, variants or homologs have at least 50%, 55%, 60%, 65%, 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In aspects, the protein is the protein as identified by its NCBI sequence reference. In aspects, the protein is the protein as identified by its NCBI sequence reference or functional fragment or homolog thereof.

The term "Krüppel associated box domain" or "KRAB domain" as provided herein refers to a category of transcriptional repression domains present in approximately 400 human zinc finger protein-based transcription factors. KRAB domains typically include about 45 to about 75 amino acid residues. A description of KRAB domains, including their function and use, may be found, for example, in Ecco, G., Imbeault, M., Trono, D., KRAB zinc finger proteins, Development 144, 2017; Lambert et al. The human transcription factors, Cell 172, 2018; Gilbert et al., Cell (2013); and Gilbert et al., Cell (2014), all of which are incorporated herein by reference in their entirety. In aspects, the KRAB domain is a KRAB domain of Kox 1. In aspects, the KRAB domain includes the sequence set forth by SEQ ID NO:16. In aspects, the KRAB domain is the sequence of SEQ ID NO:16. In aspects, the KRAB domain includes an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:16. In aspects, the KRAB domain includes an amino acid sequence that has at least 75% sequence identity to SEQ ID NO:16. In aspects, the KRAB domain includes an amino acid sequence that has at least 80% sequence identity to SEQ ID NO:16. In aspects, the KRAB domain includes an amino acid sequence that has at least 85% sequence identity to SEQ ID NO:16. In aspects, the KRAB domain includes an amino acid sequence that has at least 90% sequence identity to SEQ ID NO:16. In aspects, the KRAB domain includes an amino acid sequence that has at least 95% sequence identity to SEQ ID NO:16.

The term "DNA methyltransferase" as provided herein refers to an enzyme that catalyzes the transfer of a methyl group to DNA. Non-limiting examples of DNA methyltransferases include Dnmt1, Dnmt3A, Dnmt3B, and Dnmt3L. In aspects, the DNA methyltransferase is a bacterial cytosine methyltransferase and/or a bacterial non-cytosine methyltransferase. Depending on the specific DNA methyltransferase, different regions of DNA are methylated. For example, Dnmt3A typically targets CpG dinucleotides for methylation. Through DNA methylation, DNA methyltransferases can modify the activity of a DNA segment (e.g., gene expression) without altering the DNA sequence. In aspects, DNA methylation results in repression of gene transcription and/or modulation of methylation sensitive transcription factors or CTCF. As described herein, fusion proteins may include one or more (e.g., two) DNA metyltransferases. When a DNA methyltransferase is included as part of a fusion protein, the DNA methyltransferase may be referred to as a "DNA methyltransferase domain." In aspects, a DNA methyltransferase domain includes one or more DNA methyltransferases. In aspects, a DNA methyltransferase domain includes two DNA methyltransferases. In aspects, the DNA methyltransferase domain is Dnmt3A. In aspects, the DNA methyltransferase domain has the amino acid sequence of SEQ ID NO:26. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:26. In aspects, the DNA methyltransferase domain has an amino acid sequence that has at least 75% sequence identity to SEQ ID NO:26. In aspects, the DNA methyltransferase domain has an amino acid sequence that has at least 80% sequence identity to SEQ ID NO:26. In aspects, the DNA methyltransferase domain has an amino acid sequence that has at least 85% sequence identity to SEQ ID NO:26. In aspects, the DNA methyltransferase domain has an amino acid sequence that has at least 90% sequence identity to SEQ ID NO:26. In aspects, the DNA methyltransferase domain has an amino acid sequence that has at least 95% sequence identity to SEQ ID NO:26. In aspects, the DNA methyltransferase domain is Dnmt3L. In aspects, the DNA methyltransferase domain has the amino acid sequence of SEQ ID NO:28. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:28. In aspects, the DNA methyltransferase domain has an amino acid sequence that has at least 75% sequence identity to SEQ ID NO:28. In aspects, the DNA methyltransferase domain has an amino acid sequence that has at least 80% sequence identity to SEQ ID NO:28. In aspects, the DNA methyltransferase domain has an amino acid sequence that has at least 85% sequence identity to SEQ ID NO:28. In aspects, the DNA methyltransferase domain has an amino acid sequence that has at least 90% sequence identity to SEQ ID NO:28. In aspects, the DNA methyltransferase domain has an amino acid sequence that has at least 95% sequence identity to SEQ ID NO:28. In aspects, the DNA methyltransferase domain includes Dnmt3A and Dnmt3L. In aspects, the DNA methyltransferase domain has the amino acid sequence of SEQ ID NO:33. In aspects, the DNA methyltransferase domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:33. In aspects, the DNA methyltransferase domain has an amino acid sequence that has at least 75% sequence identity to SEQ ID NO:33. In aspects, the DNA methyltransferase domain has an amino acid sequence that has at least 80% sequence identity to SEQ ID NO:33. In aspects, the DNA methyltransferase domain has an amino acid sequence that has at least 85% sequence identity to SEQ ID NO:33. In aspects, the DNA methyltransferase domain has an amino acid sequence that has at least 90% sequence identity to SEQ ID NO:33. In aspects, the DNA methyltransferase domain has an amino acid sequence that has at least 95% sequence identity to SEQ ID NO:33. A description of Dnmt3A-3L domain structure and use may be found, for example, in Siddique et al, Targeted methylation and gene silencing of VEGF-A in human cells by using a designed Dnmt3a-Dnmt3L single-chain fusion protein with increased DNA methylation activity, J. Mol. Biol. 425, 2013 and Stepper et al, Efficient targeted DNA methylation with chimeric dCas9-Dnmt3a-Dnmt3L methyltransferase, Nucleic Acids Res. 45, 2017, which are incorporated herein by reference in their entirety and for all purposes.

A "Dnmt3A", "Dnmt3a," "DNA (cytosine-5)-methyltransferase 3A" or "DNA methyltransferase 3a" protein as referred to herein includes any of the recombinant or naturally-occurring forms of the Dnmt3A enzyme or variants or homologs thereof that maintain Dnmt3A enzyme activity (e.g. within at least 50%, 55%, 60%, 65%, 70%, 75%, 80%, 85%, 90%, 91%, 92%, 93%, 94%, 95%, 96%, 97%, 98%, 99% or 100% activity compared to Dnmt3A). In aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Dnmt3A protein. In aspects, the Dnmt3A protein is substantially identical to the protein identified by the UniProt reference number Q9Y6K1 or a variant or homolog having substantial identity thereto. In aspects, the Dnmt3A polypeptide is encoded by a nucleic acid sequence identified by the NCBI reference sequence Accession number NM_022552, homologs or functional fragments thereof. In aspects, Dnmt3A includes the sequence set forth by SEQ ID NO:26. In aspects, Dnmt3A is the sequence set forth by SEQ ID NO:26. In aspects, Dnmt3A has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:26. In aspects, the DNA methyltransferase domain has an amino acid sequence that has at least 75% sequence identity to SEQ ID NO:26. In aspects, the DNA methyltransferase domain has an amino acid sequence that has at least 80% sequence identity to SEQ ID NO:26. In aspects, the DNA methyltransferase domain has an amino acid sequence that has at least 85% sequence identity to SEQ ID NO:26. In aspects, Dnmt3A has an amino acid sequence that has at least 90% sequence identity to SEQ ID NO:26. In aspects, Dnmt3A has an amino acid sequence that has at least 95% sequence identity to SEQ ID NO:26.

A "Dnmt3L", "DNA (cytosine-5)-methyltransferase 3L" or "DNA methyltransferase 3L" protein as referred to herein includes any of the recombinant or naturally-occurring forms of the Dnmt3L enzyme or variants or homologs thereof that maintain Dnmt3L enzyme activity (e.g., within at least 50%, 55%, 60%, 65%, 70%, 75%, 80%, 85%, 90%, 91%, 92%, 93%, 94%, 95%, 96%, 97%, 98%, 99% or 100% activity compared to Dnmt3L). In aspects, the variants or homologs have at least 50%, 55%, 60%, 65%, 70%, 75%, 80%, 85%, 90%, 91%, 92%, 93%, 94%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Dnmt3L protein. In aspects, the Dnmt3L protein is substantially identical to the protein identified by the UniProt reference number Q9CWR8 or a variant or homolog having substantial identity thereto. In aspects, the Dnmt3L protein is identical to the protein identified by the UniProt reference number Q9CWR8. In aspects, the Dnmt3L protein has at least 75% sequence identity to the amino acid sequence of the protein identified by the UniProt reference number Q9CWR8. In aspects, the Dnmt3L protein has at least 80% sequence identity to the amino acid sequence of the protein identified by the UniProt reference number Q9CWR8. In aspects, the Dnmt3L protein has at least 85% sequence identity to the amino acid sequence of the protein identified by the UniProt reference number Q9CWR8. In aspects, the Dnmt3L protein has at least 95% sequence identity to the amino acid sequence of the protein identified by the UniProt reference number Q9CWR8.

In aspects, the Dnmt3L protein is substantially identical to the protein identified by the UniProt reference number Q9UJW or a variant or homolog having substantial identity thereto. In aspects, the Dnmt3L protein is identical to the protein identified by the UniProt reference number Q9UJW. In aspects, the Dnmt3L protein has at least 50% sequence identity to the amino acid sequence of the protein identified by the UniProt reference number Q9UJW. In aspects, the Dnmt3L protein has at least 55% sequence identity to the protein identified by the UniProt reference number Q9UJW. In aspects, the Dnmt3L protein has at least 60% sequence identity to the amino acid sequence of the protein identified by the UniProt reference number Q9UJW. In aspects, the Dnmt3L protein has at least 65% sequence identity to the amino acid sequence of the protein identified by the UniProt reference number Q9UJW. In aspects, the Dnmt3L protein has at least 70% sequence identity to the amino acid sequence of the protein identified by the UniProt reference number Q9UJW. In aspects, the Dnmt3L protein has at least 75% sequence identity to the amino acid sequence of the protein identified by the UniProt reference number Q9UJW. In aspects, the Dnmt3L protein has at least 80% sequence identity to the amino acid sequence of the protein identified by the UniProt reference number Q9UJW. In aspects, the Dnmt3L protein has at least 85% sequence identity to the amino acid sequence of the protein identified by the UniProt reference number Q9UJW. In aspects, the Dnmt3L protein has at least 90% sequence identity to the amino acid sequence of the protein identified by the UniProt reference number Q9UJW. In aspects, the Dnmt3L protein has at least 95% sequence identity to the amino acid sequence of the protein identified by the UniProt reference number Q9UJW. In aspects, the Dnmt3L polypeptide is encoded by a nucleic acid sequence identified by the NCBI reference sequence Accession number NM_001081695, or homologs or functional fragments thereof. In aspects, Dnmt3L includes the sequence set forth by SEQ ID NO:28. In aspects, Dnmt3L is the sequence set forth by SEQ ID NO:28. In aspects, Dnmt3L has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:28. In aspects, Dnmt3L has an amino acid sequence that has at least 50% sequence identity to SEQ ID NO:28. In aspects, Dnmt3L has an amino acid sequence that has at least 55% sequence identity to SEQ ID NO:28. In aspects, Dnmt3L has an amino acid sequence that has at least 60% sequence identity to SEQ ID NO:28. In aspects, Dnmt3L has an amino acid sequence that has at least 65% sequence identity to SEQ ID NO:28. In aspects, Dnmt3L has an amino acid sequence that has at least 97% sequence identity to SEQ ID NO:28. In aspects, Dnmt3L has an amino acid sequence that has at least 75% sequence identity to SEQ ID NO:28. In aspects, Dnmt3L has an amino acid sequence that has at least 80% sequence identity to SEQ ID NO:28. In aspects, Dnmt3L has an amino acid sequence that has at least 85% sequence identity to SEQ ID NO:28. In aspects, Dnmt3L has an amino acid sequence that has at least 90% sequence identity to SEQ ID NO:28. In aspects, Dnmt3L has an amino acid sequence that has at least 95% sequence identity to SEQ ID NO:28.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). The Cpf1 enzyme belongs to a putative type V CRISPR-Cas system. Both type II and type V systems are included in Class II of the CRISPR-Cas system.

A "nuclear localization sequence" or "nuclear localization signal" or "NLS" is a peptide that directs proteins to the nucleus. In aspects, the NLS includes five basic, positively charged amino acids. The NLS may be located anywhere on the peptide chain. In aspects, the NLS is an NLS derived from SV40. In aspects, the NLS includes the sequence set forth by SEQ ID NO:25. In aspects, the NLS is the sequence set forth by SEQ ID NO:25. In aspects, NLS has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 25. In aspects, NLS has an amino acid sequence that has at least 75% sequence identity to SEQ ID NO:25. In aspects, NLS has an amino acid sequence that has at least 80% sequence identity to SEQ ID NO:25. In aspects, NLS has an amino acid sequence that has at least 85% sequence identity to SEQ ID NO:25. In aspects, NLS has an amino acid sequence that has at least 90% sequence identity to SEQ ID NO:25. In aspects, NLS has an amino acid sequence that has at least 95% sequence identity to SEQ ID NO:25. In aspects, NLS has an amino acid sequence of SEQ ID NO:25.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include nanoparticle encapsulation of the nucleic acids that encode the fusion protein (e.g., lipid nanoparticles, gold nanoparticles, and the like), calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

A "peptide linker" as provided herein is a linker including a peptide moiety. In embodiments, the peptide linker is a divalent peptide, such as an amino acid sequence attached at the N-terminus and the C-terminus to the remainder of the compound (e.g., fusion protein provided herein. The peptide linker may be a peptide moiety (a divalent peptide moiety) capable of being cleaved (e.g., a P2A cleavable polypeptide). A peptide linker as provided herein may also be referred to interchangeably as an amino acid linker. In aspects, the peptide linker includes 1 to about 80 amino acid residues. In aspects, the peptide linker includes 1 to about 70 amino acid residues. In aspects, the peptide linker includes 1 to about 60 amino acid residues. In aspects, the peptide linker includes 1 to about 50 amino acid residues. In aspects, the peptide linker includes 1 to about 40 amino acid residues. In aspects, the peptide linker includes 1 to about 30 amino acid residues. In aspects, the peptide linker includes 1 to about 25 amino acid residues. In aspects, the peptide linker includes 1 to about 20 amino acid residues. In aspects, the peptide linker includes about 2 to about 20 amino acid residues. In aspects, the peptide linker includes about 2 to about 19 amino acid residues. In aspects, the peptide linker includes about 2 to about 18 amino acid residues. In aspects, the peptide linker includes about 2 to about 17 amino acid residues. In aspects, the peptide linker includes about 2 to about 16 amino acid residues. In aspects, the peptide linker includes about 2 to about 15 amino acid residues. In aspects, the peptide linker includes about 2 to about 14 amino acid residues. In aspects, the peptide linker includes about 2 to about 13 amino acid residues. In aspects, the peptide linker includes about 2 to about 12 amino acid residues. In aspects, the peptide linker includes about 2 to about 11 amino acid residues. In aspects, the peptide linker includes about 2 to about 10 amino acid residues. In aspects, the peptide linker includes about 2 to about 9 amino acid residues. In aspects, the peptide linker includes about 2 to about 8 amino acid residues. In aspects, the peptide linker includes about 2 to about 7 amino acid residues. In aspects, the peptide linker includes about 2 to about 6 amino acid residues. In aspects, the peptide linker includes about 2 to about 5 amino acid residues. In aspects, the peptide linker includes about 2 to about 4 amino acid residues. In aspects, the peptide linker includes about 2 to about 3 amino acid residues. In aspects, the peptide linker includes about 3 to about 19 amino acid residues. In aspects, the peptide linker includes about 3 to about 18 amino acid residues. In aspects, the peptide linker includes about 3 to about 17 amino acid residues. In aspects, the peptide linker includes about 3 to about 16 amino acid residues. In aspects, the peptide linker includes about 3 to about 15 amino acid residues. In aspects, the peptide linker includes about 3 to about 14 amino acid residues. In aspects, the peptide linker includes about 3 to about 13 amino acid residues. In aspects, the peptide linker includes about 3 to about 12 amino acid residues. In aspects, the peptide linker includes about 3 to about 11 amino acid residues. In aspects, the peptide linker includes about 3 to about 10 amino acid residues. In aspects, the peptide linker includes about 3 to about 9 amino acid residues. In aspects, the peptide linker includes about 3 to about 8 amino acid residues. In aspects, the peptide linker includes about 3 to about 7 amino acid residues. In aspects, the peptide linker includes about 3 to about 6 amino acid residues. In aspects, the peptide linker includes about 3 to about 5 amino acid residues. In aspects, the peptide linker includes about 3 to about 4 amino acid residues. In aspects, the peptide linker includes about 10 to about 20 amino acid residues. In aspects, the peptide linker includes about 15 to about 20 amino acid residues. In aspects, the peptide linker includes about 2 amino acid residues. In aspects, the peptide linker includes about 3 amino acid residues. In aspects, the peptide linker includes about 4 amino acid residues. In aspects, the peptide linker includes about 5 amino acid residues. In aspects, the peptide linker includes about 6 amino acid residues. In aspects, the peptide linker includes about 7 amino acid residues. In aspects, the peptide linker includes about 8 amino acid residues. In aspects, the peptide linker includes about 9 amino acid residues. In aspects, the peptide linker includes about 10 amino acid residues. In aspects, the peptide linker includes about 11 amino acid residues. In aspects, the peptide linker includes about 12 amino acid residues. In aspects, the peptide linker includes about 13 amino acid residues. In aspects, the peptide linker includes about 14 amino acid residues. In aspects, the peptide linker includes about 15 amino acid residues. In aspects, the peptide linker includes about 16 amino acid residues. In aspects, the peptide linker includes about 17 amino acid residues. In aspects, the peptide linker includes about 18 amino acid residues. In aspects, the peptide linker includes about 19 amino acid residues. In aspects, the peptide linker includes about 20 amino acid residues. In aspects, the peptide linker includes about 21 amino acid residues. In aspects, the peptide linker includes about 22 amino acid residues. In aspects, the peptide linker includes about 23 amino acid residues. In aspects, the peptide linker includes about 24 amino acid residues. In aspects, the peptide linker includes about 25 amino acid residues.

In aspects, the peptide linker includes the sequence set forth by SEQ ID NO:17. In aspects, the peptide linker is the sequence set forth by SEQ ID NO:17. In aspects, the peptide linker includes the sequence set forth by SEQ ID NO:18. In aspects, the peptide linker is the sequence set forth by SEQ ID NO:18. In aspects, the peptide linker includes the sequence set forth by SEQ ID NO:19. In aspects, the peptide linker is the sequence set forth by SEQ ID NO:19. In aspects, the peptide linker includes the sequence set forth by SEQ ID NO:20. In aspects, the peptide linker is the sequence set forth by SEQ ID NO:20. In aspects, the peptide linker includes the sequence set forth by SEQ ID NO:21. In aspects, the peptide linker is the sequence set forth by SEQ ID NO:21. In aspects, the peptide linker includes the sequence set forth by SEQ ID NO:22. In aspects, the peptide linker is the sequence set forth by SEQ ID NO:22. In aspects, the peptide linker includes the sequence set forth by SEQ ID NO:27. In aspects, the peptide linker is the sequence set forth by SEQ ID NO:27. In aspects, the peptide linker includes the sequence set forth by SEQ ID NO:24. In aspects, the peptide linker is the sequence set forth by SEQ ID NO:24. In aspects, the peptide linker includes the sequence set forth by SEQ ID NO:29. In aspects, the peptide linker is the sequence set forth by SEQ ID NO:29. In aspects, the peptide linker is an XTEN polypeptide. In aspects, the peptide linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:17, 18, 19, 20, 21, 22, 24, 27, or 29. In aspects, the peptide linker has an amino acid sequence that has at least 90% sequence identity to SEQ ID NO:17, 18, 19, 20, 21, 22, 24, 27, or 29.

In aspects, the peptide linker has an amino acid sequence that has at least 90% sequence identity to SEQ ID NO:17. In aspects, the peptide linker has an amino acid sequence that has at least 90% sequence identity to SEQ ID NO:18. In aspects, the peptide linker has an amino acid sequence that has at least 90% sequence identity to SEQ ID NO:19. In aspects, the peptide linker has an amino acid sequence that has at least 90% sequence identity to SEQ ID NO:20. In aspects, the peptide linker has an amino acid sequence that has at least 90% sequence identity to SEQ ID NO:21. In aspects, the peptide linker has an amino acid sequence that has at least 90% sequence identity to SEQ ID NO:22. In aspects, the peptide linker has an amino acid sequence that has at least 90% sequence identity to SEQ ID NO:24. In aspects, the peptide linker has an amino acid sequence that has at least 90% sequence identity to SEQ ID NO:27. In aspects, the peptide linker has an amino acid sequence that has at least 90% sequence identity to SEQ ID NO:29. In aspects, the peptide linker has an amino acid sequence that has at least 95% sequence identity to SEQ ID NO:17, 18, 19, 20, 21, 22, 24, 27, or 29. In aspects, the peptide linker has an amino acid sequence that has at least 95% sequence identity to SEQ ID NO:17. In aspects, the peptide linker has an amino acid sequence that has at least 95% sequence identity to SEQ ID NO:18. In aspects, the peptide linker has an amino acid sequence that has at least 95% sequence identity to SEQ ID NO:19. In aspects, the peptide linker has an amino acid sequence that has at least 95% sequence identity to SEQ ID NO:20. In aspects, the peptide linker has an amino acid sequence that has at least 95% sequence identity to SEQ ID NO:21. In aspects, the peptide linker has an amino acid sequence that has at least 95% sequence identity to SEQ ID NO:22. In aspects, the peptide linker has an amino acid sequence that has at least 95% sequence identity to SEQ ID NO:24. In aspects, the peptide linker has an amino acid sequence that has at least 95% sequence identity to SEQ ID NO:27. In aspects, the peptide linker has an amino acid sequence that has at least 95% sequence identity to SEQ ID NO:29.

The terms "XTEN," "XTEN linker," or "XTEN polypeptide" as used herein refer to an recombinant polypeptide (e.g. unstructured recombinant peptide) lacking hydrophobic amino acid residues. The development and use of XTEN can be found in, for example, Schellenberger et al., Nature Biotechnology 27, 1186-1190 (2009), which is incorporated herein by reference in its entirety and for all purposes. In aspects, the XTEN linker includes the sequence set forth by SEQ ID NO:31. In aspects, the XTEN linker is the sequence set forth by SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158 1}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, $T_m$, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

A detectable moiety is a monovalent detectable agent or a detectable agent capable of forming a bond with another composition. In aspects, the detectable agent is an HA tag. In aspects, the HA tag includes the sequence set forth by SEQ ID NO:24. In aspects, the HA tag is the sequence set forth by SEQ ID NO:24. In aspects, the HA tag has an amino acid sequence that has at least 80% sequence identity to SEQ ID NO:24. In aspects, the HA tag has an amino acid sequence that has at least 85% sequence identity to SEQ ID NO:24. In aspects, the HA tag has an amino acid sequence that has at least 90% sequence identity to SEQ ID NO:24. In aspects, the HA tag has an amino acid sequence that has at least 95% sequence identity to SEQ ID NO:24. In aspects, the detectable agent is blue fluorescent protein (BFP). In aspects, the BFP includes the sequence set forth by SEQ ID NO:30. In aspects, the BFP is the sequence set forth by SEQ ID NO:30. In aspects, the BFP has an amino acid sequence that has at least 80% sequence identity to SEQ ID NO:30. In aspects, the BFP has an amino acid sequence that has at least 85% sequence identity to SEQ ID NO:30. In aspects, the BFP has an amino acid sequence that has at least 90% sequence identity to SEQ ID NO:30. In aspects, the BFP has an amino acid sequence that has at least 95% sequence identity to SEQ ID NO:30.

Radioactive substances (e.g., radioisotopes) that may be used as imaging and/or labeling agents in accordance with the aspects of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158 1}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the aspects of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, $T_m$, Yb and Lu.

"Contacting" is used in accordance with its plain ordinary meaning and refers to the process of allowing at least two distinct species to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a fusion protein as provided herein and a nucleic acid sequence (e.g., target DNA sequence).

As defined herein, the term "inhibition", "inhibit", "inhibiting," "repression," "repressing," "silencing," "silence" and the like when used in reference to a composition as provided herein (e.g., fusion protein, complex, nucleic acid, vector) refer to negatively affecting (e.g., decreasing) the activity (e.g., transcription) of a nucleic acid sequence (e.g., decreasing transcription of a gene) relative to the activity of the nuclei acid sequence (e.g., transcription of a gene) in the absence of the composition (e.g., fusion protein, complex, nucleic acid, vector). In aspects, inhibition refers to reduction of a disease or symptoms of disease (e.g., cancer). Thus, inhibition includes, at least in part, partially or totally blocking activation (e.g., transcription), or decreasing, preventing, or delaying activation (e.g., transcription) of the nucleic acid sequence. The inhibited activity (e.g., transcription) may be 90%, 80%, 70%, 60%, 50%, 40%, 30%, 20%, 10%, or less than that in a control. In aspects, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

Fusion Proteins

Provided herein are, inter alia, fusion proteins that can turn off genes permanently (e.g., irreversibly) and reversibly in mammalian cells using CRISPR-based epigenome editing. In embodiments, the fusion protein includes a single polypeptide fusion of four proteins (e.g., catalytically inactive Cas9 (e.g., dCas9), a KRAB domain, Dnmt3A and Dnmt3L) which can be expressed transiently in cells. The fusion protein can be directed to a specific site in a mammalian genome using a polynucleotide complementary to a target nucleic acid sequence (e.g., DNA sequence) and that further includes a sequence (i.e., binding sequence) capable of binding the fusion protein. Once properly positioned and without intending to be bound by a theory, the fusion protein adds DNA methylation and/or repressive chromatin marks to the target nucleic acid, resulting in gene silencing that is inheritable across subsequent cell divisions. In this way, the fusion protein can perform epigenome editing that bypasses the need to generate DNA double-strand breaks in the host genome, making it a safe and reversible way of manipulating the genome of a living organism.

In embodiments, the fustion protein comprises a nuclease-deficient RNA-guided DNA endonuclease enzyme; a KRAB domain, and a DNA methyltransferase domain. In aspects, the fusion protein comprises, from N-terminus to C-terminus, a DNA methyltransferase domain, a nuclease-deficient RNA-guided DNA endonuclease enzyme, and KRAB domain. In aspects, the fusion protein comprises, from N-terminus to C-terminus, a KRAB domain a nuclease-deficient RNA-guided DNA endonuclease enzyme, and a DNA methyltransferase domain. In embodiments, the fustion protein further comprises one or more peptide linkers. In aspects, the fusion protein further comprises one or more detectable tags. In aspects, the fusion protein further comprises one or more nuclear localization sequences. In aspects, the fusion protein further comprises one or more peptide linkers, one or more detectable tags, one or more nuclear localization sequences, or a combination of two or more of the foregoing. When the fusion protein comprises one or more peptide linkers, each peptide liner can be the same or different. When the fusion protein comprises one or more detectable tags, each detectable tag can be the same or different. In aspects, the fusion protein comprises from 1 to 10 detectable tags. In aspects, the fusion protein comprises from 1 to 9 detectable tags. In aspects, the fusion protein comprises from 1 to 8 detectable tags. In aspects, the fusion protein comprises from 1 to 7 detectable tags. In aspects, the fusion protein comprises from 1 to 6 detectable tags. In aspects, the fusion protein comprises from 1 to 5 detectable tags. In aspects, the fusion protein comprises from 1 to 4 detectable tags. In aspects, the fusion protein comprises from 1 to 3 detectable tags. In aspects, the fusion protein comprises from 1 to 2 detectable tags. In aspects, the fusion protein comprises 1 detectable tag. In aspects, the fusion protein comprises 2 detectable tags. In aspects, the fusion protein comprises 3 detectable tags. In aspects, the fusion protein comprises 4 detectable tags. In aspects, the fusion protein comprises 5 detectable tags.

In embodiments, the fusion protein comprises the structure: A-B-C, or B-A-C or C-A-B, or C-B-A, or B-C-A, or A-C-B; where A comprises a nuclease-deficient RNA-guided DNA endonuclease enzyme; B comprises a KRAB domain, C comprises a DNA methyltransferase domain; and wherein the component on the left is the N-terminus and the component on the right is the C-terminus. In aspects, the fusion protein further comprises one or more peptide linkers and one or more detectable tags. In aspects, A-B, B-A, B-C, C-B, A-C, and C-A are each independently linked together via a covalent bond, a peptide linker, a detectable tag, a nuclear localization sequence, or a combination of two or more thereof. The peptide linker can be any known in the art (e.g., P2A cleavable peptide, XTEN linker, and the like). In aspects, the fusion protein comprises other components, such as detectable tags (e.g., HA tag, blue fluorescent protein, and the like).

In embodiments, the fusion protein comprises the structure: $A-L_1-B-L_2-C$, where A comprises a nuclease-deficient RNA-guided DNA endonuclease enzyme; B comprises a KRAB domain, C comprises a DNA methyltransferase domain, $L_1$ is a covalent bond or a peptide linker, and $L_2$ is a covalent bond or a peptide linker; and where A is at the N-terminus and C is at the C-terminus. In aspects, A is covalently linked to B via a peptide linker. In aspects, A is covalently linked to B via a covalent bond. In aspects, B is covalently linked to C via a peptide linker. In aspects, B is covalently linked to C via a covalent bond. The peptide linker can be any known in the art (e.g., P2A cleavable peptide, XTEN linker, and the like). In aspects, the fusion protein comprises other components, such as detectable tags, nuclear localization sequences, and the like. In aspects, $L_1$ is a covalent bond, a peptide linker, a detectable tag, a nuclear localization sequence, or a combination thereof. In aspects, $L_2$ is a covalent bond, a peptide linker, a detectable tag, a nuclear localization sequence, or a combination thereof.

Figure 5:
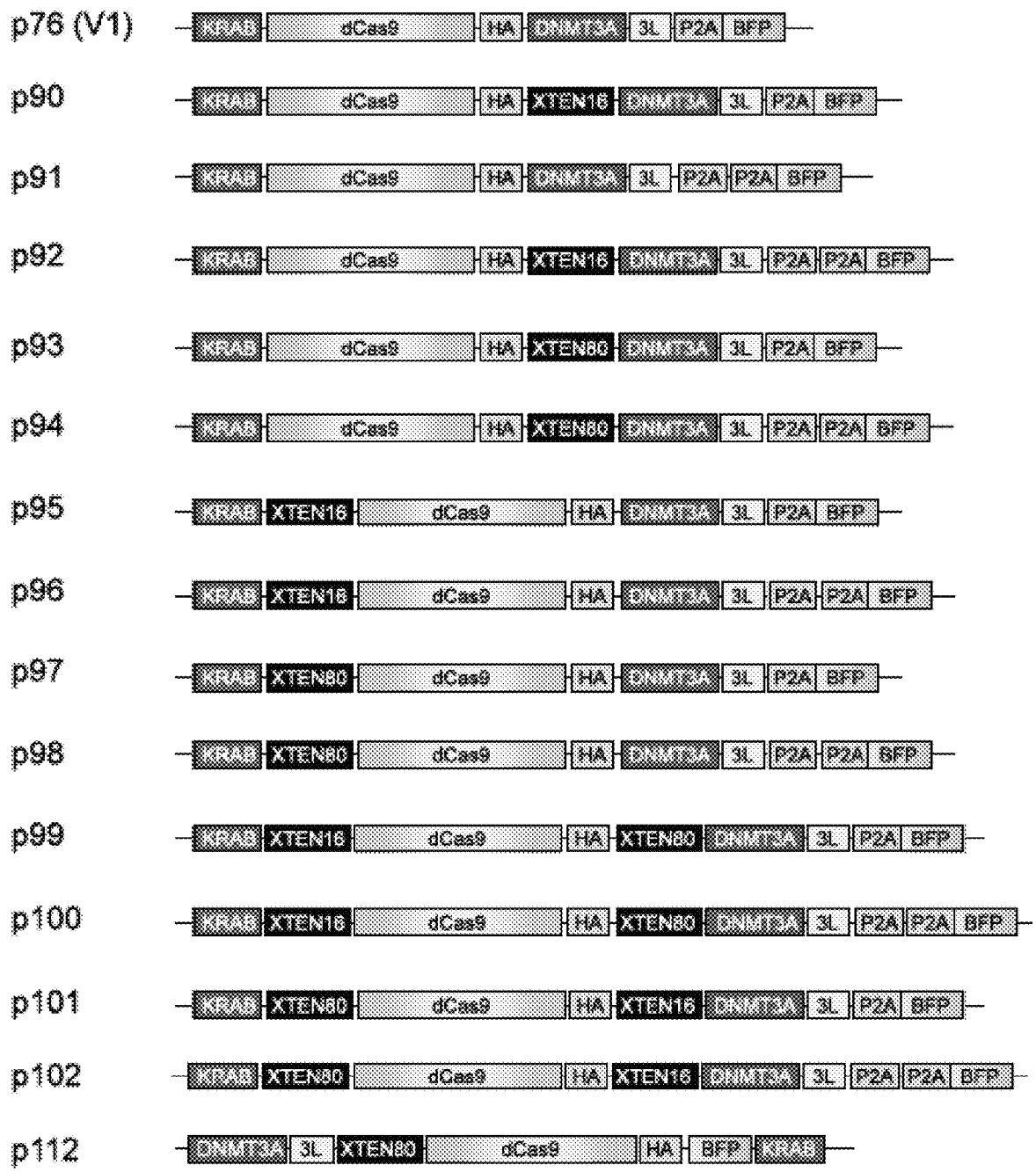
FIG. 5 provides schematics of the fusion proteins p76, p90-p102, and p112 which correspond to SEQ ID NOS:1-15, respectively.

In embodiments, the fusion protein comprises the structure: $B-L_1-A-L_2-C$, where A comprise a nuclease-deficient RNA-guided DNA endonuclease enzyme; B comprises a KRAB domain, C comprises a DNA methyltransferase domain, $L_1$ is a covalent bond or a peptide linker, and $L_2$ is a covalent bond or a peptide linker; and where B is at the N-terminus and C is at the C-terminus. In aspects, $L_1$ is a peptide linker. In aspects, $L_1$ is a covalent bond. In aspects, $L_2$ is a peptide linker. In aspects, $L_2$ is a covalent bond. The peptide linker can be any known in the art or described herein (e.g., P2A cleavable peptide, XTEN linker, and the like). In aspects, the fusion protein comprises other components, such as detectable tags. In aspects, $L_1$ is a covalent bond, a peptide linker, a detectable tag, or a combination thereof. In aspects, $L_2$ is a covalent bond, a peptide linker, a detectable tag, or a combination thereof. In aspects, the fusion protein further comprises a nuclear localization sequence. Exemplary fusion proteins comprising the structure: B-L$_1$-A-L$_2$-C include p76, p90, p91, p92, p93, p94, p95, p96, p97, p98, p99, p100, p101, and p102 (FIG. 5)

In embodiments, the fusion protein comprises the structure: B-L$_3$-A-L$_4$-C-L$_5$-D; where A comprises a nuclease-deficient RNA-guided DNA endonuclease enzyme; B comprises a KRAB domain, C comprises a DNA methyltransferase domain, D is absent or D comprises one or more detectable tags, L$_3$ comprises a covalent bond, a peptide linker, a detectable tag, or a combination of two or more thereof, L$_4$ comprises a covalent bond, a peptide linker, a detectable tag, or a combination of two or more thereof, L$_5$ is absent or L$_5$ comprises a covalent bond or a peptide linker; and where B is at the N-terminus and D is at the C-terminus. In aspects, L$_3$ is a peptide linker. In aspects, L$_3$ is a covalent bond. In aspects, L$_3$ comprises a peptide linker and a detectable tag. In aspects, L$_3$ comprises a detectable tag. In aspects, L$_4$ is a peptide linker. In aspects, L$_4$ comprises a peptide linker and a detectable tag. In aspects, L$_4$ is a covalent bond. In aspects, L$_4$ comprises a detectable tag. In aspects, L$_5$ is a peptide linker. In aspects, L$_5$ is a covalent bond. In aspects, D comprises one or a plurality of detectable tags. In aspects, D comprises one detectable tag. In aspects, D comprises two detectable tags. In aspects, D comprises three detectable tags. In aspects, D comprises a plurality of detectable tags. D can be any detectable tag known in the art and/or described herein (e.g., HA tag, blue fluorescent protein, and the like). In aspects L$_5$ and D are absent. When L$_3$, L$_4$, L$_5$, and D comprise two or more detectable tags, each detectable tag is the same or different. The peptide linker can be any known in the art and/or described herein (e.g., P2A cleavable peptide, XTEN linker, and the like). In aspects, the fusion protein further comprises a nuclear localization sequence. Exemplary fusion proteins comprising the structure: B-L$_3$-A-L$_4$-C-L$_5$-D include p76, p90, p91, p92, p93, p94, p95, p96, p97, p98, p99, p100, p101, and p102, as shown in FIG. 5.

In embodiments, the fusion protein comprises the structure: C-L$_3$-A-L$_4$-B-L$_5$-D, where A comprises a nuclease-deficient RNA-guided DNA endonuclease enzyme; B comprises a KRAB domain, C comprises a DNA methyltransferase domain, D is absent or D comprises one or more detectable tags, L$_3$ comprises a covalent bond, a peptide linker, a detectable tag, or a combination of two or more thereof, L$_4$ comprises a covalent bond, a peptide linker, a detectable tag, or a combination of two or more thereof, L$_5$ is absent or L$_5$ comprises a covalent bond or a peptide linker; and where C is at the N-terminus and D is at the C-terminus. In aspects, L$_3$ is a peptide linker. In aspects, L$_3$ is a covalent bond. In aspects, L$_3$ comprises a detectable tag. In aspects, L$_3$ comprises a peptide linker and a detectable tag. In aspects, L$_4$ a peptide linker. In aspects, L$_4$ is a covalent bond. In aspects, L$_4$ comprises a detectable tag. In aspects, L$_4$ comprises a peptide linker and a detectable tag. In aspects, L$_5$ a peptide linker. In aspects, L$_5$ is a covalent bond. In aspects, D comprises one or a plurality of detectable tags. In aspects, D comprises one detectable tag. In aspects, D comprises two detectable tags. In aspects, D comprises three detectable tags. In aspects, D comprises a plurality of detectable tags. D can be any detectable tag known in the art and/or described herein (e.g., HA tag, blue fluorescent protein, and the like). In aspects L$_5$ and D are absent. When L$_3$, L$_4$, L$_5$, and D comprise two or more detectable tags, each detectable tag is the same or different. The peptide linker can be any known in the art and/or described herein (e.g., P2A cleavable peptide, XTEN linker, and the like). In aspects, the fusion protein further comprises a nuclear localization sequence. Exemplary fusion proteins comprising the structure: C-L$_3$-A-L$_4$-B-L$_5$-D include p112, as shown in FIG. 5.

The term "nuclease-deficient RNA-guided DNA endonuclease enzyme" and the like refer, in the usual and customary sense, to an RNA-guided DNA endonuclease (e.g. a mutated form of a naturally occurring RNA-guided DNA endonuclease) that targets a specific phosphodiester bond within a DNA polynucleotide, wherein the recognition of the phosphodiester bond is facilitated by a separate polynucleotide sequence (for example, a RNA sequence (e.g., single guide RNA (sgRNA)), but is incapable of cleaving the target phosphodiester bond to a significant degree (e.g. there is no measurable cleavage of the phosphodiester bond under physiological conditions). A nuclease-deficient RNA-guided DNA endonuclease thus retains DNA-binding ability (e.g. specific binding to a target sequence) when complexed with a polynucleotide (e.g., sgRNA), but lacks significant endonuclease activity (e.g. any amount of detectable endonuclease activity). In aspects, the nuclease-deficient RNA-guided DNA endonuclease enzyme is dCas9, ddCpf1, a nuclease-deficient Cas9 variant, or a nuclease-deficient Class II CRISPR endonuclease.

In embodiments, the nuclease-deficient RNA-guided DNA endonuclease enzyme is dCas9. The terms "dCas9" or "dCas9 protein" as referred to herein is a Cas9 protein in which both catalytic sites for endonuclease activity are defective or lack activity. In aspects, the dCas9 protein has mutations at positions corresponding to D10A and H840A of *S. pyogenes* Cas9. In aspects, the dCas9 protein lacks endonuclease activity due to point mutations at both endonuclease catalytic sites (RuvC and HNH) of wild type Cas9. The point mutations can be D10A and H840A. In aspects, the dCas9 has substantially no detectable endonuclease (e.g., endodeoxyribonuclease) activity. In aspects, dCas9 includes the amino acid sequence of SEQ ID NO:23. In aspects, dCas9 has the amino acid sequence of SEQ ID NO:23. In aspects, dCas9 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:23. In aspects, dCas9 has an amino acid sequence that has at least 75% sequence identity to SEQ ID NO:23. In aspects, dCas9 has an amino acid sequence that has at least 80% sequence identity to SEQ ID NO:23. In aspects, dCas9 has an amino acid sequence that has at least 85% sequence identity to SEQ ID NO:23. In aspects, dCas9 has an amino acid sequence that has at least 90% sequence identity to SEQ ID NO:23. In aspects, dCas9 has an amino acid sequence that has at least 95% sequence identity to SEQ ID NO:23.

A "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In aspects, the Cas9 protein is substantially identical to the protein identified by the UniProt reference number Q99ZW2 or a variant or homolog having substantial identity thereto. In aspects, the Cas9 protein has at least 75% sequence identity to the amino acid sequence of the protein identified by the UniProt reference number Q99ZW2. In aspects, the Cas9 protein has at least 80% sequence identity to the amino acid sequence of the protein identified by the UniProt reference number Q99ZW2. In aspects, the Cas9 protein has at least 85% sequence identity to the amino acid sequence of the protein identified by the UniProt reference number Q99ZW2. In aspects, the Cas9 protein has at least 90% sequence identity to the amino acid sequence of the protein identified by the UniProt reference number Q99ZW2. In aspects, the Cas9 protein has at least 95% sequence identity to the amino acid sequence of the protein identified by the UniProt reference number Q99ZW2.

In embodiments, the nuclease-deficient RNA-guided DNA endonuclease enzyme is "ddCpf1" or "ddCas12a". The terms "DNAse-dead Cpf1" or "ddCpf1" refer to mutated *Acidaminococcus* sp. Cpf1 (AsCpf1) resulting in the inactivation of Cpf1 DNAse activity. In aspects, ddCpf1 includes an E993A mutation in the RuvC domain of AsCpf1. In aspects, the ddCpf1 has substantially no detectable endonuclease (e.g., endodeoxyribonuclease) activity. In aspects, ddCpf1 includes the amino acid sequence of SEQ ID NO:34. In aspects, ddCpf1 has the amino acid sequence of SEQ ID NO:34. In aspects, ddCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:34. In aspects, ddCpf1 has an amino acid sequence that has at least 75% sequence identity to SEQ ID NO:34. In aspects, ddCpf1 has an amino acid sequence that has at least 80% sequence identity to SEQ ID NO:34. In aspects, ddCpf1 has an amino acid sequence that has at least 85% sequence identity to SEQ ID NO:34. In aspects, ddCpf1 has an amino acid sequence that has at least 90% sequence identity to SEQ ID NO:34. In aspects, ddCpf1 has an amino acid sequence that has at least 95% sequence identity to SEQ ID NO:34.

In embodiments, the nuclease-deficient RNA-guided DNA endonuclease enzyme is dLbCpf1. The term "dLbCpf1: refers to mutated Cpf1 from Lachnospiraceae bacterium ND2006 (LbCpf1) that lacks DNAse activity. In aspects, dLbCpf1 includes a D832A mutation. In aspects, the dLbCpf1 has substantially no detectable endonuclease (e.g., endodeoxyribo-nuclease) activity.

In aspects, dLbCpf1 includes the amino acid sequence of SEQ ID NO:35. In aspects, dLbCpf1 has the amino acid sequence of SEQ ID NO:35. In aspects, dLbCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:35. In aspects, dLbCpf1 has an amino acid sequence that has at least 75% sequence identity to SEQ ID NO:35. In aspects, dLbCpf1 has an amino acid sequence that has at least 80% sequence identity to SEQ ID NO:35. In aspects, dLbCpf1 has an amino acid sequence that has at least 85% sequence identity to SEQ ID NO:35. In aspects, dLbCpf1 has an amino acid sequence that has at least 90% sequence identity to SEQ ID NO:35. In aspects, dLbCpf1 has an amino acid sequence that has at least 95% sequence identity to SEQ ID NO:35.

In embodiments, the nuclease-deficient RNA-guided DNA endonuclease enzyme is dFnCpf1. The term "dFnCpf1" refers to mutated Cpf1 from *Francisella novicida* U112 (FnCpf1) that lacks DNAse activity. In aspects, dFnCpf1 includes a D917A mutation. In aspects, the dFnCpf1 has substantially no detectable endonuclease (e.g., endodeoxyribo-nuclease) activity. In aspects, dFnCpf1 includes the amino acid sequence of SEQ ID NO: 36. In aspects, dFnCpf1 has the amino acid sequence of SEQ ID NO: 36. In aspects, dFnCpf1 has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:36. In aspects, dFnCpf1 has an amino acid sequence that has at least 75% sequence identity to SEQ ID NO:36. In aspects, dFnCpf1 has an amino acid sequence that has at least 80% sequence identity to SEQ ID NO:36. In aspects, dFnCpf1 has an amino acid sequence that has at least 85% sequence identity to SEQ ID NO:36. In aspects, dFnCpf1 has an amino acid sequence that has at least 90% sequence identity to SEQ ID NO:36. In aspects, dFnCpf1 has an amino acid sequence that has at least 95% sequence identity to SEQ ID NO:36.

A "Cpf1" or "Cpf1 protein" as referred to herein includes any of the recombinant or naturally-occurring forms of the Cpf1 (CRISPR from *Prevotella* and *Francisella* 1) endonuclease or variants or homologs thereof that maintain Cpf1 endonuclease enzyme activity (e.g. within at least 50%, 80%, 90%, 95%, 96%, 97%, 98%, 99% or 100% activity compared to Cpf1). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cpf1 protein. In aspects, the Cpf1 protein is substantially identical to the protein identified by the UniProt reference number U2UMQ6 or a variant or homolog having substantial identity thereto. In aspects, the Cpf1 protein is identical to the protein identified by the UniProt reference number U2UMQ6. In aspects, the Cpf1 protein has at least 75% sequence identity to the amino acid sequence of the protein identified by the UniProt reference number U2UMQ6. In aspects, the Cpf1 protein has at least 80% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 85% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 90% sequence identity to the amino acid sequence of the protein identified by the UniProt reference number U2UMQ6. In aspects, the Cpf1 protein is identical to the protein identified by the UniProt reference number U2UMQ6. In aspects, the Cpf1 protein has at least 95% sequence identity to the amino acid sequence of the protein identified by the UniProt reference number U2UMQ6.

In embodiments, the nuclease-deficient RNA-guided DNA endonuclease enzyme is a nuclease-deficient Cas9 variant. The term "nuclease-deficient Cas9 variant" refers to a Cas9 protein having one or more mutations that increase its binding specificity to PAM compared to wild type Cas9 and further include mutations that render the protein incapable of or having severely impaired endonuclease activity. Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). The binding specificity of nuclease-deficient Cas9 variants to PAM can be determined by any method known in the art. Descriptions and uses of known Cas9 variants may be found, for example, in Shmakov et al., Diversity and evolution of class 2 CRISPR-Cas systems. Nat. Rev. Microbiol. 15, 2017 and Cebrian-Serrano et al, CRISPR-Cas orthologues and variants: optimizing the repertoire, specificity and delivery of genome engineering tools. Mamm. Genome 7-8, 2017, which are incorporated herein by reference in their entirety and for all purposes. Exemplary Cas9 variants are listed in the Table 4 below.

TABLE 4

| Cas9 Variants | PAM domains | References |
|---|---|---|
| Strep pyogenes (Sp) Cas9 | NGG | Hsu et al. 2014 Cell |
| Staph aureus (Sa) Cas9 | NNGRRT or NNGRR NNGGGT, NNGAAT, NNGAGT (Zetsche) | Ran et al. 2015 Nature |
| SpCas9 VQR mutant (D1135V, R1335Q, T1337R) | NGAG > NGAT = NGAA > NGAC NGCG | Kleinstiver et al. 2015 Nature |
| SpCas9 VRER mutant (D1135V/G1218R/ R1335E/T1337R) | NGCG | Kleinstiver et al. 2015 Nature |
| SpCas9 D1135E | NGG, greater fidelity, less cutting at NAG and NGA sites | Kleinstiver et al. 2015 Nature |
| eSpCas9 1.1 mutant (K848A/K1003A/R1060A) | NGG | Slaymaker et al. Science 2015 |
| SpCas9 HF1 (Q695A, Q926A, N497A, R661A) | NGG | Kleinstiver et al. 2016 Nature |
| AsCpf1 | TTTN (5' of sgRNA) | Zetsche et al. 2015 Cell |
| HypaCas9 (N692A, M694A, Q695A, H698A) | | Chen et al., Nature volume 550, pages 407-410 (19 Oct. 2017) |

In embodiments, the nuclease-deficient RNA-guided DNA endonuclease enzyme is a nuclease-deficient Class II CRISPR endonuclease. The term "nuclease-deficient Class II CRISPR endonuclease" as used herein refers to any Class II CRISPR endonuclease having mutations resulting in reduced, impaired, or inactive endonuclease activity.

In embodiments, the DNA methyltransferase domain is a Dnmt3A-3L domain. A "Dnmt3A-3L domain" as provided herein refers to a protein including both Dnmt3A and Dnmt3L. In aspects, the Dnmt3A and the Dnmt3L are covalently linked. In aspects, the Dnmt3A is covalently linked to the Dnmt3L through a peptide linker. In aspects, the peptide linker includes the sequence set forth by SEQ ID NO:27. In aspects, the peptide linker is the sequence set forth by SEQ ID NO:27. In aspects, the peptide linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:27. In aspects, the peptide linker has an amino acid sequence that has at least 90% sequence identity to SEQ ID NO:27. In aspects, the peptide linker has an amino acid sequence that has at least 95% sequence identity to SEQ ID NO:27. In aspects, the Dnmt3A-3L domain includes the sequence set forth by SEQ ID NO:33. In aspects, the Dnmt3A-3L domain is the sequence set forth by SEQ ID NO:33. In aspects, the Dnmt3A-3L domain has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:33. In aspects, the Dnmt3A-3L domain has an amino acid sequence that has at least 75% sequence identity to SEQ ID NO:33. In aspects, the Dnmt3A-3L domain has an amino acid sequence that has at least 80% sequence identity to SEQ ID NO:33. In aspects, the Dnmt3A-3L domain has an amino acid sequence that has at least 85% sequence identity to SEQ ID NO:33. In aspects, the Dnmt3A-3L domain has an amino acid sequence that has at least 90% sequence identity to SEQ ID NO:33. In aspects, the Dnmt3A-3L domain has an amino acid sequence that has at least 95% sequence identity to SEQ ID NO:33.

In embodiments, the peptide linker is a XTEN linker. In aspects, the XTEN linker includes about 16 to about 80 amino acid residues. In aspects, the XTEN linker includes about 17 to about 80 amino acid residues. In aspects, the XTEN linker includes about 18 to about 80 amino acid residues. In aspects, the XTEN linker includes about 19 to about 80 amino acid residues. In aspects, the XTEN linker includes about 20 to about 80 amino acid residues. In aspects, the XTEN linker includes about 30 to about 80 amino acid residues. In aspects, the XTEN linker includes about 40 to about 80 amino acid residues. In aspects, the XTEN linker includes about 50 to about 80 amino acid residues. In aspects, the XTEN linker includes about 60 to about 80 amino acid residues. In aspects, the XTEN linker includes about 70 to about 80 amino acid residues. In aspects, the XTEN linker includes about 16 to about 70 amino acid residues. In aspects, the XTEN linker includes about 16 to about 60 amino acid residues. In aspects, the XTEN linker includes about 16 to about 50 amino acid residues. In aspects, the XTEN linker includes about 16 to about 40 amino acid residues. In aspects, the XTEN linker includes about 16 to about 35 amino acid residues. In aspects, the XTEN linker includes about 16 to about 30 amino acid residues. In aspects, the XTEN linker includes about 16 to about 25 amino acid residues. In aspects, the XTEN linker includes about 16 to about 20 amino acid residues. In aspects, the XTEN linker includes about 16 amino acid residues. In aspects, the XTEN linker includes about 17 amino acid residues. In aspects, the XTEN linker includes about 18 amino acid residues. In aspects, the XTEN linker includes about 19 amino acid residues. In aspects, the XTEN linker includes about 20 amino acid residues.

In embodiments, the XTEN linker includes the sequence set forth by SEQ ID NO:31. In aspects, the XTEN linker is the sequence set forth by SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:31. In aspects, the XTEN linker has an amino acid sequence that has at least 85% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:32. In aspects, the XTEN linker has an amino acid sequence that has at least 75% sequence identity to SEQ ID NO:32. In aspects, the XTEN linker has an amino acid sequence that has at least 80% sequence identity to SEQ ID NO:32. In aspects, the XTEN linker has an amino acid sequence that has at least 85% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

The fusion protein may include amino acid sequences useful for targeting the fusion protein to specific regions of a cell (e.g., cytoplasm, nucleus). Thus, in aspects, the fusion protein further includes a nuclear localization signal (NLS) peptide. In aspects, the NLS includes the sequence set forth by SEQ ID NO:25. In aspects, the NLS is the sequence set forth by SEQ ID NO:25. In aspects, the NLS has an amino acid sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO: 25. In aspects, the NLS has an amino acid sequence that has at least 75% sequence identity to SEQ ID NO:25. In aspects, the NLS has an amino acid sequence that has at least 80% sequence identity to SEQ ID NO:25. In aspects, the NLS has an amino acid sequence that has at least 85% sequence identity to SEQ ID NO:25. In aspects, the NLS has an amino acid sequence that has at least 90% sequence identity to SEQ ID NO:25. In aspects, the NLS has an amino acid sequence that has at least 95% sequence identity to SEQ ID NO:25.

In embodiments, the fusion protein includes, from N-terminus to C-terminus, a KRAB domain, a nuclease-deficient RNA-guided DNA endonuclease enzyme, and a DNA methyltransferase domain.

In embodiments, the nuclease-deficient RNA-guided DNA endonuclease enzyme is dCas9 and the DNA methyltransferase domain is a Dnmt3A-3L domain.

In embodiments, the dCas9 is covalently linked to the KRAB domain via a peptide linker and wherein the dCas9 is covalently linked to the Dnmt3A-3L domain via a peptide linker.

In embodiments, peptide linker is an XTEN linker. In aspects, the XTEN linker includes the sequence set forth by SEQ ID NO:31. In aspects, the XTEN linker is the sequence set forth by SEQ ID NO:31. In aspects, the XTEN linker has an amino acid sequence that has at least 75% sequence identity to SEQ ID NO:31. In aspects, the XTEN linker has an amino acid sequence that has at least 80% sequence identity to SEQ ID NO:31. In aspects, the XTEN linker has an amino acid sequence that has at least 85% sequence identity to SEQ ID NO:31. In aspects, the XTEN linker has an amino acid sequence that has at least 90% sequence identity to SEQ ID NO:31. In aspects, the XTEN linker has an amino acid sequence that has at least 95% sequence identity to SEQ ID NO:31. In aspects, the XTEN linker includes the sequence set forth by SEQ ID NO:32. In aspects, the XTEN linker is the sequence set forth by SEQ ID NO:32. In aspects, the XTEN linker has an amino acid sequence that has at least 75% sequence identity to SEQ ID NO:32. In aspects, the XTEN linker has an amino acid sequence that has at least 80% sequence identity to SEQ ID NO:32. In aspects, the XTEN linker has an amino acid sequence that has at least 85% sequence identity to SEQ ID NO:32. In aspects, the XTEN linker has an amino acid sequence that has at least 90% sequence identity to SEQ ID NO:32. In aspects, the XTEN linker has an amino acid sequence that has at least 95% sequence identity to SEQ ID NO:32.

In embodiments, the fusion protein includes the amino acid sequence of SEQ ID NO: 1, 2, 3, 4, 5, 6, 7, 8, 9, 10, 11 12, 13, 14 or 15. In aspects, the fusion protein includes the amino acid sequence of SEQ ID NO:1. In aspects, the fusion protein is the amino acid sequence of SEQ ID NO:1. In aspects, the fusion protein includes the amino acid sequence of SEQ ID NO:2. In aspects, the fusion protein is the amino acid sequence of SEQ ID NO:2 In aspects, the fusion protein includes the amino acid sequence of SEQ ID NO:3. In aspects, the fusion protein is the amino acid sequence of SEQ ID NO:3. In aspects, the fusion protein includes the amino acid sequence of SEQ ID NO:4. In aspects, the fusion protein is the amino acid sequence of SEQ ID NO:4. In aspects, the fusion protein includes the amino acid sequence of SEQ ID NO:5. In aspects, the fusion protein is the amino acid sequence of SEQ ID NO:5. In aspects, the fusion protein includes the amino acid sequence of SEQ ID NO:6. In aspects, the fusion protein is the amino acid sequence of SEQ ID NO:6. In aspects, the fusion protein includes the amino acid sequence of SEQ ID NO:7. In aspects, the fusion protein is the amino acid sequence of SEQ ID NO:7. In aspects, the fusion protein includes the amino acid sequence of SEQ ID NO:8. In aspects, the fusion protein is the amino acid sequence of SEQ ID NO:8. In aspects, the fusion protein includes the amino acid sequence of SEQ ID NO:9. In aspects, the fusion protein is the amino acid sequence of SEQ ID NO:9. In aspects, the fusion protein includes the amino acid sequence of SEQ ID NO:10. In aspects, the fusion protein is the amino acid sequence of SEQ ID NO:10. In aspects, the fusion protein includes the amino acid sequence of SEQ ID NO:11. In aspects, the fusion protein is the amino acid sequence of SEQ ID NO:11. In aspects, the fusion protein includes the amino acid sequence of SEQ ID NO:12. In aspects, the fusion protein is the amino acid sequence of SEQ ID NO:12. In aspects, the fusion protein includes the amino acid sequence of SEQ ID NO:13. In aspects, the fusion protein is the amino acid sequence of SEQ ID NO:13. In aspects, the fusion protein includes the amino acid sequence of SEQ ID NO:14. In aspects, the fusion protein is the amino acid sequence of SEQ ID NO:14. In aspects, the fusion protein includes the amino acid sequence of SEQ ID NO:15. In aspects, the fusion protein is the amino acid sequence of SEQ ID NO:15.

In embodiments, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1, 2, 3, 4, 5, 6, 7, 8, 9, 10, 11 12, 13, 14 or 15. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:2. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:5. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:6. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:7. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:8. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:9. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:10. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:11. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:12. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:13. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:14. In aspects, the fusion protein includes an amino acid sequence having at least 75%, 80% 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:15.

In embodiments, the fusion protein includes an amino acid sequence having at least 75% sequence identity to SEQ ID NO:1, 2, 3, 4, 5, 6, 7, 8, 9, 10, 11 12, 13, 14 or 15. In aspects, the fusion protein includes an amino acid sequence having at least 75% sequence identity to SEQ ID NO:1. In aspects, the fusion protein includes an amino acid sequence having at least 75% sequence identity to SEQ ID NO:2. In aspects, the fusion protein includes an amino acid sequence having at least 75% sequence identity to SEQ ID NO:3. In aspects, the fusion protein includes an amino acid sequence having at least 75% sequence identity to SEQ ID NO:4. In aspects, the fusion protein includes an amino acid sequence having at least 75% sequence identity to SEQ ID NO:5. In aspects, the fusion protein includes an amino acid sequence having at least 75% sequence identity to SEQ ID NO:6. In aspects, the fusion protein includes an amino acid sequence having at least 75% sequence identity to SEQ ID NO:7. In aspects, the fusion protein includes an amino acid sequence having at least 75% sequence identity to SEQ ID NO:8. In aspects, the fusion protein includes an amino acid sequence having at least 75% sequence identity to SEQ ID NO:9. In aspects, the fusion protein includes an amino acid sequence having at least 75% sequence identity to SEQ ID NO:10. In aspects, the fusion protein includes an amino acid sequence having at least 75% sequence identity to SEQ ID NO:11. In aspects, the fusion protein includes an amino acid sequence having at least 75% sequence identity to SEQ ID NO:12. In aspects, the fusion protein includes an amino acid sequence having at least 75% sequence identity to SEQ ID NO:13. In aspects, the fusion protein includes an amino acid sequence having at least 75% sequence identity to SEQ ID NO:14. In aspects, the fusion protein includes an amino acid sequence having at least 75% sequence identity to SEQ ID NO:15.

In embodiments, the fusion protein includes an amino acid sequence having at least 80% sequence identity to SEQ ID NO:1, 2, 3, 4, 5, 6, 7, 8, 9, 10, 11 12, 13, 14 or 15. In aspects, the fusion protein includes an amino acid sequence having at least 80% sequence identity to SEQ ID NO:1. In aspects, the fusion protein includes an amino acid sequence having at least 80% sequence identity to SEQ ID NO:2. In aspects, the fusion protein includes an amino acid sequence having at least 80% sequence identity to SEQ ID NO:3. In aspects, the fusion protein includes an amino acid sequence having at least 80% sequence identity to SEQ ID NO:4. In aspects, the fusion protein includes an amino acid sequence having at least 80% sequence identity to SEQ ID NO:5. In aspects, the fusion protein includes an amino acid sequence having at least 80% sequence identity to SEQ ID NO:6. In aspects, the fusion protein includes an amino acid sequence having at least 80% sequence identity to SEQ ID NO:7. In aspects, the fusion protein includes an amino acid sequence having at least 80% sequence identity to SEQ ID NO:8. In aspects, the fusion protein includes an amino acid sequence having at least 80% sequence identity to SEQ ID NO:9. In aspects, the fusion protein includes an amino acid sequence having at least 80% sequence identity to SEQ ID NO:10. In aspects, the fusion protein includes an amino acid sequence having at least 80% sequence identity to SEQ ID NO:11. In aspects, the fusion protein includes an amino acid sequence having at least 80% sequence identity to SEQ ID NO:12. In aspects, the fusion protein includes an amino acid sequence having at least 80% sequence identity to SEQ ID NO:13. In aspects, the fusion protein includes an amino acid sequence having at least 80% sequence identity to SEQ ID NO:14. In aspects, the fusion protein includes an amino acid sequence having at least 80% sequence identity to SEQ ID NO:15.

In embodiments, the fusion protein includes an amino acid sequence having at least 85% sequence identity to SEQ ID NO:1, 2, 3, 4, 5, 6, 7, 8, 9, 10, 11 12, 13, 14 or 15. In aspects, the fusion protein includes an amino acid sequence having at least 85% sequence identity to SEQ ID NO:1. In aspects, the fusion protein includes an amino acid sequence having at least 85% sequence identity to SEQ ID NO:2. In aspects, the fusion protein includes an amino acid sequence having at least 85% sequence identity to SEQ ID NO:3. In aspects, the fusion protein includes an amino acid sequence having at least 85% sequence identity to SEQ ID NO:4. In aspects, the fusion protein includes an amino acid sequence having at least 85% sequence identity to SEQ ID NO:5. In aspects, the fusion protein includes an amino acid sequence having at least 85% sequence identity to SEQ ID NO:6. In aspects, the fusion protein includes an amino acid sequence having at least 85% sequence identity to SEQ ID NO:7. In aspects, the fusion protein includes an amino acid sequence having at least 85% sequence identity to SEQ ID NO:8. In aspects, the fusion protein includes an amino acid sequence having at least 85% sequence identity to SEQ ID NO:9. In aspects, the fusion protein includes an amino acid sequence having at least 85% sequence identity to SEQ ID NO:10. In aspects, the fusion protein includes an amino acid sequence having at least 85% sequence identity to SEQ ID NO:11. In aspects, the fusion protein includes an amino acid sequence having at least 85% sequence identity to SEQ ID NO:12. In aspects, the fusion protein includes an amino acid sequence having at least 85% sequence identity to SEQ ID NO:13. In aspects, the fusion protein includes an amino acid sequence having at least 85% sequence identity to SEQ ID NO:14. In aspects, the fusion protein includes an amino acid sequence having at least 85% sequence identity to SEQ ID NO:15.

In embodiments, the fusion protein includes an amino acid sequence having at least 90% sequence identity to SEQ ID NO:1, 2, 3, 4, 5, 6, 7, 8, 9, 10, 11 12, 13, 14 or 15. In aspects, the fusion protein includes an amino acid sequence having at least 90% sequence identity to SEQ ID NO:1. In aspects, the fusion protein includes an amino acid sequence having at least 90% sequence identity to SEQ ID NO:2. In aspects, the fusion protein includes an amino acid sequence having at least 90% sequence identity to SEQ ID NO:3. In aspects, the fusion protein includes an amino acid sequence having at least 90% sequence identity to SEQ ID NO:4. In aspects, the fusion protein includes an amino acid sequence having at least 90% sequence identity to SEQ ID NO:5. In aspects, the fusion protein includes an amino acid sequence having at least 90% sequence identity to SEQ ID NO:6. In aspects, the fusion protein includes an amino acid sequence having at least 90% sequence identity to SEQ ID NO:7. In aspects, the fusion protein includes an amino acid sequence having at least 90% sequence identity to SEQ ID NO:8. In aspects, the fusion protein includes an amino acid sequence having at least 90% sequence identity to SEQ ID NO:9. In aspects, the fusion protein includes an amino acid sequence having at least 90% sequence identity to SEQ ID NO:10. In aspects, the fusion protein includes an amino acid sequence having at least 90% sequence identity to SEQ ID NO:11. In aspects, the fusion protein includes an amino acid sequence having at least 90% sequence identity to SEQ ID NO:12. In aspects, the fusion protein includes an amino acid sequence having at least 90% sequence identity to SEQ ID NO:13. In aspects, the fusion protein includes an amino acid sequence having at least 90% sequence identity to SEQ ID NO:14. In aspects, the fusion protein includes an amino acid sequence having at least 90% sequence identity to SEQ ID NO:15.

In embodiments, the fusion protein includes an amino acid sequence having at least 95% sequence identity to SEQ ID NO:1, 2, 3, 4, 5, 6, 7, 8, 9, 10, 11 12, 13, 14 or 15. In aspects, the fusion protein includes an amino acid sequence having at least 95% sequence identity to SEQ ID NO:1. In aspects, the fusion protein includes an amino acid sequence having at least 95% sequence identity to SEQ ID NO:2. In aspects, the fusion protein includes an amino acid sequence having at least 95% sequence identity to SEQ ID NO:3. In aspects, the fusion protein includes an amino acid sequence having at least 95% sequence identity to SEQ ID NO:4. In aspects, the fusion protein includes an amino acid sequence having at least 95% sequence identity to SEQ ID NO:5. In aspects, the fusion protein includes an amino acid sequence having at least 95% sequence identity to SEQ ID NO:6. In aspects, the fusion protein includes an amino acid sequence having at least 95% sequence identity to SEQ ID NO:7. In aspects, the fusion protein includes an amino acid sequence having at least 95% sequence identity to SEQ ID NO:8. In aspects, the fusion protein includes an amino acid sequence having at least 95% sequence identity to SEQ ID NO:9. In aspects, the fusion protein includes an amino acid sequence having at least 95% sequence identity to SEQ ID NO:10. In aspects, the fusion protein includes an amino acid sequence having at least 95% sequence identity to SEQ ID NO:11. In aspects, the fusion protein includes an amino acid sequence having at least 95% sequence identity to SEQ ID NO:12. In aspects, the fusion protein includes an amino acid sequence having at least 95% sequence identity to SEQ ID NO:13. In aspects, the fusion protein includes an amino acid sequence having at least 95% sequence identity to SEQ ID NO:14. In aspects, the fusion protein includes an amino acid sequence having at least 95% sequence identity to SEQ ID NO:15.

Complexes

In order for the fusion protein to carry out epigenome editing, the fusion protein interacts with (e.g. is non-covalently bound to) a polynucleotide (e.g., sgRNA) that is complementary to a target polynucleotide sequence (e.g., a target DNA sequence to be edited) and further includes a sequence (i.e., a binding sequence) to which the nuclease-deficient RNA-guided DNA endonuclease enzyme of the fusion protein as described herein can bind. By forming this complex, the fusion protein is appropriately positioned to perform epigenome editing. The term "complex" refers to a composition that includes two or more components, where the components bind together to make a functional unit. In aspects, a complex described herein includes a fusion protein described herein and a polynucleotide described herein. Thus, in an aspect is provided a fusion protein as described herein, including embodiments and aspects thereof, and a polynucleotide including: (1) a DNA-targeting sequence that is complementary to a target polynucleotide sequence; and (2) a binding sequence for the nuclease-deficient RNA-guided DNA endonuclease enzyme, wherein the nuclease-deficient RNA-guided DNA endonuclease enzyme is bound to the polynucleotide via the binding sequence (e.g., an amino acid sequence capable of binding to the DNA-targeting sequence).

A DNA-targeting sequence refers to a polynucleotide that includes a nucleotide sequence complementary to the target polynucleotide sequence (DNA or RNA). In aspects, a DNA-targeting sequence can be a single RNA molecule (single RNA polynucleotide), which may include a "single-guide RNA," or "sgRNA." In aspects, the DNA-targeting sequence includes two RNA molecules (e.g., joined together via hybridization at the binding sequence (e.g., dCas9-binding sequence). In aspects, the DNA-targeting sequence (e.g., sgRNA) is at least 50%, 55%, 60%, 65%, 70%, 75%, 80%, 85%, 90%, 95%, 96%, 97%, 98% or 99% complementary to the target polynucleotide sequence. In aspects, the DNA-targeting sequence (e.g., sgRNA) is at least 50%, 55%, 60%, 65%, 70%, 75%, 80%, 85%, 90%, 95%, 96%, 97%, 98% or 99% complementary to the sequence of a cellular gene. In aspects, the DNA-targeting sequence (e.g., sgRNA) binds a cellular gene sequence.

In aspects, the DNA-targeting sequence (e.g., sgRNA) is at least 75% complementary to the sequence of a cellular gene. In aspects, the DNA-targeting sequence (e.g., sgRNA) is at least 80% complementary to the sequence of a cellular gene. In aspects, the DNA-targeting sequence (e.g., sgRNA) binds a cellular gene sequence. In aspects, the DNA-targeting sequence (e.g., sgRNA) is at least 85% complementary to the sequence of a cellular gene. In aspects, the DNA-targeting sequence (e.g., sgRNA) binds a cellular gene sequence. In aspects, the DNA-targeting sequence (e.g., sgRNA) is at least 90% complementary to the sequence of a cellular gene. In aspects, the DNA-targeting sequence (e.g., sgRNA) binds a cellular gene sequence. In aspects, the DNA-targeting sequence (e.g., sgRNA) is at least 95% complementary to the sequence of a cellular gene. In aspects, the DNA-targeting sequence (e.g., sgRNA) binds a cellular gene sequence.

A "target polynucleotide sequence" as provided herein is a nucleic acid sequence present in, or expressed by, a cell, to which a guide sequence (or a DNA-targeting sequence) is designed to have complementarity, where hybridization between a target sequence and a guide sequence (or a DNA-targeting sequence) promotes the formation of a CRISPR complex. Full complementarity is not necessarily required, provided there is sufficient complementarity to cause hybridization and promote formation of a CRISPR complex. In aspects, the target polynucleotide sequence is an exogenous nucleic acid sequence. In aspects, the target polynucleotide sequence is an endogenous nucleic acid sequence.

The target polynucleotide sequence may be any region of the polynucleotide (e.g., DNA sequence) suitable for epigenome editing. In aspects, the target polynucleotide sequence is part of a gene. In aspects, the target polynucleotide sequence is part of a transcriptional regulatory sequence. In aspects, the target polynucleotide sequence is part of a promoter, enhancer or silencer. In aspects, the target polynucleotide sequence is part of a promoter. In aspects, the target polynucleotide sequence is part of an enhancer. In aspects, the target polynucleotide sequence is part of a silencer.

In embodiments, the target polynucleotide sequence is a hypomethylated nucleic acid sequence. A "hypomethylated nucleic acid sequence" is used herein according to the standard meaning in the art and refers to a loss or lack of methyl groups on the 5-methylcytosine nucleotide (e.g., in CpG). The loss or lack of methyl groups may be relative to a standard control. Hypomethylation may occur, for example, in aging cells or in cancer (e.g., early stages of neoplasia) relative to the younger cell or non-cancer cell, respectively. Thus, the complex may be useful for reestablishing normal (e.g. non-aged of non-diseased) methylation levels.

In embodiments, the target polynucleotide sequence is within about 3000 base pairs (bp) flanking a transcription start site. In aspects, the target polynucleotide sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking a transcription start site.

In embodiments, the target polynucleotide sequence is at, near, or within a promoter sequence. In aspects, the target polynucleotide sequence is within a CpG island. In aspects, the target polynucleotide sequence is known to be associated with a disease or condition characterized by DNA hypomethylation.

In embodiments, exemplary target polynucleotide sequences include those described in Tables 1 and 2. In aspects, the target polynucleotide sequence include the sequence of SEQ ID NO:37, 39, 41, 43, 45, 47, 49, 51, 53, 55, 57, 59, 61, 63, 65, 67, 69, 71, 73, 75, 77, 79, 81, 83, 85, 87, 89, 91, 93, or 95. In aspects, the target polynucleotide sequence include an amino acid sequence having at least 80%, 85%, 90%, 91%, 92%, 93%, 94%, 95%, 96%, 97%, 98%, or 99% sequence identity to SEQ ID NO:37, 39, 41, 43, 45, 47, 49, 51, 53, 55, 57, 59, 61, 63, 65, 67, 69, 71, 73, 75, 77, 79, 81, 83, 85, 87, 89, 91, 93, or 95. In aspects, the target polynucleotide sequence is SEQ ID NO:37. In aspects, the target polynucleotide sequence is SEQ ID NO:39. In aspects, the target polynucleotide sequence is SEQ ID NO:41. In aspects, the target polynucleotide sequence is SEQ ID NO:43. In aspects, the target polynucleotide sequence is SEQ ID NO:45. In aspects, the target polynucleotide sequence is SEQ ID NO:47. In aspects, the target polynucleotide sequence is SEQ ID NO:49. In aspects, the target polynucleotide sequence is SEQ ID NO:51. In aspects, the target polynucleotide sequence is SEQ ID NO:53. In aspects, the target polynucleotide sequence is SEQ ID NO:55. In aspects, the target polynucleotide sequence is SEQ ID NO:57. In aspects, the target polynucleotide sequence is SEQ ID NO:59. In aspects, the target polynucleotide sequence is SEQ ID NO:61. In aspects, the target polynucleotide sequence is SEQ ID NO:63. In aspects, the target polynucleotide sequence is SEQ ID NO:65. In aspects, the target polynucleotide sequence is SEQ ID NO:67. In aspects, the target polynucleotide sequence is SEQ ID NO:69. In aspects, the target polynucleotide sequence is SEQ ID NO:71. In aspects, the target polynucleotide sequence is SEQ ID NO:73. In aspects, the target polynucleotide sequence is SEQ ID NO:75. In aspects, the target polynucleotide sequence is SEQ ID NO:77. In aspects, the target polynucleotide sequence is SEQ ID NO:79. In aspects, the target polynucleotide sequence is SEQ ID NO:81. In aspects, the target polynucleotide sequence is SEQ ID NO:83. In aspects, the target polynucleotide sequence is SEQ ID NO:85. In aspects, the target polynucleotide sequence is SEQ ID NO:87. In aspects, the target polynucleotide sequence is SEQ ID NO:89. In aspects, the target polynucleotide sequence is SEQ ID NO:91. In aspects, the target polynucleotide sequence is SEQ ID NO:93. In aspects, the target polynucleotide sequence is SEQ ID NO:95.

In aspects, the target polynucleotide sequence has at least 75%, 80%, 85%, 90%, 91%, 92%, 93%, 94%, 95%, 96%, 97%, 98%, or 99% sequence identity to SEQ ID NO:37. In aspects, the target polynucleotide sequence has at least 75%, 80%, 85%, 90%, 91%, 92%, 93%, 94%, 95%, 96%, 97%, 98%, or 99% sequence identity to SEQ ID NO:39. In aspects, the target polynucleotide sequence has at least 75%, 80%, 85%, 90%, 91%, 92%, 93%, 94%, 95%, 96%, 97%, 98%, or 99% sequence identity to SEQ ID NO:41. In aspects, the target polynucleotide sequence has at least 75%, 80%, 85%, 90%, 91%, 92%, 93%, 94%, 95%, 96%, 97%, 98%, or 99% sequence identity to SEQ ID NO:43. In aspects, the target polynucleotide sequence is SEQ ID NO:45. In aspects, the target polynucleotide sequence has at least 75%, 80%, 85%, 90%, 91%, 92%, 93%, 94%, 95%, 96%, 97%, 98%, or 99% sequence identity to SEQ ID NO:47. In aspects, the target polynucleotide sequence has at least 75%, 80%, 85%, 90%, 91%, 92%, 93%, 94%, 95%, 96%, 97%, 98%, or 99% sequence identity to SEQ ID NO:49. In aspects, the target polynucleotide sequence has at least 75%, 80%, 85%, 90%, 91%, 92%, 93%, 94%, 95%, 96%, 97%, 98%, or 99% sequence identity to SEQ ID NO:51. In aspects, the target polynucleotide sequence has at least 75%, 80%, 85%, 90%, 91%, 92%, 93%, 94%, 95%, 96%, 97%, 98%, or 99% sequence identity to SEQ ID NO:53. In aspects, the target polynucleotide sequence has at least 75%, 80%, 85%, 90%, 91%, 92%, 93%, 94%, 95%, 96%, 97%, 98%, or 99% sequence identity to SEQ ID NO:55. In aspects, the target polynucleotide sequence has at least 75%, 80%, 85%, 90%, 91%, 92%, 93%, 94%, 95%, 96%, 97%, 98%, or 99% sequence identity to SEQ ID NO:57. In aspects, the target polynucleotide sequence has at least 75%, 80%, 85%, 90%, 91%, 92%, 93%, 94%, 95%, 96%, 97%, 98%, or 99% sequence identity to SEQ ID NO:59. In aspects, the target polynucleotide sequence has at least 75%, 80%, 85%, 90%, 91%, 92%, 93%, 94%, 95%, 96%, 97%, 98%, or 99% sequence identity to SEQ ID NO:61. In aspects, the target polynucleotide sequence has at least 75%, 80%, 85%, 90%, 91%, 92%, 93%, 94%, 95%, 96%, 97%, 98%, or 99% sequence identity to SEQ ID NO:63. In aspects, the target polynucleotide sequence has at least 75%, 80%, 85%, 90%, 91%, 92%, 93%, 94%, 95%, 96%, 97%, 98%, or 99% sequence identity to SEQ ID NO:65. In aspects, the target polynucleotide sequence has at least 75%, 80%, 85%, 90%, 91%, 92%, 93%, 94%, 95%, 96%, 97%, 98%, or 99% sequence identity to SEQ ID NO:67. In aspects, the target polynucleotide sequence has at least 75%, 80%, 85%, 90%, 91%, 92%, 93%, 94%, 95%, 96%, 97%, 98%, or 99% sequence identity to SEQ ID NO:69. In aspects, the target polynucleotide sequence has at least 75%, 80%, 85%, 90%, 91%, 92%, 93%, 94%, 95%, 96%, 97%, 98%, or 99% sequence identity to SEQ ID NO:71. In aspects, the target polynucleotide sequence has at least 75%, 80%, 85%, 90%, 91%, 92%, 93%, 94%, 95%, 96%, 97%, 98%, or 99% sequence identity to SEQ ID NO:73. In aspects, the target polynucleotide sequence has at least 75%, 80%, 85%, 90%, 91%, 92%, 93%, 94%, 95%, 96%, 97%, 98%, or 99% sequence identity to SEQ ID NO:75. In aspects, the target polynucleotide sequence has at least 75%, 80%, 85%, 90%, 91%, 92%, 93%, 94%, 95%, 96%, 97%, 98%, or 99% sequence identity to SEQ ID NO:77. In aspects, the target polynucleotide sequence has at least 75%, 80%, 85%, 90%, 91%, 92%, 93%, 94%, 95%, 96%, 97%, 98%, or 99% sequence identity to SEQ ID NO:79. In aspects, the target polynucleotide sequence has at least 75%, 80%, 85%, 90%, 91%, 92%, 93%, 94%, 95%, 96%, 97%, 98%, or 99% sequence identity to SEQ ID NO:81. In aspects, the target polynucleotide sequence has at least 75%, 80%, 85%, 90%, 91%, 92%, 93%, 94%, 95%, 96%, 97%, 98%, or 99% sequence identity to SEQ ID NO:83. In aspects, the target polynucleotide sequence has at least 75%, 80%, 85%, 90%, 91%, 92%, 93%, 94%, 95%, 96%, 97%, 98%, or 99% sequence identity to SEQ ID NO:85. In aspects, the target polynucleotide sequence has at least 75%, 80%, 85%, 90%, 91%, 92%, 93%, 94%, 95%, 96%, 97%, 98%, or 99% sequence identity to SEQ ID NO:87. In aspects, the target polynucleotide sequence has at least 75%, 80%, 85%, 90%, 91%, 92%, 93%, 94%, 95%, 96%, 97%, 98%, or 99% sequence identity to SEQ ID NO:89. In aspects, the target polynucleotide sequence has at least 75%, 80%, 85%, 90%, 91%, 92%, 93%, 94%, 95%, 96%, 97%, 98%, or 99% sequence identity to SEQ ID NO:91. In aspects, the target polynucleotide sequence has at least 75%, 80%, 85%, 90%, 91%, 92%, 93%, 94%, 95%, 96%, 97%, 98%, or 99% sequence identity to SEQ ID NO:93. In aspects, the target polynucleotide sequence has at least 75%, 80%, 85%, 90%, 91%, 92%, 93%, 94%, 95%, 96%, 97%, 98%, or 99% sequence identity to SEQ ID NO:95.

In aspects, the target polynucleotide sequence has at least 90% sequence identity to SEQ ID NO:37. In aspects, the target polynucleotide sequence has at least 90% sequence identity to SEQ ID NO:39. In aspects, the target polynucleotide sequence has at least 90% sequence identity to SEQ ID NO:41. In aspects, the target polynucleotide sequence has at least 90% sequence identity to SEQ ID NO:43. In aspects, the target polynucleotide sequence is SEQ ID NO:45. In aspects, the target polynucleotide sequence has at least 90% sequence identity to SEQ ID NO:47. In aspects, the target polynucleotide sequence has at least 90% sequence identity to SEQ ID NO:49. In aspects, the target polynucleotide sequence has at least 90% sequence identity to SEQ ID NO:51. In aspects, the target polynucleotide sequence has at least 90% sequence identity to SEQ ID NO:53. In aspects, the target polynucleotide sequence has at least 90% sequence identity to SEQ ID NO:55. In aspects, the target polynucleotide sequence has at least 90% sequence identity to SEQ ID NO:57. In aspects, the target polynucleotide sequence has at least 90% sequence identity to SEQ ID NO:59. In aspects, the target polynucleotide sequence has at least 90% sequence identity to SEQ ID NO:61. In aspects, the target polynucleotide sequence has at least 90% sequence identity to SEQ ID NO:63. In aspects, the target polynucleotide sequence has at least 90% sequence identity to SEQ ID NO:65. In aspects, the target polynucleotide sequence has at least 90% sequence identity to SEQ ID NO:67. In aspects, the target polynucleotide sequence has at least 90% sequence identity to SEQ ID NO:69. In aspects, the target polynucleotide sequence has at least 90% sequence identity to SEQ ID NO:71. In aspects, the target polynucleotide sequence has at least 90% sequence identity to SEQ ID NO:73. In aspects, the target polynucleotide sequence has at least 90% sequence identity to SEQ ID NO:75. In aspects, the target polynucleotide sequence has at least 90% sequence identity to SEQ ID NO:77. In aspects, the target polynucleotide sequence has at least 90% sequence identity to SEQ ID NO:79. In aspects, the target polynucleotide sequence has at least 90% sequence identity to SEQ ID NO:81. In aspects, the target polynucleotide sequence has at least 90% sequence identity to SEQ ID NO:83. In aspects, the target polynucleotide sequence has at least 90% sequence identity to SEQ ID NO:85. In aspects, the target polynucleotide sequence has at least 90% sequence identity to SEQ ID NO:87. In aspects, the target polynucleotide sequence has at least 90% sequence identity to SEQ ID NO:89. In aspects, the target polynucleotide sequence has at least 90% sequence identity to SEQ ID NO:91. In aspects, the target polynucleotide sequence has at least 90% sequence identity to SEQ ID NO:93. In aspects, the target polynucleotide sequence has at least 90% sequence identity to SEQ ID NO:95.

In aspects, the target polynucleotide sequence has at least 95% sequence identity to SEQ ID NO:37. In aspects, the target polynucleotide sequence has at least 95% sequence identity to SEQ ID NO:39. In aspects, the target polynucleotide sequence has at least 95% sequence identity to SEQ ID NO:41. In aspects, the target polynucleotide sequence has at least 95% sequence identity to SEQ ID NO:43. In aspects, the target polynucleotide sequence is SEQ ID NO:45. In aspects, the target polynucleotide sequence has at least 95% sequence identity to SEQ ID NO:47. In aspects, the target polynucleotide sequence has at least 95% sequence identity to SEQ ID NO:49. In aspects, the target polynucleotide sequence has at least 95% sequence identity to SEQ ID NO:51. In aspects, the target polynucleotide sequence has at least 95% sequence identity to SEQ ID NO:53. In aspects, the target polynucleotide sequence has at least 95% sequence identity to SEQ ID NO:55. In aspects, the target polynucleotide sequence has at least 95% sequence identity to SEQ ID NO:57. In aspects, the target polynucleotide sequence has at least 95% sequence identity to SEQ ID NO:59. In aspects, the target polynucleotide sequence has at least 95% sequence identity to SEQ ID NO:61. In aspects, the target polynucleotide sequence has at least 95% sequence identity to SEQ ID NO:63. In aspects, the target polynucleotide sequence has at least 95% sequence identity to SEQ ID NO:65. In aspects, the target polynucleotide sequence has at least 95% sequence identity to SEQ ID NO:67. In aspects, the target polynucleotide sequence has at least 95% sequence identity to SEQ ID NO:69. In aspects, the target polynucleotide sequence has at least 95% sequence identity to SEQ ID NO:71. In aspects, the target polynucleotide sequence has at least 95% sequence identity to SEQ ID NO:73. In aspects, the target polynucleotide sequence has at least 95% sequence identity to SEQ ID NO:75. In aspects, the target polynucleotide sequence has at least 95% sequence identity to SEQ ID NO:77. In aspects, the target polynucleotide sequence has at least 95% sequence identity to SEQ ID NO:79. In aspects, the target polynucleotide sequence has at least 95% sequence identity to SEQ ID NO:81. In aspects, the target polynucleotide sequence has at least 95% sequence identity to SEQ ID NO:83. In aspects, the target polynucleotide sequence has at least 95% sequence identity to SEQ ID NO:85. In aspects, the target polynucleotide sequence has at least 95% sequence identity to SEQ ID NO:87. In aspects, the target polynucleotide sequence has at least 95% sequence identity to SEQ ID NO:89. In aspects, the target polynucleotide sequence has at least 95% sequence identity to SEQ ID NO:91. In aspects, the target polynucleotide sequence has at least 95% sequence identity to SEQ ID NO:93. In aspects, the target polynucleotide sequence has at least 95% sequence identity to SEQ ID NO:95.

In embodiments, the complex includes dCas9 bound to the polynucleotide through binding a binding sequence of the polynucleotide and thereby forming a ribonucleoprotein complex. In aspects, the binding sequence forms a hairpin structure. In aspects, the binding sequence is 30-100 nt, 35-50 nt, 37-47 nt, or 42 nt in length.

In embodiments, the binding sequence (e.g., Cas9-binding sequence) interacts with or binds to a Cas9 protein (e.g., dCas9 protein), and together they bind to the target polynucleotide sequence recognized by the DNA-targeting sequence. The binding sequence (e.g., Cas9-binding sequence) includes two complementary stretches of nucleotides that hybridize to one another to form a double stranded RNA duplex (a dsRNA duplex). These two complementary stretches of nucleotides may be covalently linked by intervening nucleotides known as linkers or linker nucleotides (e.g., in the case of a single-molecule polynucleotide), and hybridize to form the double stranded RNA duplex (dsRNA duplex, or "Cas9-binding hairpin") of the binding sequence (e.g., Cas9-binding sequence), thus resulting in a stem-loop structure. Alternatively, in some aspects, the two complementary stretches of nucleotides may not be covalently linked, but instead are held together by hybridization between complementary sequences (e.g., a two-molecule polynucleotide).

The binding sequence (e.g., Cas9-binding sequence) can have a length of from 10 nucleotides to 100 nucleotides, e.g., from 10 nucleotides (nt) to 20 nt, from 20 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In aspects, the binding sequence has a length of from 15 nucleotides (nt) to 80 nt. In aspects, the binding sequence has a length of from 15 nt to 50 nt. In aspects, the binding sequence has a length of from 15 nt to 40 nt. In aspects, the binding sequence has a length of from 15 nt to 30 nt. In aspects, the binding sequence has a length of from 37 nt to 47 nt (e.g., 42 nt). In aspects, the binding sequence has a length of from 15 nt to 25 nt.

The dsRNA duplex of the binding sequence (e.g., Cas9-binding sequence) can have a length from 6 base pairs (bp) to 50 bp. For example, the dsRNA duplex of the binding sequence (e.g., Cas9-binding sequence) can have a length from 6 bp to 40 bp, from 6 bp to 30 bp, from 6 bp to 25 bp, from 6 bp to 20 bp, from 6 bp to 15 bp, from 8 bp to 40 bp, from 8 bp to 30 bp, from 8 bp to 25 bp, from 8 bp to 20 bp or from 8 bp to 15 bp. In aspects, the dsRNA duplex of the binding sequence (e.g., Cas9-binding sequence) has a length from 8 bp to 10 bp. In aspects, the dsRNA duplex of the binding sequence (e.g., Cas9-binding sequence) has a length from 10 bp to 15 bp. In aspects, the dsRNA duplex of the binding sequence (e.g., Cas9-binding sequence) has a length from 15 bp to 18 bp. In aspects, the dsRNA duplex of the binding sequence (e.g., Cas9-binding sequence) has a length from 18 bp to 20 bp. In aspects, the dsRNA duplex of the binding sequence (e.g., Cas9-binding sequence) has a length from 20 bp to 25 bp. In aspects, the dsRNA duplex of the binding sequence (e.g., Cas9-binding sequence) has a length from 25 bp to 30 bp. In aspects, the dsRNA duplex of the binding sequence (e.g., Cas9-binding sequence) has a length from 30 bp to 35 bp. In aspects, the dsRNA duplex of the binding sequence (e.g., Cas9-binding sequence) has a length from 35 bp to 40 bp. In aspects, the dsRNA duplex of the binding sequence (e.g., Cas9-binding sequence) has a length from 40 bp to 50 bp.

In embodiments, the exemplary polynucleotide that forms a complex with a fusion protein described herein includes those described in Tables 1 and 2 as sgRNA. In aspects, the polynucleotide that forms a complex with a fusion protein described herein includes the sequence of SEQ ID NO: 38, 40, 42, 44, 46, 48, 50, 52, 54, 56, 58, 60, 62, 64, 66, 68, 70, 72, 74, 76, 78, 80, 82, 84, 86, 88, 90, 92, or 94 or their corresponding RNA sequence. In aspects, the polynucleotide that forms a complex with a fusion protein described herein includes the sequence having at least 80%, 85%, 90%, 91%, 92%, 93%, 94%, 95%, 96%, 97%, 98%, or 99% sequence identity to SEQ ID NO:38, 40, 42, 44, 46, 48, 50, 52, 54, 56, 58, 60, 62, 64, 66, 68, 70, 72, 74, 76, 78, 80, 82, 84, 86, 88, 90, 92, or 94 or their corresponding RNA sequence. In aspects, the polynucleotide that forms a complex with a fusion protein described herein includes the sequence of SEQ ID NO:38. In aspects, the polynucleotide that forms a complex with a fusion protein described herein includes the sequence of SEQ ID NO:40. In aspects, the polynucleotide that forms a complex with a fusion protein described herein includes the sequence of SEQ ID NO:42. In aspects, the polynucleotide that forms a complex with a fusion protein described herein includes the sequence of SEQ ID NO:44. In aspects, the polynucleotide that forms a complex with a fusion protein described herein includes the sequence of SEQ ID NO:46. In aspects, the polynucleotide that forms a complex with a fusion protein described herein includes the sequence of SEQ ID NO:48. In aspects, the polynucleotide that forms a complex with a fusion protein described herein includes the sequence of SEQ ID NO:50. In aspects, the polynucleotide that forms a complex with a fusion protein described herein includes the sequence of SEQ ID NO:52. In aspects, the polynucleotide that forms a complex with a fusion protein described herein includes the sequence of SEQ ID NO:54. In aspects, the polynucleotide that forms a complex with a fusion protein described herein includes the sequence of SEQ ID NO:56. In aspects, the polynucleotide that forms a complex with a fusion protein described herein includes the sequence of SEQ ID NO:58. In aspects, the polynucleotide that forms a complex with a fusion protein described herein includes the sequence of SEQ ID NO:60. In aspects, the polynucleotide that forms a complex with a fusion protein described herein includes the sequence of SEQ ID NO:62. In aspects, the polynucleotide that forms a complex with a fusion protein described herein includes the sequence of SEQ ID NO:64. In aspects, the polynucleotide that forms a complex with a fusion protein described herein includes the sequence of SEQ ID NO:66. In aspects, the polynucleotide that forms a complex with a fusion protein described herein includes the sequence of SEQ ID NO:68. In aspects, the polynucleotide that forms a complex with a fusion protein described herein includes the sequence of SEQ ID NO:70. In aspects, the polynucleotide that forms a complex with a fusion protein described herein includes the sequence of SEQ ID NO:72. In aspects, the polynucleotide that forms a complex with a fusion protein described herein includes the sequence of SEQ ID NO:74. In aspects, the polynucleotide that forms a complex with a fusion protein described herein includes the sequence of SEQ ID NO:76. In aspects, the polynucleotide that forms a complex with a fusion protein described herein includes the sequence of SEQ ID NO:78. In aspects, the polynucleotide that forms a complex with a fusion protein described herein includes the sequence of SEQ ID NO:80. In aspects, the polynucleotide that forms a complex with a fusion protein described herein includes the sequence of SEQ ID NO:82. In aspects, the polynucleotide that forms a complex with a fusion protein described herein includes the sequence of SEQ ID NO:84. In aspects, the polynucleotide that forms a complex with a fusion protein described herein includes the sequence of SEQ ID NO:86. In aspects, the polynucleotide that forms a complex with a fusion protein described herein includes the sequence of SEQ ID NO:88. In aspects, the polynucleotide that forms a complex with a fusion protein described herein includes the sequence of SEQ ID NO:90. In aspects, the polynucleotide that forms a complex with a fusion protein described herein includes the sequence of SEQ ID NO:92. In aspects, the polynucleotide that forms a complex with a fusion protein described herein includes the sequence of SEQ ID NO:94.

Nucleic Acids and Vectors

The fusion protein described herein, including embodiments and aspects thereof, may be provided as a nucleic acid sequence that encodes for the fusion protein. Thus, in an aspect is provided a nucleic acid sequence encoding the fusion protein described herein, including embodiments and aspects thereof. In an aspect is provided a nucleic acid sequence encoding the fusion protein described herein (including the DNA-targeting sequence), including embodiments and aspects thereof. In aspects, the nucleic acid sequence encodes for a fusion protein described herein, including fusion proteins having amino acid sequences with certain % sequence identities described herein. In aspects, the nucleic acid is RNA. In aspects, the nucleic acid is messenger RNA. In aspects, the messenger RNA is messenger RNP. In aspects, the nucleic acid sequence encodes for the fusion proteins described herein, including embodiments and aspects thereof. In aspects, the nucleic acid sequence encodes for the fusion protein of SEQ ID NO:1. In aspects, the nucleic acid sequence encodes for the fusion protein of SEQ ID NO:2. In aspects, the nucleic acid sequence encodes for the fusion protein of SEQ ID NO:3. In aspects, the nucleic acid sequence encodes for the fusion protein of SEQ ID NO:4. In aspects, the nucleic acid sequence encodes for the fusion protein of SEQ ID NO:5. In aspects, the nucleic acid sequence encodes for the fusion protein of SEQ ID NO:6. In aspects, the nucleic acid sequence encodes for the fusion protein of SEQ ID NO:7. In aspects, the nucleic acid sequence encodes for the fusion protein of SEQ ID NO:8. In aspects, the nucleic acid sequence encodes for the fusion protein of SEQ ID NO:9. In aspects, the nucleic acid sequence encodes for the fusion protein of SEQ ID NO:10. In aspects, the nucleic acid sequence encodes for the fusion protein of SEQ ID NO:11. In aspects, the nucleic acid sequence encodes for the fusion protein of SEQ ID NO:12. In aspects, the nucleic acid sequence encodes for the fusion protein of SEQ ID NO:13. In aspects, the nucleic acid sequence encodes for the fusion protein of SEQ ID NO:14. In aspects, the nucleic acid sequence encodes for the fusion protein of SEQ ID NO:15.

It is further contemplated that the nucleic acid sequence encoding the fusion protein as described herein, including embodiments and aspects thereof, may be included in a vector. Therefore, in an aspect is provided a vector including a nucleic acid sequence as described herein, including embodiments and aspects thereof. In aspects, the vector comprises a nucleic acid sequence that encodes for a fusion protein described herein, including fusion proteins having amino acid sequences with certain % sequence identities described herein. In aspects, the nucleic acid is messenger RNA. In aspects, the messenger RNA is messenger RNP. In aspects, the vector comprises a nucleic acid sequence that encodes for the fusion protein of SEQ ID NO:1. In aspects, the vector comprises a nucleic acid sequence that encodes for the fusion protein of SEQ ID NO:2. In aspects, the vector comprises a nucleic acid sequence that encodes for the fusion protein of SEQ ID NO:3. In aspects, the vector comprises a nucleic acid sequence that encodes for the fusion protein of SEQ ID NO:4. In aspects, the vector comprises a nucleic acid sequence that encodes for the fusion protein of SEQ ID NO:5. In aspects, the vector comprises a nucleic acid sequence that encodes for the fusion protein of SEQ ID NO:6. In aspects, the vector comprises a nucleic acid sequence that encodes for the fusion protein of SEQ ID NO:7. In aspects, the vector comprises a nucleic acid sequence that encodes for the fusion protein of SEQ ID NO:8. In aspects, the vector comprises a nucleic acid sequence that encodes for the fusion protein of SEQ ID NO:9. In aspects, the vector comprises a nucleic acid sequence that encodes for the fusion protein of SEQ ID NO:10. In aspects, the vector comprises a nucleic acid sequence that encodes for the fusion protein of SEQ ID NO:11. In aspects, the vector comprises a nucleic acid sequence that encodes for the fusion protein of SEQ ID NO:12. In aspects, the vector comprises a nucleic acid sequence that encodes for the fusion protein of SEQ ID NO:13. In aspects, the vector comprises a nucleic acid sequence that encodes for the fusion protein of SEQ ID NO:14. In aspects, the vector comprises a nucleic acid sequence that encodes for the fusion protein of SEQ ID NO:15.

In embodiments, the vector further includes a polynucleotide, wherein the polynucleotide includes: (1) a DNA-targeting sequence that is complementary to a target polynucleotide sequence; and (2) a binding sequence for the nuclease-deficient RNA-guided DNA endonuclease enzyme. Thus, one or more vectors may include all necessary components for preforming epigenome editing.

Cells

The compositions described herein may be incorporated into a cell. Inside the cell, the compositions as described herein, including embodiments and aspects thereof, may perform epigenome editing. Accordingly, in an aspect is provided a cell including a fusion protein as described herein, including embodiments and aspects thereof, a nucleic acid as described herein, including embodiments and aspects thereof, a complex as described herein, including embodiments and aspects thereof, or a vector as described herein, including embodiments and aspects thereof. In aspects is provided a cell including a fusion protein as described herein, including embodiments and aspects thereof. In aspects is provided a cell including a nucleic acid as described herein, including embodiments and aspects thereof. In aspects is provided a cell including a complex as described herein, including embodiments and aspects thereof. In aspects is provided a cell including a vector as described herein, including embodiments and aspects thereof. In aspects, the cell is a eukaryotic cell. In aspects, the cell is a mammalian cell.

Methods

It is contemplated that the compositions described herein may be used for epigenome editing, and more particularly epigenome editing resulting in the repression or silencing of target nucleic acid sequences (e.g., genes). Without intending to be bound by any theory, silencing may result from methylation of and/or the introduction of repressive chromatin markers (e.g., mono-, di-, or tri-methylation of specific histones (e.g., H3K9, H3K27), deacetylation, acetylation, phosphorylation, ubiquitination) on chromatin containing a target nucleic acid sequence. Without intending to be bound by any theory, the method can be used to change epigenetic state by, for example, closing chromatin via methylation or introducing repressive chromatin markers on chromatin containing the target nuclei acid sequence (e.g., gene). Without intending to be bound by any theory, it is contemplated that the Dnmt3A-3L fusion functions to add methyl marks at CG DNA sites found in CpG islands and the KRAB domain recruits epigenetic factors that modify the histones by introducing repressive marks. Without intending to be bound by any theory, DNA is methylated at the C nucleotide of CG sequences found in CpG islands (i.e., adding methyl marks at the C nucleotide of CG DNA sites found in CpG islands).

In an aspect is provided a method of silencing a target nucleic acid sequence in a cell, including delivering a first polynucleotide encoding a fusion protein as described herein, including embodiments and aspects thereof, to a cell containing the target nucleic acid; and delivering to the cell a second polynucleotide including: (i) a DNA-targeting sequence that is complementary to the target nucleic acid sequence; and (ii) a binding sequence for the nuclease-deficient RNA-guide DNA endonuclease enzyme. Without intending to be bound by any theory, the fusion protein silences the target nucleic acid sequence in the cell by methylating a chromatin containing the target nucleic acid sequence and/or by introducing repressive chromatin marks to a chromatin containing the target nucleic acid sequence. Without intending to be bound by any theory, methylating a chromatin means that DNA is methylated at the C nucleotide of CG sequences found in CpG islands (i.e., adding methyl marks at the C nucleotide of CG DNA sites found in CpG islands). In aspects, the sequence that is within about 3000 base pairs of the target nucleic acid sequence is methylated. In aspects, the sequence that is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs of the target nucleic acid sequence is methylated.

The term "repressive chromatin markers" as used herein refers to modifications made to the chromatin that result in silencing (e.g., decreasing or inhibiting of transcription) of the target nucleic acid sequence (e.g., a gene). Examples of repressive chromatin markers include, but are not limited to, mono-, di-, and/or tri-methylation, acetylation/deacetylation, phosphorylation, and ubiquitination of histones (e.g., H3K9, H3K27, H3K79, H2BK5).

In embodiments, silencing refers to a complete suppression of transcription. In aspects, silencing refers to a significant decrease in transcription compared to control levels of transcription.

In embodiments, the first polynucleotide is contained within a first vector. In aspects, the first polynucleotide is contained within a second vector. In aspects, the first vector and the second vector are the same. In aspects, the first vector is different from the second vector.

In embodiments, the polynucleotide described herein is delivered into the cell by any method known in the art, for example, by transfection, electroporation or transduction.

Alternatively, in an aspect is provided a method of silencing a target nucleic acid sequence in a cell, including delivering a complex as described herein, including embodiments and aspects thereof, to a cell containing the target nucleic acid. Without intending to be bound by any theory, the complex silences the target nucleic acid sequence in the cell by methylating a chromatin containing the target nucleic acid sequence and/or by introducing repressive chromatin marks to a chromatin containing the target nucleic acid sequence.

In embodiments, the cell is a mammalian cell.

In embodiments, the method has a specificity that is 2-fold higher than a specificity to a non-target nucleic acid sequence. In aspects, the method has a specificity that is at least 2-fold (e.g., 2-, 3-, 4-, 5-, 6-, 7-, 8-, 9-, 10-, 15-, 20-, 25-fold) higher than a specificity to a non-target nucleic acid sequence. Methods for determining specificity are well known in the art and include, but are not limited to, RNA-seq, bisulfite sequencing, chromatin immunoprecipitation, flow cytometry, and qPCR. Thus, in aspects, specificity is determined by RNA-seq. In aspects, specificity is determined by bisulfite sequencing. In aspects, specificity is determined by chromatin immunoprecipitation. In aspects, specificity is determined by flow cytometry. In aspects, specificity is determined by qPCR.

In aspects, the complex is delivered into the cell via any methods known in the art, for example, via ribonucleoprotein (RNP) delivery.

Embodiments N1—N41

Embodiment N1. A fusion protein comprising a nuclease-deficient RNA-guided DNA endonuclease enzyme, a Krüppel associated box domain, and a DNA methyltransferase domain.

Embodiment N2. The fusion protein of Embodiment N1, wherein the nuclease-deficient RNA-guided DNA endonuclease enzyme is dCas9, ddCpf1, a nuclease-deficient Cas9 variant, or a nuclease-deficient Class II CRISPR endonuclease.

Embodiment N3. The fusion protein of Embodiment N1 or N2, wherein the DNA methyltransferase domain is a Dnmt3A-3L domain.

Embodiment N4. The fusion protein of Embodiment N1, wherein the fusion protein comprises, from N-terminus to C-terminus, the DNA methyltransferase domain, the nuclease-deficient RNA-guided DNA endonuclease enzyme, and the Krüppel associated box domain Embodiment N5. The fusion protein of Embodiment N4, wherein the nuclease-deficient RNA-guided DNA endonuclease enzyme is dCas9 and the DNA methyltransferase domain is a Dnmt3A-3L domain Embodiment N6. The fusion protein of Embodiment N5, wherein the nuclease-deficient RNA-guided DNA endonuclease enzyme is dCas9 and the DNA methyltransferase domain is a Dnmt3A-3L domain Embodiment N7. The fusion protein of Embodiment N6, wherein the peptide linker is a XTEN linker.

Embodiment N8. The fusion protein of Embodiment N1, wherein the fusion protein comprises, from N-terminus to C-terminus, the Krüppel associated box, the nuclease-deficient RNA-guided DNA endonuclease enzyme, and the DNA methyltransferase domain Embodiment N9. The fusion protein of Embodiment N8, wherein the nuclease-deficient RNA-guided DNA endonuclease enzyme is dCas9 and the DNA methyltransferase domain is a Dnmt3A-3L domain.

Embodiment N10. The fusion protein of Embodiment N9, wherein the dCas9 is covalently linked to the Dnmt3A-3L domain via a peptide linker and wherein the Krüppel associated box domain is covalently linked to the dCas9 via a peptide linker.

Embodiment N11. The fusion protein of Embodiment N10, wherein the peptide linker is a XTEN linker.

Embodiment N12. The fusion protein of anyone of Embodiments N1 to N3, wherein the nuclease-deficient RNA-guided DNA endonuclease enzyme is covalently linked to the Krüppel associated box domain via a peptide linker.

Embodiment N13. The fusion protein of anyone of Embodiments N1 to N3, wherein the nuclease-deficient RNA-guided DNA endonuclease enzyme is covalently linked to the DNA methyltransferase domain via a peptide linker.

Embodiment N14. The fusion protein of anyone of Embodiments N1 to N3, wherein the Krüppel associated box domain is covalently linked to the DNA methyltransferase domain via a peptide linker.

Embodiment N15. The fusion protein of anyone of Embodiments N12 to N14, wherein the peptide linker is a XTEN linker.

Embodiment N16. The fusion protein of Embodiment N15, wherein the XTEN linker comprises about 16 to 80 amino acid residues.

Embodiment N17. The fusion protein of anyone of Embodiments N1 to N16, further comprising a nuclear localization signal peptide.

Embodiment N18. The fusion protein of Embodiment N1, wherein the fusion protein comprises the amino acid sequence of SEQ ID NO: 1, 2, 3, 4, 5, 6, 7, 8, 9, 10, 11 12, 13, 14, or 15.

Embodiment N19. A nucleic acid sequence encoding the fusion protein of anyone of Embodiments N1 to N18.

Embodiment N20. The nucleic acid sequence of Embodiment N19, wherein the nucleic acid sequence is messenger RNA.

Embodiment N21. A complex comprising: (i) a fusion protein of anyone of Embodiments N1 to N18; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

Embodiment N22. The complex of Embodiment N21, wherein the target polynucleotide sequence is part of a gene.

Embodiment N23. The complex of Embodiment N21, wherein the target polynucleotide sequence is part of a transcriptional regulatory sequence.

Embodiment N24. The complex of Embodiment N21, wherein the target polynucleotide sequence is part of a promoter, enhancer, or silencer.

Embodiment N25. The complex of Embodiment N21, wherein the target polynucleotide sequence is within about 3000 bp flanking a transcription start site.

Embodiment N26. A vector comprising the nucleic acid sequence of Embodiment N19 or N20.

Embodiment N27. The vector of Embodiment N26, further comprising a polynucleotide, wherein the polynucleotide comprises: (a) a DNA-targeting sequence that is complementary to a target polynucleotide sequence; and (b) a binding sequence for the nuclease-deficient RNA-guided DNA endonuclease enzyme.

Embodiment N28. A cell comprising the fusion protein of anyone of Embodiments N1 to N18; the nucleic acid of Embodiment N19 or N20; the complex of anyone of Embodiments N21 to N25, or the vector of Embodiment N26 or N27.

Embodiment N29. The cell of Embodiment N28, wherein the cell is a eukaryotic cell.

Embodiment N30. The cell of Embodiment N28, wherein the cell is a mammalian cell.

Embodiment N31. A method of silencing a target nucleic acid sequence in a cell, comprising: (i) delivering a first polynucleotide encoding a fusion protein of any one of Embodiments N1 to N18 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme Embodiment N32. The method of Embodiment N31, wherein the fusion protein silences the target nucleic acid sequence in the cell by methylating a chromatin containing the target nucleic acid sequence and/or by introducing repressive chromatin marks to a chromatin containing the target nucleic acid sequence.

Embodiment N33. The method of Embodiment N31 or N32, wherein the first polynucleotide is contained within a first vector.

Embodiment N34. The method of anyone of Embodiments N31 to N33, wherein the first polynucleotide is contained within a second vector.

Embodiment N35. The method of Embodiment N34, wherein the first vector and the second vector are the same.

Embodiment N36. The method of Embodiment N34, wherein the first vector is different from the second vector.

Embodiment N37. The method of Embodiment N31, wherein the cell is a mammalian cell.

Embodiment N38. The method of Embodiment N31, wherein the method has a specificity that is 2-fold higher than a specificity to a non-target nucleic acid sequence.

Embodiment N39. A method of silencing a target nucleic acid sequence in a cell, the method comprising delivering the complex of any one of Embodiments N21 to N25 to a cell containing the target nucleic acid.

Embodiment N40. The method of Embodiment N39, wherein the complex silences the target nucleic acid sequence in the cell by methylating a chromatin containing the target nucleic acid sequence and/or by introducing repressive chromatin marks to a chromatin containing the target nucleic acid sequence.

Embodiment N41. The method of Embodiment N39 or N40, wherein the cell is a mammalian cell.

Embodiment N42. The method of any one of Embodiments N39 to N41, wherein the method has a specificity that is 2-fold higher than a specificity to a non-target nucleic acid sequence.

Embodiments 1 to 36

Embodiment 1. A fusion protein comprising a nuclease-deficient RNA-guided DNA endonuclease enzyme, a Krüppel associated box (KRAB) domain, and a DNA methyltransferase domain.

Embodiment 2. The fusion protein of Embodiment 1, wherein the nuclease-deficient RNA-guided DNA endonuclease enzyme is dCas9, ddCpf1, a nuclease-deficient Cas9 variant, or a nuclease-deficient Class II CRISPR endonuclease.

Embodiment 3. The fusion protein of Embodiment 1 or 2, wherein the DNA methyltransferase domain is a Dnmt3A-3L domain.

Embodiment 4. The fusion protein of any one of Embodiments 1 to 3, wherein the nuclease-deficient RNA-guided DNA endonuclease enzyme is covalently linked to the KRAB domain via a peptide linker.

Embodiment 5. The fusion protein of any one of Embodiments 1 to 4, wherein the nuclease-deficient RNA-guided DNA endonuclease enzyme is covalently linked to the DNA methyltransferase domain via a peptide linker.

Embodiment 6. The fusion protein of any one of Embodiments 1 to 5, wherein the KRAB domain is covalently linked to the DNA methyltransferase domain via a peptide linker.

Embodiment 7. The fusion protein of any one of Embodiments 4 to 6, wherein the peptide linker is a XTEN linker.

Embodiment 8. The fusion protein of Embodiment 7, wherein the XTEN linker comprises about 16 to 80 amino acid residues.

Embodiment 9. The fusion protein of any one of Embodiments 1 to 8, further comprising a nuclear localization signal peptide.

Embodiment 10. The fusion protein of any one of Embodiments 1 to 9, wherein the fusion protein comprises, from N-terminus to C-terminus, a KRAB domain, a nuclease-deficient RNA-guided DNA endonuclease enzyme, and a DNA methyltransferase domain.

Embodiment 11. The fusion protein of anyone of Embodiments 1 to 10, wherein the nuclease-deficient RNA-guided DNA endonuclease enzyme is dCas9 and the DNA methyltransferase domain is a Dnmt3A-3L domain.

Embodiment 12. The fusion protein of Embodiment 11, wherein the dCas9 is covalently linked to the KRAB domain via a peptide linker and wherein the dCas9 is covalently linked to the Dnmt3A-3L domain via a peptide linker.

Embodiment 13. The fusion protein of Embodiment 12, wherein the peptide linker is a XTEN linker.

Embodiment 14. The fusion protein of any one of Embodiments 1 to 13, wherein the fusion protein comprises the amino acid sequence of SEQ ID NO:1, 2, 3, 4, 5, 6, 7, 8, 9, 10, 11 12, 13, 14, or 15.

Embodiment 15. A nucleic acid sequence encoding the fusion protein of anyone of Embodiments 1 to 14.

Embodiment 16. A complex comprising: (i) a fusion protein of any one of Embodiments 1 to 14; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

Embodiment 17. The complex of Embodiment 16, wherein the target polynucleotide sequence is part of a gene.

Embodiment 18. The complex of Embodiment 16, wherein the target polynucleotide sequence is part of a transcriptional regulatory sequence.

Embodiment 19. The complex of Embodiment 16, wherein the target polynucleotide sequence is part of a promoter, enhancer, or silencer.

Embodiment 20. The complex of Embodiment 16, wherein the target polynucleotide sequence is a hypomethylated nucleic acid sequence.

Embodiment 21. The complex of Embodiment 16, wherein the target polynucleotide sequence is within about 3000 bp flanking a transcription start site.

Embodiment 22. A vector comprising the nucleic acid sequence of Embodiment 15.

Embodiment 23. The vector of Embodiment 17, further comprising a polynucleotide, wherein the polynucleotide comprises: (a) a DNA-targeting sequence that is complementary to a target polynucleotide sequence; and (b) a binding sequence for the nuclease-deficient RNA-guided DNA endonuclease enzyme.

Embodiment 24. A cell comprising the fusion protein of any one of Embodiments 1 to 14; the nucleic acid of Embodiment 15; the complex of any one of Embodiments 16 to 21; or the vector of Embodiment 22 or 23.

Embodiment 25. The cell of Embodiment 18, wherein the cell is a eukaryotic cell.

Embodiment 26. The cell of Embodiment 18, wherein the cell is a mammalian cell.

Embodiment 27. A method of silencing a target nucleic acid sequence in a cell, comprising: (i) delivering a first polynucleotide encoding a fusion protein according to any one of Embodiments 1 to 14 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme, wherein the fusion protein silences the target nucleic acid sequence in the cell by methylating a chromatin containing the target nucleic acid sequence and/or by introducing repressive chromatin marks to a chromatin containing the target nucleic acid sequence Embodiment 28. The method of Embodiment 27, wherein the first polynucleotide is contained within a first vector.

Embodiment 29. The method of Embodiment 27, wherein the first polynucleotide is contained within a second vector.

Embodiment 30. The method of Embodiment 28 or 29, wherein the first vector and the second vector are the same.

Embodiment 31. The method of Embodiment 28 or 29, wherein the first vector is different from the second vector.

Embodiment 32. The method of anyone of Embodiments 27 to 31, wherein the cell is a mammalian cell.

Embodiment 33. The method of any one of Embodiments 27 to 32, wherein the method has a specificity that is 2-fold higher than a specificity to a non-target nucleic acid sequence.

Embodiment 34. A method of silencing a target nucleic acid sequence in a cell, the method comprising delivering the complex of any one of Embodiments 16 to 20 to a cell containing the target nucleic acid, wherein the complex silences the target nucleic acid sequence in the cell by: (i) methylating a chromatin containing the target nucleic acid sequence, (ii) introducing repressive chromatin marks to a chromatin containing the target nucleic acid sequence, or (iii) methylating a chromatin containing the target nucleic acid sequence and introducing repressive chromatin marks to a chromatin containing the target nucleic acid sequence.

Embodiment 35. The method of Embodiment 34, wherein the cell is a mammalian cell.

Embodiment 36. The method of Embodiment 34 or 35, wherein the method has a specificity that is 2-fold higher than a specificity to a non-target nucleic acid sequence.

EXAMPLES

Embodiments and aspects herein are further illustrated by the following examples. The examples are merely intended to illustrate embodiments and aspects, and are not to be construed to limit the scope herein.

Figure 1B:
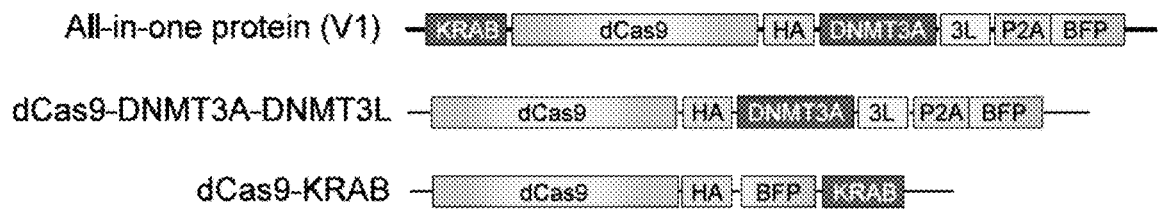

Example 1 dCas9-fused epigenetic modulators tested for permanent gene silencing. The initial version (V1, p76 (SEQ ID NO:1)) of the all-in-one protein (FIG. 1A) has the KRAB domain fused to the —N-terminus of dCas9 (SEQ ID NO:23), separated by a GGSGGGS (SEQ ID NO:17) linker, and Dnmt3A-Dnmt3L at the C-terminus of dCas9 (separated by a EASGSGRASPGIPGSTR (SEQ ID NO:19) linker). Another all-in-one proteins that combined the KRAB domain (SEQ ID NO:16), dCas9 (D10A, H208A), Dnmt3A-Dnmt3L (SEQ ID NO:33; where SEQ ID NO:26 is Dnmt3A and SEQ ID NO:28 is Dnmt3L) into one polypeptide (FIG. 1i). With reference to FIG. 1B, the dCas9-KRAB protein was adapted from Gilbert et al., Cell 2013 for CRISPR interference (CRISPRi) applications, and the dCas9-Dnmt3A-Dnmt3L fusion was adapted from Stepper et al., Nucleic Acids Research, 2016.

Figure 1C:
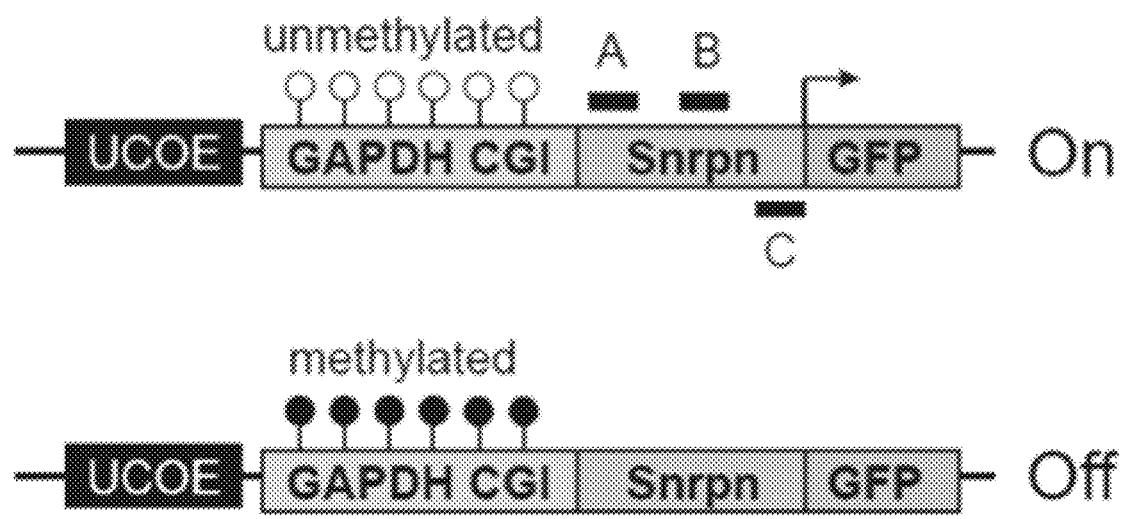
Figure 1D:
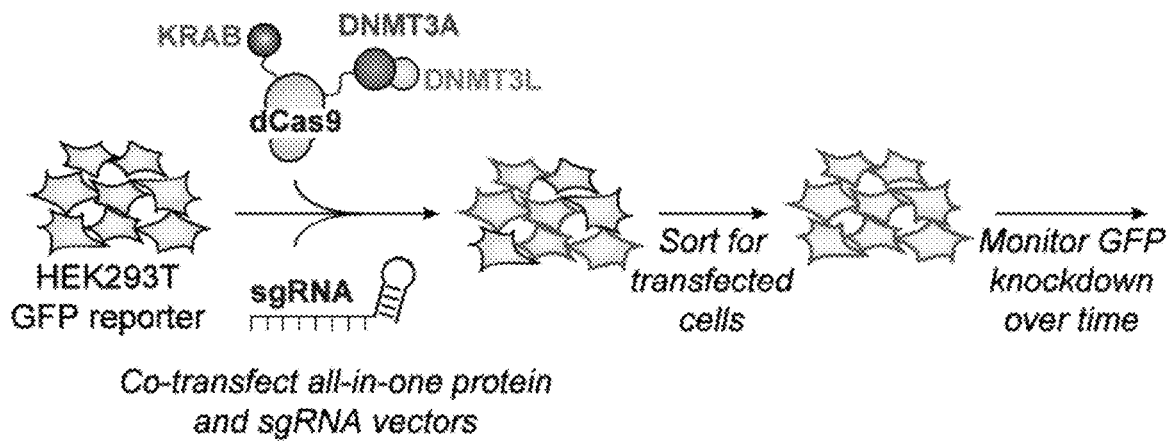
Figure 1E:
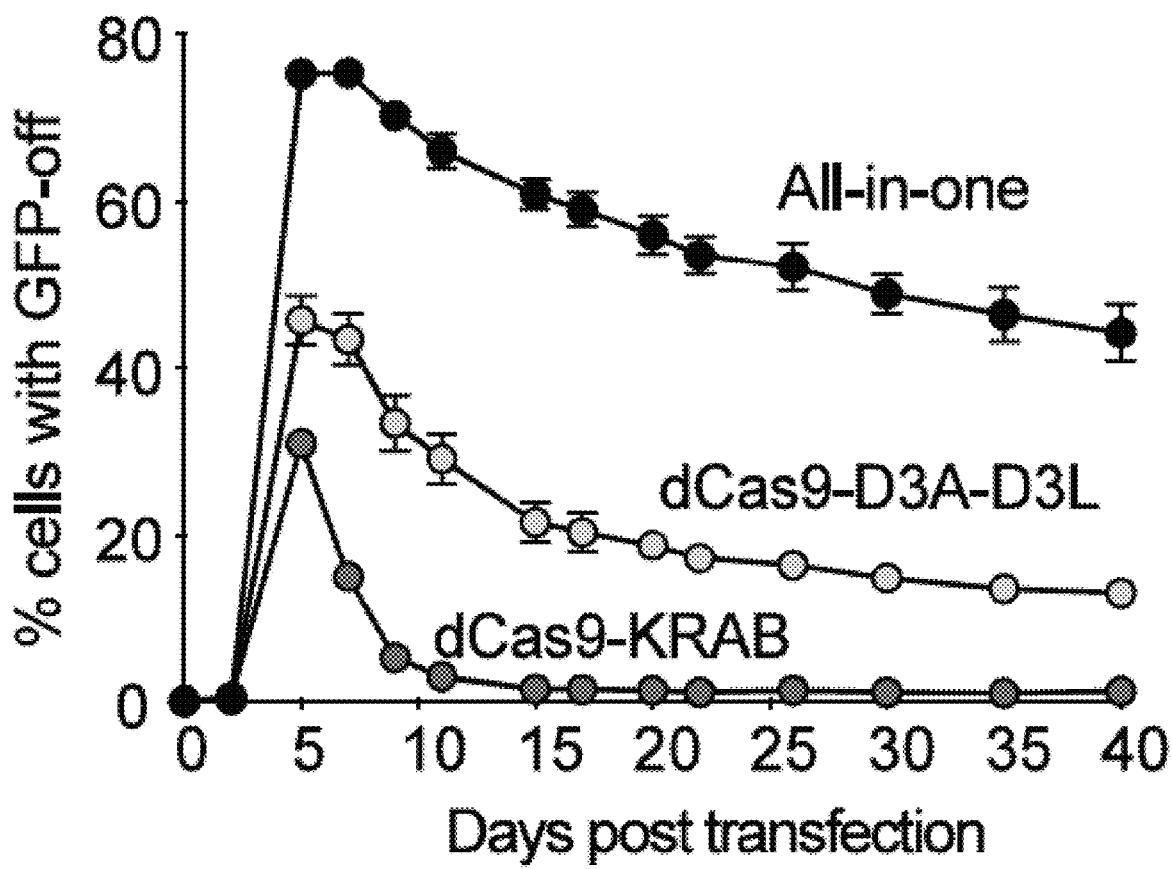

The activity of the V1 epigenetic editor was tested in HEK293T cells using a DNA-methylation sensitive GFP reporter (adapted from Stelzer et al., Cell 2015) to assess long-term silencing by the all-in-one protein (FIG. 1C). A ubiquitous chromatin opening element (UCOE) was added upstream of the GAPDH CpG island (CGI) to prevent background silencing of the lentiviral vector in mammalian cells. The gfp gene is turned off when the GAPDH CGI is methylated. A, B and C denote positions we encoded single guide RNAs (sgRNA) to target in the promoter. These targeted sequences and corresponding sgRNA sequences are listed in the Table 1 below. Two plasmids were co-transfected into cells, one encoding the hit-and-run protein and the other plasmid encoding a sgRNA (FIG. 1D). Two days post-transfection, cells that express the hit-and-run protein and sgRNA-expressing vector are sorted. GFP fluorescence is assessed over time by flow cytometry. A population of cells undergoing long-term silencing of the GFP reporter was observed when the all-in-one protein is expressed with sgRNAs (FIG. 1E). The number of cells undergoing long-term silencing was higher than dCas9-Dnmt3A-Dnmt3L (lacking the KRAB domain).

TABLE 1

| Name | Targeted sequence (5' to 3') | sgRNA sequence (5' to 3') |
|---|---|---|
| A (JKNg156) | ACTGCGGAAATTTGAGCGT (SEQ ID NO: 37) | ACGCTCAAATTTCC GCAGT (SEQ ID NO: 38) |
| B (JKNg158) | AGGCAATGGCTGCACATGC (SEQ ID NO: 39) | GCATGTGCAGCCAT TGCCT (SEQ ID NO: 40) |
| C (JKNg160) | GACGCTTGGTTCTGAGGAG (SEQ ID NO: 41) | CTCCTCAGAACCAA GCGTC (SEQ ID NO: 42) |

Silencing of the GFP reporter is dependent on the sgRNA sequence, with guide C resulting in the highest level of silencing among the three sgRNA sequences tested. Pooling the sgRNAs encoding different sequences did not have a significant change in gene silencing.

Example 2

Figure 2D:
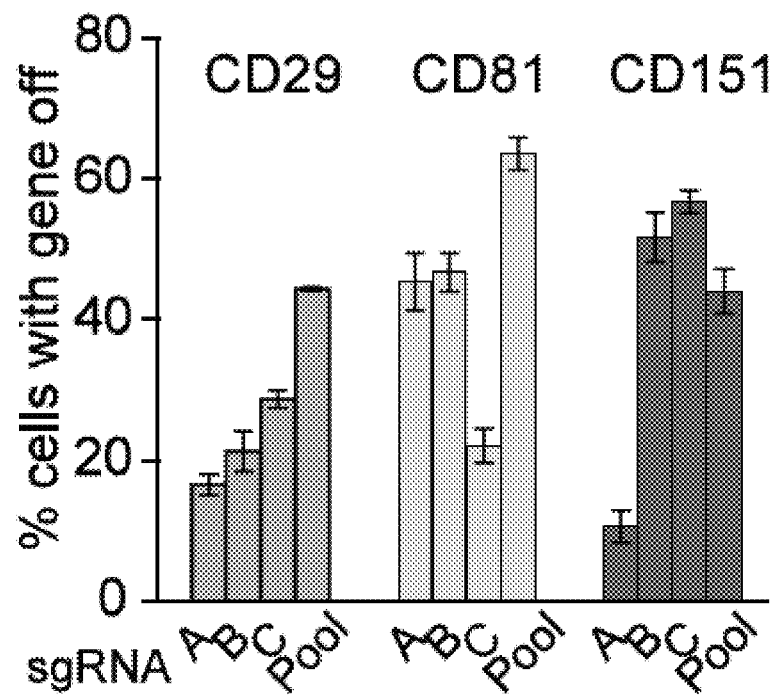

Three genes (CD29, CD81, CD151) were targeted for long term silencing using the hit-and-run fusion protein. All three proteins are cell surface-localized and knockdown was assessed by cell surface antibody staining of cells, followed by flow cytometry. Representative flow cytometry data are shown in FIGS. 2A-2C taken 22 days post-transfection. Quadrant IV represents cells that have turned off the gene, indicated by the percentage of cells with the gene off. The lack of cells in Quadrants I and II signify that the hit-and-run protein (marked by BFP) is no longer present in the cells. FIG. 2D provides quantification of silencing of CD29, CD81 and CD151 with three different sgRNA sequences or a pool of all three sgRNAs. The targeted DNA sequences and their sgRNAs used in this experiment are summarized in Table 2.

TABLE 2

| Name | Targeted sequence (5' to 3') | sgRNA sequence (5' to 3') |
|---|---|---|
| CD29, sgRNA-A | TCCGGAAACGCATTCCTCT (SEQ ID NO: 43) | AGAGGAATGCGTTT CCGGA (SEQ ID NO: 44) |
| CD29, sgRNA-B | CCGCGTCAGCCCGGCCCGG (SEQ ID NO: 45) | CCGGGCCGGGCTGA CGCGG (SEQ ID NO: 46) |
| CD29, sgRNA-C | CGACTCCCGCTGGGCCTCT (SEQ ID NO: 47) | AGAGGCCCAGCGGG AGTCG (SEQ ID NO: 48) |
| CD81, sgRNA-A | ccgttgcgcgctcgctctc (SEQ ID NO: 49) | gagagcgagcgcgc aacgg (SEQ ID NO: 50) |
| CD81, sgRNA-B | CCGCGCATCCTGCCAGGCC (SEQ ID NO: 51) | GGCCTGGCAGGATG CGCGG (SEQ ID NO: 52) |
| CD81, sgRNA-C | CCAACTTGGCGCGTTTCGG (SEQ ID NO:53) | CCGAAACGCGCCAA GTTGG (SEQ ID NO: 54) |
| CD151, sgRNA-A | ACCACGCGTCCGAGTCCGG (SEQ ID NO: 55) | CCGGACTCGGACGC GTGGT (SEQ ID NO: 56) |
| CD151, sgRNA-B | TGCTCATTGTCCCTGGACA (SEQ ID NO: 57) | TGTCCAGGGACAAT GAGCA (SEQ ID NO: 58) |
| CD151, sgRNA-C | GGACACCCTGCTCATTGTC (SEQ ID NO: 59) | GACAATGAGCAGGG TGTCC (SEQ ID NO: 60) |

Figure 2E:
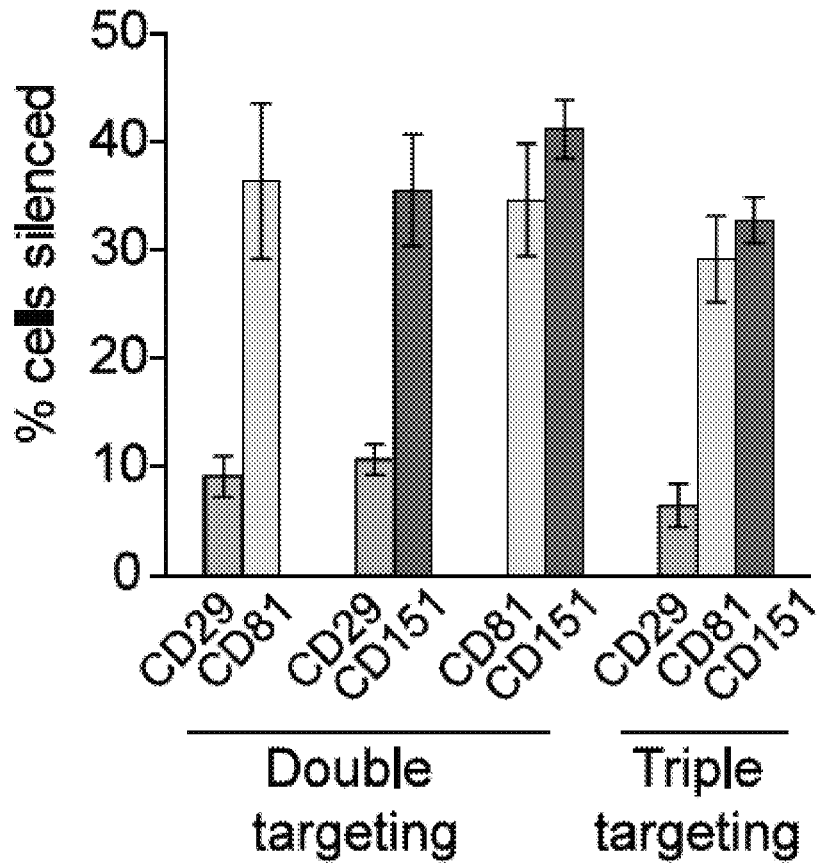

Two or three genes were simultaneously targeted to show that the all-in-protein can be multiplexed by co-delivery of sgRNAs targeting different genes. NT sgRNA refers to non-targeting sgRNA control. The results are shown in FIG. 2E.

Figure 2F:
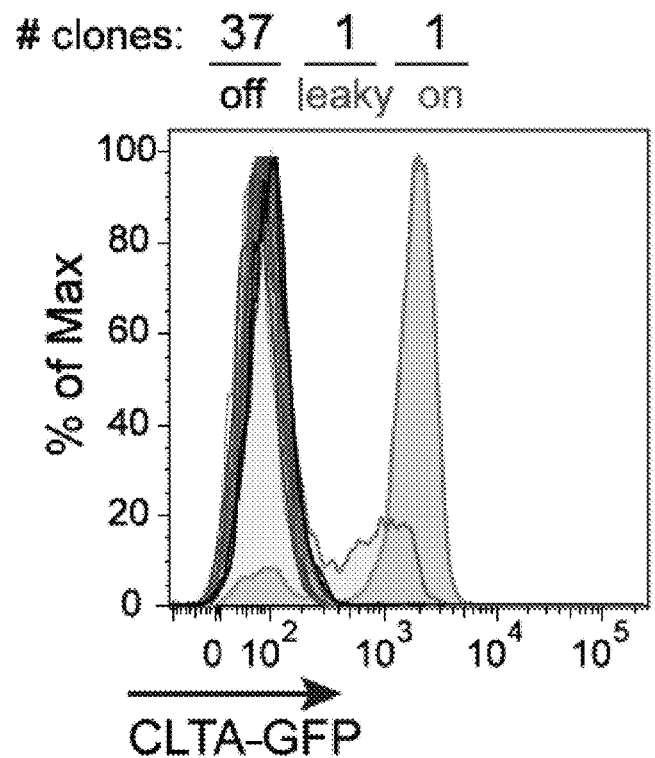

Gene silencing of cells that started as a single clone were followed and it was observed the majority of cells have maintained the targeted CLTA gene off (37 out of 39 clones). The plot in FIG. 2F represents a time point taken 9 months post transfection of the all-in-one protein and sgRNA targeting the CLTA gene.

The system described herein can target any genes in the mammalian genomes, especially those that contain CpG islands at the gene promoter. The Dnmt3A-Dnmt3L canonically targets CpG dinucleotides. Examples of genes that can be targeted include, but are not limited to, CXCR4, CD4, CD8, CD45, PD-1, CLTA-4, TGFBR, TCRa, TCRb, B2M.

Example 3

Figure 3A:
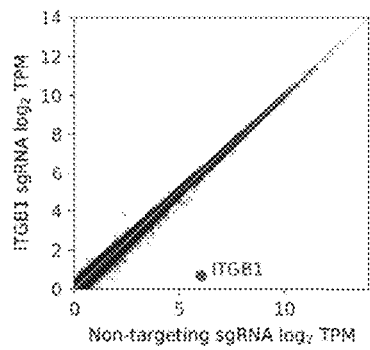
FIGS. 3A-3I describe long-term silencing of endogenous genes.
Figure 3B:
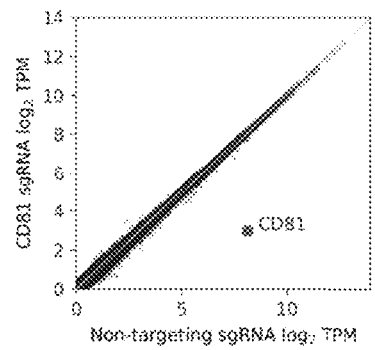
Figure 3C:
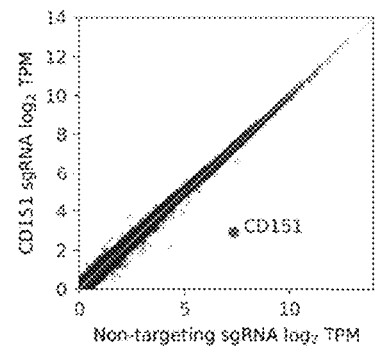
Figure 3D:
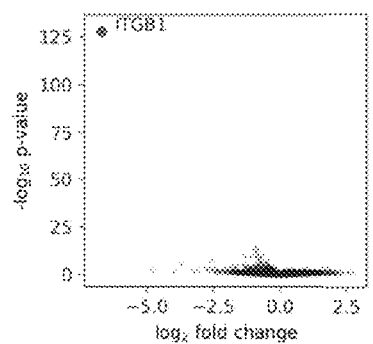
Figure 3E:
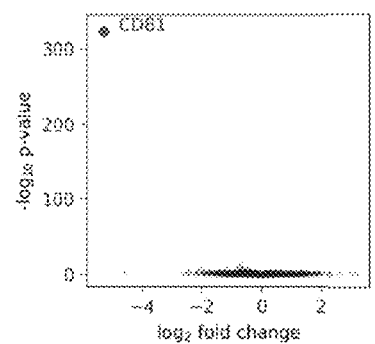
Figure 3F:
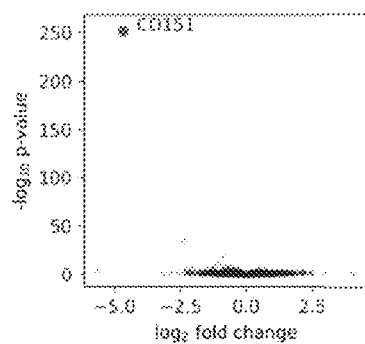
Figure 3G:
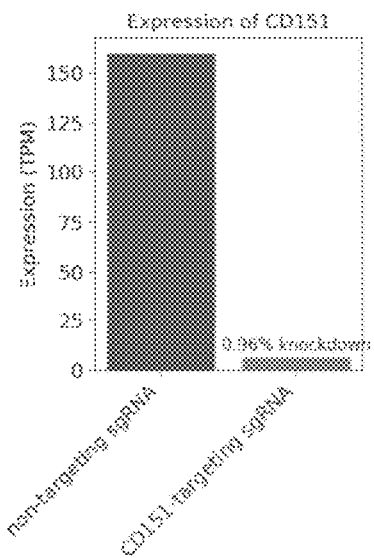
Figure 3H:
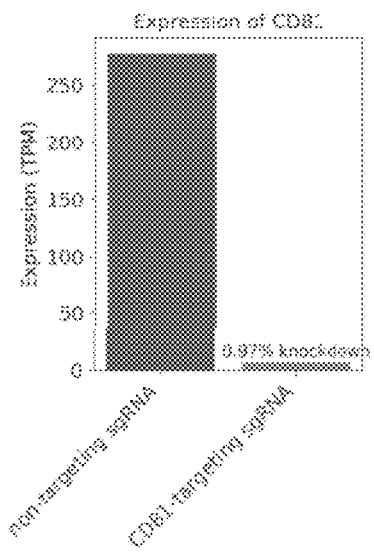
Figure 3I:
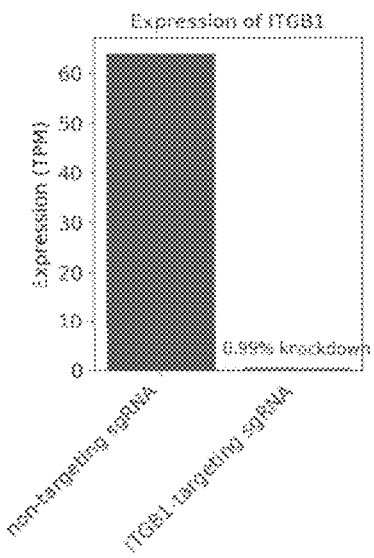

Cells were harvested that lost expression of ITGB1 (CD29), CD81 and CD151 thirty-six days post-transfection and analyzed their RNA expression profiles were analyzed. As shown in FIGS. 3A-3C, successful knockdown of the targeted genes was detected compared to the non-targeting sgRNA control. FIGS. 3D-3F are volcano plots show that the targeted gene is the only significant gene knocked down for each experiment, signifying high specificity of gene silencing. FIGS. 3G-3I are the quantification of transcript levels showing greater than 96% knockdown of the targeted gene.

Example 4

Figure 4A:
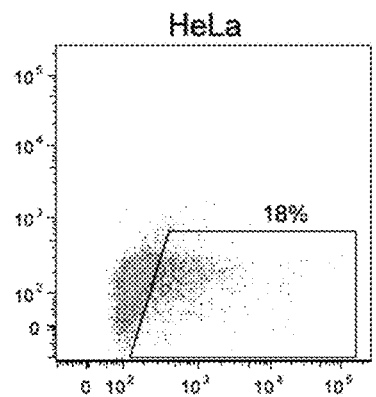
FIGS. 4A-4H describe long-term gene silencing in different mammalian cell lines.
Figure 4B:
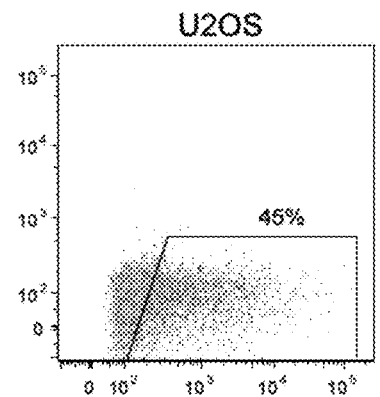
Figure 4C:
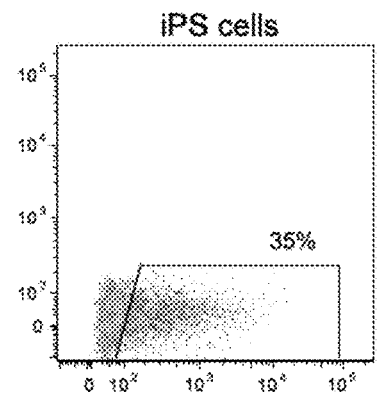
Figure 4D:
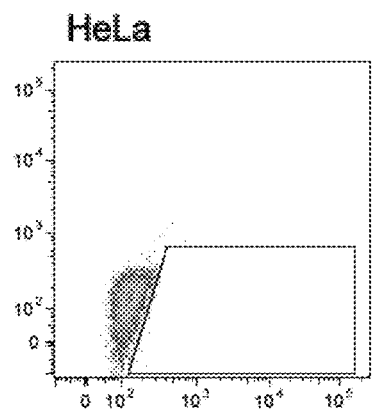
Figure 4E:
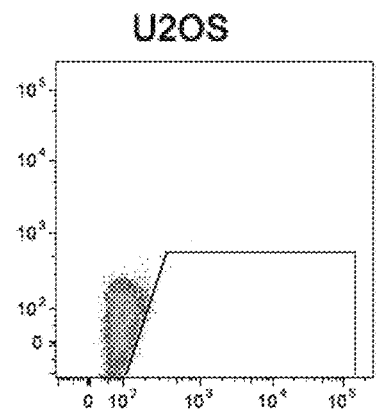
Figure 4F:
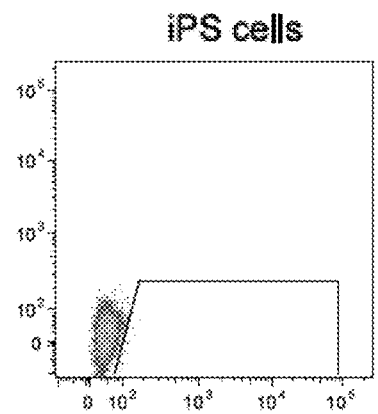
Figure 4G:
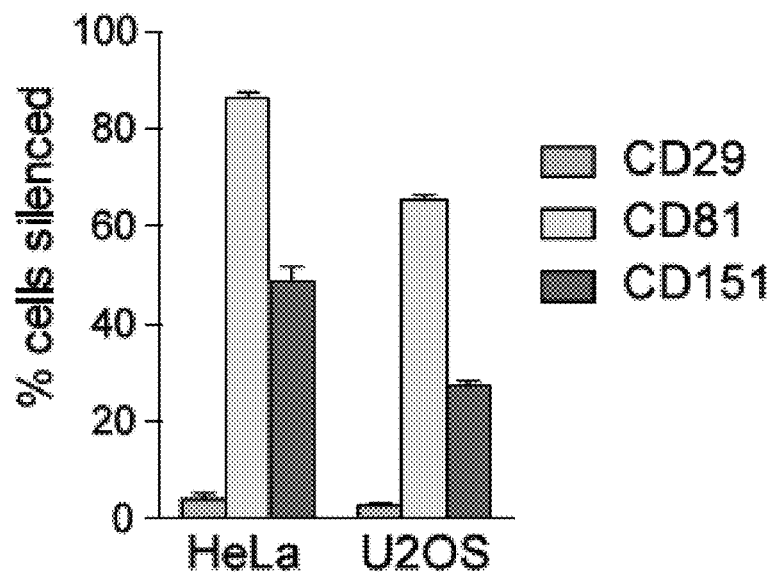
Figure 4H:
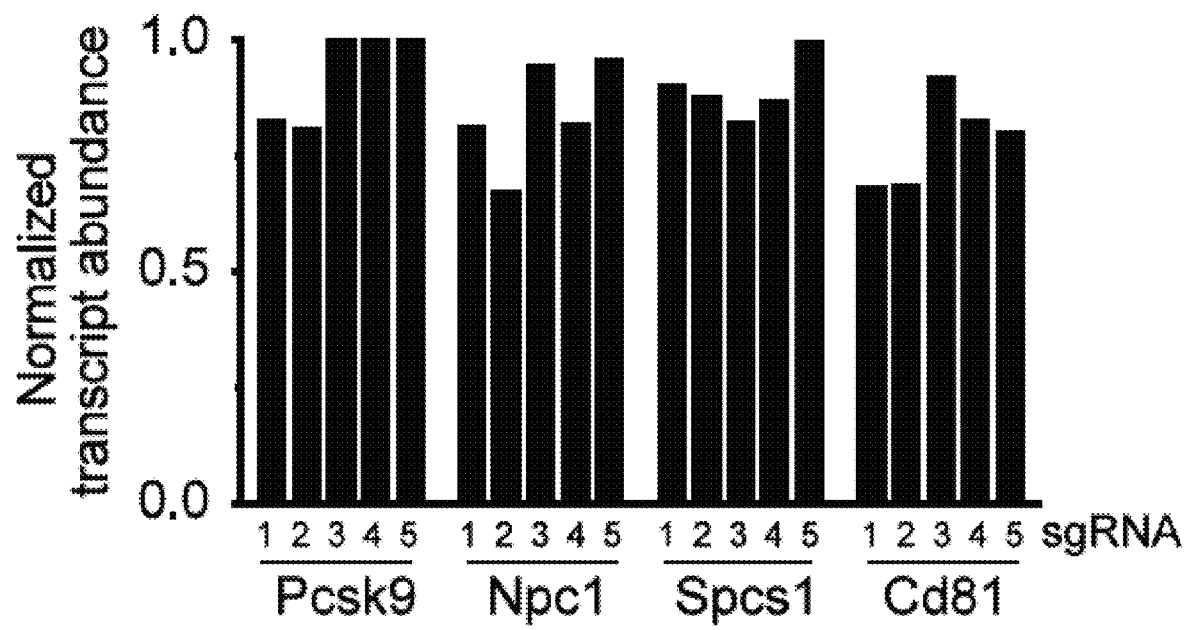

The all-in-one protein can be transfected and expressed in HeLa (cervical), U2OS (bone) and human induced pluripotent stem cells (iPSC). Flow cytometry plots in FIGS. 4A-4F show BFP expression, which is fused to the protein. Three endogenous genes in HeLa and U2OS cells (i.e., CD29, CD81, and CD151) were targeted. As shown in FIG. 4G, stable silencing, measured at 18 days post-transfection, was detected. Gene silencing in AML12 mouse hepatocyte cell lines was detected when targeting Pcsk9, Npc1, Spcs1 and Cd81. Silencing was detected by qPCR, measured 14 days post transfection, as shown in FIG. 4H. The sgRNA sequences used in this experiment are summarized in Table 3

TABLE 3

| Name | Targeted sequence (5' to 3') | sgRNA sequence (5' to 3') |
|---|---|---|
| Pcsk9 sgRNA-1 | TCCGGAAACGCATTCCTCT (SEQ ID NO: 43) | AGAGGAATGCGTTTCCGGA (SEQ ID NO: 44) |
| Pcsk9 sgRNA-2 | ACCGGCAGCCTGCGCGTCC (SEQ ID NO: 61) | GGACGCGCAGGCTGCCGGT (SEQ ID NO: 62) |
| Pcsk9 sgRNA-3 | CGATGGGCACCCACTGCTC (SEQ ID NO: 63) | GAGCAGTGGGTGCCCATCG (SEQ ID NO: 64) |
| Pcsk9 sgRNA-4 | CCTTCACGTGGACGCGCAG (SEQ ID NO: 65) | CTGCGCGTCCACGTGAAGG (SEQ ID NO: 66) |
| Pcsk9 sgRNA-5 | CGTGAAGGTGGAAGCCTTC (SEQ ID NO: 67) | GAAGGCTTCCACCTTCACG (SEQ ID NO: 68) |
| Npc1 sgRNA-1 | CTCCTTGGTCAGGCGCCGG (SEQ ID NO: 69) | CCGGCGCCTGACCAAGGAG (SEQ ID NO: 70) |
| Npc1 sgRNA-2 | TGGTCAGGCGCCGGTTCCG (SEQ ID NO: 71) | CGGAACCGGCGCCTGACCA (SEQ ID NO: 72) |
| Npc1 sgRNA-3 | TAGAGGTCGCCTTCTCCTC (SEQ ID NO: 73) | GAGGAGAAGGCGACCTCTA (SEQ ID NO: 74) |
| Npc1 sgRNA-4 | CGACGCTCGGGTCGCGGTG (SEQ ID NO: 75) | CACCGCGACCCGAGCGTCG (SEQ ID NO: 76) |
| Npc1 sgRNA-5 | ATGCTGTCGCCGCGCGGGG (SEQ ID NO: 77) | CCCCGCGCGGCGACAGCAT (SEQ ID NO: 78) |
| Spcs1 sgRNA-1 | CTCACCCTCACCGGAGCCA (SEQ ID NO: 79) | TGGCTCCGGTGAGGGTGAG (SEQ ID NO: 80) |
| Spcs1 sgRNA-2 | CCGCAAACTTTACTCCTTA (SEQ ID NO: 81) | TAAGGAGTAAAGTTTGCGG (SEQ ID NO: 82) |
| Spcs1 sgRNA-3 | CTCGGAGACATCCGCTTCC (SEQ ID NO: 60) | GGAAGCGGATGTCTCCGAG (SEQ ID NO: 60) |
| Spcs1 sgRNA-4 | CTCCTAAGATTGGCTTCAC (SEQ ID NO: 83) | GTGAAGCCAATCTTAGGAG (SEQ ID NO: 84) |
| Spcs1 sgRNA-5 | CCGGAGCCACTCCTAAGAT (SEQ ID NO: 85) | ATCTTAGGAGTGGCTCCGG (SEQ ID NO: 86) |
| Cd81 sgRNA-1 | TTCTCTACCCTACGTCTCA (SEQ ID NO: 87) | TGAGACGTAGGGTAGAGAA (SEQ ID NO: 88) |
| Cd81 sgRNA-2 | TACGTCTCATTCTCCGCAA (SEQ ID NO: 89) | TTGCGGAGAATGAGACGTA (SEQ ID NO: 90) |
| Cd81 sgRNA-3 | GCTAGGCCTCCAGCCCTTC (SEQ ID NO: 91) | GAAGGGCTGGAGGCCTAGC (SEQ ID NO: 92) |
| Cd81 sgRNA-4 | ACAGGTGGCGCCGCAACTT (SEQ ID NO: 93) | AAGTTGCGGCGCCACCTGT (SEQ ID NO: 94) |
| Cd81 sgRNA-5 | AGCCGGAGGCGCGAGAGTC (SEQ ID NO: 95) | GACTCTCGCGCCTCCGGCT (SEQ ID NO: 96) |

Example 5

FIG. 5 provides a schematic of the all-in-one protein constructs that were designed and tested for gene silencing. The initial design (p76, V1) of SEQ ID NO:1 was modified to encode XTEN linkers (e.g., 16 amino acids (SEQ ID NO: 31) or 80 amino acids (SEQ ID NO:32)) at either the N or C terminus of dCas9 (SEQ ID NO:29). All vectors contain HA tags (SEQ ID NO:24) at the C-terminus of dCas9. In aspects, CAG promoter is used since it provides good expression, for example, in constructs p76, and p90-102, p112 (V2). With reference to FIG. 5, the protein constructs of p90 to p102 correspond to SEQ ID NOS:2-14, respectively, and protein construct p112 corresponds to SEQ ID NO: 15.

Example 6

Figure 6A:
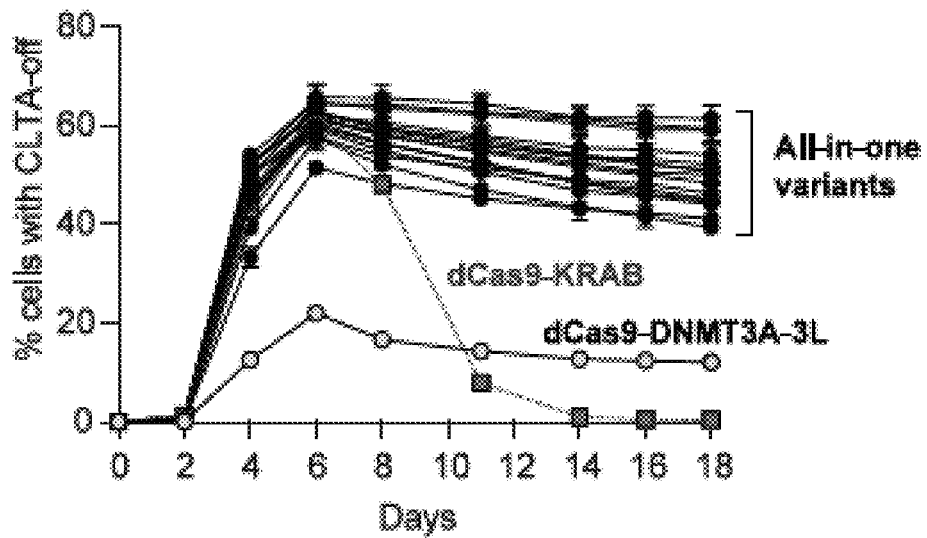
FIGS. 6A-6E describe gene silencing activities of all-in-one protein variants.
Figure 6B:
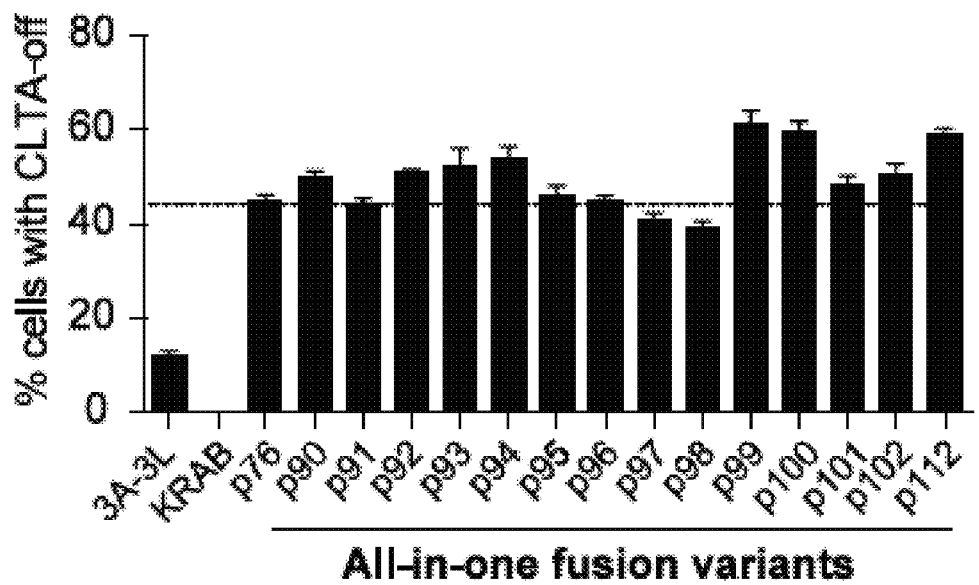
Figure 6C:
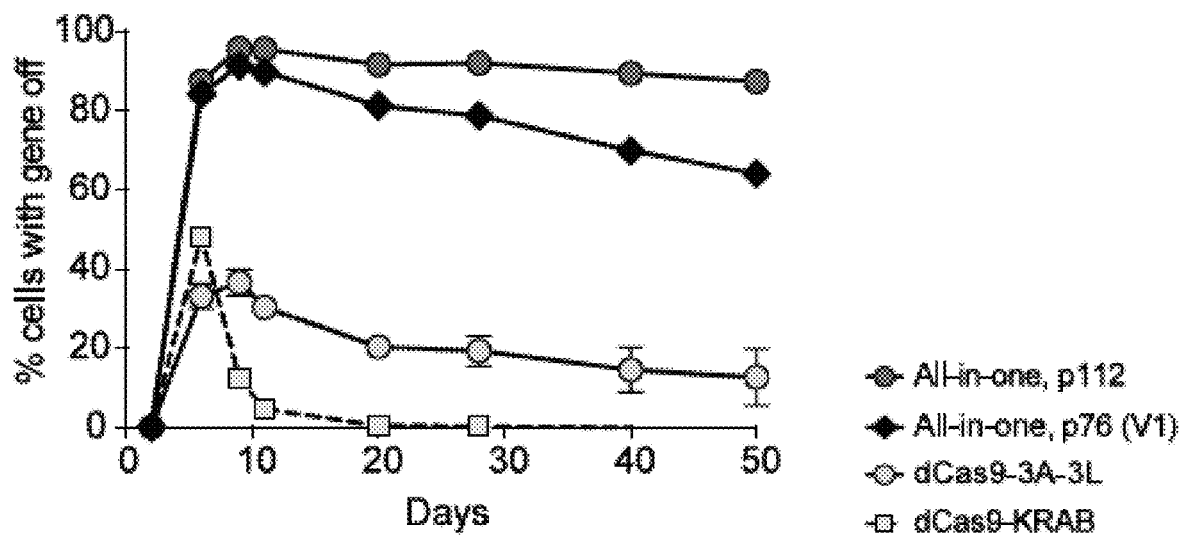
Figure 6D:
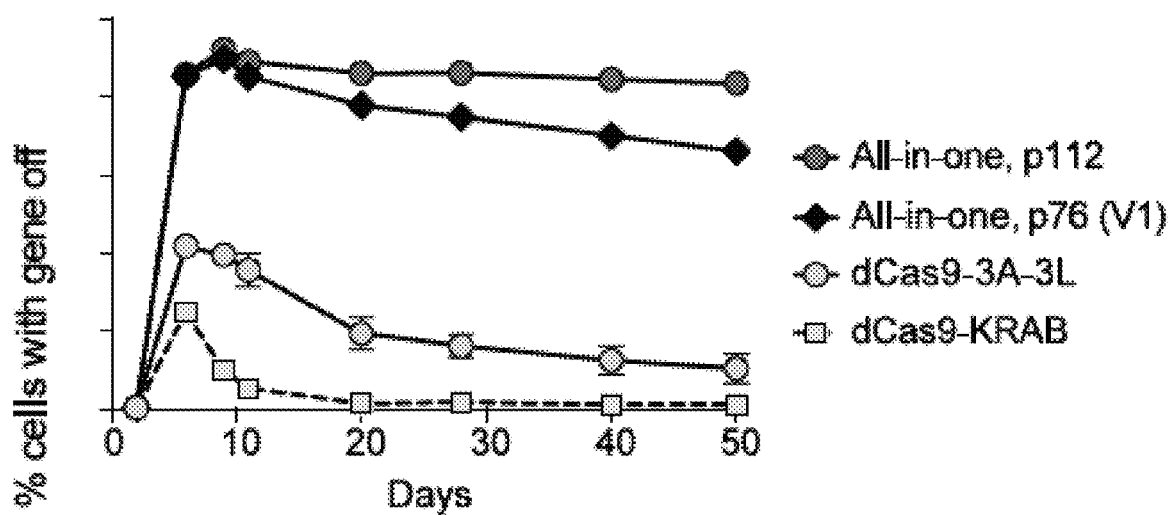
Figure 6E:
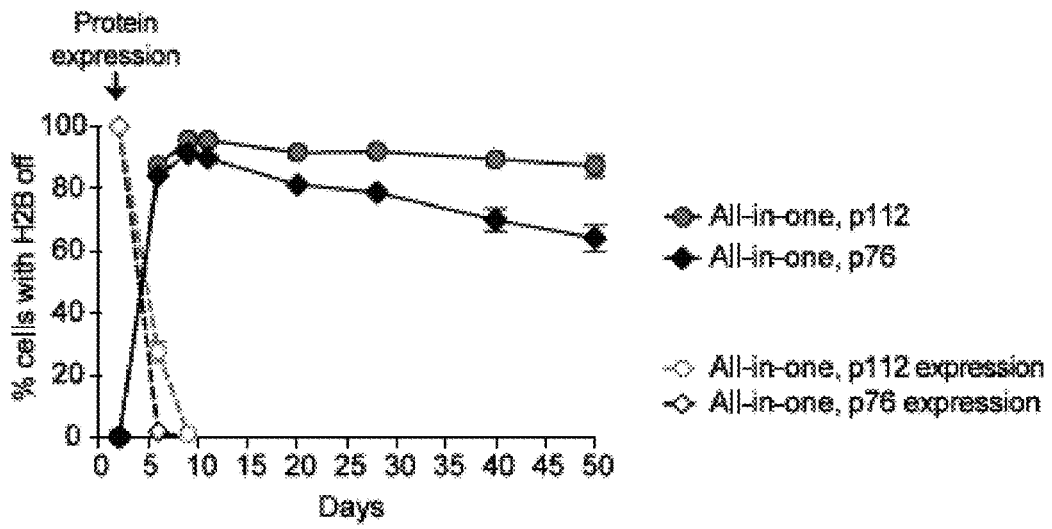

The protein constructs shown in FIG. 5 were tested for silencing of the CLTA gene in HEK293T cells for 18 days post-transfection (FIGS. 6A-6B). Variable levels of gene silencing activities were detected, including a panel of variants with more durable gene silencing compared to the p76 (V1) design such as p99 (SEQ ID NO:11), p100 (SEQ ID NO:12), and p112 (SEQ ID NO:15). FIGS. 6A and 6B show tat the dCas9-KRAB and dCas9-Dnmt3A-Dnmt3L constructs showed transient and lower efficiency of long term silencing.

p76 (SEQ ID NO:1), p112 (SEQ ID NO:15) were tested for silencing the HIST2H2BE (H2B) endogenous gene and a synthetic Snrpn-GFP reporter gene stably expressed in HEK293T cells (FIGS. 6C-6D). Cells were followed for 50 days post-transfection. The p112 variant sustained gene silencing at a higher efficiency than the p76 (V1) design. The dCas9-Dnmt3A-Dnmt3L and dCas9-KRAB fusion proteins have transient and lower efficiency of long term silencing. FIG. 6E provides a plot of protein expression of p76 and p112 over the 50 day time course to turn off the HIST2H2BE (H2B) gene. Protein levels were measured by flow cytometry detection of BFP, which is co-expressed with the all-in-one protein.

Example 7

Figure 7A:
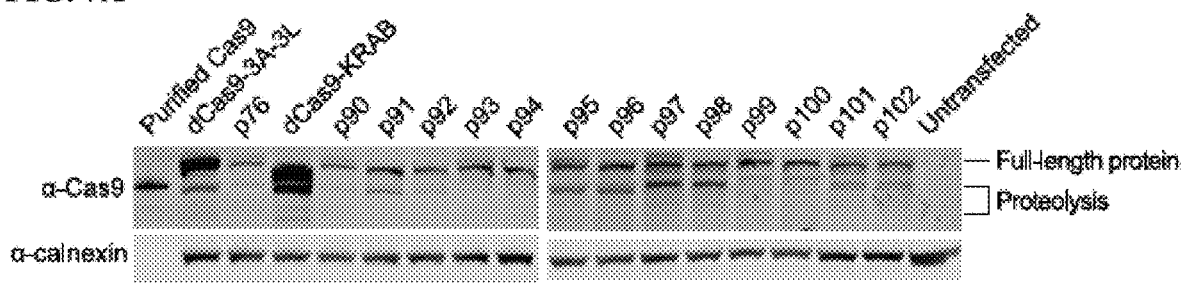
FIGS. 7A-7B provide Western blots of all-in-one-protein variants.

Western blot analysis was performed with the all-in-one protein variants p76, p90-p102 using an antibody against *Streptococcus pyogenes* Cas9. With reference to FIG. 7A, the top band represents full-length protein and smaller-sized bands represent proteolysis of the all-in-one protein. Variants that show little proteolysis, such as p99 (SEQ ID NO:11), p100 (SEQ ID NO:12), and p102 (SEQ ID NO:14), exhibited higher efficiency of gene silencing. Variants with high levels of proteolysis, such as p96 (SEQ ID NO:8) and p97 (SEQ ID NO:9), led to lower efficiency of sustained gene silencing.

Figure 7B:

Western blot analysis was performed with the all-in-one protein variants to detect free Dnmt3A that is cleaved from the fusion protein. As shown in FIG. 7B, variants that had little or no detectable free Dnmt3, such as p92 (SEQ ID NO:4), p100 (SEQ ID NO:12), p101 (SEQ ID NO:13), and p102 (SEQ ID NO:14), had higher efficiency of sustained gene silencing compared to variants with detectable cleaved Dnmt3A, i.e., p76 (SEQ ID NO:1), p91 (SEQ ID NO:3), p96 (SEQ ID NO:8), p98 (SEQ ID NO:10).

Example 8

Figure 8A:
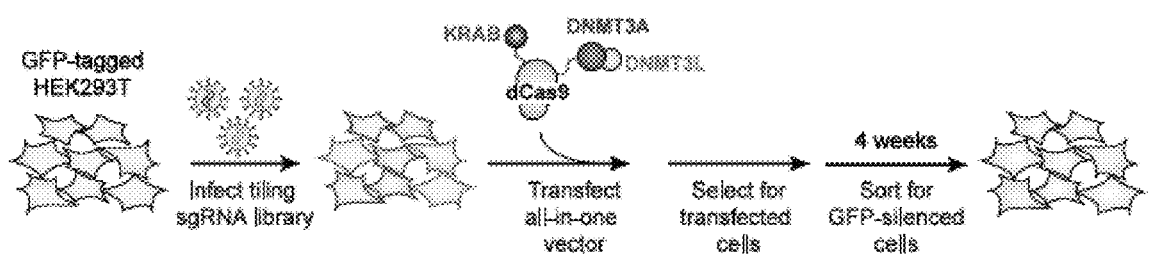
FIGS. 8A-8E describe pooled screen to determine optimal sgRNAs.
Figure 8B:
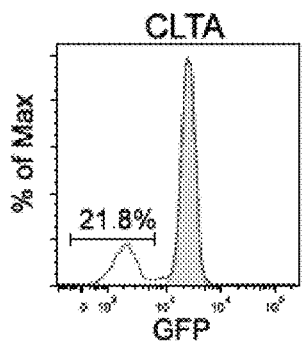
Figure 8C:
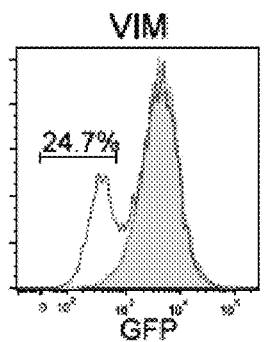
Figure 8D:
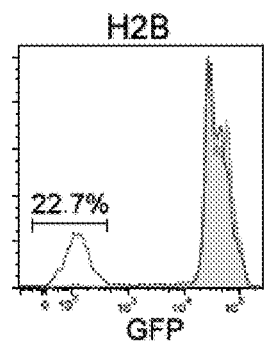
Figure 8E:
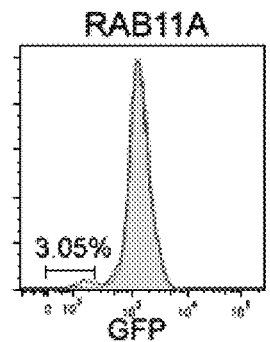
Figure 9A:
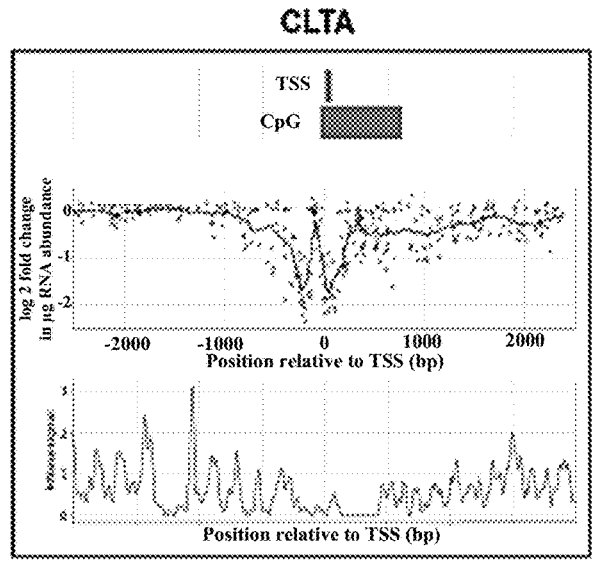
FIGS. 9A-9D are maps of sgRNA functionality across the transcription start site of the targeted gene, including CLTA (FIG. 9A), H2B (FIG. 9B), RAB11 (FIG. 9C), and VIM (FIG. 9D). The transcription start site (TSS) and CpG island are annotated above each plot. Each dot represents one sgRNA and its efficacy in long term gene silencing is plotted as the log 2 fold change in sgRNA abundance. Nucleosome occupancy (bottom plot) is plotted from MNase signal.
Figure 9B:
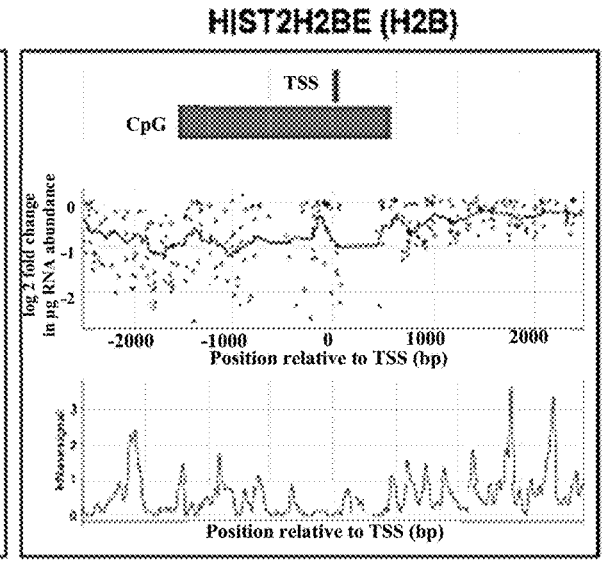
Figure 9C:
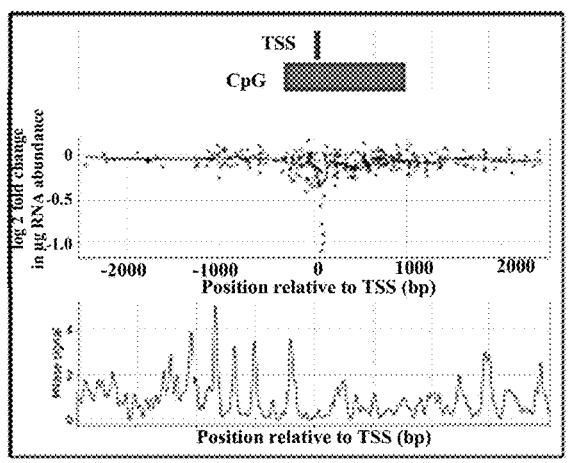
Figure 9D:
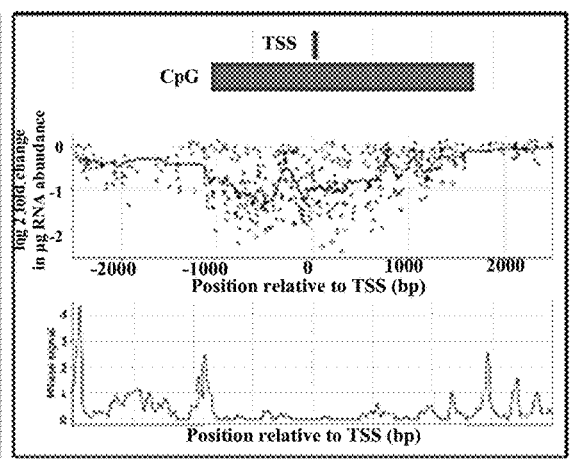

A pooled screen was assayed, as shown in FIG. 8A, to determine the optimal sgRNAs that leads to long term gene silencing. Four HEK293T cell lines were used, each with a different gene with a GFP tag (CLTA, VIM, HIST2H2BE (H2B), and RAB11A). Tiling libraries consisting of sgRNAs that span +/−2.5 kb from the transcription start site (TSS) of each gene were stably expressed in cells by lentiviral delivery, followed by transient expression plasmid DNA expressing the all-in-one protein. Four weeks post-transfection, cells that maintained gene silencing were sorted to determine the sgRNA identity. FIGS. 8B-8E are flow cytometry histograms showing the percent of cells undergoing gene silencing four weeks post-transfection.

FIGS. 9A-9D are maps of sgRNA functionality across the transcription start site of the targeted gene (CLTA, H2B, RAB11, VIM). The transcription start site (TSS) and CpG island are annotated above each plot. Each dot represents one sgRNA and its efficacy in long term gene silencing is plotted as the log 2 fold change in sgRNA abundance. Nucleosome occupancy (bottom plot) is plotted from MNase signal.

Example 9

Figure 10A:
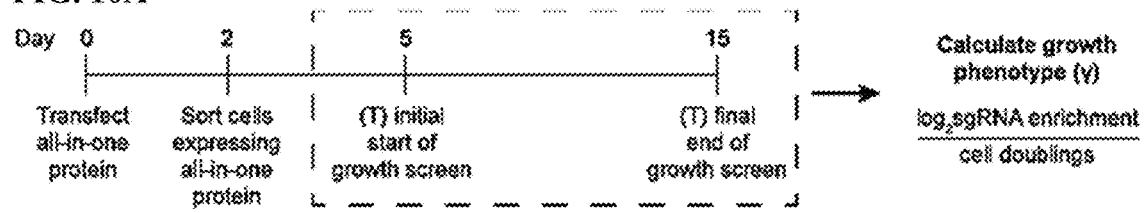
FIGS. 10A-10E describe functional sgRNAs for long term gene silencing.
Figure 10B:
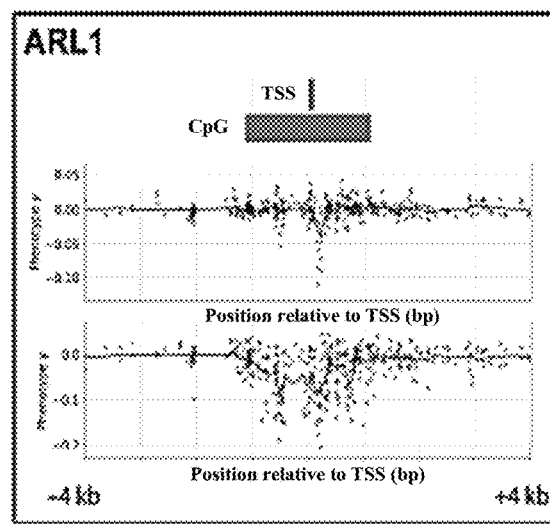
Figure 10C:
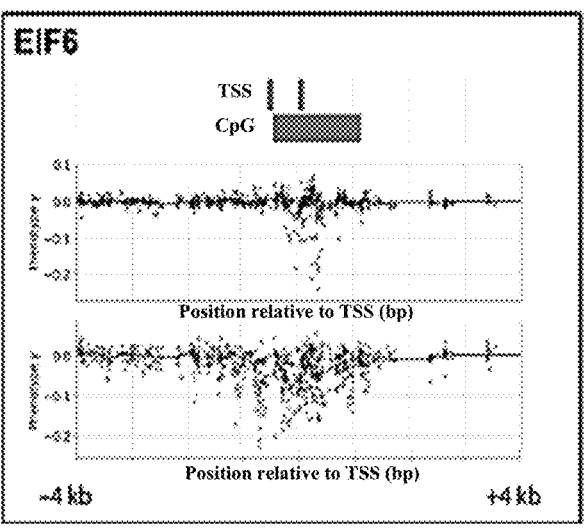
Figure 10D:
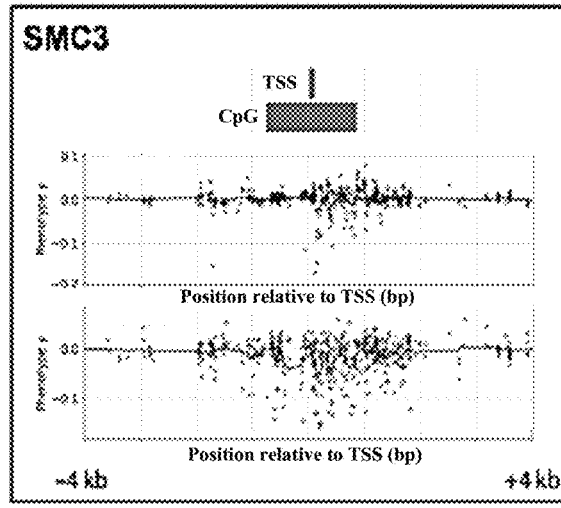
Figure 10E:
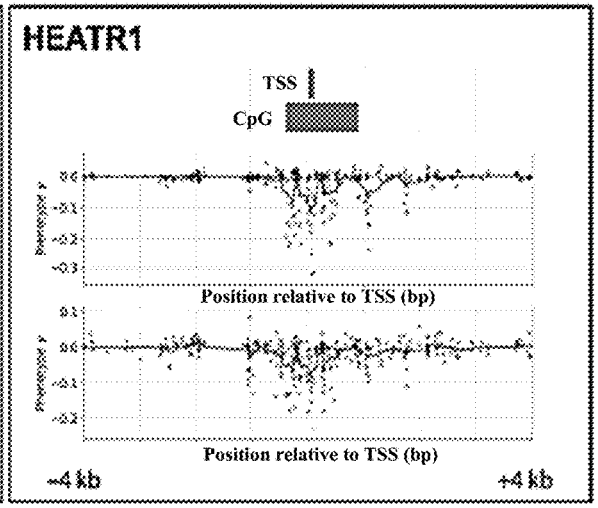

FIG. 10A shows the workflow of a pooled screen in HEK293T cells to determine optimal sgRNA targeting positions for the all-in-one protein, adapted from a previous ricin tiling screen in K562 cells to determine optimal sgRNAs for dCas9-KRAB (Gilbert, Horlbeck et al., Cell 2014). The sgRNAs are first stably expressed in HEK293T cells by lentiviral delivery, followed by transient transfection of a plasmid encoding the all-in-one protein (Day 0). Cells expressing the all-in-one protein are sorted (Day 2) and allowed to grow for three more days. Cells are split on Day 5, from which half are harvested as an initial time point, and the other half are passaged for ten more days (Day 15) for a final time point. The growth phenotype (γ) is calculated as the log 2 sgRNA enrichment divided by the number of cell doublings between T(initial) and T(final).

FIGS. 10B-10E are representative plots showing growth phenotypes for four genes (ARL1, EIF6, SMC3, HEATR1) from existing dCas9-KRAB/CRISPRi datasets in K562 cells (Gilbert, Horlbeck et al., 2014) and with the all-in-one protein (bottom plot). Each dot represents an sgRNA. The TSS and annotated CpG island are shown for each gene. The functional sgRNAs using the all-in-one protein spans a wider range than the functional sgRNAs, signifying a broader range of effective targeting.

Example 10

Figure 11A:
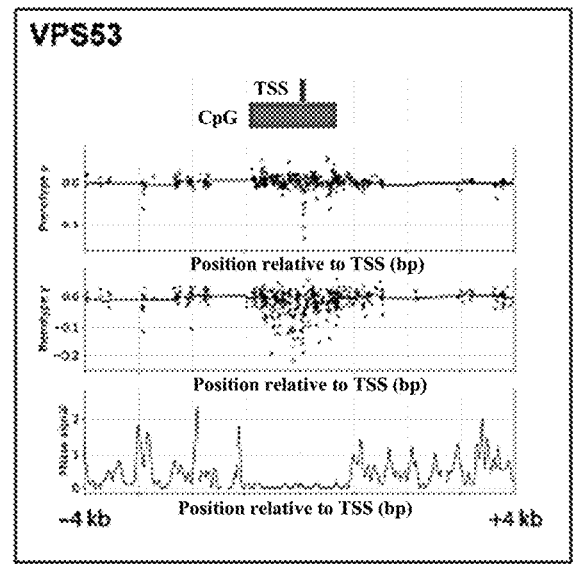
FIGS. 11A-11B provide a comparison of growth phenotypes and nucleosome positioning (from MNase signal) for VPS53 (FIG. 11A) and VPS54 (FIG. 11B) showing the location of functional sgRNAs at nucleosome-depleted regions.
Figure 11B:
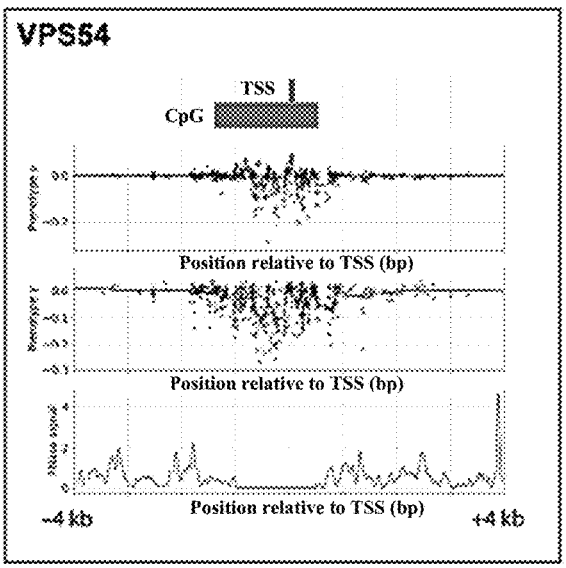

FIGS. 11A-11B provide a comparison of growth phenotypes and nucleosome positioning (from MNase signal) for VPS53 and VPS54 and show the location of functional sgRNAs at nucleosome-depleted regions. Furthermore, the range of functional sgRNAs is broader when using the all-in-one protein compared to dCas9-KRAB/CRISPRi.

Example 11

Figure 12A:
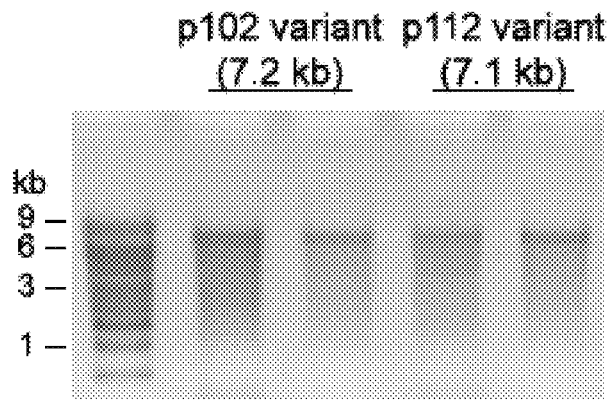
FIGS. 12A-12C show the delivery of the all-in-one protein by mRNA expression
Figure 12B:
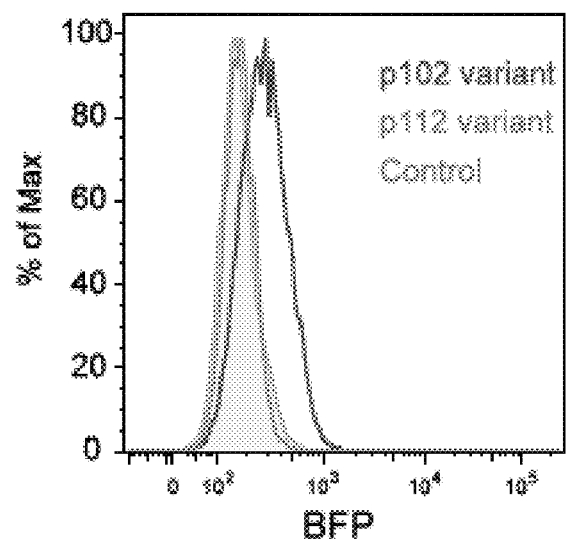
Figure 12C:
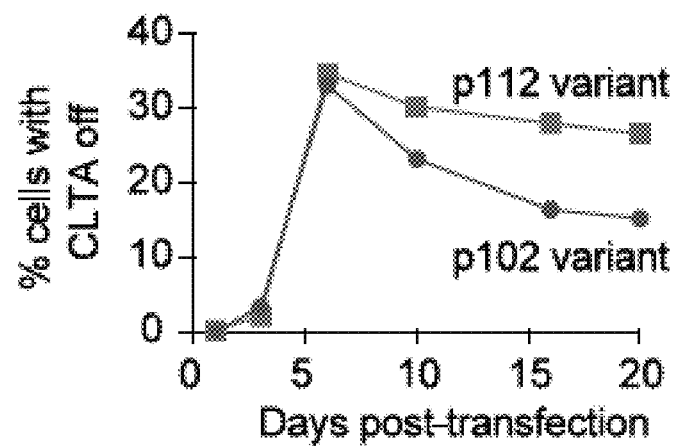

The in vitro transcription of two all-in-one variants (p102 (SEQ ID NO:14) and p112 (SEQ ID NO:15)) show full length synthesis of each design (FIG. 12A). FIG. 12B provides a flow cytometry plot showing expression of p102 and p112 one day post-transfection of mRNA into HEK293T cells. FIG. 12C shows the time course of CLTA endogenous gene silencing in HEK293T cells after transfecting mRNA expressing the p102 and p112 all-in-one variants.

Example 12

Figure 13A:
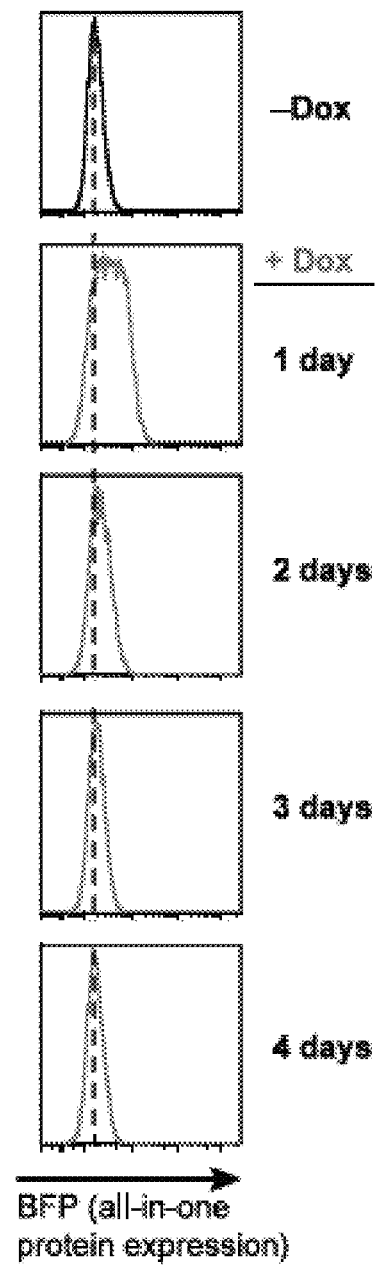
FIGS. 13A-13G describe controlled expression of the all-in-one protein by doxycycline induction.
Figure 13B:
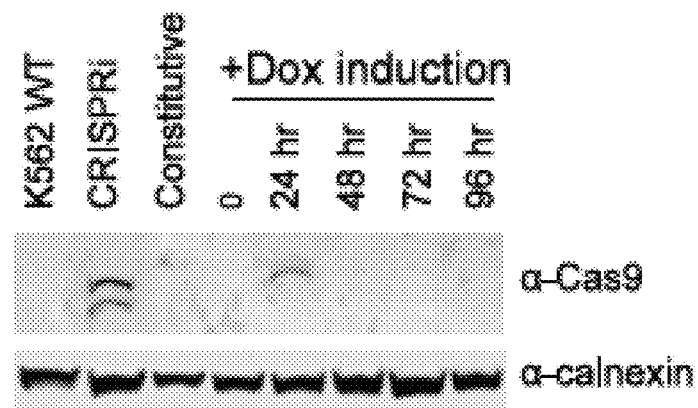
Figure 13C:
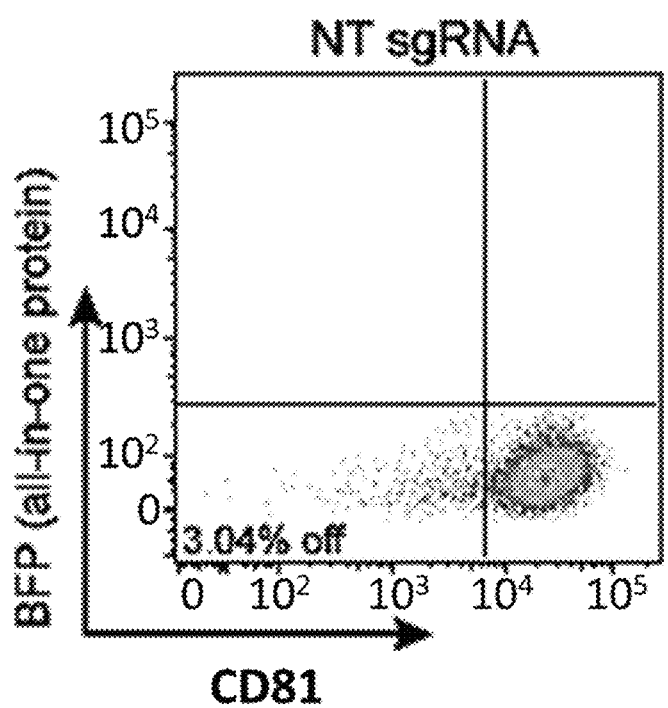
Figure 13D:
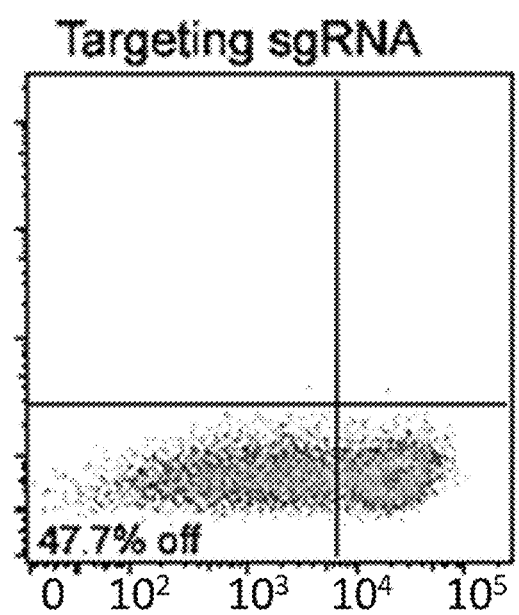
Figure 13E:
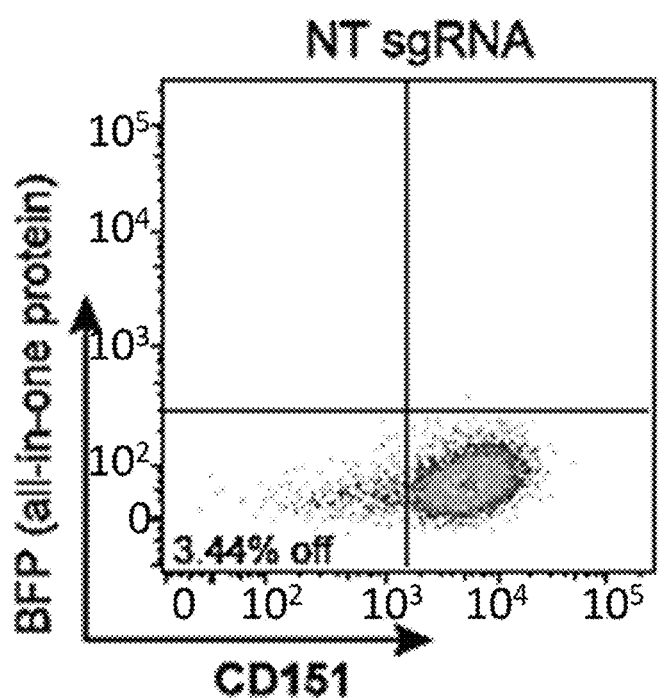
Figure 13F:
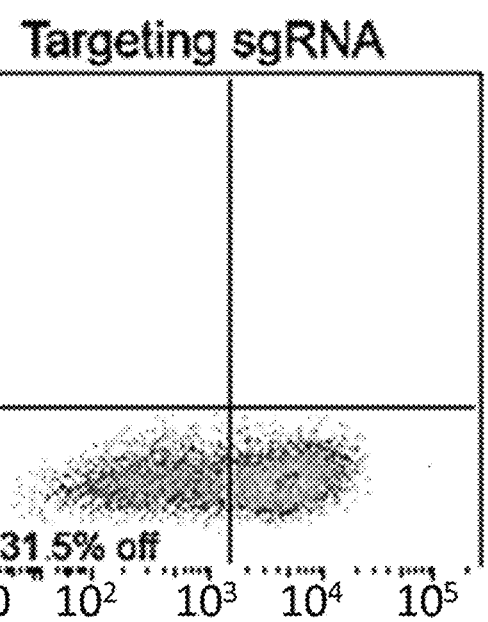
Figure 13G:
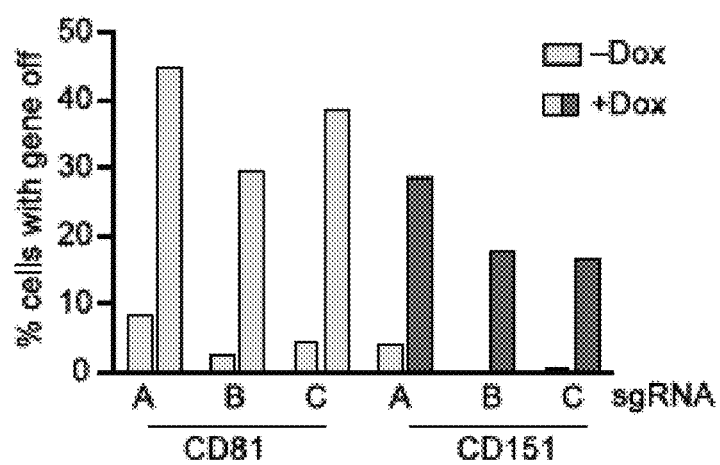

FIG. 13A provides flow cytometry plots showing induced expression of the all-in-one protein by addition of doxycycline in K562 cells that stably encode the all-in-one protein under a doxycycline-inducible promoter. Protein expression was followed for four days after doxycycline induction. The dotted lines in the panels in FIG. 13A represent the baseline median BFP fluorescence without doxycycline administration. Western blots of cells were performed to detect expression of the all-in-one protein before and after doxycycline treatment (FIG. 13B). The presence of the all-in-one protein is not detectable by 96 hours post-induction. Flow cytometry plots of CD81 and CD151 knockdown 14 days post-doxycycline treatment of K562 cells are shown in FIGS. 13C-13F. The percent of cells with the targeted gene knocked down is shown. There is no detectable expression of the all-in-one protein, as no cells are present in the BFP+ quadrants. Quantification of CD81 and CD151 knockdown 14 days post-doxycycline treatment or without doxycycline treatment is shown in FIG. 13G.

REFERENCES

Ecco et al, Development 144, 2017. Lambert et al, Cell 172, 2018. Siddique et al., J. Mol. Biol., 425, 2013. Stepper et al, Nucleic Acids Res., 45, 2017. Shmakov et al., Nat. Rev. Microbiol. 15, 2017. Cebrian-Serrano et al, Mamm. Genome 7-8, 2017. Pulecio et al., Cell Stem Cell 21, 2017.

Informal Sequence Listing

SEQ ID NO:1 (p76 (all-in-one protein sequence, version 1): KRAB (bold; from Gilbert et al., Cell, 2013, 2014), Linkers (underlined), dCas9 (italics), HA tag (lowercase), SV40 NLS (lowercase italics), Dnmt3A (bold italics; residues 612-912; from Siddique et al., JMB, 2013; Stepper et al., NAR, 2016), 27 amino acid linker (italics underlined; from Siddique et al., JMB, 2013; Stepper et al., NAR, 2016), Dnmt3L (bold underlined; from Siddique et al., JMB, 2013; Stepper et al., NAR, 2016), P2A peptide cleavage sequence (lowercase bold), BFP (lowercase underlined

DAKSLTAWSRTLVTFKDVFVDFTREEWKLLDTAQQIVYRNVMLENYKNLV

SLGYQLTKPDVILRLEKGEEP<u>GGSGGGS</u>MDKKYSIGLAIGTNSVGWAVIT

*DEYKVPSKKEKVLGNTDRHSIKKNLIGALLFDSGETAEATRLKRTARRRY*

*TRRKNRICYLQEIFSNEMAKVDDSFFHRLEESFLVEEDKKHERHPIFGNI*

*VDEVAYHEKYPTIYHLRKKLVDSTDKADLRLIYLALAHMIKFRGHFLIEG*

*DLNPDNSDVDKLFIQLVQTYNQLFEENPINASGVDAKAILSARLSKSRRL*

*ENLIAQLPGEKKNGLFGNLIALSLGLTPNFKSNFDLAEDAKLQLSKDTYD*

*DDLDNLLAQIGDQYADLFLAAKNLSDAILLSDILRVNTEITKAPLSASMI*

*KRYDEHHQDLTLLKALVRQQLPEKYKEIFFDQSKNGYAGYIDGGASQEEF*

*YKFIKPILEMIDGTEELLVKLNREDLLRKQRTFDNGSIPHQIHLGELHAI*

*LRRQEDFYPFLKDNREKIEKILTFRIPYYVGPLARGNSRFAWMTRKSEET*

*ITPWNFEEVVDKGASAQSFIERMTNFDKNLPNEKVLPKHSLLYEYFTVYN*

*ELTKVKYVTEGMRKPAFLSGEQKKAIVDLLFKTNRKVTVKQLKEDYFKKI*

*ECFDSVEISGVEDRFNASLGTYHDLLKIIKDKDFLDNEENEDILEDIVLT*

*LTLFEDREMIEERLKTYAHLFDDKVMKQLKRRRYTGWGRLSRKLINGIRD*

*KQSGKTILDFLKSDGFANRNFMQLIHDDSLTFKEDIQKAQVSGQGDSLHE*

*HIANLAGSPAIKKGILQTVKVVDELVKVMGRHKPENIVIEMARENQTTQK*

*GQKNSREMKRIEEGIKELGSQILKEHPVENTQLQNEKLYLYYLQNGRDMY*

*VDQELDINRLSDYDVDAIVPQSFLKDDSIDNKVLTRSDKNRGKSDNVPSE*

*EVVKKMKNYWRQLLNAKLITQRKEDNLTKAERGGLSELDKAGFIKRQLVE*

*TRQITKHVAQILDSRMNTKYDENDKLIREVKVITLKSKLVSDFRKDFQFY*

*KVREINNYHHAHDAYLNAVVGTALIKKYPKLESEFVYGDYKVYDVRKMIA*

*KSEQEIGKATAKYFFYSNIMNFFKTEITLANGEIRKRPLIEINGETGEIV*

*WDKGRDFATVRKVLSMPQVNIVKKTEVQTGGFSKESILPKRNSDKLIARK*

*KDWDPKKYGGFDSPTVAYSVLVVAKVEKGKSKKLKSVKELLGITIMERSS*

*FEKNPIDFLEAKGYKEVKKDLIIKLPKYSLFELENGRKRMLASAGELQKG*

*NELALPSKYVNFLYLASHYEKLKGSPEDNEQKQLFVEQHKHYLDEIIEQI*

*SEFSKRVILADANLDKVLSAYNKHRDKPIREQAENIIHLFTLTNLGAPAA*

*FKYFDTTIDRKRYTSTKEVLDATLIHQSITGLYETRIDLSQLGGD*<u>SRAD</u>y pydvpdya<u>SGS</u>pkkkrkv<u>EASGSGRASPGIPGSTR</u>*NHDQEFDPPKV*

*YPPVPAEKRKPIRVLSLFDGIATGLLVLKDLGIQVDRYIASEVCED*

*SITVGMVRHQGKIMYVGDVRSVTQKHIQEWGPFDLVIG*

*GSPCNDLSIVNPARKGLYEGTGRLFFEFYRLLHDARPKE*

*GDDRPFFWLFENVVAMGVSDKRDISRFLESNPVMIDAKEVSAA*

*HRARYFWGNLPGMNRPLASTVNDKLELQECLEHGRIAKF*

*SKVRTITTRSNSIKQGKDQHFPVFMNEKEDILWCTEME*

*RVFGFPVHYTDVSNMSRLARQRLLGRSWSVPVIRHLFAPLKEYFACV*

<u>SSGNSNANSRGPSFSSGLVPLSLRGSH</u>MGPMEIYKTVSAWKRQPVRVLSL

FRNIDKVLKSLGFLESGSGSGGGTLKYVEDVTNVVRRDVEKWGPFDLVYG

STQPLGSSCDRCPGWYMFQFHRILQYALPRQESQRPFFWIFMDNLLLTED

DQETTTRFLQTEAVTLQDVRGRDYQNAMRVWSNIPGLKSKHAPLTPKEEE

YLQAQVRSRSKLDAPKVDLLVKNCLLPLREYFKYFSQNSLPL<u>SRAD</u>pkkk rkv<u>GSG</u>atnfsllkqagdveenpgp<u>selikenmhmklymeqtvdnhhfkc</u>

<u>tsegegkpyegtqtmrikvveggplpfafdilatsflygsktfinhtqgi</u>

<u>pdffkqsfpeqftwervttyedqqvltatqdtslqdqcliynvkirqvnf</u>

<u>tsnqpvmqkktlqweaftetlypadqqleqrndmalklvqqshlianikt</u>

<u>tyrskkpaknlkmpqvyyvdyrlerikeannetyveqhevavarycdlps</u>

<u>klqhkln</u>*

SEQ ID NO:2 (p90 (KRAB-dCas9-XTEN16-Dnmt3A-Dnmt3L-P2A-BFP): KRAB (bold, from Gilbert et al., Cell, 2013, 2014); Linkers (underlined), dCas9 (italics); HA tag (lowercase), SV40 NLS (lowercase italics), XTEN16 (uppercase, 16 amino acid sequence), Dnmt3A (bold italics; from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNLV

SLGYQLTKPDVILRLEKGEEP<u>GGSGGGS</u>MDKKYSIGLAIGTNSVGWAVIT

*DEYKVPSKKFKVLGNTDRHSIKKNLIGALLFDSGETAEATRLKRTARRRY*

*TRRKNRICYLQEIFSNEMAKVDDSFFHRLEESFLVEEDKKHERHPIFGNI*

*VDEVAYHEKYPTIYHLRKKLVDSTDKADLRLIYLALAHMIKFRGHFLIEG*

*DLNPDNSDVDKLFIQLVQTYNQLFEENPINASGVDAKAILSARLSKSRRL*

*ENLIAQLPGEKKNGLFGNLIALSLGLTPNFKSNFDLAEDAKLQLSKDTYD*

*DDLDNLLAQIGDQYADLFLAAKNLSDAILLSDILRVNTEITKAPLSASMI*

*KRYDEHHQDLTLLKALVRQQLPEKYKEIFFDQSKNGYAGYIDGGASQEEF*

*YKFIKPILEKMDGTEELLVKLNREDLLRKQRTFDNGSIPHQIHLGELHAI*

*LRRQEDFYPFLKDNREKIEKILTFRIPYYVGPLARGNSRFAWMTRKSEET*

*ITPWNFEEVVDKGASAQSFIERMTNFDKNLPNEKVLPKHSLLYEYFTVYN*

*ELTKVKYVTEGMRKPAFLSGEQKKAIVDLLFKTNRKVTVKQLKEDYFKKI*

*ECFDSVEISGVEDRFNASLGTYHDLLKIIKDKDFLDNEENEDILEDIVLT*

*LTLFEDREMIEERLKTYAHLFDDKVMKQLKRRRYTGWGRLSRKLINGIRD*

*KQSGKTILDFLKSDGFANRNFMQLIHDDSLTFKEDIQKAQVSGQGDSLHE*

*HIANLAGSPAIKKGILQTVKVVDELVKVMGRHKPENIVIEMARENQTTQK*

*GQKNSRERMKRIEEGIKELGSQILKEHPVENTQLQNEKLYLYYLQNGRDMY*

*VDQELDINRLSDYDVDAIVPQSFLKDDSIDNKVLTRSDKNRGKSDNVPSE*

*EVVKKMKNYWRQLLNAKLITQRKFDNLTKAERGGLSELDKAGFIKRQLVE*

*TRQITKHVAQILDSRMNTKYDENDKLIREVKVITLKSKLVSDFRKDFQFY*

*KVREINNYHHAHDAYLNAVVGTALIKKYPKLESEFVYGDYKVYDVRKMIA*

*KSEQEIGKATAKYFFYSNIMNFFKTEITLANGEIRKRPLIETNGETGEIV*

*WDKGRDFATVRKVLSMPQVNIVKKTEVQTGGFSKESILPKRNSDKLIARK*

*KDWDPKKYGGFDSPTVAYSVLVVAKVEKGKSKKLKSVKELLGITIMERSS*

-continued

FEKNPIDFLEAKGYKEVKKDLIIKLPKYSLFELENGRKRMLASAGELQKG

NELALPSKYVNFLYLASHYEKLKGSPEDNEQKQLFVEQHKHYLDEIIEQI

SEFSKRVILADANLDKVLSAYNKHRDKPIREQAENIIHLFTLTNLGAPAA

FKYFDTTIDRKRYTSTKEVLDATLIHQSITGLYETRIDLSQLGGDSRADy pydvpdyaSGSpkkkrkvSPGSGSETPGTSESATPESNHDQEFDPP

KVYPPVPAEKRKPIRVLSLFDGIATGLLVLKD

LGIQVDRYIASEVCEDSITVGMVRHQGKIM

YVGDVRSVTQKHIQEWGPFDLVIGGSPCNDL

SIVNPARKGLYEGTGRLFFEFYRLLHDARP

KEGDDRPFFWLFENVVAMGVSDKRDISRFL

ESNPVMIDAKEVSAAHRARYFWGNLPGMN

RPLASTVNDKLELQECLEHGRIAKFSKVRTI

TTRSNSIKQGKDQHFPVFMNEKEDILWCTE

MERVFGFPVHYTDVSNMSRLARQR

LLGRSWSVPVIRHLFAPLKEYFACV

SSGNSNANSRGPSFSSGLVPLSLRGSHMGPMEIYKTVSAWKRQPVRVLSL

FRNIDKVLKSLGFLESGSGSGGGTLKYVEDVTNVVRRDVEKWGPFDLVYG

STQPLGSSCDRCPGWYMFQFHRILQYALPRQESQRPFFWIFMDNLLLTED

DQETTTRFLQTEAVTLQDVRGRDYQNAMRVWSNIPGLKSKHAPLTPKEEE

YLQAQVRSRSKLDAPKVDLLVKNCLLPLREYFKYFSQNSLPLSRADpkkk rkvGSGatnfsllkqagdveenpgpselikenmhmklymeqtvdnhhfkc tseqeqkpyeqtqtmrikvveqqplpfafdilatsflyqsktfinhtqqi pdffkqsfpeqftwervttyedqqvltatqdtslqdqcliynvkirqvnf tsnqpvmqkktlqweaftetlypadqqleqrndmalklvqqshlianikt tyrskkpaknlkmpqvyyvdyrlerikeannetyveqhevavarycdlps klqhkln*

SEQ ID NO:3 (p91 (KRAB-dCas9-Dnmt3A-Dnmt3L-P2A-P2A-BFP): KRAB (bold, from Gilbert et al., Cell, 2013, 2014), Linkers (underlined), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP(lowercase underlined))

DAKSLTAWSRTLVTFKDVFVDFTREEWKLLDTAQQIVYRNVMLENYKNLV

SLGYQLTKPDVILRLEKGEEPGGSGGGSMDKKYSIGLAIGTNSVGWAVIT

DEYKVPSKKFKVLGNTDRHSIKKNLIGALLFDSGETAEATRLKRTARRRY

TRRKNRICYLQEIFSNEMAKVDDSFFHRLEESELVEEDKKHERHPIFGNI

VDEVAYHEKYPTIYHLRKKLVDSTDKADLRLIYLALAHMIKFRGHFLIEG

DLNPDNSDVDKLFIQLVQTYNQLFEENPINASGVDAKAILSARLSKSRRL

ENLIAQLPGEKKNGLFGNLIALSLGLTPNFKSNFDLAEDAKLQLSKDTYD

-continued

DDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEF

YKFIKPILEKMDGTEELLVKLNREDLLRKQRTEDNGSIPHQIHLGELHAI

LRRQEDFYPFLKDNREKIEKILTFRIPYYVGPLARGNSRFAWMTRKSEET

ITPWNFEEVVDKGASAQSFIERMTNFDKNLPNEKVLPKHSLLYEYFTVYN

ELTKVKYVTEGMRKPAFLSGEQKKAIVDLLFKTNRKVTVKQLKEDYFKKI

ECFDSVEISGVEDRFNASLGTYHDLLKIIKDKDFLDNEENEDILEDIVLT

LTLFEDREMIEERLKTYAHLFDDKVMKQLKRRRYTGWGRLSRKLINGIRD

KQSGKTILDFLKSDGFANRNFMQLIHDDSLTFKEDIQKAQVSGQGDSLHE

HIANLAGSPAIKKGILQTVKVVDELVKVMGRHKPENIVIEMARENQTTQK

GQKNSRERMKRIEEGIKELGSQILKEHPVENTQLQNEKLYLYYLQNGRDM

YVDQELDINRLSDYDVDAIVPQSFLKDDSIDNKVLTRSDKNRGKSDNVPS

EEVVKKMKNYWRQLLNAKLITQRKFDNLTKAERGGLSELDKAGFIKRQLV

ETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMI

AKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERS

SFEKNPIDFLEAKGYKEVKKDLIIKLPKYSLFELENGRKRMLASAGELQK

GNELALPSKYVNFLYLASHYEKLKGSPEDNEQKQLFVEQHKHYLDEIIEQ

ISEFSKRVILADANLDKVLSAYNKHRDKPIREQAENIIHLFTLTNLGAPA

AFKYFDTTIDRKRYTSTKEVLDATLIHQSITGLYETRIDLSQLGGDSRAD ypydvpdyaSGSpkkkrkvEASGSGRASPGIPGSTRNHDQEFDPPKV

YPPVPAEKRKPIRVLSLFDGIATGLLVLKDLGIQ

VDRYIASEVCEDSITVGMVRHQGKIMYV

GDVRSVTQKHIQEWGPFDLVIGGSPCNDLSIVN

PARKGLYEGTGRLFFEFYRLLHDARPKE

GDDRPFFWLFENVVAMGVSDKRDISRFLESNP

VMIDAKEVSAAHRARYFWGNLPGMNRP

LASTVNDKLELQECLEHGRIAKFSKVRTITTRS

NSIKQGKDQHFPVFMNEKEDILWCTEME

RVFGFPVHYTDVSNMSRLARQRLLGRSWSVPVIRHLFAPLKEYFACV

SSGNSNANSRGPSFSSGLVPLSLRGSHMGPMEIYKTVSAWKRQPVRVLSL

FRNIDKVLKSLGFLESGSGSGGGTLKYVEDVTNVVRRDVEKWGPFDLVYG

STQPLGSSCDRCPGWYMFQFHRILQYALPRQESQRPFFWIFMDNLLLTED

DQETTTRFLQTEAVTLQDVRGRDYQNAMRVWSNIPGLKSKHAPLTPKEEE

YLQAQVRSRSKLDAPKVDLLVKNCLLPLREYFKYFSQNSLPLSRADpkkk rkvGSGatnfsllkqagdveenpgpGSGatnfsllkqagdveenpgpsel ikenmhmklymeqtvdnhhfkctseqeqkpyeqtqtmrikvveqqplpfa fdilatsflyqsktfinhtqqipdffkqsfpeqftwervttyedqqvlta tqdtslqdqcliynvkirqvnftsnqpvmqkktlqweaftetlypadqql egrndmalklvggshlianikttyrskkpaknlkmpgvyyvdyrlerike
annetyveqhevavarycdlpsklqhkln*

SEQ ID NO: 4 (p92 (KRAB-dCas9-XTEN16-Dnmt3A-Dnmt3L-P2A-P2A-BFP): KRAB (bold, from Gilbert et al., Cell, 2013, 2014), Linkers (underlined), dCas9 (italics), HA tag (lowercase), SV40 NLS (lowercase italics), XTEN16 (16 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL
VSLGYQLTKPDVILRLEKGEEPGGSGGGSMDKKYSIGLAIGTNSVGWAV
ITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITK
APLSASMIKRYDEHHQDLTLLKALVRQQLPEKYKEIFFDQSKNGYAGYI
DGGASQEEFYKFIKPILEKMDGTEELLVKLNREDLLRKQRTFDNGSIPH
QIHLGELHAILRRQEDFYPFLKDNREKIEKILTFRIPYYVGPLARGNSR
FAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKV
TVKQLKEDYFKKIECFDSVEISGVEDRFNASLGTYHDLLKIIKDKDFLD
NEENEDILEDIVLTLTLFEDREMIEERLKTYAHLFDDKVMKQLKRRRYT
GWGRLSRKLINGIRDKQSGKTILDFLKSDGFANRNFMQLIHDDSLTFKE
DIQKAQVSGQGDSLHEHIANLAGSPAIKKGILQTVKVVDELVKVMGRHK
PENIVIEMARENQTTQKGQKNSRERMKRIEEGIKELGSQILKEHPVENT
QLQNEKLYLYYLQNGRDMYVDQELDINRLSDYDVDAIVPQSFLKDDSID
NKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIR
EVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKT
EVQTGGFSKESILPKRNSDKLIARKKDWDPKKYGGFDSPTVAYSVLVVA
KVEKGKSKKLKSVKELLGITIMERSSFEKNPIDFLEAKGYKEVKKDLII
KLPKYSLFELENGRKRMLASAGELQKGNELALPSKYVNFLYLASHYEKL
KGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVL
DATLIHQSITGLYETRIDLSQLGGDSRADypydvpdyaSGSpkkkrkvS PGSGSETPGTSESATPESNHDQEFDPP
KVYPPVPAEKRKPIRVLSLFDGIATGLLVLKDL
GIQVDRYIASEVCEDSITVGMVRHQGKIM
YVGDVRSVTQKHIQEWGPFDLVIGGSPCNDLS
IVNPARKGLYEGTGRLFFEFYRLLHDARP
KEGDDRPFFWLFENVVAMGVSDKRDISRFLE
SNPVMIDAKEVSAAHRARYFWGNLPGMN
RPLASTVNDKLELQECLEHGRIAKFSKVRTITT
RSNSIKQGKDQHFPVFMNEKEDILWCTE
MERVFGFPVHYTDVSNMSRLARQRLLGRSWSVPVIRHLFAPLKEYFACV
SSGNSNANSRGPSFSSGLVPLSLRGSHMGPMEIYKTVSAWKRQPVRVLS
LFRNIDKVLKSLGFLESGSGSGGGTLKYVEDVTNVVRRDVEKWGPFDLV
YGSTQPLGSSCDRCPGWYMFQFHRILQYALPRQESQRPFFWIFMDNLLL
TEDDQETTTRFLQTEAVTLQDVRGRDYQNAMRVWSNIPGLKSKHAPLTP
KEEEYLQAQVRSRSKLDAPKVDLLVKNCLLPLREYFKYFSQNSLPLSRA
DpkkkrkvGSGatnfsllkqagdveenpgpGSGatnfsllkqagdveen
pgpselikenmhmklymeqtvdnhhfkctseqeqkpyeqtqtmrikvve
qqplpfafdilatsflyqsktfinhtqqipdffkqsfpeqftwervtty
edqqvltatqdtslqdqcliynvkirqvnftsnqpvmqkktlqweafte
tlypadqqleqrndmalklvggshlianikttyrskkpaknlkmpgvyy
vdyrlerikeannetyveqhevavarycdlpsklqhkln*

SEQ ID NO:5 (p93 (KRAB-dCas9-XTEN80-Dnmt3A-Dnmt3L-P2A-BFP): KRAB (bold, from Gilbert et al., Cell, 2013, 2014), Linkers (underlined), dCas9 (italics), HA tag (lowercase), SV40 NLS (lowercase italics), XTEN80 (80 amino acid sequence), Dnmt3A (bold italics, from Siddique et al., JMB, 2013; Stepper et al., NAR, 2016), 27 amino acid linker (italics underlined; from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL
VSLGYQLTKPDVILRLEKGEEPGGSGGGSMDKKYSIGLAIGTNSVGWAV
ITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITK
APLSASMIKRYDEHHQDLTLLKALVRQQLPEKYKEIFFDQSKNGYAGYI
DGGASQEEFYKFIKPILEKMDGTEELLVKLNREDLLRKQRTFDNGSIPH
QIHLGELHAILRRQEDFYPFLKDNREKIEKILTFRIPYYVGPLARGNSR
FAWMTRKSEETITPWNFEEVVDKGASAQSFIERMTNFDKNLPNEKVLPK

-continued

HSLLYEYFTVYNELTKVKYVTEGMRKPAFLSGEQKKAIVDLLFKTNRKV
TVKQLKEDYFKKIECFDSVEISGVEDRFNASLGTYHDLLKIIKDKDFLD
NEENEDILEDIVLTLTLFEDREMIEERLKTYAHLFDDKVMKQLKRRRYT
GWGRLSRKLINGIRDKQSGKTILDFLKSDGFANRNFMQLIHDDSLTFKE
DIQKAQVSGQGDSLHEHIANLAGSPAIKKGILQTVKVVDELVKVMGRHK
PENIVIEMARENQTTQKGQKNSRERMKRIEEGIKELGSQILKEHPVENT
QLQNEKLYLYYLQNGRDMYVDQELDINRLSDYDVDAIVPQSFLKDDSID
NKVLTRSDKNRGKSDNVPSEEVVKKMKNYWRQLLNAKLITQRKFDNLTK
AERGGLSELDKAGFIKRQLVETRQITKHVAQILDSRNINTKYDENDKLI
REVKVITLKSKLVSDFRKDFQFYKVREINNYHHAHDAYLNAVVGTALIK
KYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKK
TEVQTGGFSKESILPKRNSDKLIARKKDWDPKKYGGFDSPTVAYSVLVV
AKVEKGKSKKLKSVKELLGITIMERSSFEKNPIDFLEAKGYKEVKKDLI
IKLPKYSLFELENGRKRMLASAGELQKGNELALPSKYVNFLYLASHYEK
LKGSPEDNEQKQLFVEQHKHYLDEIIEQISEFSKRVILADANLDKVLSA
YNKHRDKPIREQAENIIHLFTLTNLGAPAAFKYFDTTIDRKRYTSTKEV
LDATLIHQSITGLYETRIDLSQLGGD<u>SRAD</u>ypydvpdya<u>SGS</u>pkkkrkv
<u>SPGGGPSSGAPPPSGGSPAGSPTSTEEGTSESATPESGPGTSTEPSEGS
APGSPAGSPTSTEEGTSTEPSEGSAPGTSTEPSE</u>*NHDQEFDPPK*
*VYPPVPAEKRKPIRVLSLFDGIATGLLVLKDLGI*
*QVDRYIASEVCEDSITVGMVRHQGKIMY*
*VGDVRSVTQKHIQEWGPFDLVIGGSPCNDLSIV*
*NPARKGLYEGTGRLFFEFYRLLHDARPK*
*EGDDRPFFWLFENVVAMGVSDKRDISRFLESN*
*PVMIDAKEVSAAHRARYFWGNLPGMNR*
*PLASTVNDKLELQECLEHGRIAKFSKVRTITTRS*
*NSIKQGKDQHFPVFMNEKEDILWCTEM*
*ERVFGFPVHYTDVSNMSRLARQRLL*
*GRSWSVPVIRHLFAPLKEYFACV*<u>SSGNSNANSRGPSFSSGLVPLSLRGSH</u>
MGPMEIYKTVSAWKRQPVRVLSLFRNIDKVLKSLGFLESGSGSGGGTLKY
VEDVTNVVRRDVEKWGPFDLVYGSTQPLGSSCDRCPGWYMFQFHRILQYA
LPRQESQRPFFWIFMDNLLLTEDDQETTTRFLQTEAVTLQDVRGRDYQNA
MRVWSNIPGLKSKHAPLTPKEEEYLQAQVRSRSKLDAPKVDLLVKNCLLP
LREYFKYFSQNSLPL<u>SRAD</u>pkkkrkv<u>GSG</u>atnfsllkqagdveenpgpse
likenmhmklymegtvdnhhfkctsegegkpyegtqtmrikvveggplpf
afdilatsflygsktfinhtqgipdffkqsfpeqftwervttyedgqylt
atqdtslqdgcliynvkirqvnftsnqpvmqkktlqweaftetlypadgq
legrndmalklvggshlianikttyrskkpaknlkmpgvyyvdyrlerik
eannetyveqhevavarycdlpsklqhkln*

SEQ ID NO:6 (p94 (KRAB-dCas9-XTEN80-Dnmt3A-Dnmt3L-P2A-P2A-BFP): KRAB (bold, from Gilbert et al., Cell, 2013, 2014), Linkers (underlined), dCas9 (italics), HA tag (lowercase), SV40 NLS (lowercase italics), XTEN80 (80 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL
VSLGYQLTKPDVILRLEKGEEP<u>GGSGGGS</u>MDKKYSIGLAIGTNSVGWAV
ITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITK
APLSASMIKRYDEHHQDLTLLKALVRQQLPEKYKEIFFDQSKNGYAGYI
DGGASQEEFYKFIKPILEKMDGTEELLVKLNREDLLRKQRTFDNGSIPH
QIHLGELHAILRRQEDFYPFLKDNREKIEKILTFRIPYYVGPLARGNSR
FAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKV
TVKQLKEDYFKKIECFDSVEISGVEDRFNASLGTYHDLLKIIKDKDFLD
NEENEDILEDIVLTLTLFEDREMIEERLKTYAHLFDDKVMKQLKRRRYT
GWGRLSRKLINGIRDKQSGKTILDFLKSDGFANRNFMQLIHDDSLTFKE
DIQKAQVSGQGDSLHEHIANLAGSPAIKKGILQTVKVVDELVKVMGRHK
PENIVIEMARENQTTQKGQKNSRERMKRIEEGIKELGSQILKEHPVENT
QLQNEKLYLYYLQNGRDMYVDQELDINRLSDYDVDAIVPQSFLKDDSID
NKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIR
EVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKT
EVQTGGFSKESILPKRNSDKLIARKKDWDPKKYGGFDSPTVAYSVLVVA
KVEKGKSKKLKSVKELLGITIMERSSFEKNPIDFLEAKGYKEVKKDLII
KLPKYSLFELENGRKRMLASAGELQKGNELALPSKYVNFLYLASHYEKL
KGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVL
DATLIHQSITGLYETRIDLSQLGGD<u>SRAD</u>ypydvpdya<u>SGS</u>pkkkrkv<u>S
PGGGPSSGAPPPSGGSPAGSPTSTEEGTSESATPESGPGTSTEPSEGSA
PGSPAGSPTSTEEGTSTEPSEGSAPGTSTEPSE</u>*NHDQEFDPPK*
*VYPPVPAEKRKPIRVLSLFDGIATGLLVLKDLG*

IQVDRYIASEVCEDSITVGMVRHQGKIMY

VGDVRSVTQKHIQEWGPFDLVIGGSPCNDLSI

VNPARKGLYEGTGRLFFEFYRLLHDARPK

EGDDRPFFWLFENVVAMGVSDKRDISRFLES

NPVMIDAKEVSAAHRARYFWGNLPGMNR

PLASTVNDKLELQECLEHGRIAKFSKVRTITT

RSNSIKQGKDQHFPVFMNEKEDILWCTEM

ERVFGFPVHYTDVSNMSRLARQRLLGR

SWSVPVIRHLFAPLKEYFACVSSGNSNANSRGPSFSSGLVPLSLRGSH

MGPMEIYKTVSAWKRQPVRVLSLFRNIDKVLKSLGFLESGSGSGGGTLK

YVEDVTNVVRRDVEKWGPFDLVYGSTQPLGSSCDRCPGWYMFQFHRILQ

YALPRQESQRPFFWIFMDNLLLTEDDQETTTRFLQTEAVTLQDVRGRDY

QNAMRVWSNIPGLKSKHAPLTPKEEEYLQAQVRSRSKLDAPKVDLLVKN

CLLPLREYFKYFSQNSLPLSRADpkkkrkvGSGatnfsllkqagdveen pgpGSGatnfsllkqagdveenpgpselikenmhmklymegtvdnhhfk ctseqeqkpyeqtqtmrikvveqqplpfafdilatsflyqsktfinhtq qipdffkqsfpeqftwervttyedqqvltatqdtslqdqcliynvkirq vnftsnqpvmqkktlqweaftetlypadqqleqrndmalklvqqshlia nikttyrskkpaknlkmpqvyyvdyrlerikeannetyveqhevavary cdlpsklqhkln*

SEQ ID NO:7 (p95 (KRAB-XTEN16-dCas9-Dnmt3A-Dnmt3L-P2A-BFP): KRAB (bold, from Gilbert et al., Cell, 2013, 2014), Linkers (underlined), XTEN16 (16 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL

VSLGYQLTKPDVILRLEKGEEPSGSETPGTSESATPESMDKKYSIGLAI

GTNSVGWAVITDEYKVPSKKFKVLGNTDRHSIKKNLIGALLFDSGETAE

ATRLKRTARRRYTRRKNRICYLQEIFSNEMAKVDDSFFHRLEESFLVEE

DKKHERHPIFGNIVDEVAYHEKYPTIYHLRKKLVDSTDKADLRLIYLAL

AHMIKFRGHFLIEGDLNPDNSDVDKLFIQLVQTYNQLFEENPINASGVD

AKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDI

LRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQR

TFDNGSIPHQIHLGELHAILRRQEDFYPFLKDNREKIEKILTFRIPYYV

GPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLK

IIKDKDFLDNEENEDILEDIVLTLTLFEDREMIEERLKTYAHLFDDKVM

KQLKRRRYTGWGRLSRKLINGIRDKQSGKTILDFLKSDGFANRNFMQLI

HDDSLTFKEDIQKAQVSGQGDSLHEHIANLAGSPAIKKGILQTVKVVDE

LVKVMGRHKPENIVIEMARENQTTQKGQKNSRERMKRIEEGIKELGSQI

LKEHPVENTQLQNEKLYLYYLQNGRDMYVDQELDINRLSDYDVDAIVPQ

SFLKDDSIDNKVLTRSDKNRGKSDNVPSEEVVKKWKNYWRQLLNAKLIT

QRKFDNLTKAERGGLSELDKAGFIKRQLVETRQITKHVAQILDSRMNTK

YDENDKLIREVKVITLKSKLVSDFRKDFQFYKVREINNYHHAHDAYLNA

VVGTALIKKYPKLESEFVYGDYKVYDVRKMIAKSEQEIGKATAKYFFYS

NIMNFFKTEITLANGEIRKRPLIETNGETGEIVWDKGRDFATVRKVLSM

PQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGY

KEVKKDLIIKLPKYSLFELENGRKRMLASAGELQKGNELALPSKYVNFL

YLASHYEKLKGSPEDNEQKQLFVEQHKHYLDEIIEQISEFSKRVILADA

NLDKVLSAYNKHRDKPIREQAENIIHLFTLTNLGAPAAFKYFDTTIDRK

RYTSTKEVLDATLIHQSITGLYETRIDLSQLGGDSRADypydvpdyaSG

SpkkkrkvEASGSGRASPGIPGSTRNH

DQEFDPPKVYPPVPAEKRKPIRVLSLFDGIATGL

LVLKDLGIQVDRYIASEVCEDSITVGMV

RHQGKIMYVGDVRSVTQKHIQEWGPFDLVIGG

SPCNDLSIVNPARKGLYEGTGRLFFEFYR

LLHDARPKEGDDRPFFWLFENVVAMGVSDKR

DISRFLESNPVMIDAKEVSAAHRARYFW

GNLPGMNRPLASTVNDKLELQECLEHGRIAKF

SKVRTITTRSNSIKQGKDQHFPVFMNEKE

DILWCTEMERVFGFPVHYTDVSNMSRLA

RQRLLGRSWSVPVIRHLFAPLKEYFACVSSGNSNANSRGPSFSSGLVPL

SLRGSHMGPMEIYKTVSAWKRQPVRVLSLFRNIDKVLKSLGFLESGSGS

GGGTLKYVEDVTNVVRRDVEKWGPFDLVYGSTQPLGSSCDRCPGWYMFQ

FHRILQYALPRQESQRPFFWIFMDNLLLTEDDQETTTRFLQTEAVTLQD

VRGRDYQNAMRVWSNIPGLKSKHAPLTPKEEEYLQAQVRSRSKLDAPKV

DLLVKNCLLPLREYFKYFSQNSLPLSRADpkkkrkvGSGatnfsllkqa gdveenpgpselikenmhmklymegtvdnhhfkctseqeqkpyeqtqtm rikvveqqplpfafdilatsflyqsktfinhtqqipdffkqsfpeqftw ervttyedqqvltatqdtslqdqcliynvkirqvnftsnqpvmqkktlq weaftetlypadqqleqrndmalklvqgshlianikttyrskkpaknlk mpqvyyvdyrlerikeannetyveqhevavarycdlpsklqhkln*

SEQ ID NO:8 (p96 (KRAB-XTEN16-dCas9-Dnmt3A-Dnmt3L-P2A-P2A-BFP): KRAB (bold, from Gilbert et al., Cell, 2013, 2014), Linkers (underlined), XTEN16 (16 amino acid sequence), dCas9 (italics), HA tag (lowercase), SV40

NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold); BFP (lowercase underlined))

DAKSLTAWSRTLVTFKDVFVDFTREEWKLLDTAQQIVYRNVMLENYKNL

VSLGYQLTKPDVILRLEKGEEPSGSETPGTSESATPES*MDKKYSIGLAI*

*GTNSVGWAVITDEYKVPSKKFKVLGNTDRHSIKKNLIGALLFDSGETAE*

*ATRLKRTARRRYTRRKNRICYLQEIFSNEMAKVDDSFFHRLEESFLVEE*

*DKKHERHPIFGNIVDEVAYHEKYPTIYHLRKKLVDSTDKADLRLIYLAL*

*AHMIKFRGHFLIEGDLNPDNSDVDKLFIQLVQTYNQLFEENPINASGVD*

*AKAILSARLSKSRRLENLIAQLPGEKKNGLFGNLIALSLGLTPNFKSNF*

*DLAEDAKLQLSKDTYDDDLDNLLAQIGDQYADLFLAAKNLSDAILLSDI*

*LRVNTEITKAPLSASMIKRYDEHHQDLTLLKALVRQQLPEKYKEIFFDQ*

*SKNGYAGYIDGGASQEEFYKFIKPILEKMDGTEELLVKLNREDLLRKQR*

*TFDNGSIPHQIHLGELHAILRRQEDFYPFLKDNREKIEKILTFRIPYYV*

*GPLARGNSRFAWMTRKSEETITPWNFEEVVDKGASAQSFIERMTNFDKN*

*LPNEKVLPKHSLLYEYFTVYNELTKVKYVTEGMRKPAFLSGEQKKAIVD*

*LLFKTNRKVTVKQLKEDYFKKIECFDSVEISGVEDRFNASLGTYHDLLK*

*IIKDKDFLDNEENEDILEDIVLTLTLFEDREMIEERLKTYAHLFDDKVM*

*KQLKRRRYTGWGRLSRKLINGIRDKQSGKTILDFLKSDGFANRNFMQLI*

*HDDSLTFKEDIQKAQVSGQGDSLHEHIANLAGSPAIKKGILQTVKVVDE*

*LVKVMGRHKPENIVIEMARENQTTQKGQKNSRERMKRIEEGIKELGSQI*

*LKEHPVENTQLQNEKLYLYYLQNGRDMYVDQELDINRLSDYDVDAIVPQ*

*SFLKDDSIDNKVLTRSDKNRGKSDNVPSEEVVKKMKNYWRQLLNAKLIT*

*QRKFDNLTKAERGGLSELDKAGFIKRQLVETRQITKHVAQILDSRMNTK*

*YDENDKLIREVKVITLKSKLVSDFRKDFQFYKVREINNYHHAHDAYLNA*

*VVVGTALIKKYPKLESEFVYGDYKVYDVRKMIAKSEQEIGKATAKYFFYS*

*NIMNFFKTEITLANGEIRKRPLIETNGETGEIVWDKGRDFATVRKVLSM*

*PQVNIVKKTEVQTGGFSKESILPKRNSDKLIARKKDWDPKKYGGFDSPT*

*VAYSVLVVAKVEKGKSKKLKSVKELLGITIMERSSFEKNPIDFLEAKGY*

*KEVKKDLIIKLPKYSLFELENGRKRMLASAGELQKGNELALPSKYVNFL*

*YLASHYEKLKGSPEDNEQKQLFVEQHKHYLDEIIEQISEFSKRVILADA*

*NLDKVLSAYNKHRDKPIREQAENIIHLFTLTNLGAPAAFKYFDTTIDRK*

*RYTSTKEVLDATLIHQSITGLYETRIDLSQLGGD*<u>SRAD</u>pydvpdya<u>SG</u>

<u>Sp</u>*kkkrkv*<u>EASGSGRASPGIPGSTR</u>*NH*

*DQEFDPPKVYPPVPAEKRKPIRVLSLFDGIAT*

*GLLVLKDLGIQVDRYIASEVCEDSITVGMV*

*RHQGKIMYVGDVRSVTQKHIQEWGPFDLVIG*

*GSPCNDLSIVNPARKGLYEGTGRLFFEFYR*

*LLHDARPKEGDDRPFFWLFENVVAMGVSDK*

*RDISRFLESNPVMIDAKEVSAAHRARYFW*

*GNLPGMNRPLASTVNDKLELQECLEHGRIAK*

*FSKVRTITTRSNSIKQGKDQHFPVFMNEKE*

*DILWCTEMERVFGFPVHYTDVSNMSRL*

*ARQRLLGRSWSVPVIRHLFAPLKEYFACV*<u>SSGNSNANSRGPSFSSGLVP</u>

<u>LSLRGSH</u>MGPMEIYKTVSAWKRQPVRVLSLFRNIDKVLKSLGFLESGSG

SGGGTLKYVEDVTNVVRRDVEKWGPFDLVYGSTQPLGSSCDRCPGWYMF

QFHRILQYALPRQESQRPFFWIFMDNLLLTEDDQETTTRFLQTEAVTLQ

DVRGRDYQNAMRVWSNIPGLKSKHAPLTPKEEEYLQAQVRSRSKLDAPK

VDLLVKNCLLPLREYFKYFSQNSLPL<u>SRAD</u>*pkkkrkv*<u>GSG</u>atnfsllkq agdveenpgp<u>GSG</u>atnfsllkqagdveenpgp<u>selikenmhmklymeqt</u>

<u>vdnhhfkctsegegkpyegtqtmrikvveggplpfafdilatsflygsk</u>

<u>tfinhtqgipdffkqsfpeqftwervttyedqqvltatqdtslqdgcli</u>

<u>ynvkirgvnftsngpvmqkktlgweaftetlypadgglegrndmalklv</u>

<u>qgshlianikttyrskkpaknlkmpqvyyvdyrlerikeannetyveqh</u>

<u>evavarycdlpsklghkln</u>*

SEQ ID NO:9 (p97 (KRAB-XTEN80-dCas9-Dnmt3A-Dnmt3L-P2A-BFP): KRAB (bold, from Gilbert et al., Cell, 2013, 2014), Linkers (underlined), XTEN80 (80 amino acid sequence), dCas9 (italics); HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL

VSLGYQLTKPDVILRLEKGEEPGGPSSGAPPPSGGSPAGSPTSEEGTS

ESATPESGPGTSTEPSEGSAPGSPAGSPTSEEGTSTEPSEGSAPGTST

EPSE*MDKKYSIGLAIGTNSVGWAVITDEYKVPSKKFKVLGNTDRHSIKK*

*NLIGALLFDSGETAEATRLKRTARRRYTRRKNRICYLQEIFSNEMAKVD*

*DSFFHRLEESFLVEEDKKHERHPIFGNIVDEVAYHEKYPTIYHLRKKLV*

*DSTDKADLRLIYLALAHMIKFRGHFLIEGDLNPDNSDVDKLFIQLVQTY*

*NQLFEENPINASGVDAKAILSARLSKSRRLENLIAQLPGEKKNGLFGNL*

*IALSLGLTPNFKSNFDLAEDAKLQLSKDTYDDDLDNLLAQIGDQYADLF*

*LAAKNLSDAILLSDILRVNTEITKAPLSASMIKRYDEHHQDLTLLKALV*

*RQQLPEKYKEIFFDQSKNGYAGYIDGGASQEEFYKFIKPILEKMDGTEE*

*LLVKLNREDLLRKQRTFDNGSIPHQIHLGELHAILRRQEDFYPFLKDNR*

*EKIEKILTFRIPYYVGPLARGNSRFAWMTRKSEETITPWNFEEVVDKGA*

*SAQSFIERMTNFDKNLPNEKVLPKHSLLYEYFTVYNELTKVKYVTEGMR*

*KPAFLSGEQKKAIVDLLFKTNRKVTVKQLKEDYFKKIECFDSVEISGVE*

*DRFNASLGTYHDLLKIIKDKDFLDNEENEDILEDIVLTLTLFEDREMIE*

-continued

*ERLKTYAHLFDDKVMKQLKRRRYTGWGRLSRKLINGIRDKQSGKTILDF*

*LKSDGFANRNFMQLIHDDSLTFKEDIQKAQVSGQGDSLHEHIANLAGSP*

*AIKKGILQTVKVVDELVKVMGRHKPENIVIEMARENQTTQKGQKNSRER*

*MKRIEEGIKELGSQILKEHPVENTQLQNEKLYLYYLQNGRDMYVDQELD*

*INRLSDYDVDAIVPQSFLKDDSIDNKVLTRSDKNRGKSDNVPSEEVVKM*

*KNYWRQLLNAKLITQRKFDNLTKAERGGLSELDKAGFIKRQLVETRQIT*

*KHVAQILDSRMNTKYDENDKLIREVKVITLKSKLVSDFRKDFQFYKVRE*

*INNYHHAHDAYLNAVVGTALIKKYPKLESEFVYGDYKVYDVRKMIAKSE*

*QEIGKATAKYFFYSNIMNFFKTEITLANGEIRKRPLIETNGETGEIVWD*

*KGRDFATVRKVLSMPQVNIVKKTEVQTGGFSKESILPKRNSDKLIARKK*

*DWDPKKYGGFDSPTVAYSVLVVAKVEKGKSKKLKSVKELLGITIMERSS*

*FEKNPIDFLEAKGYKEVKKDLIIKLPKYSLFELENGRKRMLASAGELQK*

*GNELALPSKYVNFLYLASHYEKLKGSPEDNEQKQLFVEQHKHYLDEIIE*

*QISEFSKRVILADANLDKVLSAYNKHRDKPIREQAENIIHLFTLTNLGA*

*PAAFKYFDTTIDRKRYTSTKEVLDATLIHQSITGLYETRIDLSQLGGDS*

<u>RAD</u>*pydvpdya*<u>SGS</u>*pkkkrkv*<u>EASGSGRASPGIPGSTR</u>NH

DQEFDPPKVYPPVPAEKRKPIRVLSLFDGIATGLL

VLKDLGIQVDRYIASEVCEDSITVGMV

RHQGKIMYVGDVRSVTQKHIQEWGPFDLVIGGS

PCNDLSIVNPARKGLYEGTGRLFFEFYR

LLHDARPKEGDDRPFFWLFENVVAMGVSDKRDI

SRFLESNPVMIDAKEVSAAHRARYFW

GNLPGMNRPLASTVNDKLELQECLEHGRIAKFSK

VRTITTRSNSIKQGKDQHFPVFMNEKE

DILWCTEMERVFGFPVHYTDVSNMS

RLARQRLLGRSWSVPVIRHLFAPLKEYFACV<u>SSGNSNANSRGPSFSSGL</u>

<u>VPLSLRGSH</u>MGPMEIYKTVSAWKRQPVRVLSLFRNIDKVLKSLGFLESG

SGSGGGTLKYVEDVTNVVRRDVEKWGPFDLVYGSTQPLGSSCDRCPGWY

MFQFHRILQYALPRQESQRPFFWIFMDNLLLTEDDQETTTRFLQTEAVT

LQDVRGRDYQNAMRVWSNIPGLKSKHAPLTPKEEEYLQAQVRSRSKLDA

PKVDLLVKNCLLPLREYFKYFSQNSLPLSRAD*pkkkrkv*GSGatnfsll kqagdveenpgp<u>selikenmhmklymegtvdnhhfkctsegegkpyegt</u>

<u>qtmrikvveqgplpfafdilatsflyqsktfinhtqqipdffkqsfpeq</u>

<u>ftwervttyedggvltatqdtslqdgcliynvkirgvnftsngpvmqkk</u>

<u>tlqweaftetlypadqqlegrndmalklvqgshlianikttyrskkpak</u>

<u>nlkmpgvyyvdyrlerikeannetyveqhevavarycdlpsklghkln</u>*

SEQ ID NO:10 (p98 (KRAB-XTEN80-dCas9-Dnmt3A-Dnmt3L-P2A-P2A-BFP): KRAB (bold, from Gilbert et al., Cell, 2013, 2014), Linkers (underlined), XTEN80 (80 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL

VSLGYQLTKPDVILRLEKGEEPGGPSSGAPPPSGGSPAGSPTSTEEGTS

ESATPESGPGTSTEPSEGSAPGSPAGSPTSTEEGTSTEPSEGSAPGTST

EPSEMDKKYS*IGLAIGTNSVGWAVITDEYKVPSKKFKVLGNTDRHSIKK*

*NLIGALLFDSGETAEATRLKRTARRRYTRRKNRICYLQEIFSNEMAKVD*

*DSFFHRLEESFLVEEDKKHERHPIFGNIVDEVAYHEKYPTIYHLRKKLV*

*DSTDKADLRLIYLALAHMIKFRGHFLIEGDLNPDNSDVDKLFIQLVQTY*

*NQLFEENPINASGVDAKAILSARLSKSRRLENLIAQLPGEKKNGLFGNL*

*IALSLGLTPNFKSNFDLAEDAKLQLSKDTYDDDLDNLLAQIGDQYADLF*

*LAAKNLSDAILLSDILRVNTEITKAPLSASMIKRYDEHHQDLTLLKALV*

*RQQLPEKYKEIFFDQSKNGYAGYIDGGASQEEFYKFIKPILEKMDGTEE*

*LLVKLNREDLLRKQRTFDNGSIPHQIHLGELHAILRRQEDFYPFLKDNR*

*EKIEKILTFRIPYYVGPLARGNSRFAWMTRKSEETITPWNFEEVVDKGA*

*SAQSFIERMTNFDKNLPNEKVLPKHSLLYEYFTVYNELTKVKYVTEGMR*

*KPAFLSGEQKKAIVDLLFKTNRKVTVKQLKEDYFKKIECFDSVEISGVE*

*DRFNASLGTYHDLLKIIKDKDFLDNEENEDILEDIVLTLTLFEDREMIE*

*ERLKTYAHLFDDKVMKQLKRRRYTGWGRLSRKLINGIRDKQSGKTILDF*

*LKSDGFANRNFMQLIHDDSLTFKEDIQKAQVSGQGDSLHEHIANLAGSP*

*AIKKGILQTVKVVDELVKVMGRHKPENIVIEMARENQTTQKGQKNSRER*

*MKRIEEGIKELGSQILKEHPVENTQLQNEKLYLYYLQNGRDMYVDQELD*

*INRLSDYDVDAIVPQSFLKDDSIDNKVLTRSDKNRGKSDNVPSEEVVKK*

*MKNYWRQLLNAKLITQRKFDNLTKAERGGLSELDKAGFIKRQLVETRQI*

*TKHVAQILDSRMNTKYDENDKLIREVKVITLKSKLVSDFRKDFQFYKVR*

*EINNYHHAHDAYLNAVVGTALIKKYPKLESEFVYGDYKVYDVRKMIAKS*

*EQEIGKATAKYFFYSNIMNFFKTEITLANGEIRKRPLIETNGETGEIVW*

*DKGRDFATVRKVLSMPQVNIVKKTEVQTGGFSKESILPKRNSDKLIARK*

*KDWDPKKYGGFDSPTVAYSVLVVAKVEKGKSKKLKSVKELLGITIMERS*

*SFEKNPIDFLEAKGYKEVKKDLIIKLPKYSLFELENGRKRMLASAGELQ*

*KGNELALPSKYVNFLYLASHYEKLKGSPEDNEQKQLFVEQHKHYLDEII*

*EQISEFSKRVILADANLDKVLSAYNKHRDKPIREQAENIIHLFTLTNLG*

*APAAFKYFDTTIDRKRYTSTKEVLDATLIHQSITGLYETRIDLSQLGGD*

<u>SRAD</u>*pydvpdya*<u>SGS</u>*pkkkrkv*<u>EASGSGRASPGIPGSTR</u>NH

DQEFDPPKVYPPVPAEKRKPIRVLSLFDGIATGL

LVLKDLGIQVDRYIASEVCEDSITVGMV

RHQGKIMYVGDVRSVTQKHIQEWGPFDLVIGG

SPCNDLSIVNPARKGLYEGTGRLFFEFYR

LLHDARPKEGDDRPFFWLFENVVAMGVSDKR

DISRFLESNPVMIDAKEVSAAHRARYFW

-continued

GNLPGMNRPLASTVNDKLELQECLEHGRIAKF

SKVRTITTRSNSIKQGKDQHFPVFMNEKE

DILWCTEMERVFGFPVHYTDVSNMSRLA

RQRLLGRSWSVPVIRHLFAPLKEYFACV SSGNSNANSRGPSFSSGLVP

LSLRGSHMGPMEIYKTVSAWKRQPVRVLSLFRNIDKVLKSLGFLESGSG

SGGGTLKYVEDVTNVVRRDVEKWGPFDLVYGSTQPLGSSCDRCPGWYMF

QFHRILQYALPRQESQRPFFWIFMDNLLLTEDDQETTTRFLQTEAVTLQ

DVRGRDYQNAMRVWSNIPGLKSKHAPLTPKEEEYLQAQVRSRSKLDAPK

VDLLVKNCLLPLREYFKYFSQNSLPLSRADpkkkrkvGSGatnfsllkq agdveenpgpGSGatnfsllkqagdveenpgpselikenmhmklymeqt vdnhhfkctsegegkpyegtqtmrikvveggplpfafdilatsflygsk tfinhtqgipdffkqsfpeqftwervttyedqqvltatqdtslqdqcli ynvkirgvnftsngpvmqkktlgweaftetlypadgglegrndmalklv ggshlianikttyrskkpaknlkmpqvyyvdyrlerikeannetyveqh evavarycdlpsklghkln*

SEQ ID NO:11 (p99 (KRAB-XTEN16-dCas9-XTEN80-Dnmt3A-Dnmt3L-P2A-BFP): KRAB (bold, from Gilbert et al., Cell, 2013, 2014), XTEN16 (16 amino acid sequence), dCas9 (italics), HA tag (lowercase), Linkers (underlined), SV40 NLS (lowercase italics), XTEN80 (lowercase italics bold, 80 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (old underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL

VSLGYQLTKPDVILRLEKGEEPSGSETPGTSESATPESMDKKYSIGLAI

GTNSVGWAVITDEYKVPSKKFKVLGNTDRHSIKKNLIGALLFDSGETAE

ATRLKRTARRRYTRRKNRICYLQEIFSNEMAKVDDSFFHRLEESFLVEE

DKKHERHPIFGNIVDEVAYHEKYPTIYHLRKKLVDSTDKADLRLIYLAL

AHMIKFRGHFLIEGDLNPDNSDVDKLFIQLVQTYNQLFEENPINASGVD

AKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDI

LRVNTEITKAPLSASMIKRYDEHHQDLTLLKALVRQQLPEKYKEIFFDQ

SKNGYAGYIDGGASQEEFYKFIKPILEKMDGTEELLVKLNREDLLRKQR

TFDNGSIPHQIHLGELHAILRRQEDFYPFLKDNREKIEKILTFRIPYYV

GPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLK

IIKDKDFLDNEENEDILEDIVLTLTLFEDREMIEERLKTYAHLFDDKVM

KQLKRRRYTGWGRLSRKLINGIRDKQSGKTILDFLKSDGFANRNFMQLI

HDDSLTFKEDIQKAQVSGQGDSLHEHIANLAGSPAIKKGILQTVKVVDE

LVKVMGRHKPENIVIEMARENQTTQKGQKNSRERMKRIEEGIKELGSQI

LKEHPVENTQLQNEKLYLYYLQNGRDMYVDQELDINRLSDYDVDAIVPQ

SFLKDDSIDNKVLTRSDKNRGKSDNVPSEEVVKKMKNYWRQLLNAKLIT

QRKFDNLTKAERGGLSELDKAGFIKRQLVETRQITKHVAQILDSRMNTK

YDENDKLIREVKVITLKSKLVSDFRKDFQFYKVREINNYHHAHDAYLNA

VVGTALIKKYPKLESEFVYGDYKVYDVRKMIAKSEQEIGKATAKYFFYS

NIMNFFKTEITLANGEIRKRPLIETNGETGEIVWDKGRDFATVRKVLSM

PQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGY

KEVKKDLIIKLPKYSLFELENGRKRMLASAGELQKGNELALPSKYVNFL

YLASHYEKLKGSPEDNEQKQLFVEQHKHYLDEIIEQISEFSKRVILADA

NLDKVLSAYNKHRDKPIREQAENIIHLFTLTNLGAPAAFKYFDTTIDRK

RYTSTKEVLDATLIHQSITGLYETRIDLSQLGGDSRADypydvpdyaSG

SpkkkrkvSPGggpssgapppsggspagsptste egtsesatpesgpgtstepsegsapgspagsptsteegtstepsegsap gtstepseNHDQEFDPPKVYPPVPAEKRKPIR

VLSLFDGIATGLLVLKDLGIQVDRYIASEVCED

SITVGMVRHQGKIMYVGDVRSVTQKHIQE

WGPFDLVIGGSPCNDLSIVNPARKGLYEGTGRL

FFEFYRLLHDARPKEGDDRPFFWLFEN

VVAMGVSDKRDISRFLESNPVMIDAKEVSAAH

RARYFWGNLPGMNRPLASTVNDKLELQE

CLEHGRIAKFSKVRTITTRSNSIKQGKDQHFP

VFMNEKEDILWCTEMERVFGFPVHYTDVS

NMSRLARQRLLGRSWSVPVIRHLFAPLKEYFACVSSGNSNANSRGPSF

SSGLVPLSLRGSHMGPMEIYKTVSAWKRQPVRVLSLFRNIDKVLKSLGF

LESGSGSGGGTLKYVEDVTNVVRRDVEKWGPFDLVYGSTQPLGSSCDRC

PGWYMFQFHRILQYALPRQESQRPFFWIFMDNLLLTEDDQETTTRFLQT

EAVTLQDVRGRDYQNAMRVWSNIPGLKSKHAPLTPKEEEYLQAQVRSRS

KLDAPKVDLLVKNCLLPLREYFKYFSQNSLPLSRADpkkkrkvGSGatn fsllkqagdveenpgpselikenmhmklymeqtvdnhhfkctseqeqkp yegtqtmrikvveggplpfafdilatsflygsktfinhtqgipdffkqs fpeqftwervttyedqqvltatqdtslqdqcliynvkirqvnftsngpv mqkktlgweaftetlypadgglegrndmalklvggshlianikttyrsk kpaknlkmpqvyyvdyrlerikeannetyveqhevavarycdlpsklgh kln*

SEQ ID NO:12 (p100 (KRAB-XTEN16-dCas9-XTEN80-Dnmt3A-Dnmt3L-P2A-P2A-BFP): KRAB (bold, from Gilbert et al., Cell, 2013, 2014), XTEN16 (16 amino acid sequence), dCas9 (italics), HA tag (lowercase), Linkers (underlined), SV40 NLS (lowercase italics), XTEN80 (lowercase bold italics, 80 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL
VSLGYQLTKPDVILRLEKGEEPSGSETPGTSESATPESMDKKYSIGLAI
GTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEE
DKKHERHPIFGNIVDEVAYHEKYPTIYHLRKKLVDSTDKADLRLIYLAL
AHMIKFRGHFLIEGDLNPDNSDVDKLFIQLVQTYNQLFEENPINASGVD
AKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDI
LRVNTEITKAPLSASMIKRYDEHHQDLTLLKALVRQQLPEKYKEIFFDQ
SKNGYAGYIDGGASQEEFYKFIKPILEKMDGTEELLVKLNREDLLRKQR
TFDNGSIPHQIHLGELHAILRRQEDFYPFLKDNREKIEKILTFRIPYYV
GPLARGNSRFAWMTRKSEETITPWNFEEVVDKGASAQSFIERMTNFDKN
LPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLK
IIKDKDFLDNEENEDILEDIVLTLTLFEDREMIEERLKTYAHLFDDKVM
KQLKRRRYTGWGRLSRKLINGIRDKQSGKTILDFLKSDGFANRNFMQLI
HDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQI
LKEHPVENTQLQNEKLYLYYLQNGRDMYVDQELDINRLSDYDVDAIVPQ
SFLKDDSIDNKVLTRSDKNRGKSDNVPSEEVVKKMKNYWRQLLNAKLIT
QRKFDNLTKAERGGLSELDKAGFIKRQLVETRQITKHVAQILDSRMNTK
YDENDKLIREVKVITLKSKLVSDFRKDFQFYKVREINNYHHAHDAYLNA
VVGTALIKKYPKLESEFVYGDYKVYDVRKMIAKSEQEIGKATAKYFFYS
NIMNFFKTEITLANGEIRKRPLIETNGETGEIVWDKGRDFATVRKVLSM
PQVNIVKKTEVQTGGFSKESILPKRNSDKLIARKKDWDPKKYGGFDSPT
VAYSVLVVAKVEKGKSKKLKSVKELLGITIMERSSFEKNPIDFLEAKGY
KEVKKDLIIKLPKYSLFELENGRKRMLASAGELQKGNELALPSKYVNFL
YLASHYEKLKGSPEDNEQKQLFVEQHKHYLDEIIEQISEFSKRVILADA
NLDKVLSAYNKHRDKPIREQAENIITILFTLTNLGAPAAFKYFDTTIDR
KRYTSTKEVLDATLIHQSITGLYETRIDLSQLGGDSRADypydvpdyaS
GSpkkkrkvSPGggpssgapppsggspagsptste
egtsesatpesgpgtstepsegsapgspagsptsteegtstepse
gsapgtstepseNHDQEFDPPKVYPPVPAEKRKPIR
VLSLFDGIATGLLVKDLGIQVDRYIASEVCED
SITVGMVRHQGKIMYVGDVRSVTQKHIQE
WGPFDLVIGGSPCNDLSIVNPARKGLYEGT
GRLFFEFYRLLHDARPKEGDDRPFFWLFEN
VVAMGVSDKRDISRFLESNPVMIDAKEVSA AHRARYFWGNLPGMNRPLASTVNDKLELQE
CLEHGRIAKFSKVRTITTRSNSIKQGKDQHF
PVFMNEKEDILWCTEMERVFGFPVHYTDVS
NMSRLARQRLLGRSWSVPVIHLFAPLKEYFACV
SSGNSNANSRGPSFSSGLVPLSLRGSHMGPMEIYKTVSAWKRQPVRVLS
LFRNIDKVLKSLGFLESGSGSGGGTLKYVEDVTNVVRRDVEKWGPFDLV
YGSTQPLGSSCDRCPGWYMFQFHRILQYALPRQESQRPFFWIFMDNLLL
TEDDQETTTRFLQTEAVTLQDVRGRDYQNAMRVWSNIPGLKSKHAPLTP
KEEEYLQAQVRSRSKLDAPKVDLLVKNCLLPLREYFKYFSQNSLPLSRA
DpkkkrkvGSGatnfsllkqagdveenpgpGSGatnfsllkqagdveen
pgpselikenmhmklymeqtvdnhhfkctseqeqkpyeqtqtmrikvve
ggplpfafdilatsflygsktfinhtqgipdffkqsfpegftwervtty
edgqvltatqdtslqdqcliynvkirqvnftsnqpvmqkktlqweafte
tlypadgglegrndmalklvggshhanikttyrskkpaknlkmpgvyyv
dyrlerikeannetyveqhevavarycdlpsklqhkln*

SEQ ID NO:13 (p101 (KRAB-XTEN80-dCas9-XTEN16-Dnmt3A-Dnmt3L-P2A-BFP): KRAB (bold, from Gilbert et al., Cell, 2013, 2014), Linkers (underlined), XTEN80 (lowercase bold italics, 80 amino acid sequence), dCas9 (italics), HA tag (lowercase), SV40 NLS (lowercase italics), XTEN16 (16 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL
VSLGYQLTKPDVILRLEKGEEP
ggpssgapppsggspagsptsteegtsesatpes
gpgtstepsegsapgspagsptsteegtstepsegsapgtstepse
MDKKYSIGLAIGTNSVGWAVITDEYKVPSKKFKVLGNTDRHSIKKNLIG
ALLFDSGETAEATRLKRTARRRYTRRKNRICYLQEIFSNEMAKVDDSFF
HRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLF
EENPINASGVDAKAILSARLSKSRRLENLIAQLPGEKKNGLFGNLIALS
LGLTPNFKSNFDLAEDAKLQLSKDTYDDDLDNLLAQIGDQYADLFLAAK
NLSDAILLSDILRVNTEITKAPLSASMIKRYDEHHQDLTLLKALVRQQL
PEKYKEIFFDQSKNGYAGYIDGGASQEEFYKFIKPILEKMDGTEELLVK
LNREDLLRKQRTFDNGSIPHQIHLGELHAILRRQEDFYPFLKDNREKIE
KILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFN
ASLGTYHDLLKIIKDKDFLDNEENEDILEDIVLTLTLFEDREMIEERLK -continued

TYAHLFDDKMKQLKRRRYTGWGRLSRKLINGIRDKQSGKTILDFLKSDG

FANRNFMQLIHDDSLTFKEDIQKAQVSGQGDSLHEHIANLAGSPAIKKG

ILQTVKVVDELVKVMGRHKPENIVIEMARENQTTQKGQKNSREMKRIEE

GIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQ

ILDSRMNTKYDENDKLIREVKVITLKSKLVSDFRKDFQFYKVREINNYH

HAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDF

ATVRKVLSMPQVNIVKKTEVQTGGFSKESILPKRNSDKLIARKKDWDPK

KYGGFDSPTVAYSVLVVAKVEKGKSKKLKSVKELLGITIMERSSFEKNP

IDFLEAKGYKEVKKDLIIKLPKYSLFELENGRKRMLASAGELQKGNELA

LPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFK

YFDTTIDRKRYTSTKEVLDATLIHQSITGLYETRIDLSQLGGD<u>SRAD</u>yp ydvpdya<u>SGS</u>pkkkrkv<u>SPG</u>SGSETPGTSESATPES

*NHDQEFDPPKVYPPVPAEKRKPI*

*RVLSLFDGIATGLLVLKDLGIQVDRYIASEVCED*

*SITVGMVRHQGKIMYVGDVRSVTQKHIQ*

*EWGPFDLVIGGSPCNDLSIVNPARKGLYEGTGR*

*LFFEFYRLLHDARKPEGDDRPFFWLFE*

*NVVAMGVSDKRDISRFLESNPVMIDAKEVSAAH*

*RARYFWGNLPGMNRPLASTVNDKLELQ*

*ECLEHGRIAKFSKVRTITTRSNSIKQGKDQHFPV*

*FMNEKEDILWCTEMERVFGFPVHYTD*

*VSNMSRLARQRLLGRSWSVPVIRHLFAPLKEYFACV*<u>SSGNSNANSRGP</u>

<u>SFSSGLVPLSLRGSH</u>MGPMEIYKTVSAWKRQPVRVLSLFRNIDKVLKSL

GFLESGSGSGGGTLKYVEDVTNVVRRDVEKWGPFDLVYGSTQPLGSSCD

RCPGWYMFQFHRILQYALPRQESQRPFFWIFMDNLLLTEDDQETTTRFL

QTEAVTLQDVRGRDYQNAMRVWSNIPGLKSKHAPLTPKEEEYLQAQVRS

RSKLDAPKVDLLVKNCLLPLREYFKYFSQNSLPL<u>SRAD</u>pkkkrkv<u>GSG</u>a tnfsllkqagdveenpgp<u>selikenmhmklymeqtvdnhhfkctseqeq</u>

<u>kpyeqtqtmrikvveqgplpfafdilatsflyqsktfinhtqqipdffk</u>

<u>qsfpeqftwervttyedqqvltatqdtslqdqcliynvkirqvnftsnq</u>

<u>pvmqkktlqweaftetlypadqqleqrndmalklvqqshlianikttyr</u>

<u>skkpaknlkmpqvyyvdyrlerikeannetyveqhevavarycdlpskl</u>

<u>ghkln</u>*

SEQ ID NO:14 (p102 (KRAB-XTEN80-dCas9-XTEN16-Dnmt3A-Dnmt3L-P2A-BFP): KRAB (bold, from Gilbert et al., Cell, 2013, 2014), Linkers (underlined), XTEN80 (lowercase bold italics, 80 amino acid sequence), dCas9 (italics), HA tag (lowercase), SV40 NLS (lowercase italics), XTEN16 (16 amino acid sequence), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), P2A peptide cleavage sequence (lowercase bold), BFP (lowercase underlined))

DAKSLTAWSRTLVTFKDVFVDFTREEWKLLDTAQQIVYRNVMLENYKNL

VSLGYQLTKPDVILRLEKGEEP

*ggpssgapppsggspagsptsteegtsesatpes*

*gpgtstepsegsapgspagsptsteegtstepsegsapgtstepse*

MDKKYSIGLAIGTNSVGWAVITDEYKVPSKKFKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLFGNLIALS

LGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIE

KILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLK

TYAHLFDDKVMQLKRRRYTGWGRLSRKLINGIRDKQSGKTILDFLKSD

GFANRNFMQLIHDDSLTFKEDIQKAQVSGQGDSLHEHIANLAGSPAIKK

GILQTVKVVDELVKVMGRHKPENIVIEMARENQTTQKGQKNSREMKRIE

EGIKELGSQILKEHPVENTQLQNEKLYLYYLQNGRDMYVDQELDINRLS

DYDVDAIVPQSFLKDDSIDNKVLTRSDKNRGKSDNVPSEEVVKKMKNYW

RQLLNAKLITQRKFDNLTKAERGGLSELDKAGFIKRQLVETRQITKHVA

QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFDSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGD<u>SRAD</u>y pydvpdya<u>SGS</u>pkkkrkv<u>SPG</u>SGSETPGTSESATPES

*NHDQEFDPPKVYPPVPAEKRKPI*

*RVLSLFDGIATGLLVLKDLGIQVDRYIASEV*

*CEDSITVGMVRHQGKIMYVGDVRSVTQKHIQ*

*EWGPFDLVIGGSPCNDLSIVNPARKGLYEGT*

*GRLFFEFYRLLHDARPKEGDDRPFFWLFE*

*NVVAMGVSDKRDISRFLESNPVMIDAKEVSA*

*AHRARYFWGNLPGMNRPLASTVNDKLELQ*

*ECLEHGRIAKFSKVRTITTRSNSIKQGKDQHFP*

*VFMNEKEDILWCTEMERVFGFPVHYTD*

*VSNMSRLARQRLLGRSWSVPVIRHLFAPLKEYFACV<u>S</u>*

<u>SGNSNANSRGPSFSSGLVPLSLRGSH</u>MGPMEIYKTVSAWKRQPVRVLS

LFRNIDKVLKSLGFLESGSGSGGGTLKYVEDVTNVVRRDVEKWGPFDLV

YGSTQPLGSSCDRCPGWYMFQFHRILQYALPRQESQRPFFWIFMDNLLL

TEDDQETTTRFLQTEAVTLQDVRGRDYQNAMRVWSNIPGLKSKHAPLTP

KEEEYLQAQVRSRSKLDAPKVDLLVKNCLLPLREYFKYFSQNSLPLSRA

<u>D</u>pkkkrkv<u>GSG</u>atnfsllkqagdveenpgp<u>GSG</u>atnfsllkqagdveen pgp<u>selikenmhmklymeqtvdnhhfkctseqeqkpyeqtqtmrikvve</u>

<u>ggplpfafdilatsflygsktfinhtqgipdffkqsfpegftwervtty</u>

<u>edqgvltatqdtslqdqcliynvkirqvnftsnqpvmqkktlqweafte</u>

<u>tlypadgglegrndmalklvggshlianikttyrskkpaknlkmpgvyy</u>

<u>vdyrlerikeannetyveqhevavarycdlpsklqhkln</u>*

SEQ ID NO:15 (p112 (Dnmt3A-Dnmt3L-XTEN80-dCas9-BFP-KRAB); KRAB (bold, from Gilbert et al., Cell, 2013, 2014), Linkers (underlined), XTEN80 (lowercase bold italics, 80 amino acid sequence), dCas9 (italics), HA tag (lowercase), SV40 NLS (lowercase italics), Dnmt3A (bold italics, from Siddique et al., JMB, 2013; Stepper et al., NAR, 2016), 27 amino acid linker (italics underlined, from Siddique et al., JMB, 2013; Stepper et al., NAR, 2016), Dnmt3L (bold underlined, from Siddique et al., JMB, 2013; Stepper et al., NAR, 2016), BFP (lowercase underlined))

*NHDQEFDPPKVYPPVPAEKRKPIRVLSLFDGIATGLLVLKDLGIQVDRYIASEVCEDSITVG*

*MVRHQGKIMYVGDVRSVTQKHIQEWGPFDLVIGGSPCNDLSIVNPARKGLYEGTGRLFFE*

*FYRLLHDARPKEGDDRPFFWLFENVVAMGVSDKRDISRFLESNPVMIDAKEVSAAHRARY*

*FWGNLPGMNRPLASTVNDKLELQECLEHGRIAKFSKVRTITTRSNSIKQGKDQHFPVFMN*

*EKEDILWCTEMERVFGFPVHYTDVSNMSRLARQRLLGRSWSVPVIRHLFAPLKEYFACV*

<u>SSGNSNANSRGPSFSSGLVPLSLRGSH</u>MGPMEIYKTVSAWKRQPVRVLSLFRNIDKVLKSL

GFLESGSGSGGGTLKYVEDVTNVVRRDVEKWGPFDLVYGSTQPLGSSCDRCPGWYMFQFHR

ILQYALPRQESQRPFFWIFMDNLLLTEDDQETTTRFLQTEAVTLQDVRGRDYQNAMRVWSN

IPGLKSKHAPLTPKEEEYLQAQVRSRSKLDAPKVDLINKNCLLPLREYFKYFSQNSLPL

*ggpssgapppsggspagsptsteegtsesatpesgpgtstepse*

*gsapgspagsptsteegtstepsegsapgtstepse*MDKKYSIGLAIGTNSVGWAVITDE

YKVPSKKFKVLGNTDRHSIKKNLIGALLFDSGETAEATRLKRTARRRYTRRKNRICYLQEIFS

NEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILS

ARLSKSRRLENLIAQLPGEKKNGLFGNLIALSLGLTPNFKSNFDLAEDAKLQLSKDTYDDDLD

NLLAQIGDQYADLFLAAKNLSDAILLSDILRVNTEITKAPLSASMIKRYDEHHQDLTLLKALV

RQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWM

TRKSEETITPWNFEEVVDKGASAQSFIERMTNFDKNLPNEKVLPKHSLLYEYFTVYNELTKVK

YVTEGMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQLKRR

RYTGWGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKNSRER

MKRIEEGIKELGSQILKEHPVENTQLQNEKLYLYYLQNGRDMYVDQELDINRLSDYDVDAIVP

QSFLKDDSIDNKVLTRSDKNRGKSDNVPSEEVVKKMKNYWRQLLNAKLITQRKFDNLTKAERG

GLSELDKAGFIKRQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRKMIAKSEQEIGKA

-continued

```
TAKYFFYSNIMNFFKTEITLANGEIRKRPLIETNGETGEIVWDKGRDFATVRKVLSMPQVNIV
KKTEVQTGGFSKESILPKRNSDKLIARKKDWDPKKYGGFDSPTVAYSVLVVAKVEKGKSKKLK
SVKELLGITIMERSSFEKNPIDFLEAKGYKEVKKDLIIKLPKYSLFELENGRKRMLASAGELQ
KGNELALPSKYVNFLYLASHYEKLKGSPEDNEQKQLFVEQHKHYLDEIIEQISEFSKRVILAD
ANLDKVLSAYNKHRDKPIREQAENIIHLFTLTNLGAPAAFKYFDTTIDRKRYTSTKEVLDATL
IHQSITGLYETRIDLSQLGGDAypydvpdyaSLGSGSpkkkrkvEDpkkkrkvDGIGSGSNGS
SGSselikenmhmklymeqtvdnhhfkctsegeqkpyeqtqtmrikvveqqplpfafdilats
flygsktfinhtqgipdffkqsfpeqftwervttyedqgvltatqdtslqdqcliynvkirqv
nftsnqpvmqkktlqweaftetlypadqqleqrndmalklvqqshlianikttyrskkpaknl
kmpqvyyvdyrlerikeannetyveqhevavarycdlpsklqhldnGGGGGMDAKSLTAWSRT
LVTFKDVFVDFTREEWKLLDTAQQIVYRNVMLENYKNLVSLGYQLTKPDVILRLEKGEEP*
```

(KRAB; from Gilbert etal., Cell, 2013, 2014)

SEQ ID NO: 16

```
DAKSLTAWSRTLVTFKDVFVDFTREEWKLLDTAQQIVYRNVMLENYKNLVSLGYQLTKP
DVILRLEKGEEP
```

(Linker)

SEQ ID NO: 17

```
GGSGGGS
```

(Linker)

SEQ ID NO: 18

```
SGS
```

(Linker)

SEQ ID NO: 19

```
EASGSGRASPGIPGSTR
```

(Linker)

SEQ ID NO: 20

```
SRAD
```

(Linker)

SEQ ID NO: 21

```
GSG
```

(Linker

SEQ ID NO: 22

```
SPG
```

(dCas9)

SEQ ID NO: 23

```
MDKKYSIGLAIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGK
TILDFLKSDGFANRNFMQLIHDDSLTFKEDIQKAQVSGQGDSLHEHIANLAGSPAIKKGILQ
TVKVVDELVKVMGRHKPENIVIEMARENQTTQKGQKNSRERMKRIEEGIKELGSQILKEHP
```

-continued

VENTQLQNEKLYLYYLQNGRDMYVDQELDINRLSDYDVDAIVPQSFLKDDSIDNKVLTRS

DKNRGKSDNVPSEEVVKKMKNYWRQLLNAKLITQRKFDNLTKAERGGLSELDKAGFIKR

QLVETRQITKHVAQILDSRMNTKYDENDKLIREVKVITLKSKLVSDFRKDFQFYKVREINN

YHHAHDAYLNAVVGTALIKKYPKLESEFVYGDYKVYDVRKMIAKSEQEIGKATAKYFFYS

NIMNFFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSVKE

LLGITIMERSSFEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISEFSKRVILADAN

LDKVLSAYNKHRDKPIREQAENIIHLFTLTNLGAPAAFKYFDTTIDRKRYTSTKEVLDATLI

HQSITGLYETRIDLSQLGGD (HA tag)
SEQ ID NO: 24
YPYDVPDYA (SV40 NLS)
SEQ ID NO: 25
PKKKRKV (Dnmt3A; residues 612-912; from Siddique et al., JMB, 2013;
Stepper et al., NAR, 2016)
SEQ ID NO: 26
NHDQEFDPPPKVYPPVPAEKRKPIRVLSLFDGIATGLLVLKDLGIQVDRYIASEVCEDSITVG

MVRHQGKIMYVGDVRSVTQKHIQEWGPFDLVIGGSPCNDLSIVNPARKGLYEGTGRLFFEF

YRLLHDARPKEGDDRPFFWLFENVVAMGVSDKRDISRFLESNPVMIDAKEVSAAHRARYF

WGNLPGMNRPLASTVNDKLELQECLEHGRIAKFSKVRTITTRSNSIKQGKDQHFPVFMNEK

EDILWCTEMERVFGFPVHYTDVSNMSRLARQRLLGRSWSVPVIRHLFAPLKEYFACV (27 amino acid linker; from Siddique et al., JMB, 2013;
Stepper et al., NAR, 2016)
SEQ ID NO: 27
SSGNSNANSRGPSFSSGLVPLSLRGSH (Dnmt3L; from Siddique et al., JMB, 2013; Stepper et al., NAR,
2016)
SEQ ID NO: 28
MGPMEIYKTVSAWKRQPVRVLSLFRNIDKVLKSLGFLESGSGSGGGTLKYVEDVTNVVRR

DVEKWGPFDLVYGSTQPLGSSCDRCPGWYMFQFHRILQYALPRQESQRPFFWIFMDNLLL

TEDDQETTTRFLQTEAVTLQDVRGRDYQNAMRVWSNIPGLKSKHAPLTPKEEEYLQAQVR

SRSKLDAPKVDLLVKNCLLPLREYFKYFSQNSLPL (P2A peptide cleave sequence)
SEQ ID NO: 29
ATNFSLLKQAGDVEENPGP (BFP)
SEQ ID NO: 30
SELIKENMHMKLYMEGTVDNHHFKCTSEGEGKPYEGTQTMRIKVVEGGPLPFAFDILATSF

LYGSKTFINHTQGIPDFFKQSFPEGFTWERVTTYEDGGVLTATQDTSLQDGCLIYNVKIRGV

NFTSNGPVMQKKTLGWEAFTETLYPADGGLEGRNDMALKLVGGSHLIANIKTTYRSKKPA

KNLKMPGVYYVDYRLERIKEANNETYVEQHEVAVARYCDLPSKLGHKLN*

(XTEN16 (16 amino acid sequence))
SEQ ID NO: 31
SGSETPGTSESATPES (XTEN80 (80 amino acid sequence))
SEQ ID NO: 32
GGPSSGAPPPSGGSPAGSPTSTEEGTSESATPESGPGTSTEPSEGSAPGSPAGSPTSTEEGTSTE

PSEGSAPGTSTEPSE (Dnmt3A-Dnmt3L domain)

SEQ ID NO: 33

NHDQEFDPPKVYPPVPAEKRKPIRVLSLFDGIATGLLVLKDLGIQVDRYIASEVCEDSITVG

MVRHQGKIMYVGDVRSVTQKHIQEWGPFDLVIGGSPCNDLSIVNPARKGLYEGTGRLFFEF

YRLLHDARPKEGDDRPFFWLFENVVAMGVSDKRDISRFLESNPVMIDAKEVSAAHRARYF

WGNLPGMNRPLASTVNDKLELQECLEHGRIAKFSKVRTITTRSNSIKQGKDQHFPVFMNEK

EDILWCTEMERVFGFPVHYTDVSNMSRLARQRLLGRSWSVPVIRHLFAPLKEYFACVSSGN

SNANSRGPSFSSGLVPLSLRGSHMGPMEIYKTVSAWKRQPVRVLSLFRNIDKVLKSLGFLES

GSGSGGGTLKYVEDVTNVVRRDVEKWGPFDLVYGSTQPLGSSCDRCPGWYMFQFHRILQ

YALPRQESQRPFFWIFMDNLLLTEDDQETTTRFLQTEAVTLQDVRGRDYQNAMRVWSNIP

GLKSKHAPLTPKEEEYLQAQVRSRSKLDAPKVDLLVKNCLLPLREYFKYFSQNSLPL (ddAsCfp1)

SEQ ID NO: 34

MTQFEGFTNLYQVSKTLRFELIPQGKTLKHIQEQGFIEEDKARNDHYKELKPIIDRIYKTYA

DQCLQLVQLDWENLSAAIDSYRKEKTEETRNALIEEQATYRNAIHDYFIGRTDNLTDAINK

RHAEIYKGLFKAELFNGKVLKQLGTVTTTEHENALLRSFDKFTTYFSGFYENRKNVFSAEDI

STAIPHRIVQDNFPKFKENCHIFTRLITAVPSLREHFENVKKAIGIFVSTSIEEVFSFPFYNQLL

TQTQIDLYNQLLGGISREAGTEKIKGLNEVLNLAIQKNDETAHIIASLPHRFIPLFKQILSDRN

TLSFILEEFKSDEEVIQSFCKYKTLLRNENVLETAEALFNELNSIDLTHIFISHKKLETISSALC

DHWDTLRNALYERRISELTGKITKSAKEKVQRSLKHEDINLQEIISAAGKELSEAFKQKTSEI

LSHAHAALDQPLPTTLKKQEEKEILKSQLDSLLGLYHLLDWFAVDESNEVDPEFSARLTGIK

LEMEPSLSFYNKARNYATKKPYSVEKFKLNFQMPTLASGWDVNKEKNNGAILFVKNGLY

YLGIMPKQKGRYKALSFEPTEKTSEGFDKMYYDYFPDAAKMIPKCSTQLKAVTAHFQTHT

TPILLSNNFIEPLEITKEIYDLNNPEKEPKKFQTAYAKKTGDQKGYREALCKWIDFTRDFLSK

YTKTTSIDLSSLRPSSQYKDLGEYYAELNPLLYHISFQRIAEKEIMDAVETGKLYLFQIYNKD

FAKGHHGKPNLHTLYWTGLFSPENLAKTSIKLNGQAELFYRPKSRMKRMAHRLGEKMLN

KKLKDQKTPIPDTLYQELYDYVNHRLSHDLSDEARALLPNVITKEVSHEIIKDRRFTSDKFF

FHVPITLNYQAANSPSKFNQRVNAYLKEHPETPIIGIDRGERNLIYITVIDSTGKILEQRSLNTI

QQFDYQKKLDNREKERVAARQAWSVVGTIKDLKQGYLSQVIHEIVDLMIHYQAVVVLAN

LNFGFKSKRTGIAEKAVYQQFEKMLIDKLNCLVLKDYPAEKVGGVLNPYQLTDQFTSFAK

MGTQSGFLFYVPAPYTSKIDPLTGFVDPFVWKTIKNHESRKHFLEGFDFLHYDVKTGDFILH

FKMNRNLSFQRGLPGFMPAWDIVFEKNETQFDAKGTPFIAGKRIVPVIENHRFTGRYRDLY

PANELIALLEEKGIVFRDGSNILPKLLENDDSHAIDTMVALIRSVLQMRNSNAATGEDYINSP

VRDLNGVCFDSRFQNPEWPMDADANGAYHIALKGQLLLNHLKESKDLKLQNGISNQDWL

AYIQELRN (ddLbCfp1)

SEQ ID NO: 35

MSKLEKFTNCYSLSKTLRFKAIPVGKTQENIDNKRLLVEDEKRAEDYKGVKKLLDRYYLSF

INDVLHSIKLKNLNNYISLFRKKTRTEKENKELENLEINLRKEIAKAFKGNEGYKSLFKKDII

ETILPEFLDDKDEIALVNSFNGFTTAFTGFFDNRENMFSEEAKSTSIAFRCINENLTRYISNMD

IFEKVDAIFDKHEVQEIKEKILNSDYDVEDFFEGEFFNFVLTQEGIDVYNAIIGGFVTESGEKI

KGLNEYINLYNQKTKQKLPKFKPLYKQVLSDRESLSFYGEGYTSDEEVLEVFRNTLNKNSE

IFSSIKKLEKLFKNFDEYSSAGIFVKNGPAISTISKDIFGEWNVIRDKWNAEYDDIHLKKKAV

VTEKYEDDRRKSFKKIGSFSLEQLQEYADADLSVVEKLKEIIIQKVDEIYKVYGSSEKLFDA

-continued

DFVLEKSLKKNDAVVAIMKDLLDSVKSFENYIKAFFGEGKETNRDESFYGDFVLAYDILLK

VDHIYDAIRNYVTQKPYSKDKFKLYFQNPQFMGGWDKDKETDYRATILRYGSKYYLAIM

DKKYAKCLQKIDKDDVNGNYEKINYKLLPGPNKMLPKVFFSKKWMAYYNPSEDIQKIYK

NGTFKKGDMFNLNDCHKLIDFFKDSISRYPKWSNAYDFNFSETEKYKDIAGFYREVEEQGY

KVSFESASKKEVDKLVEEGKLYMFQIYNKDFSDKSHGTPNLHTMYFKLLFDENNHGQIRLS

GGAELFMRRASLKKEELVVHPANSPIANKNPDNPKKTTTLSYDVYKDKRFSEDQYELHIPI

AINKCPKNIFKINTEVRVLLKHDDNPYVIGIARGERNLLYIVVVDGKGNIVEQYSLNEIINNF

NGIRIKTDYHSLLDKKEKERFEARQNWTSIENIKELKAGYISQVVHKICELVEKYDAVIALA

DLNSGFKNSRVKVEKQVYQKFEKMLIDKLNYMVDKKSNPCATGGALKGYQITNKFESFKS

MSTQNGFIFYIPAWLTSKIDPSTGFVNLLKTKYTSIADSKKFISSFDRIMYVPEEDLFEFALDY

KNFSRTDADYIKKWKLYSYGNRIRIFRNPKKNNVFDWEEVCLTSAYKELFNKYGINYQQG

DIRALLCEQSDKAFYSSFMALMSLMLQMRNSITGRTDVDFLISPVKNSDGIFYDSRNYEAQ

ENAILPKNADANGAYNIARKVLWAIGQFKKAEDEKLDKVKIAISNKEWLEYAQTSVKH (ddFnCfp1)
SEQ ID NO: 36

MYPYDVPDYASGSGMSIYQEFVNKYSLSKTLRFELIPQGKTLENIKARGLILDDEKRAKDY

KKAKQIIDKYHQFFIEEILSSVCISEDLLQNYSDVYFKLKKSDDDNLQKDFKSAKDTIKKQIS

EYIKDSEKFKNLFNQNLIDAKKGQESDLILWLKQSKDNGIELFKANSDITDIDEALEIIKSFK

GWTTYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGENTKR

KGINEYINLYSQQINDKTLKKYKMSVLFKQILSDTESKSFVIDKLEDDSDVVTTMQSFYEQI

AAFKTVEEKSIKETLSLLFDDLKAQKLDLSKIYFKNDKSLTDLSQQVFDDYSVIGTAVLEYI

TQQIAPKNLDNPSKKEQELIAKKTEKAKYLSLETIKLALEEFNKHRDIDKQCRFEEILANFA

AIPMIFDEIAQNKDNLAQISIKYQNQGKKDLLQASAEDDVKAIKDLLDQTNNLLHKLKIFHI

SQSEDKANILDKDEHFYLVFEECYFELANIVPLYNKIRNYITQKPYSDEKFKLNFENSTLAN

GWDKNKEPDNTAILFIKDDKYYLGVMNKKNNKIFDDKAIKENKGEGYKKIVYKLLPGAN

KMLPKVFFSAKSIKFYNPSEDILRIRNHSTHTKNGSPQKGYEKFEFNIEDCRKFIDFYKQSISK

HPEWKDFGFRFSDTQRYNSIDEFYREVENQGYKLTFENISESYIDSVVNQGKLYLFQIYNKD

FSAYSKGRPNLHTLYWKALFDERNLQDVVYKLNGEAELFYRKQSIPKKITHPAKEAIANKN

KDNPKKESVFEYDLIKDKRFTEDKFFFHCPITINFKSSGANKFNDEINLLLKEKANDVHILSI

ARGERHLAYYTLVDGKGNIIKQDTFNIIGNDRMKTNYHDKLAAIEKDRDSARKDWKKINN

IKEMKEGYLSQVVHEIAKLVIEYNAIVVFEDLNFGFKRGRFKVEKQVYQKLEKMLIEKLNY

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQMRNSK

TGTELDYLISPVADVNGNFFDSRQAPKNMPQDADANGAYHIGLKGLMLLGRIKNNQEGKK

LNLVIKNEEYFEFVQRNN

What is claimed is:

1. A fusion protein comprising, from N-terminus to C-terminus:
   (i) a DNA methyltransferase domain, a nuclease-deficient RNA-guided DNA endonuclease enzyme, and a Krüppel associated box domain; or
   (ii) a Krüppel associated box domain, a nuclease-deficient RNA-guided DNA endonuclease enzyme, and a DNA methyltransferase domain.

2. The fusion protein of claim 1, wherein the nuclease-deficient RNA-guided DNA endonuclease enzyme is a nuclease-deficient Class II CRISPR endonuclease.

3. The fusion protein of claim 1, wherein the DNA methyltransferase domain comprises a Dnmt3A protein and a Dnmt3L protein (a Dnmt3A-3L domain).

4. The fusion protein of claim 1, wherein the fusion protein comprises, from N-terminus to C-terminus, the DNA methyltransferase domain, the nuclease-deficient RNA-guided DNA endonuclease enzyme, and the Krüppel associated box domain.

5. The fusion protein of claim 4, wherein the nuclease-deficient RNA-guided DNA endonuclease enzyme is dCas9 and the DNA methyltransferase domain comprises a Dnmt3A protein and a Dnmt3L protein (a Dnmt3A-3L domain); wherein the dCas9 is covalently linked to the Dnmt3A-3L domain via an XTEN linker.

6. The fusion protein of claim 1, wherein the fusion protein comprises, from N-terminus to C-terminus, the Krüppel associated box, the nuclease-deficient RNA-guided DNA endonuclease enzyme, an XTEN linker, and the DNA methyltransferase domain.

7. The fusion protein of claim 1, wherein the nuclease-deficient RNA-guided DNA endonuclease enzyme is dCas9 and the DNA methyltransferase domain comprises a Dnmt3A protein and a Dnmt3L protein (a Dnmt3A-3L domain).

8. The fusion protein of claim 7, wherein the dCas9 is covalently linked to the Dnmt3A-3L domain via a XTEN linker and wherein the Krüppel associated box domain is covalently linked to the dCas9 via a peptide linker.

9. The fusion protein of claim 1, wherein the nuclease-deficient RNA-guided DNA endonuclease enzyme is covalently linked to the Krüppel associated box domain via a peptide linker.

10. The fusion protein of claim 1, wherein the nuclease-deficient RNA-guided DNA endonuclease enzyme is covalently linked to the DNA methyltransferase domain via a peptide linker.

11. The fusion protein of claim 1, wherein the Krüppel associated box domain in (ii) is covalently linked to the DNA methyltransferase domain via an XTEN linker.

12. The fusion protein of claim 5, wherein the XTEN linker comprises about 16 to 80 amino acid residues.

13. The fusion protein of claim 1, further comprising a nuclear localization signal peptide.

14. The fusion protein of claim 1, wherein the fusion protein comprises the amino acid sequence of SEQ ID NO: 1, 2, 3, 4, 5, 6, 7, 8, 9, 10, 11 12, 13, 14, or 15.

15. A nucleic acid sequence encoding the fusion protein of claim 1.

16. A complex comprising: (i) a fusion protein of claim 1; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

17. A vector comprising a nucleic acid sequence encoding the fusion protein of claim 1.

18. A cell comprising the fusion protein of claim 1.

19. A method of silencing a target nucleic acid sequence in a cell, comprising: (i) delivering a first polynucleotide encoding a fusion protein of claim 1 to a cell containing the target nucleic acid; and (ii) delivering to the cell a second polynucleotide comprising: (a) a DNA-targeting sequence that is complementary to the target nucleic acid sequence; and (b) a binding sequence for the nuclease-deficient RNA-guide DNA endonuclease enzyme.

20. A method of silencing a target nucleic acid sequence in a cell, the method comprising delivering a complex to a cell containing the target nucleic acid; wherein the complex comprises: (i) a fusion protein of claim 1; and (ii) a polynucleotide comprising: (a) a DNA-targeting sequence that is complementary to a target polynucleotide sequence; and (b) a binding sequence for the nuclease-deficient RNA-guided DNA endonuclease enzyme, wherein the nuclease-deficient RNA-guided DNA endonuclease enzyme is bound to the polynucleotide via the binding sequence.

21. The fusion protein of claim 1, wherein the nuclease-deficient RNA-guided DNA endonuclease enzyme is dCas9 which comprises an amino acid sequence having at least 85% sequence identity to SEQ ID NO:23; ddCas12a which comprises an amino acid sequence having at least 85% sequence identity to SEQ ID NO:34; dLbCfp1 which comprises an amino acid sequence having at least 85% sequence identity to SEQ ID NO:35; or dFnCfp1 which comprises an amino acid sequence having at least 85% sequence identity to SEQ ID NO:36.

22. The fusion protein of claim 1, wherein the Krüppel associated box domain comprises an amino acid sequence having at least 85% sequence identity to SEQ ID NO:16.

23. The fusion protein of claim 3, wherein the Dnmt3A protein comprises an amino acid sequence with at least 85% sequence identity to SEQ ID NO:26, and the Dnmt3L protein comprises an amino acid sequence with at least 85% sequence identity to SEQ ID NO:28.

24. The fusion protein of claim 1, wherein the fusion protein comprises an amino acid sequence having at least 85% sequence identity to SEQ ID NO:15.

25. The fusion protein of claim 1, wherein the nuclease-deficient RNA-guided DNA endonuclease enzyme is selected from the group consisting of dCas9, ddCpf1, ddCas12a, ddLbCpf1 and ddFnCpf1.

26. A fusion protein comprising, a DNA methyltransferase domain, a nuclease-deficient RNA-guided DNA endonuclease enzyme, and a Krüppel associated box domain; wherein
(1) the nuclease-deficient RNA-guided DNA endonuclease enzyme is dCas9 which comprises an amino acid sequence having at least 85% sequence identity to SEQ ID NO:23; ddCas12a which comprises an amino acid sequence having at least 85% sequence identity to SEQ ID NO:34; dLbCfp1 which comprises an amino acid sequence having at least 85% sequence identity to SEQ ID NO:35; or dFnCfp1 which comprises an amino acid sequence having at least 85% sequence identity to SEQ ID NO:36;
(2) the Krüppel associated box domain comprises an amino acid sequence having at least 85% sequence identity to SEQ ID NO:16; and
(3) the DNA methyltransferase domain comprises a Dnmt3A protein, a Dnmt3L protein, or a Dnmt3A protein and a Dnmt3L protein; wherein the Dnmt3A protein comprises an amino acid sequence with at least 85% sequence identity to SEQ ID NO:26, and the Dnmt3L protein comprises an amino acid sequence with at least 85% sequence identity to SEQ ID NO:28.

27. The fusion protein of claim 26, wherein the Krüppel associated box domain comprises an amino acid sequence having at least 90% sequence identity to SEQ ID NO:16.

28. The fusion protein of claim 27, wherein the Krüppel associated box domain comprises an amino acid sequence having at least 95% sequence identity to SEQ ID NO:16.

29. The fusion protein of claim 28, wherein the Krüppel associated box domain comprises an amino acid sequence having at least 99% sequence identity to SEQ ID NO:16.

30. The fusion protein of claim 26, wherein the Dnmt3A protein comprises an amino acid sequence with at least 90% sequence identity to SEQ ID NO:26.

31. The fusion protein of claim 30, wherein the Dnmt3A protein comprises an amino acid sequence with at least 95% sequence identity to SEQ ID NO:26.

32. The fusion protein of claim 31, wherein the Dnmt3A protein comprises an amino acid sequence with at least 99% sequence identity to SEQ ID NO:26.

33. The fusion protein of claim 26, wherein the Dnmt3L protein comprises an amino acid sequence with at least 90% sequence identity to SEQ ID NO:28.

34. The fusion protein of claim 33, wherein the Dnmt3L protein comprises an amino acid sequence with at least 95% sequence identity to SEQ ID NO:28.

35. The fusion protein of claim 34, wherein the Dnmt3L protein comprises an amino acid sequence with at least 99% sequence identity to SEQ ID NO:28.

36. The fusion protein of claim 26, wherein the dCas9 comprises an amino acid sequence having at least 90% sequence identity to SEQ ID NO:23.

37. The fusion protein of claim 36, wherein the dCas9 comprises an amino acid sequence having at least 95% sequence identity to SEQ ID NO:23.

38. The fusion protein of claim 37, wherein the dCas9 comprises an amino acid sequence having at least 99% sequence identity to SEQ ID NO:23.

39. The fusion protein according to claim 25, wherein the Krüppel associated box domain comprises an amino acid sequence of SEQ ID NO: 16, the Dnmt3A protein comprises an amino acid sequence of SEQ ID NO: 26, the Dnmt3L protein comprises an amino acid sequence of SEQ ID NO: 28 and the dCas9 comprises an amino acid sequence of SEQ ID NO: 23.

40. The fusion protein according to claim 39, wherein the fusion protein comprises, from N-terminus to C-terminus, a DNA methyltransferase domain, a nuclease-deficient RNA-guided DNA endonuclease enzyme, and a Krüppel associated box domain.

41. The fusion protein according to claim 39, wherein the fusion protein comprises, from N-terminus to C-terminus, a DNA methyltransferase domain, a nuclease-deficient RNA-guided DNA endonuclease enzyme, and a Krüppel associated box domain.

* * * * *